(12) United States Patent
Babul

(10) Patent No.: US 8,329,744 B2
(45) Date of Patent: Dec. 11, 2012

(54) METHODS OF PREVENTING THE SEROTONIN SYNDROME AND COMPOSITIONS FOR USE THEREOF

(75) Inventor: Najib Babul, Blue Bell, PA (US)

(73) Assignee: Relmada Therapeutics, Inc., Blue Bell, PA (US)

( * ) Notice: Subject to any disclaimer, the term of this patent is extended or adjusted under 35 U.S.C. 154(b) by 258 days.

(21) Appl. No.: 12/216,645

(22) Filed: Jul. 7, 2008

(65) Prior Publication Data

US 2008/0280975 A1 Nov. 13, 2008

Related U.S. Application Data

(63) Continuation-in-part of application No. 12/223,987, filed as application No. PCT/US2006/042962 on Nov. 2, 2006, now abandoned.

(60) Provisional application No. 60/732,121, filed on Nov. 2, 2005, provisional application No. 60/929,611, filed on Jul. 5, 2007.

(51) Int. Cl.
- A01N 43/08 (2006.01)
- A01N 43/38 (2006.01)
- A01N 43/26 (2006.01)

(52) U.S. Cl. .................. 514/468; 514/410; 514/441

(58) Field of Classification Search .................. 514/183
See application file for complete search history.

(56) References Cited

U.S. PATENT DOCUMENTS

| | | | |
|---|---|---|---|
| 3,493,657 A | 2/1970 | Lewenstein | |
| 3,773,955 A | 11/1973 | Pachter | |
| 3,966,940 A | 6/1976 | Pachter | |
| 3,980,766 A | 9/1976 | Shaw | |
| 4,070,494 A | 1/1978 | Hoffmeister | |
| 4,457,933 A | 7/1984 | Gordon | |
| 4,582,835 A | 4/1986 | Lewis | |
| 4,713,243 A | 12/1987 | Schiraldi | |
| 5,378,474 A | 1/1995 | Morella et al. | |
| 5,747,058 A | 5/1998 | Tipton | |
| 5,922,341 A * | 7/1999 | Smith et al. | 424/430 |
| 5,958,452 A | 9/1999 | Oshlack | |
| 5,968,542 A | 10/1999 | Tipton | |
| 5,968,551 A | 10/1999 | Oshlack | |
| 6,227,384 B1 | 5/2001 | Saylor | |
| 6,228,863 B1 | 5/2001 | Palermo | |
| 6,261,599 B1 | 7/2001 | Oshlack | |
| 6,266,331 B1 | 7/2001 | Baker | |
| 6,309,668 B1 | 10/2001 | Bastin | |
| 6,326,027 B1 | 12/2001 | Miller | |
| 6,335,033 B2 | 1/2002 | Oshlack | |
| 6,375,957 B1 | 4/2002 | Kaiko | |
| 6,475,494 B2 | 11/2002 | Kaiko | |
| 6,559,159 B2 | 5/2003 | Carroll | |
| 6,627,635 B2 | 9/2003 | Palermo | |
| 6,638,533 B2 | 10/2003 | Krsek | |
| 6,692,771 B2 | 2/2004 | Pather | |
| 6,696,066 B2 | 2/2004 | Kaiko | |
| 6,696,088 B2 | 2/2004 | Oshlack | |
| 6,706,281 B2 | 3/2004 | Oshlack | |
| 6,743,442 B2 | 6/2004 | Oshlack | |
| 7,015,346 B2 | 3/2006 | Jenkins et al. | |
| 7,083,808 B2 | 8/2006 | Goldenheim et al. | |
| 7,144,587 B2 | 12/2006 | Oshlack et al. | |
| 7,169,752 B2 | 1/2007 | Mickle et al. | |
| 7,172,767 B2 | 2/2007 | Kaiko | |
| 7,201,920 B2 | 4/2007 | Kumar et al. | |
| 7,226,619 B1 | 6/2007 | Bear | |
| 7,399,488 B2 | 7/2008 | Hirsh | |
| 7,419,686 B2 | 9/2008 | Kaiko | |
| 7,511,054 B2 | 3/2009 | Stinchcomb et al. | |
| 7,731,758 B2 | 6/2010 | Asius et al. | |
| 2002/0192287 A1 | 12/2002 | Mooney et al. | |
| 2003/0049317 A1 | 3/2003 | Lindsay | |
| 2003/0077297 A1 * | 4/2003 | Chen et al. | 424/400 |
| 2003/0118641 A1 | 6/2003 | Maloney | |
| 2003/0124185 A1 | 7/2003 | Oshlack et al. | |
| 2003/0129229 A1 | 7/2003 | Krsek | |
| 2003/0180352 A1 | 9/2003 | Patel et al. | |
| 2004/0042964 A1 | 3/2004 | Joshi et al. | |
| 2004/0058946 A1 | 3/2004 | Buchwald et al. | |
| 2004/0101557 A1 | 5/2004 | Gibson et al. | |
| 2004/0131552 A1 | 7/2004 | Boehm | |
| 2004/0131680 A1 | 7/2004 | Goldenheim et al. | |
| 2004/0132826 A1 | 7/2004 | Hirsh | |
| 2004/0176341 A1 | 9/2004 | Chou et al. | |
| 2004/0191323 A1 | 9/2004 | Asius et al. | |
| 2004/0202717 A1 | 10/2004 | Mehta | |
| 2004/0228802 A1 | 11/2004 | Chang et al. | |

(Continued)

FOREIGN PATENT DOCUMENTS

| | | |
|---|---|---|
| GB | 05 06982.8 | 4/2005 |
| WO | WO 2006/106344 | 10/2006 |
| WO | WO 2007/056142 | 5/2007 |
| WO | WO 2007/087452 | 8/2007 |
| WO | WO 2008/033351 | 3/2008 |
| WO | WO 2008/134071 | 11/2008 |

OTHER PUBLICATIONS

Lopez, J. (The Neurobiology of Depression, Cyberounds, 2000, 4 printed pages).*
Lopez, J. "The Neurobiology of Depression" Cyberounds, 2000, 4 pages.
U.S. Appl. No. 12/223,987, Babul.

*Primary Examiner* — Sreeni Padmanabhan
*Assistant Examiner* — Timothy E Betton
(74) *Attorney, Agent, or Firm* — Dilworth Paxson LLP; Gary D. Colby

(57) ABSTRACT

The present invention is directed at methods for preventing or minimizing the intensity of the serotonin syndrome in humans and lower animals which comprises administering proserotonergic agents and serotonin surge protectors. The present invention is also directed to pharmaceutical compositions comprising proserotonergic agents and serotonin surge protectors useful for carrying out the method of the present invention.

20 Claims, 66 Drawing Sheets

U.S. PATENT DOCUMENTS

| | | |
|---|---|---|
| 2005/0020613 A1 | 1/2005 | Boehm et al. |
| 2005/0025832 A1 | 2/2005 | Lam et al. |
| 2005/0031546 A1 | 2/2005 | Bartholomaus et al. |
| 2005/0074493 A1 | 4/2005 | Mehta |
| 2005/0152843 A1 | 7/2005 | Bartholomaus et al. |
| 2005/0208047 A1 | 9/2005 | Anderson |
| 2005/0238709 A1 | 10/2005 | Lam et al. |
| 2005/0281748 A1 | 12/2005 | Hirsh |
| 2006/0002860 A1 | 1/2006 | Bartholomaus et al. |
| 2006/0003006 A1 | 1/2006 | Remon et al. |
| 2006/0034872 A1 | 2/2006 | Woolf |
| 2006/0039864 A1 | 2/2006 | Bartholomaus et al. |
| 2006/0110327 A1 | 5/2006 | Emigh et al. |
| 2006/0188447 A1 | 8/2006 | Arkenau-Maric et al. |
| 2006/0251721 A1 | 11/2006 | Cruz et al. |
| 2007/0020339 A1 | 1/2007 | Bear |
| 2007/0026065 A1 | 2/2007 | Benke et al. |
| 2007/0087977 A1 | 4/2007 | Robbins |
| 2007/0122482 A1 | 5/2007 | Holm et al. |
| 2007/0231268 A1 | 10/2007 | Emigh et al. |
| 2008/0020032 A1 | 1/2008 | Crowley |
| 2008/0069871 A1 | 3/2008 | Vaughn |
| 2008/0075768 A1 | 3/2008 | Vaughn |
| 2008/0075770 A1 | 3/2008 | Vaughn |
| 2008/0075771 A1 | 3/2008 | Vaughn |
| 2008/0076789 A1 | 3/2008 | Stinchcomb et al. |
| 2008/0152595 A1 | 6/2008 | Emigh et al. |
| 2008/0199530 A1 | 8/2008 | Hirsh |
| 2009/0082466 A1 | 3/2009 | Babul |
| 2009/0123386 A1 | 5/2009 | Young |

* cited by examiner

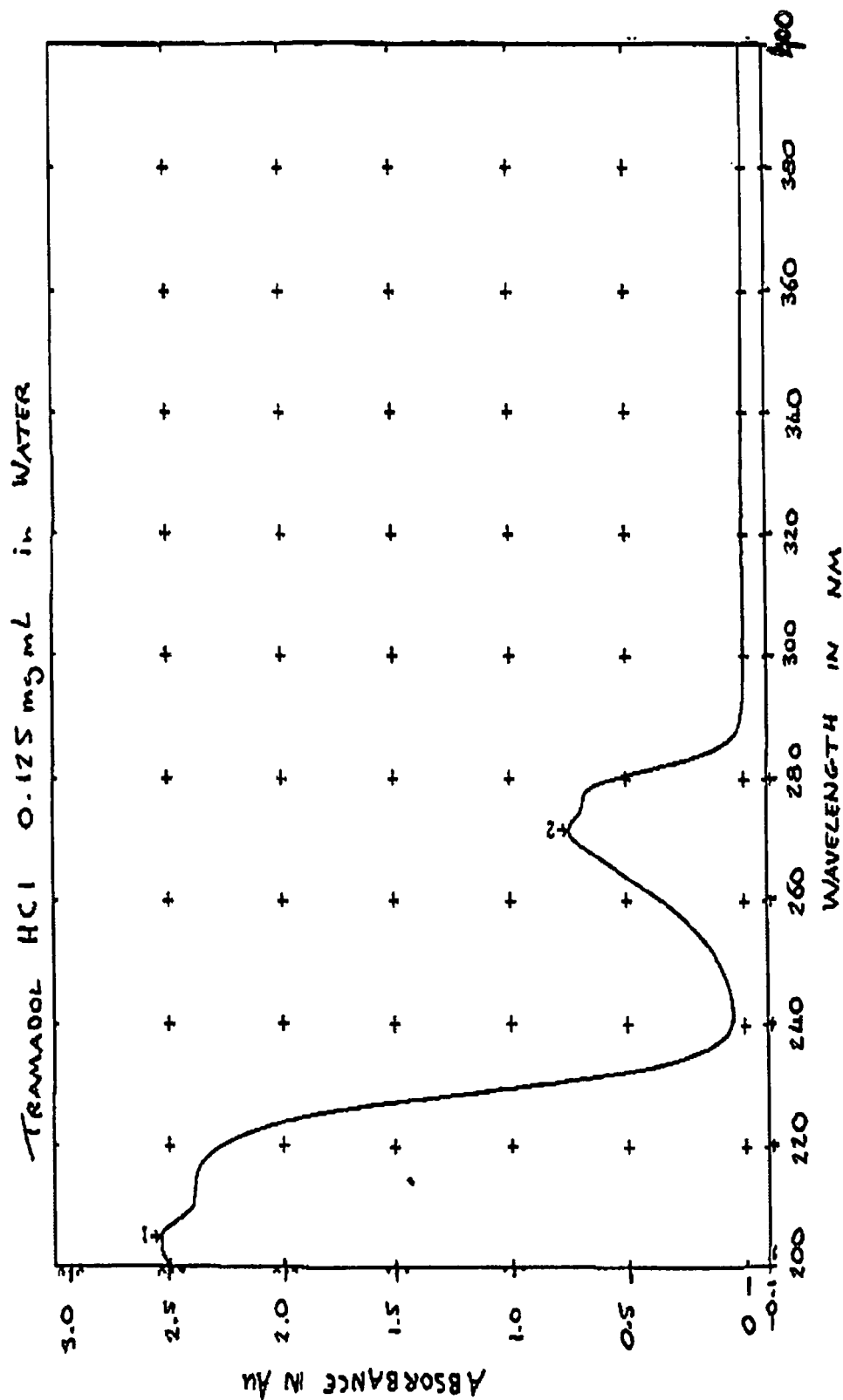
*Figure 1.* UV Spectrum of tramadol HCl in water

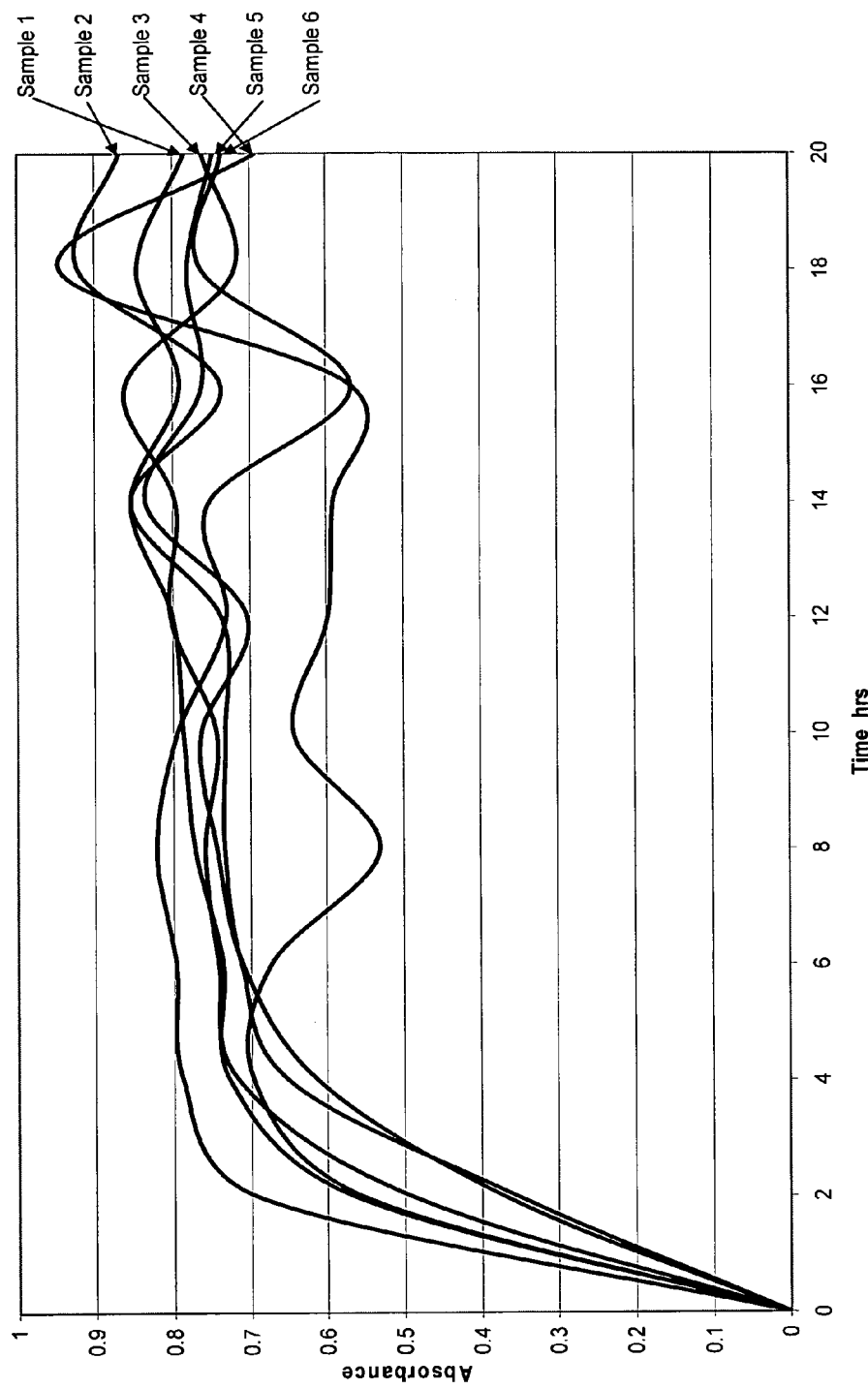
*Figure 2.* Formulation 052/014 dissolution profile

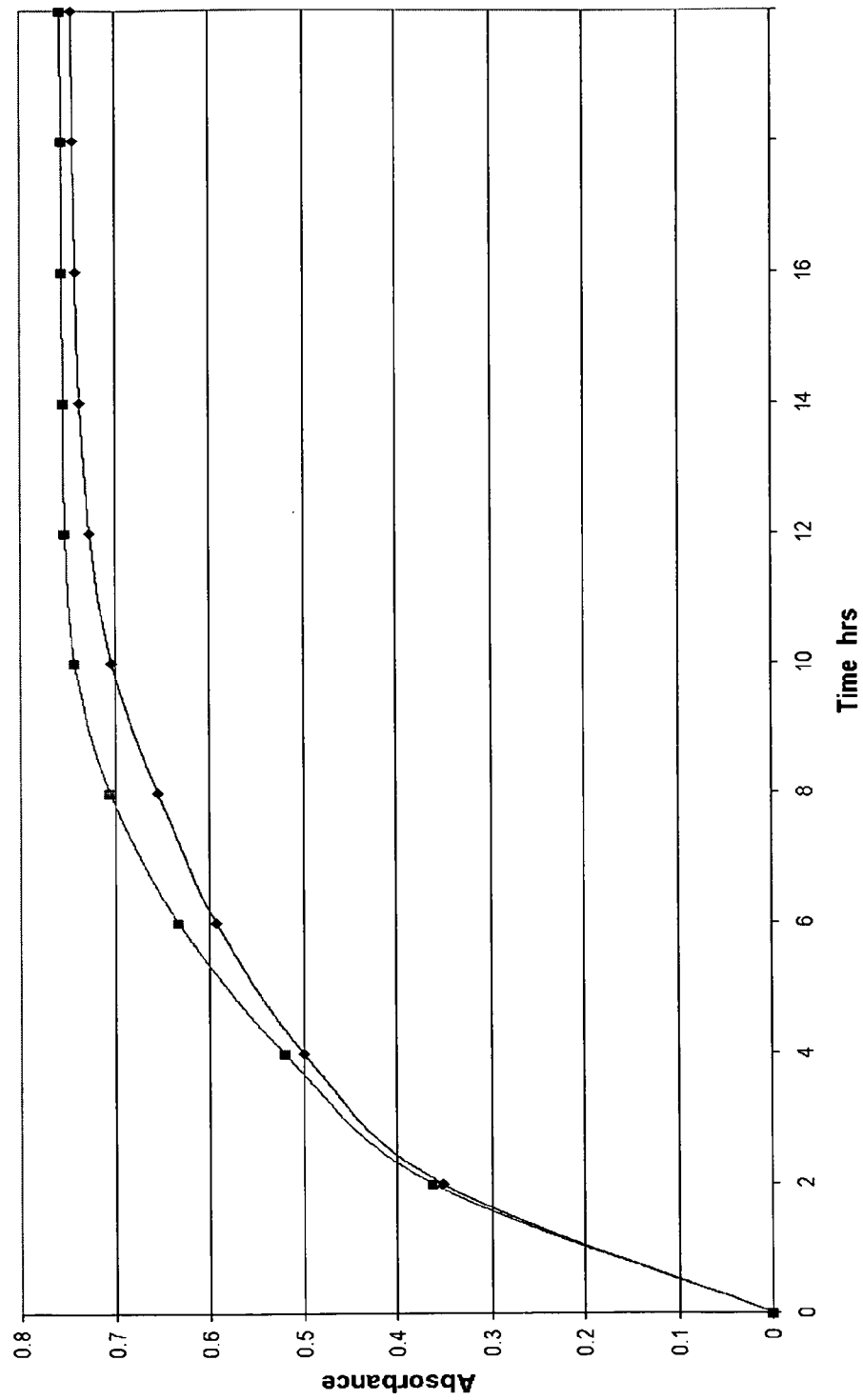
*Figure 3.* Formulation 052/015 dissolution profile

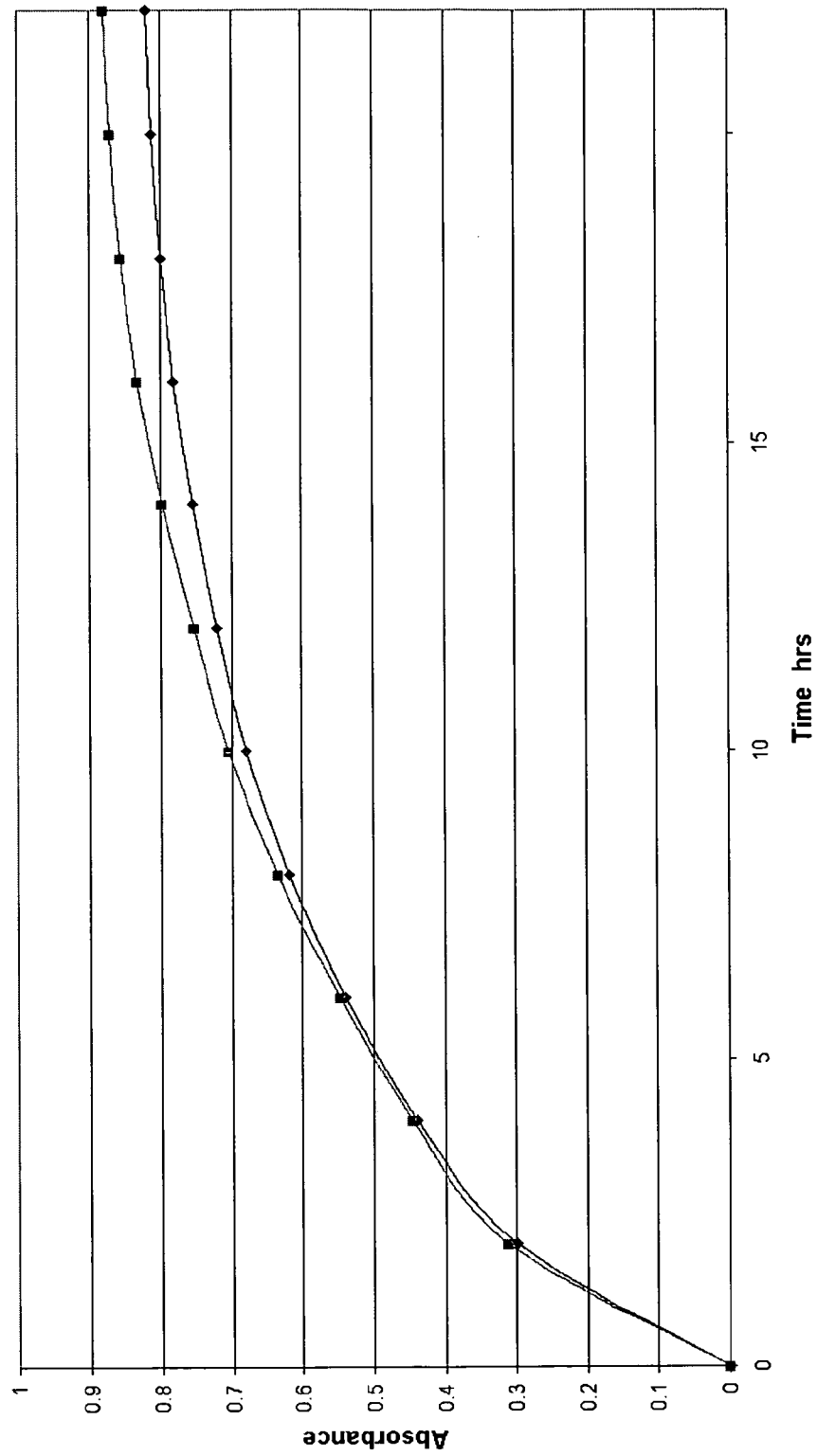
*Figure 4.* Formulation 052/019 dissolution profile, Gelucire 50/02 with Methocel K 100M

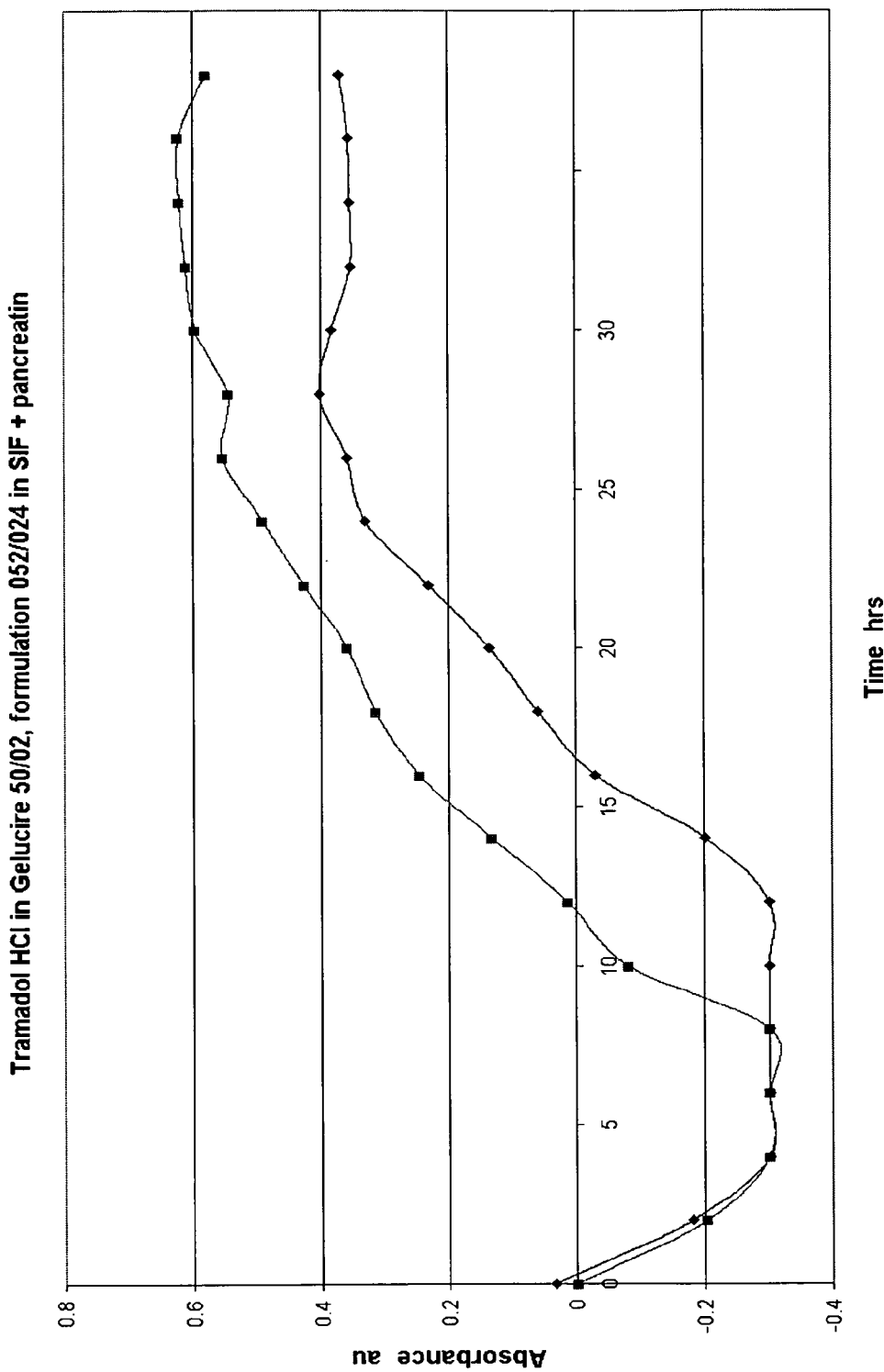
*Figure 5.* Formulation 052/024 dissolution profile

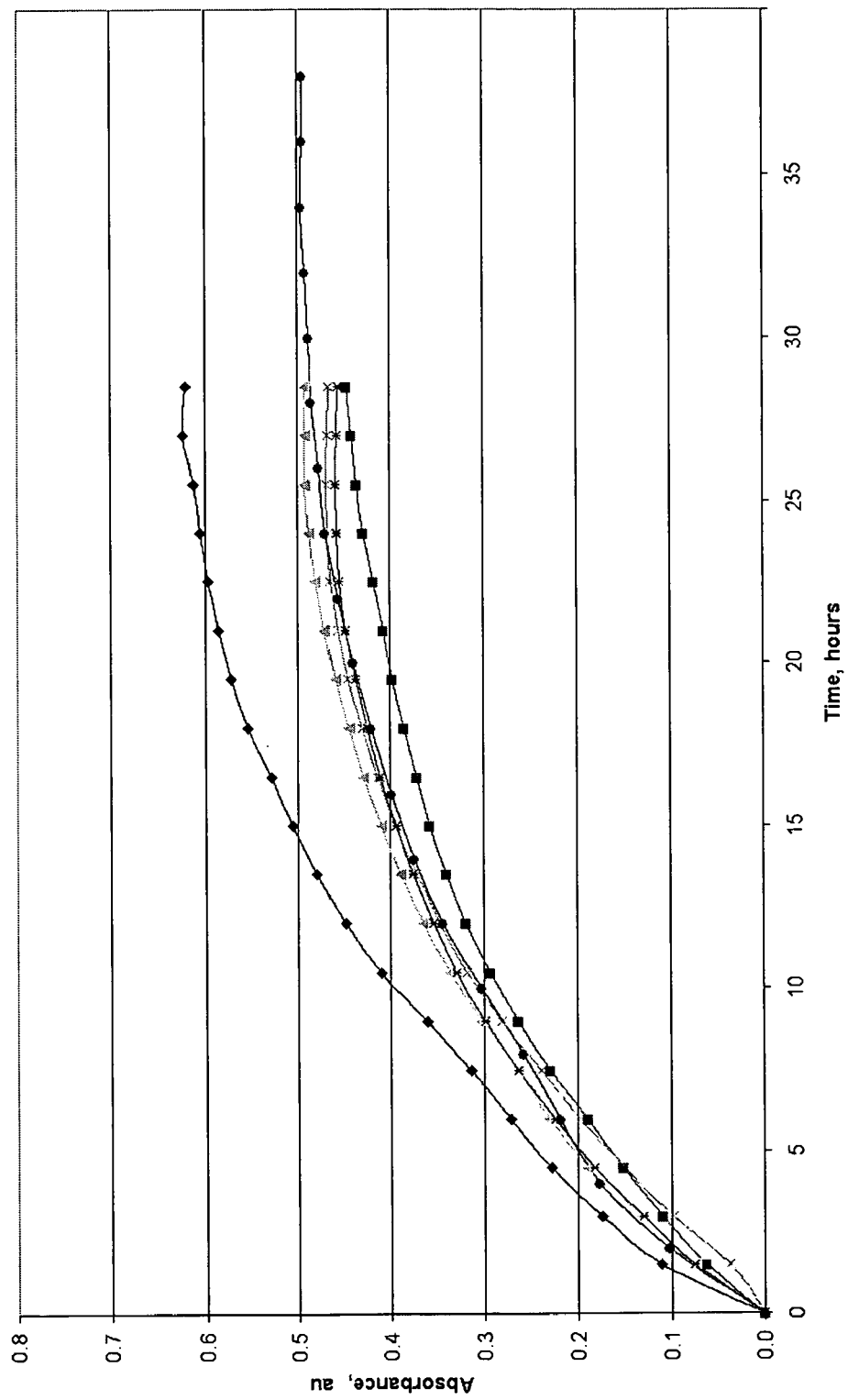
*Figure 6.* Formulation 052/024 dissolution profile in SIF containing pancreatin

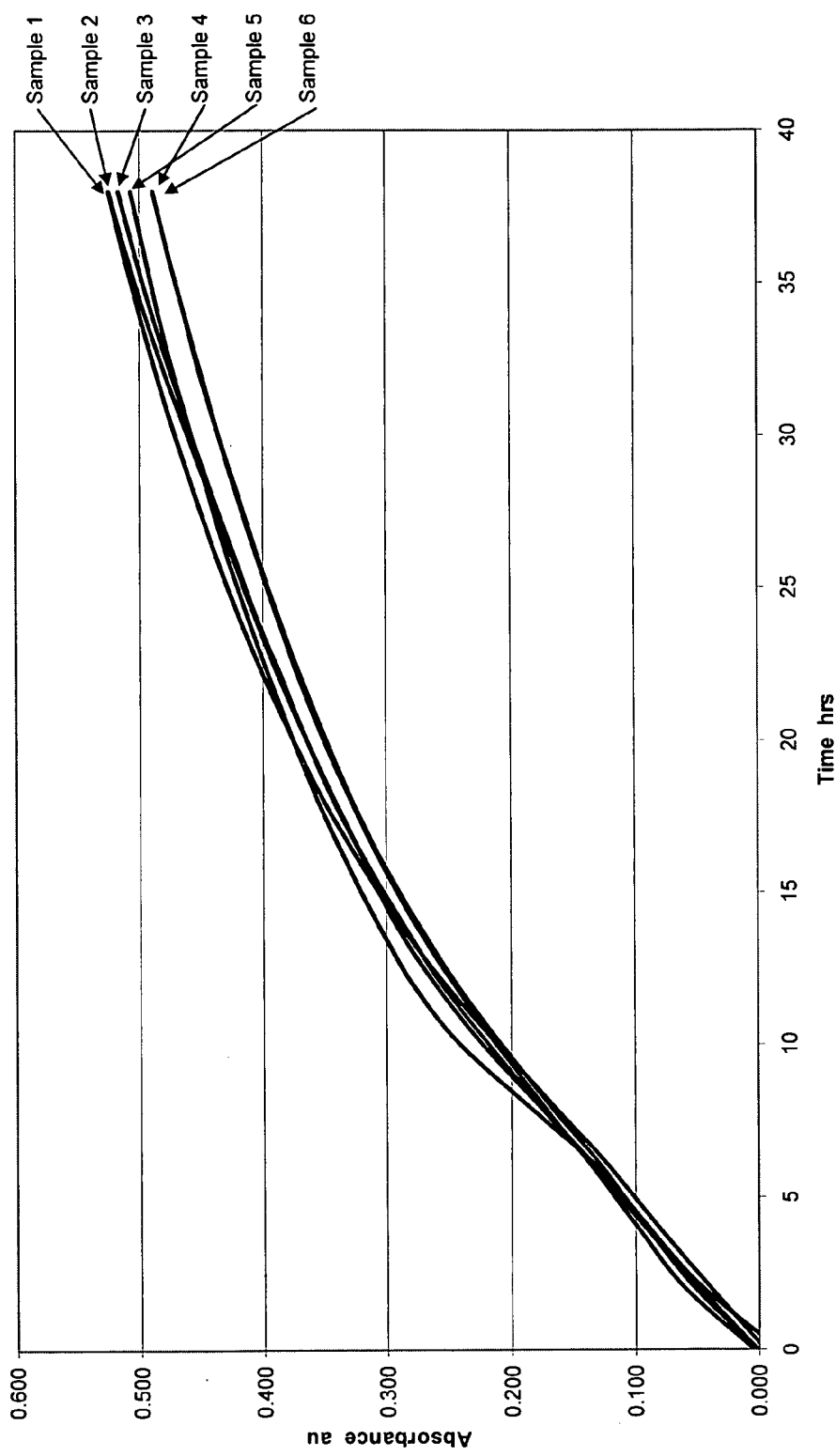
Figure 7. Dissolution profile of propranolol HCl in Gelucire 50/02 in SIF without pancreatin

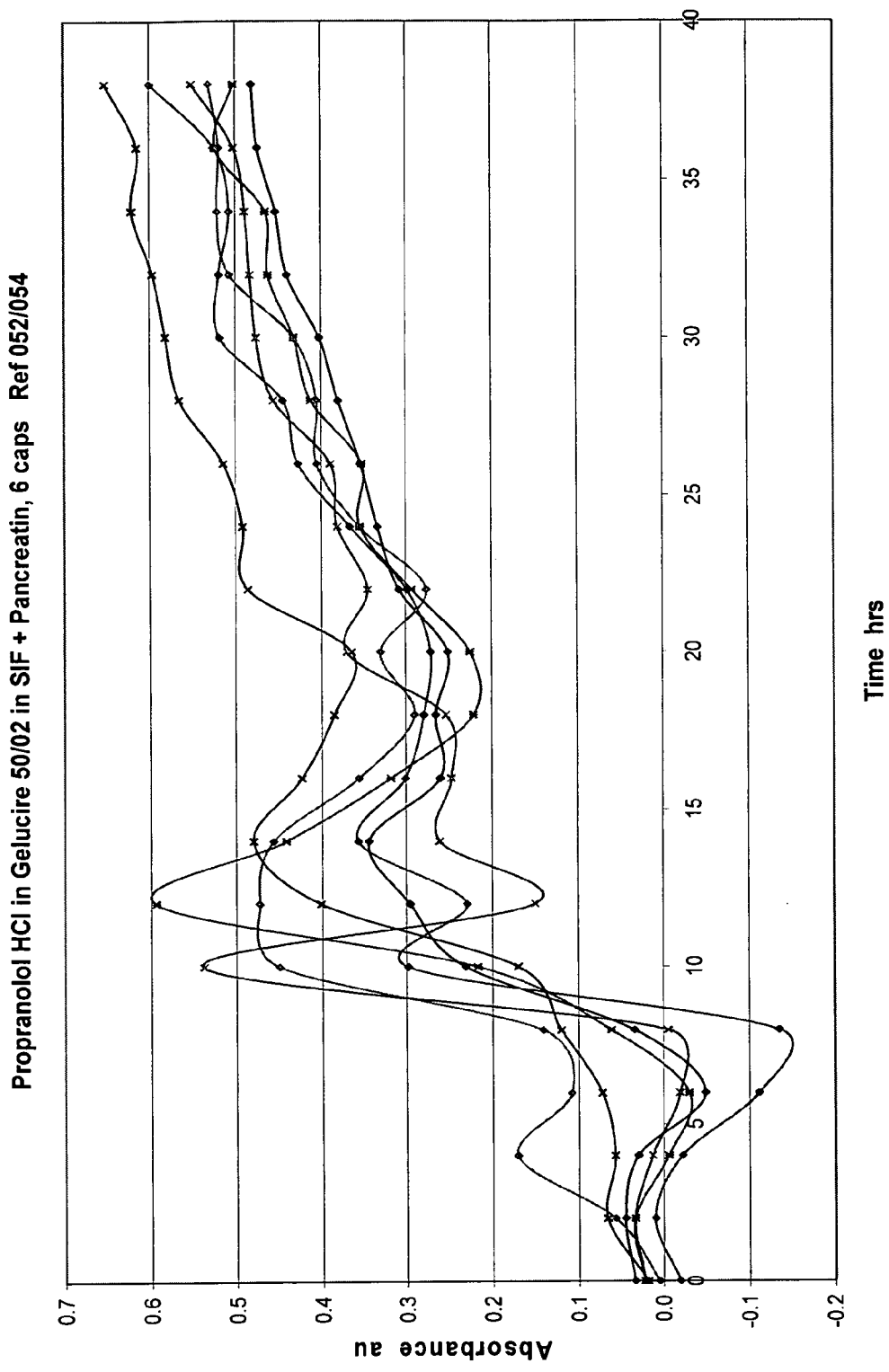
*Figure 8.* Dissolution profile of propranolol HCl in Gelucire 50/02 in SIF containing pancreatin

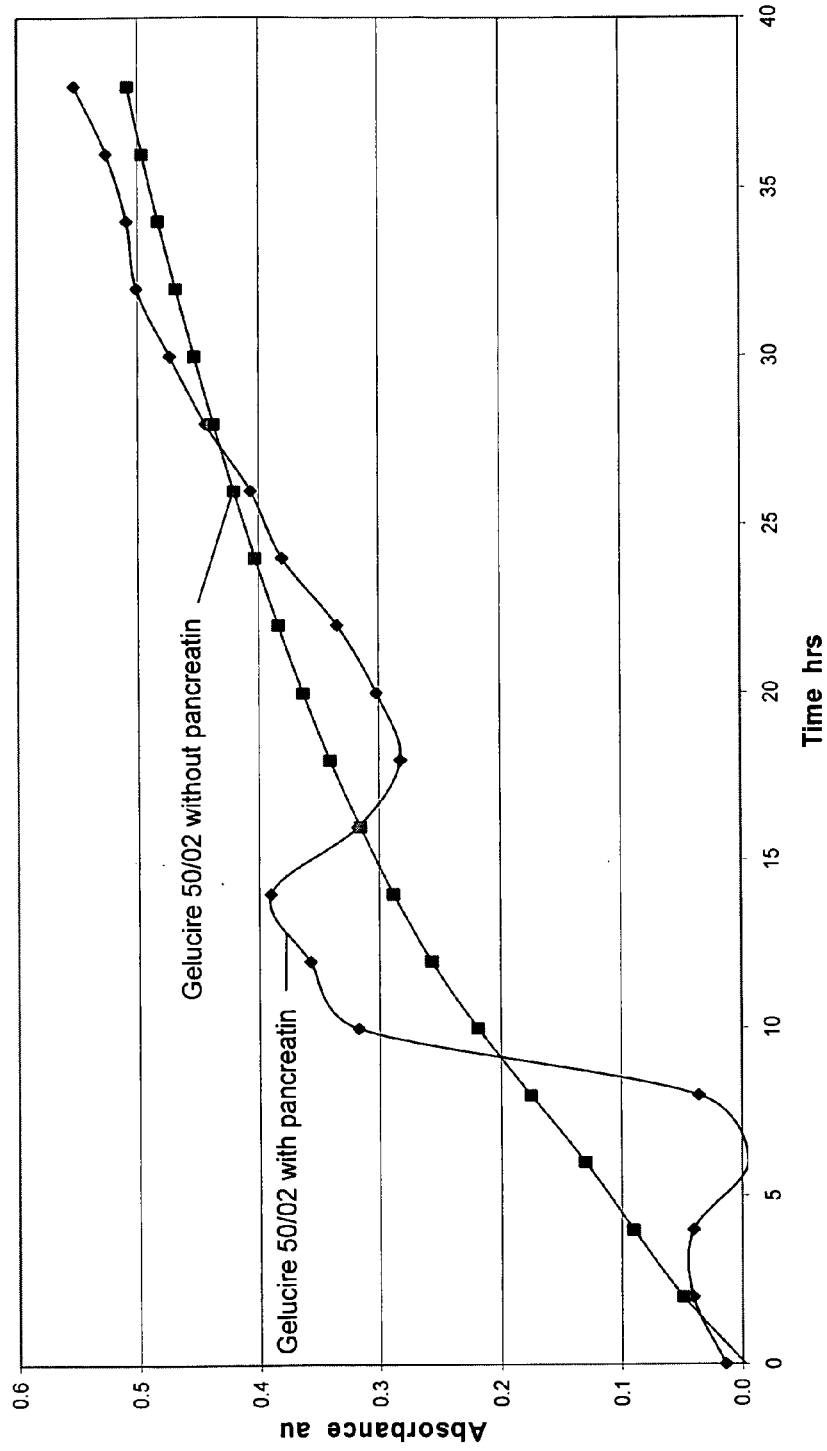
*Figure 9.* Combined averaged dissolution profiles of propranolol HCl in Gelucire 50/02 in SIF with and without pancreatin

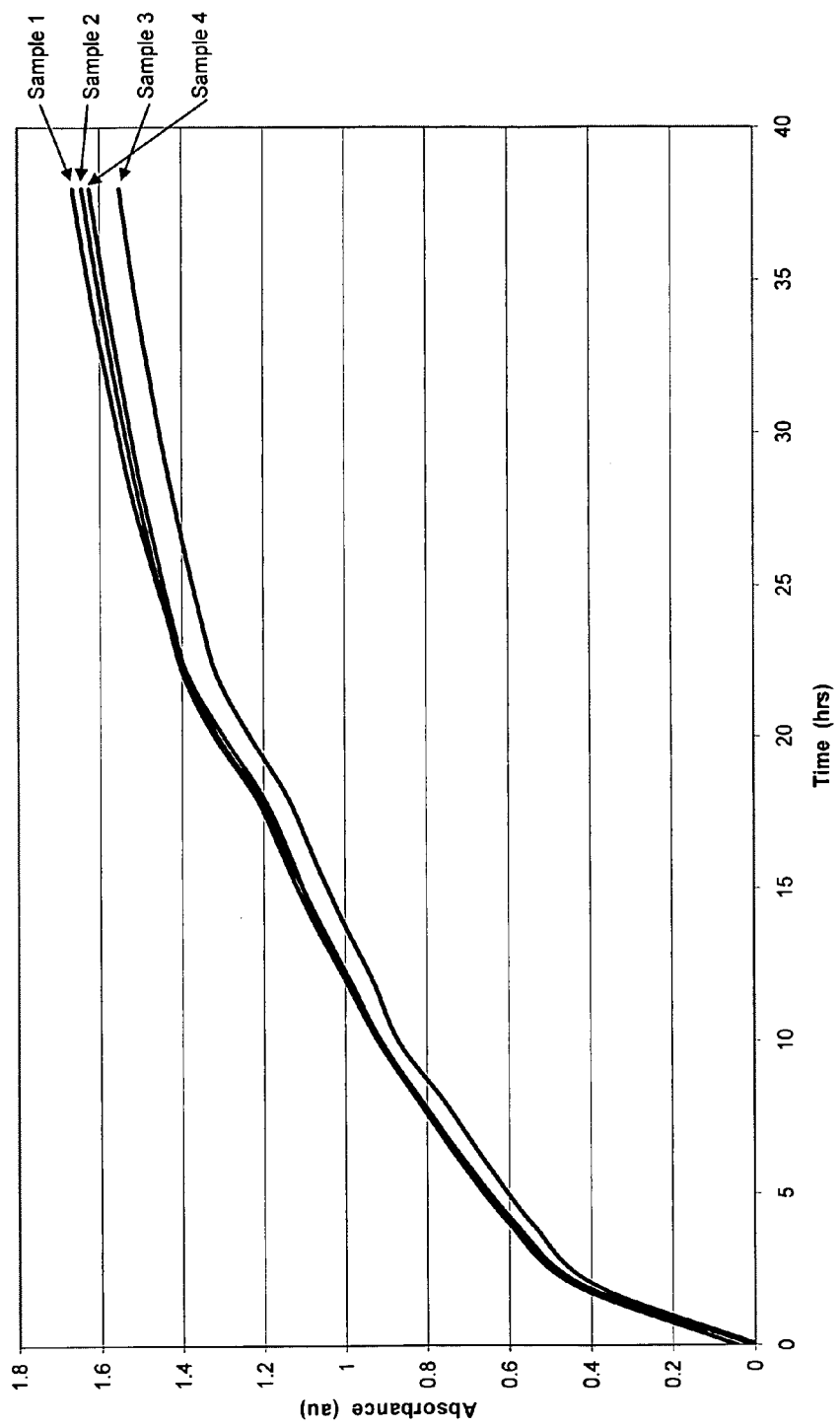
*Figure 10.* Combined dissolution profiles of Zydol XL 150 and Dromadol SR tablets in SIF

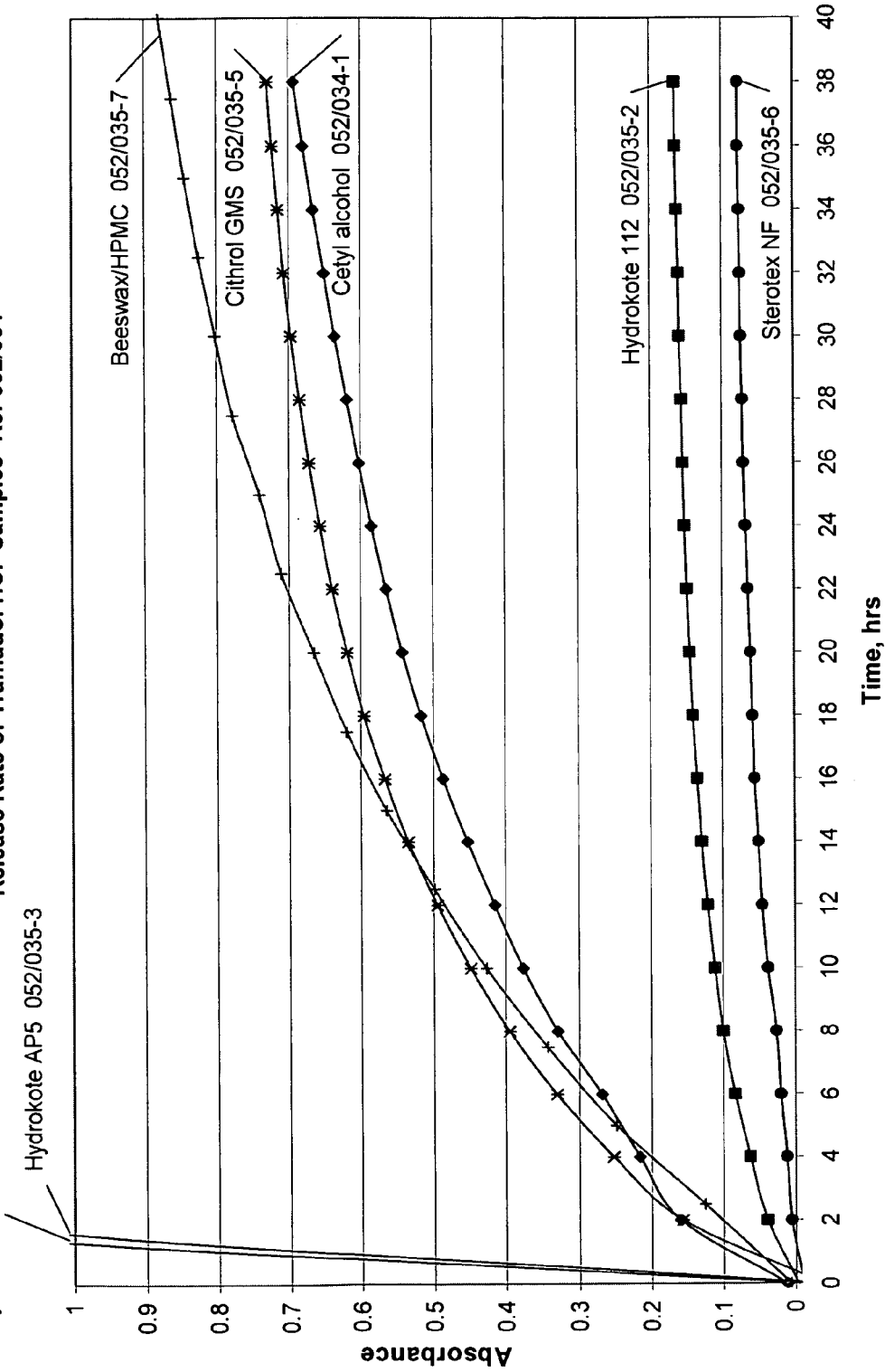
Figure 11. Combined dissolution profiles of seven different excipient formulations in SIF

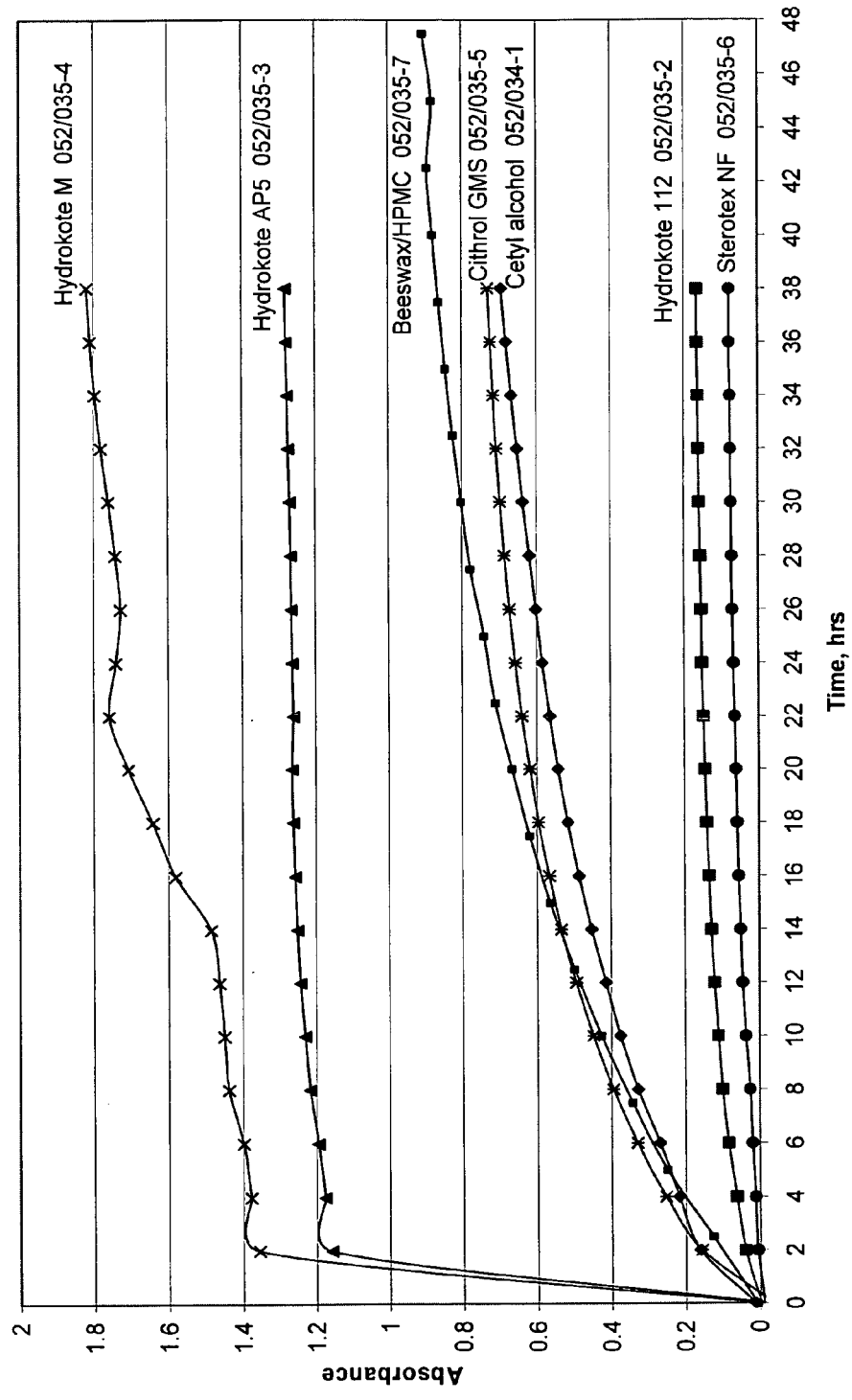
Figure 12. Combined dissolution profiles of seven different excipient formulations, extended scale

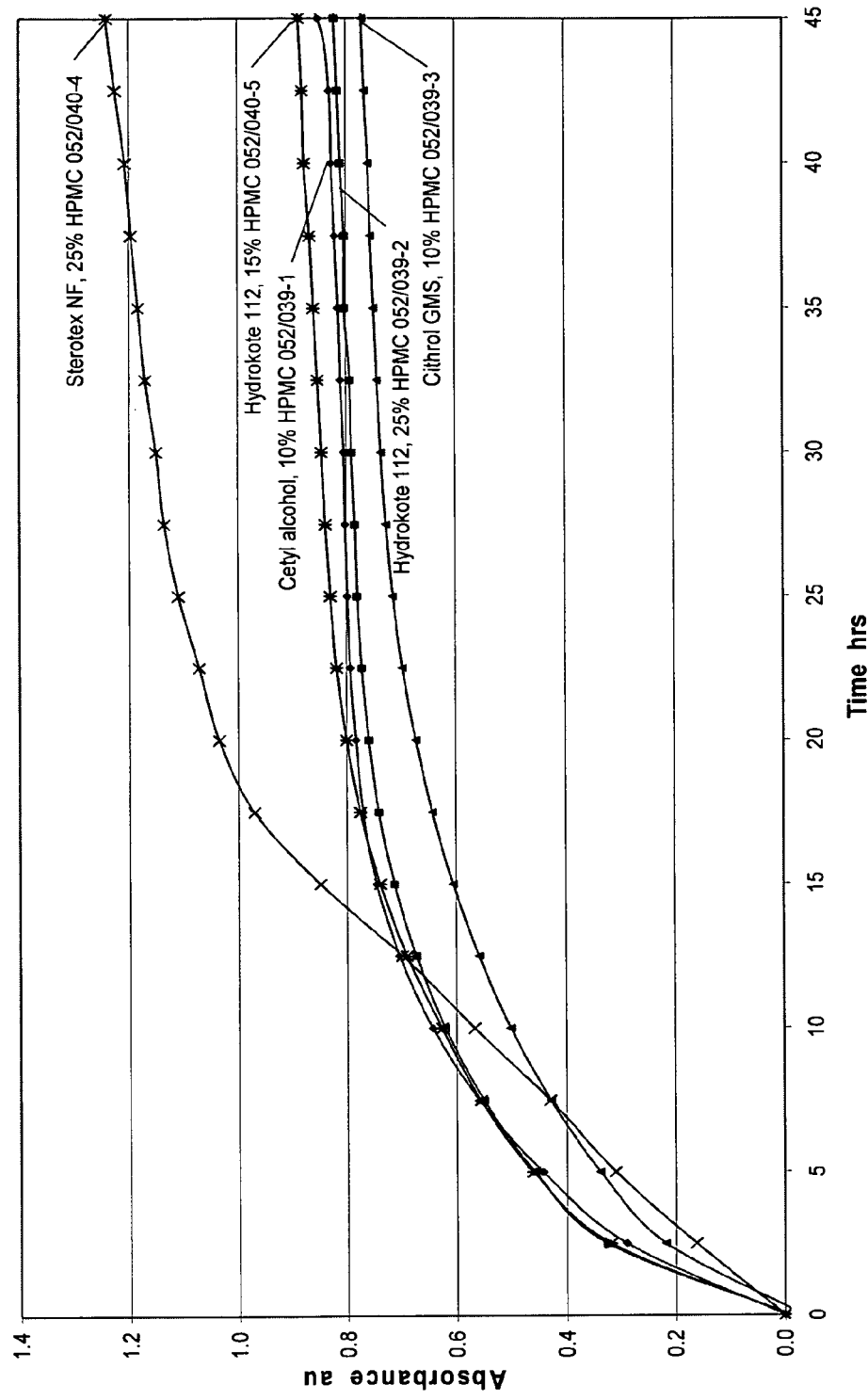
Figure 13. Combined dissolution profiles of five base excipients in HPMC modified formulations

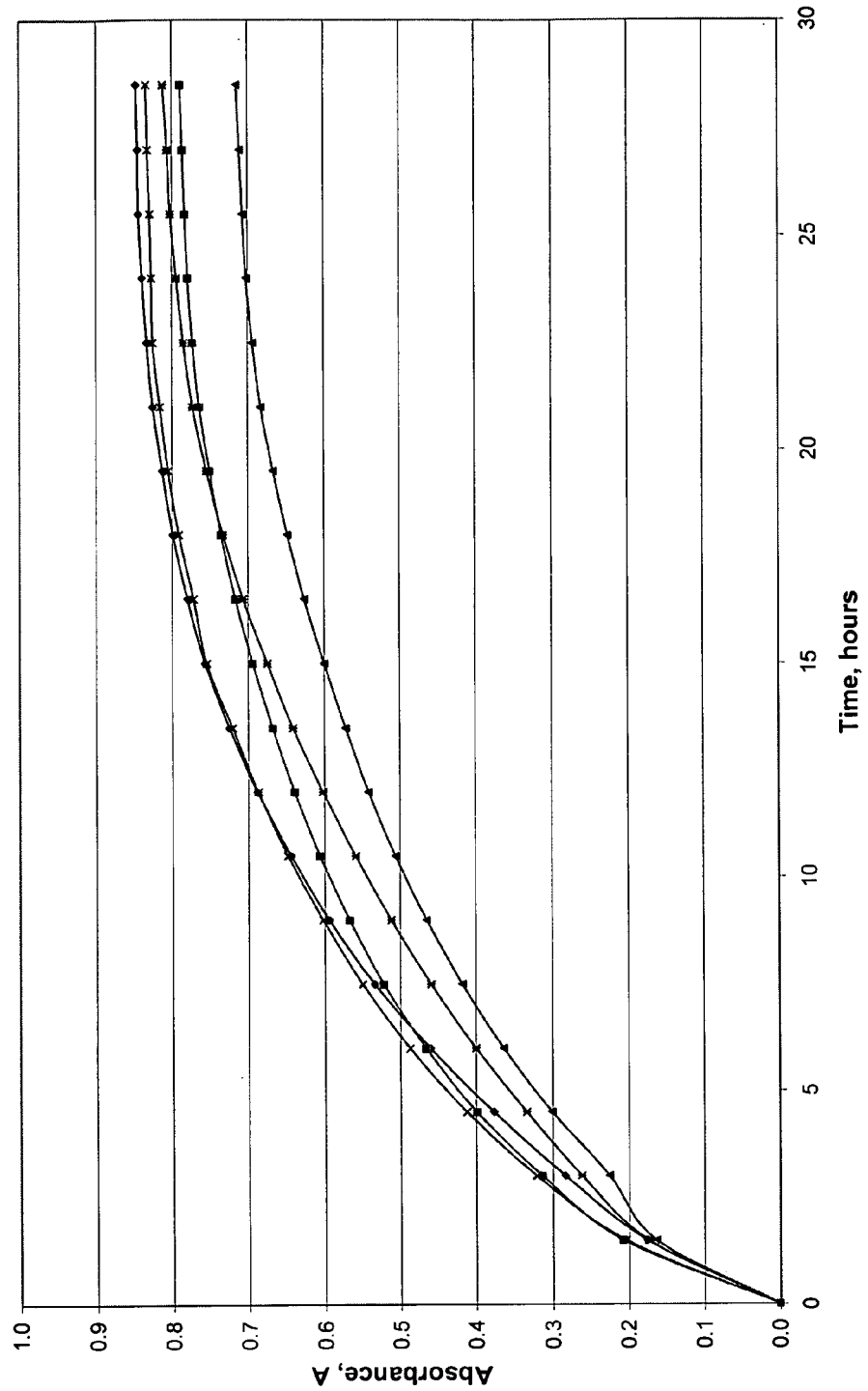
*Figure 14.* Dissolution profiles of five capsule sample of cetyl alcohol formulation with 10% HPMC

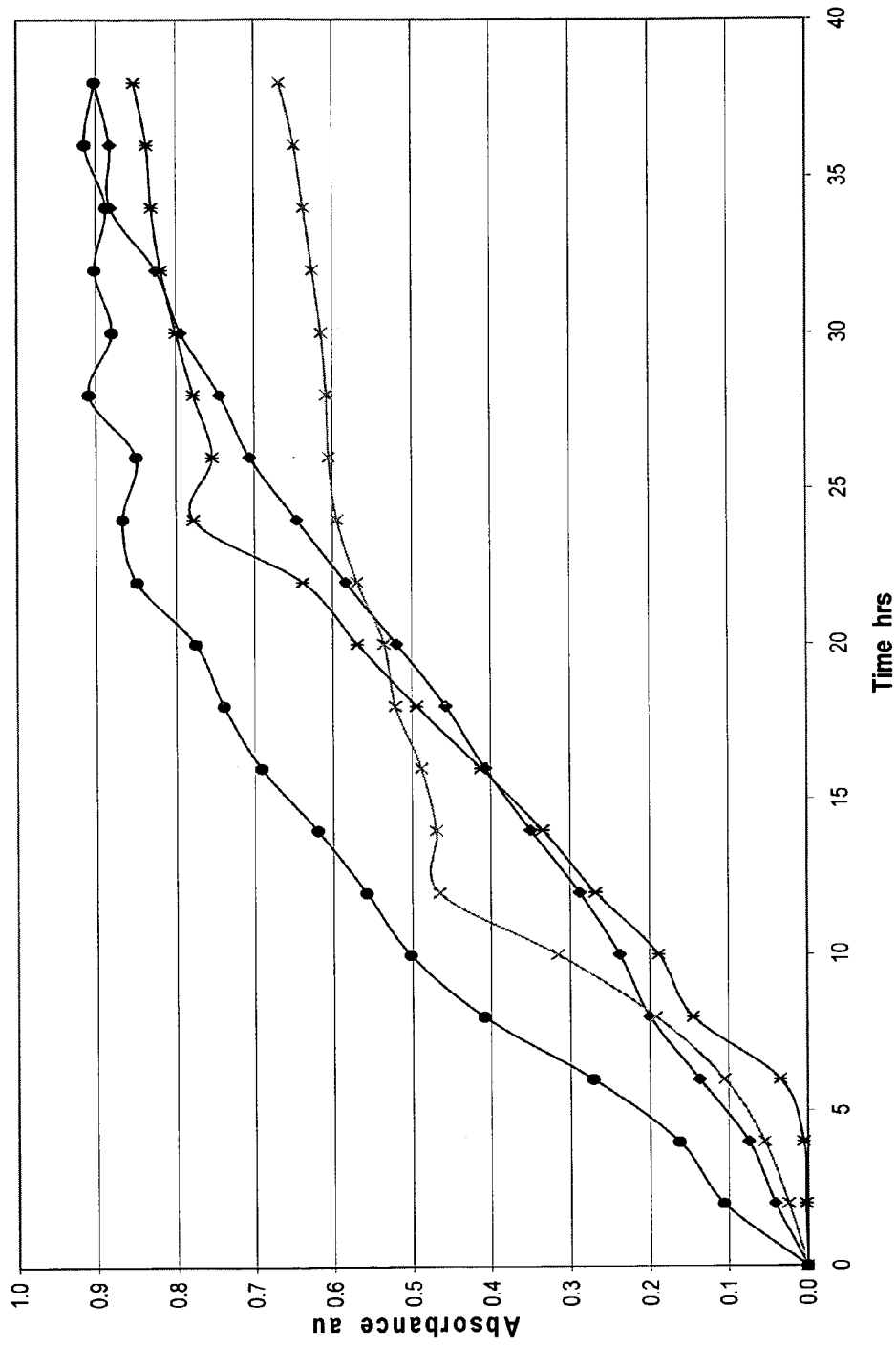
*Figure 15.* Dissolution profiles of modified Sterotex NF formulation

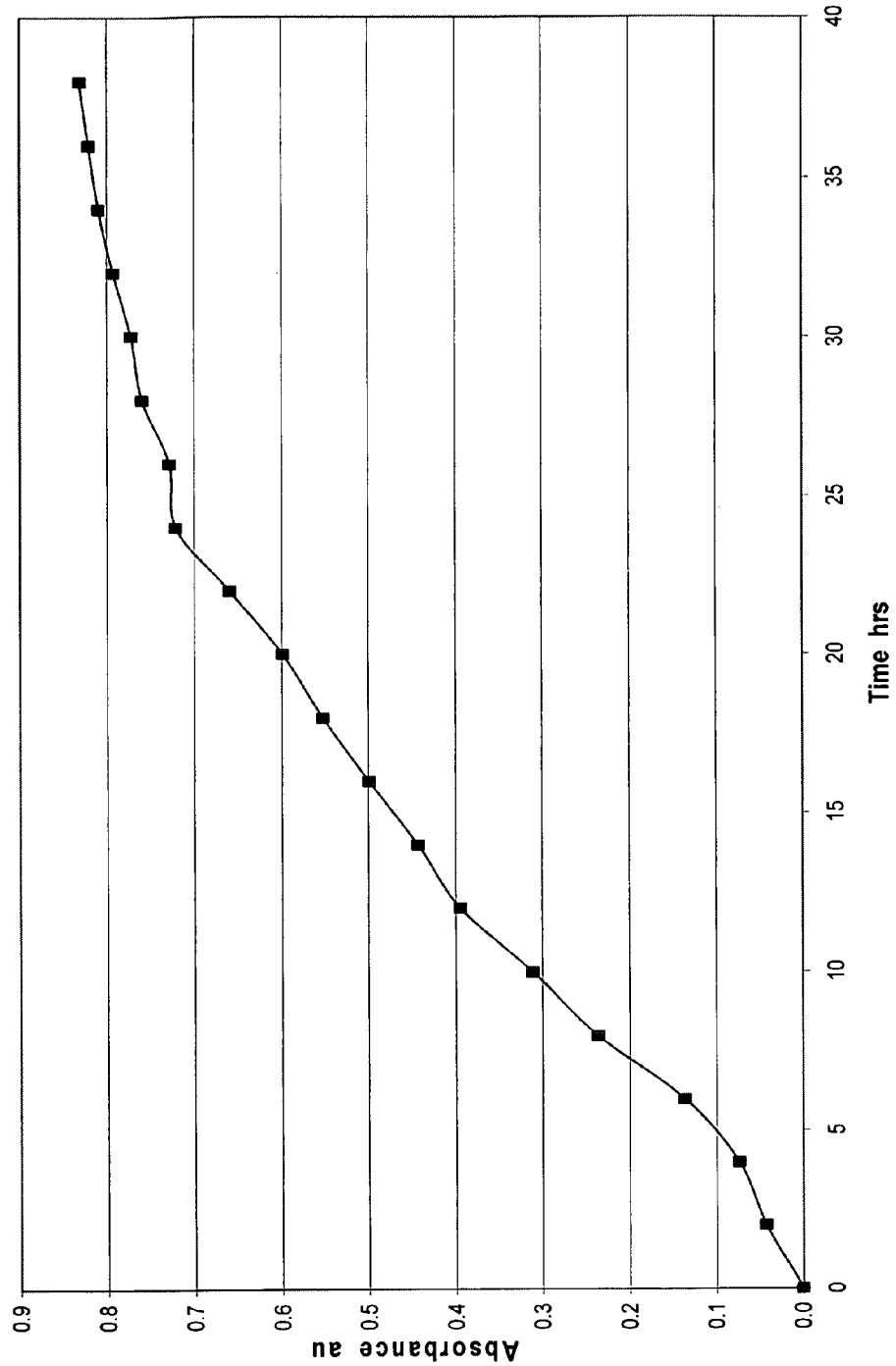
*Figure 16.* Average dissolution profiles of modified Sterotex NF formulation

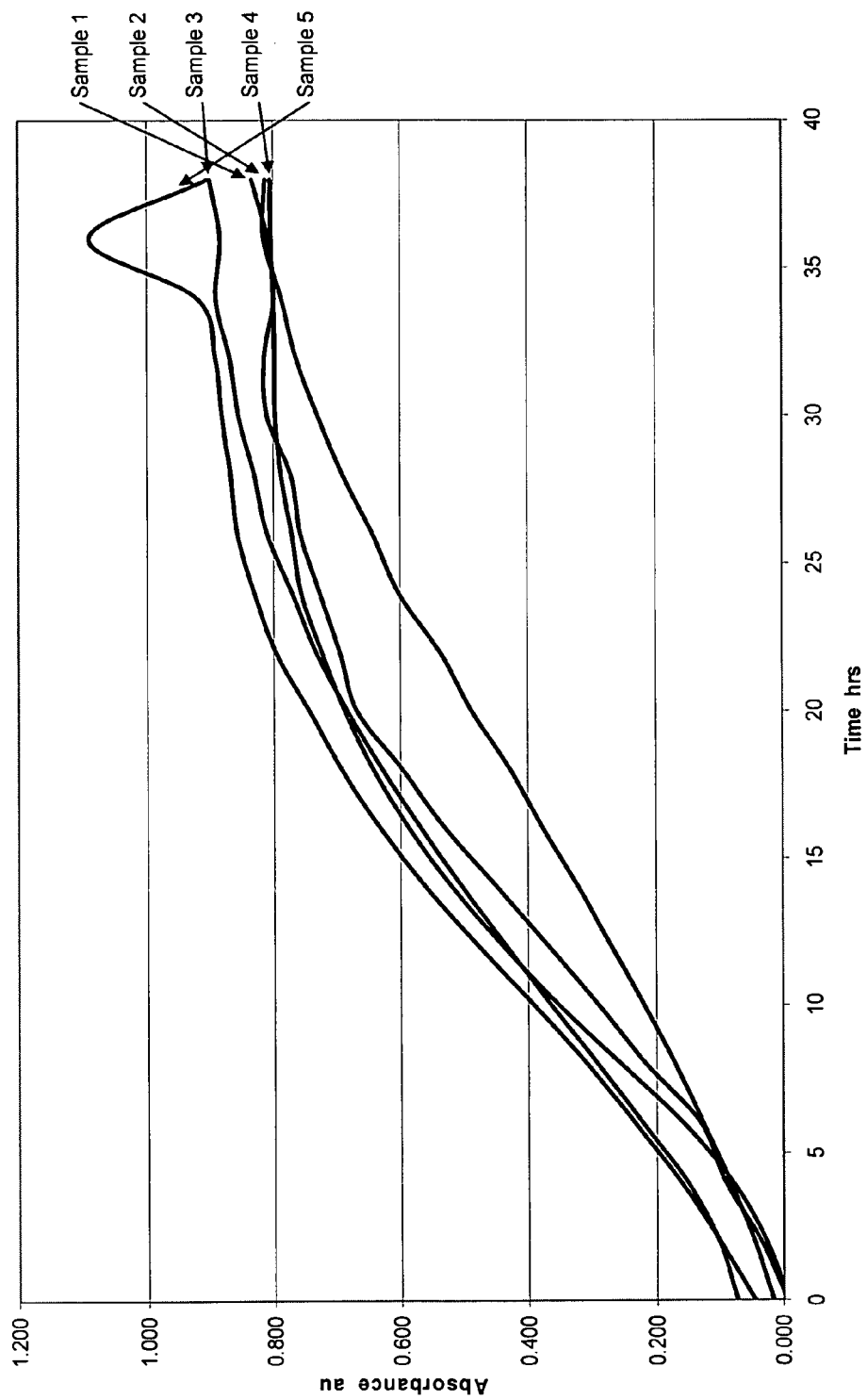
*Figure 17.* Dissolution profiles of further modified Sterotex NF formulation

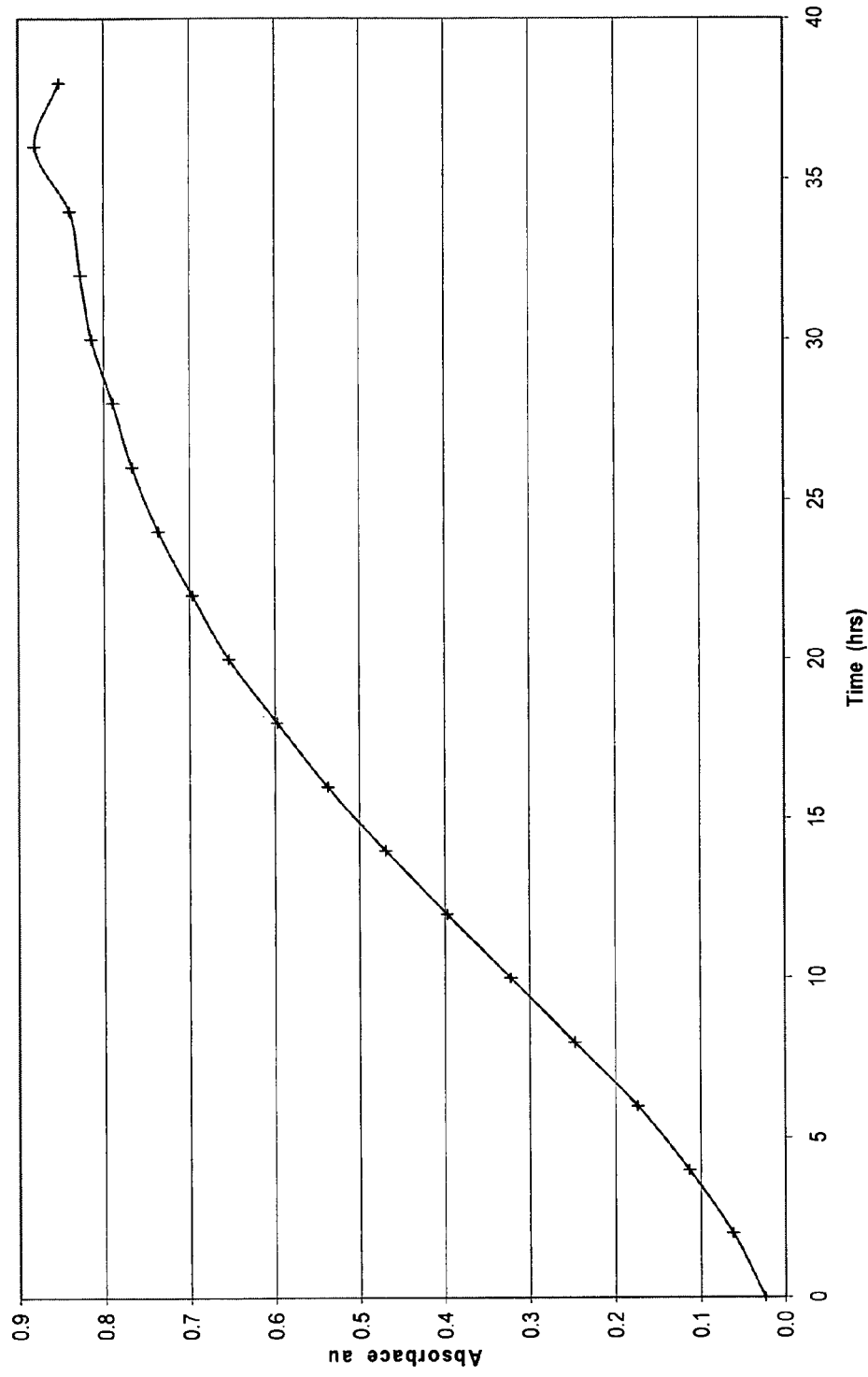
*Figure 18.* Average dissolution profiles of further modified Sterotex NF formulation

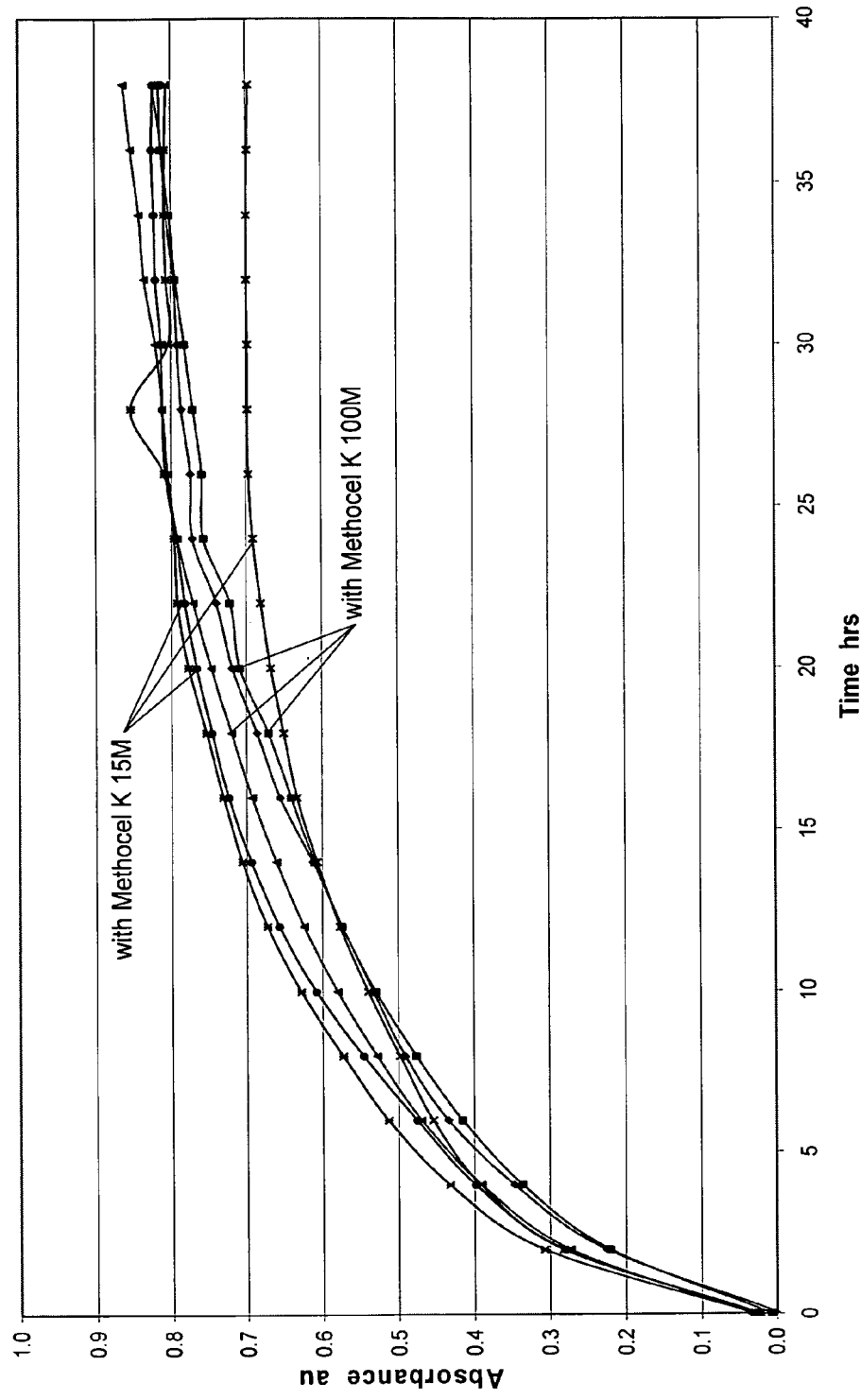
*Figure 19.* Dissolution profiles of Hydrokote formulations containing Methocel K 100M or Methocel K 15M

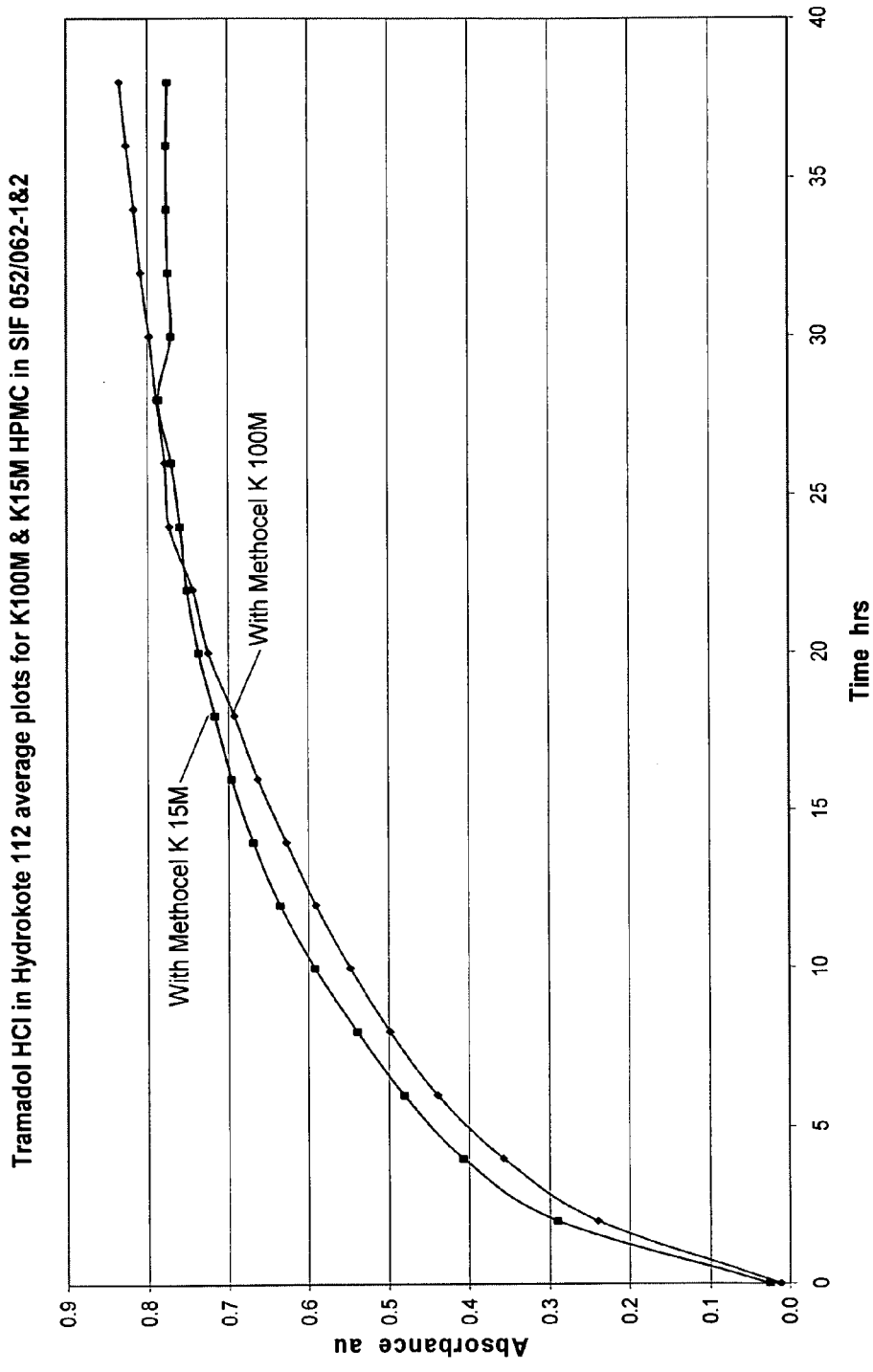
Figure 20. Averaged dissolution profiles of Hydrokote formulations containing Methocel K 100M or Methocel K 15M

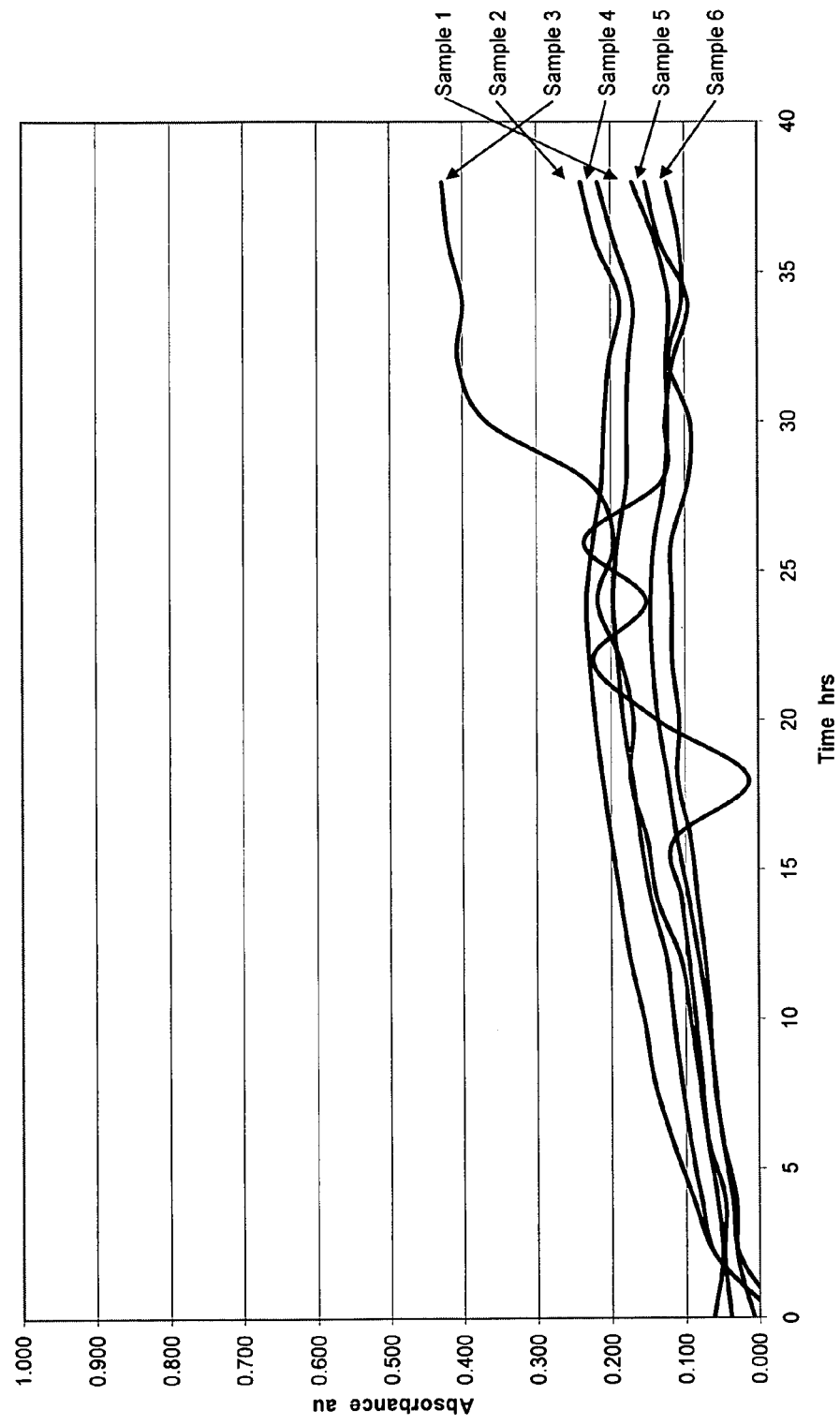
Figure 21. Dissolution profiles of 250 mg Tramadol HCl in a 550 mg Sterotex NF based formulation

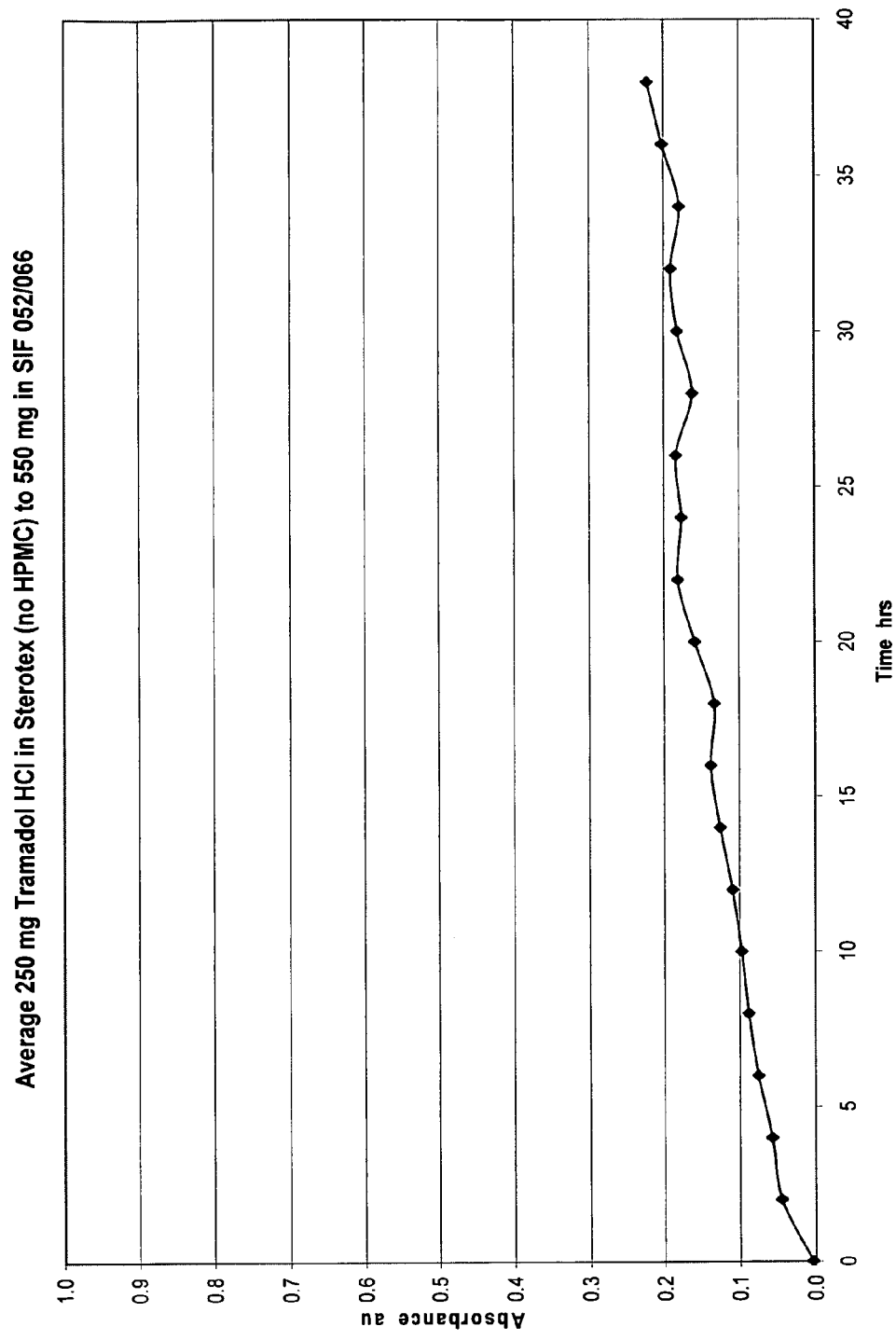
*Figure 22.* Averaged dissolution profiles of 250 mg Tramadol HCl in a 550 mg Sterotex NF based formulation

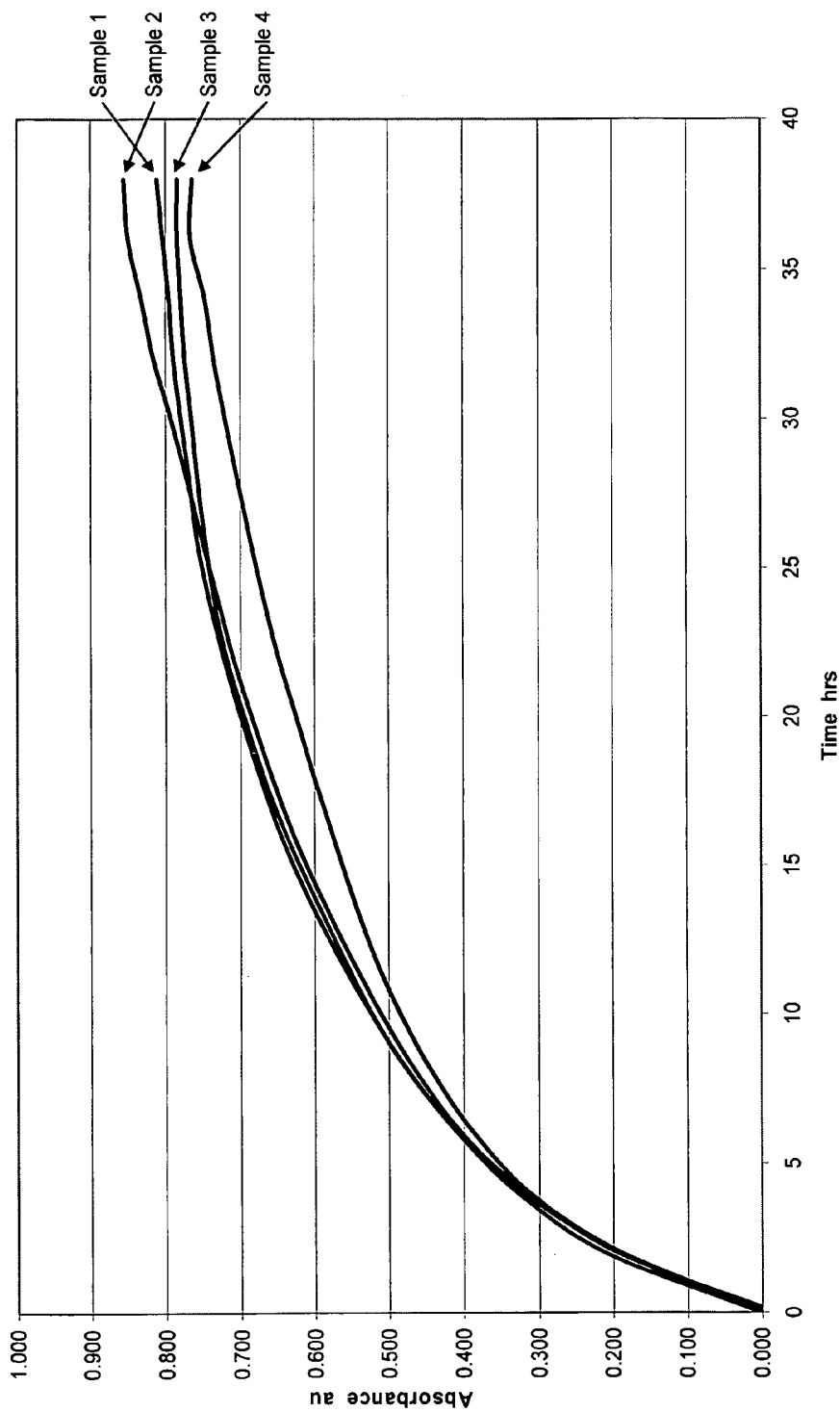
Figure 23. Dissolution profiles of 75 mg Tramadol HCl in beeswax with 20% HPMC based formulation

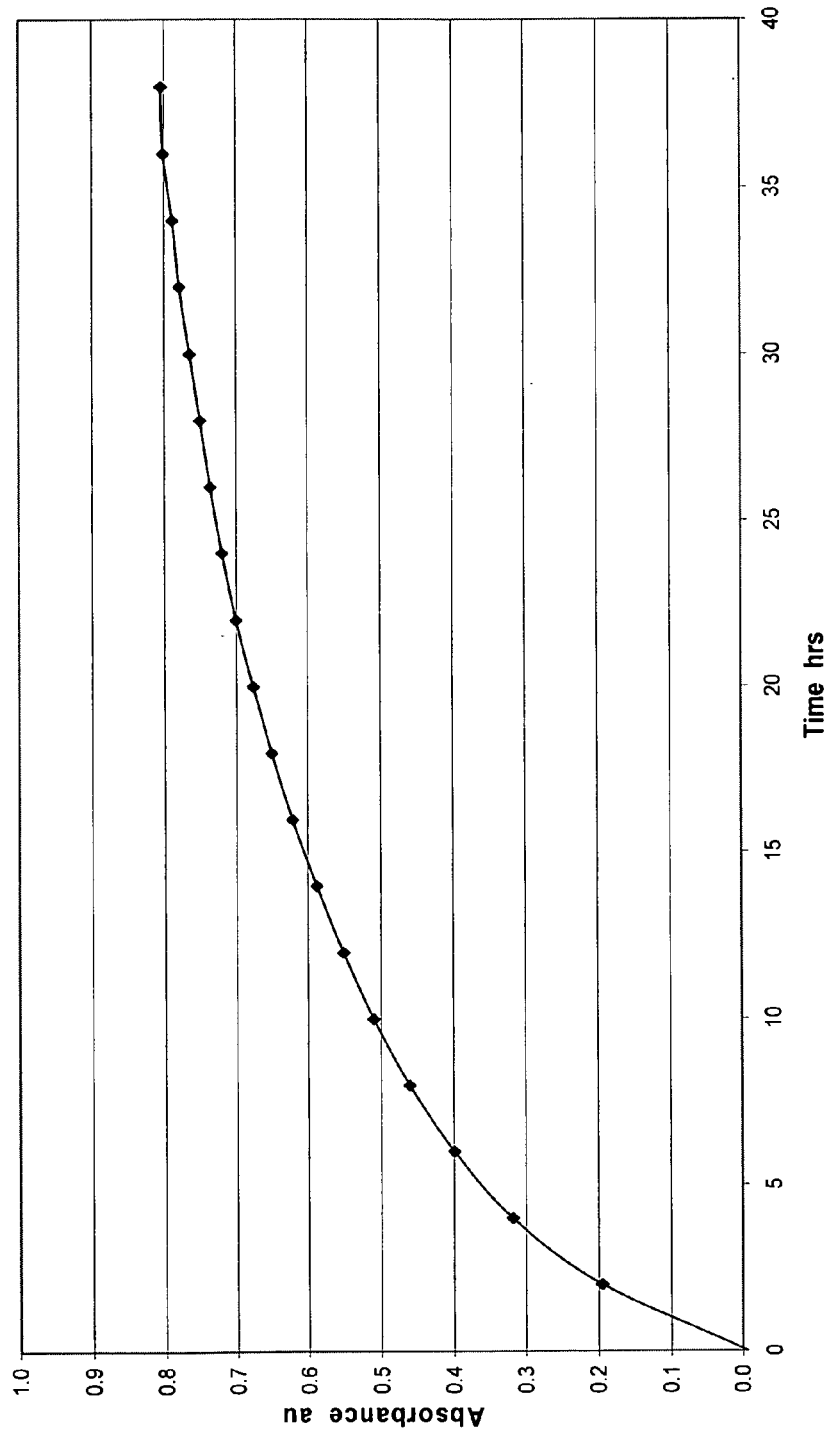
*Figure 24.* Averaged dissolution profiles of 75 mg Tramadol HCl in beeswax with 20% HPMC based formulation

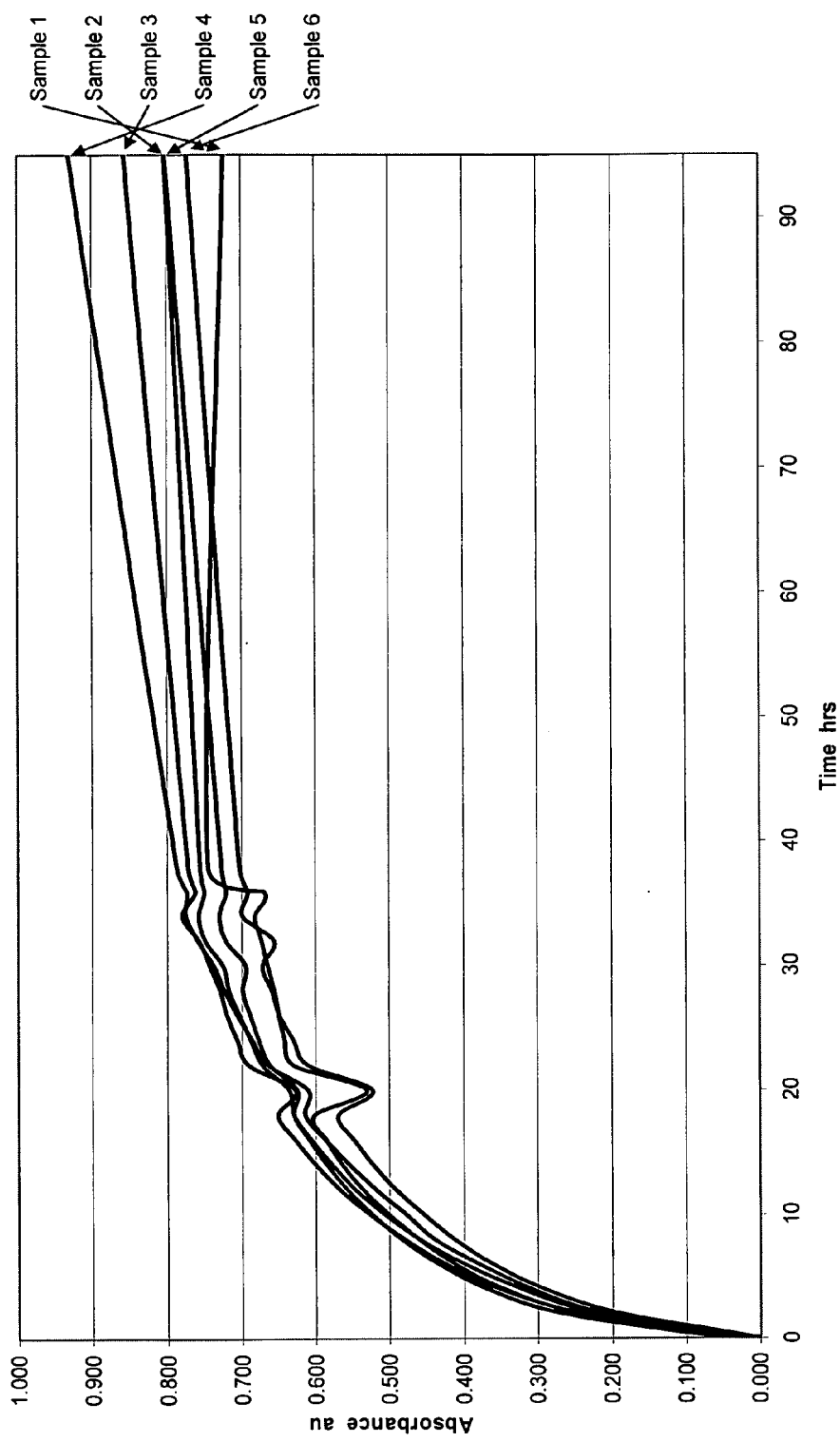
Figure 25. Dissolution profiles of 75 mg Tramadol HCl in beeswax with 23% HPMC based formulation

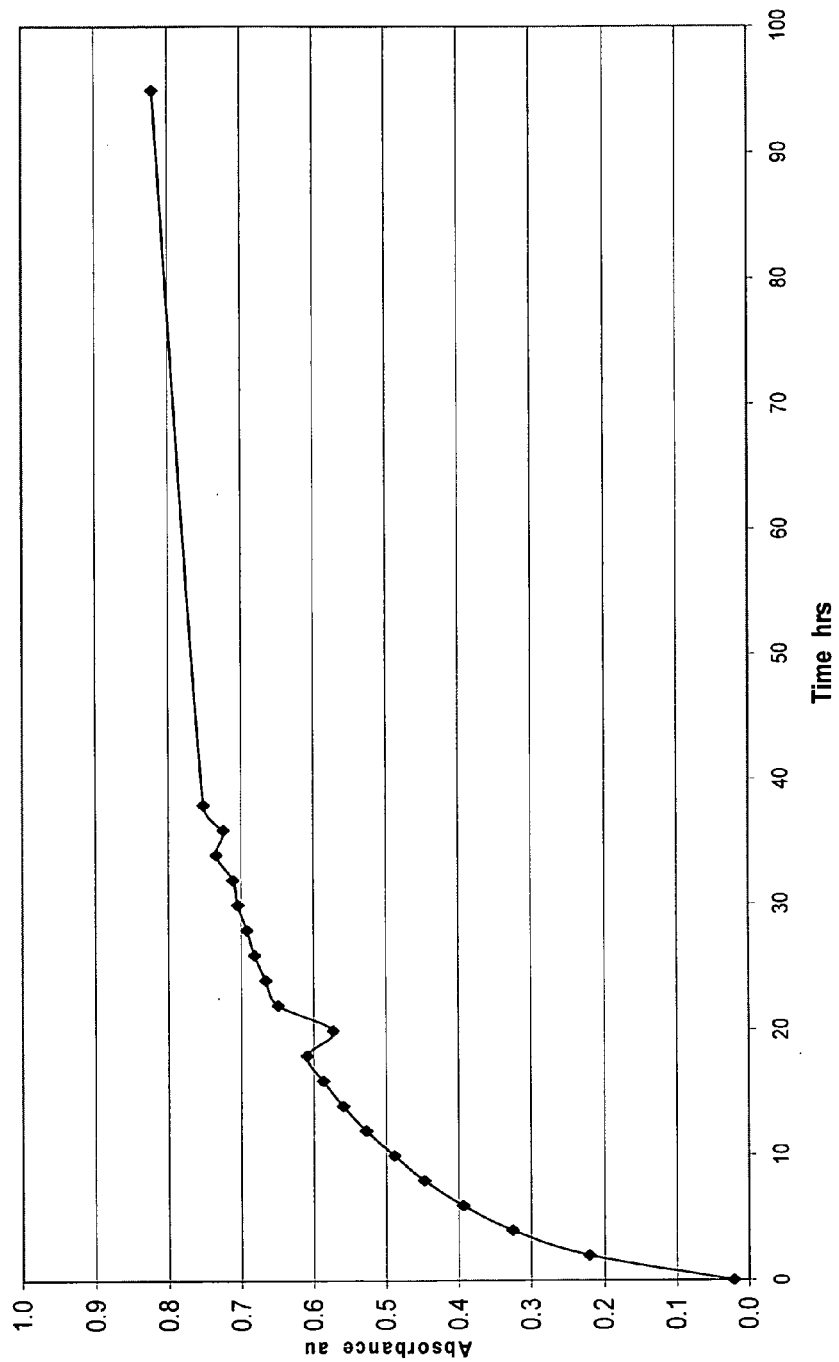
*Figure 26.* Averaged dissolution profiles of 75 mg Tramadol HCl in beeswax with 23% HPMC based formulation

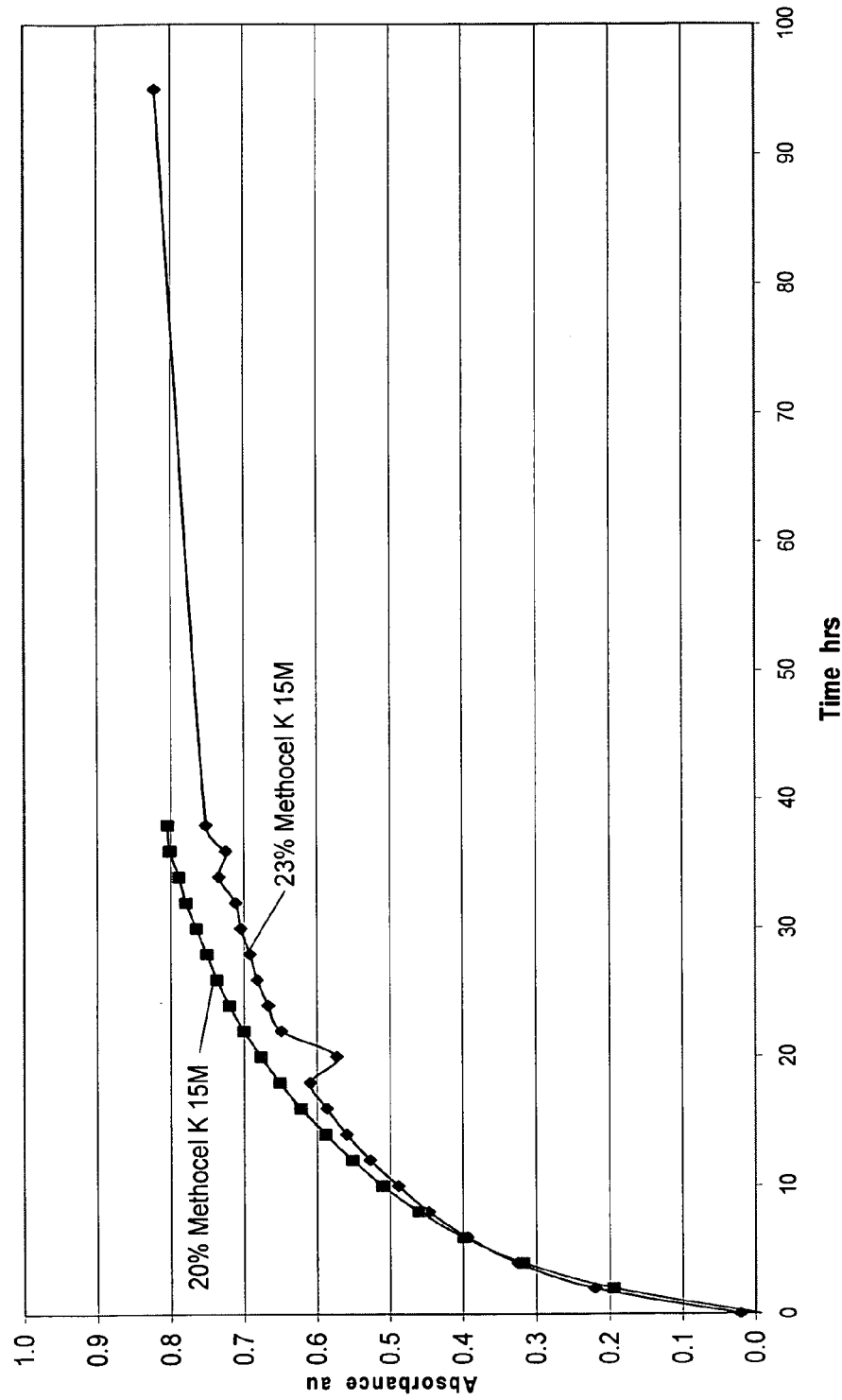
*Figure 27.* Comparison of averaged dissolution profiles of Tramadol HCl in beeswax with 20% and 23% HPMC based formulation

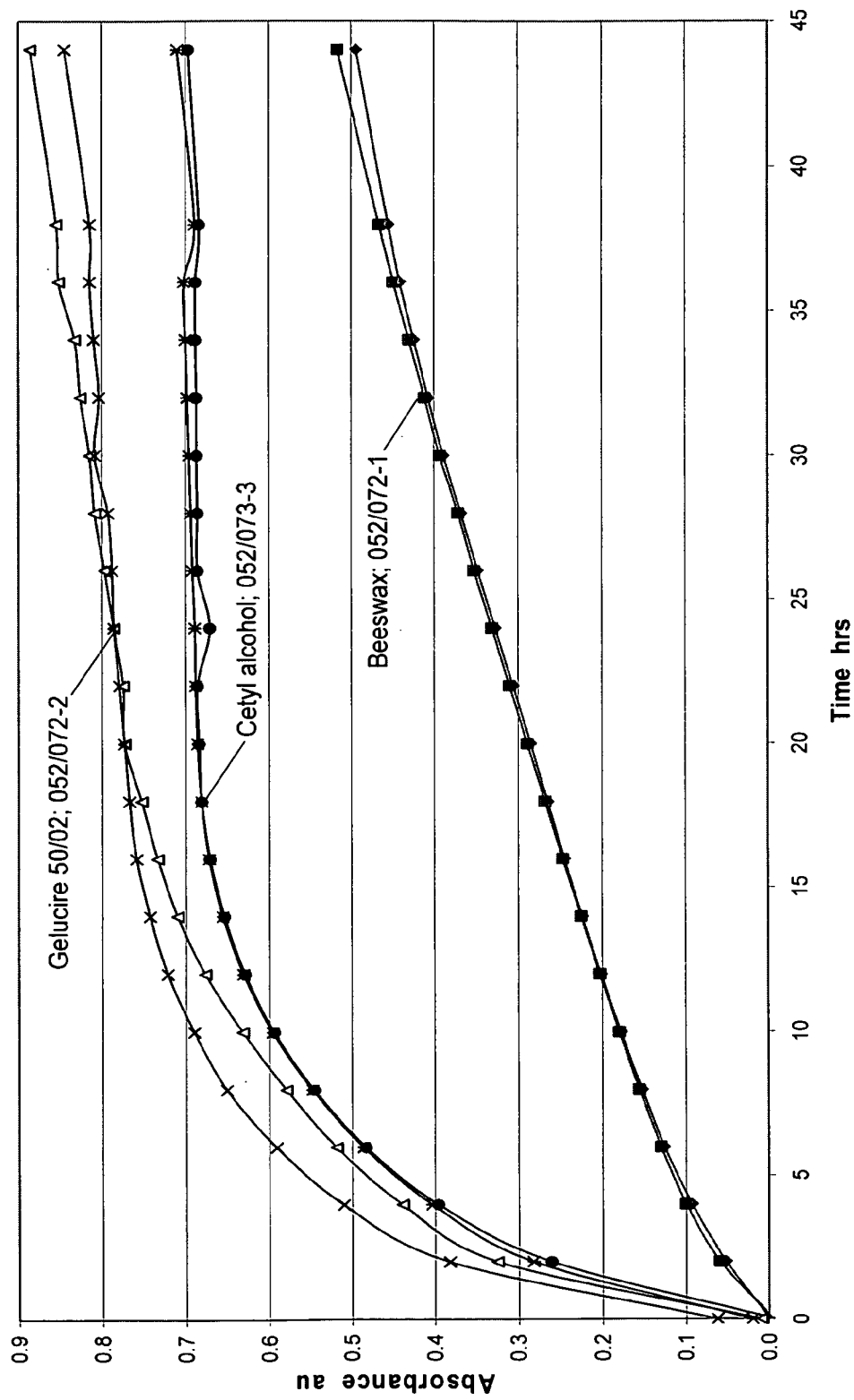
*Figure 28.* Combined dissolution profiles of first three Tramadol HCl formulations
75 mg Tramadol HCl in beeswax, Gelucire 50/02 and cetyl alcohol ; 052/072-1, 052/072-2, 052/073-3

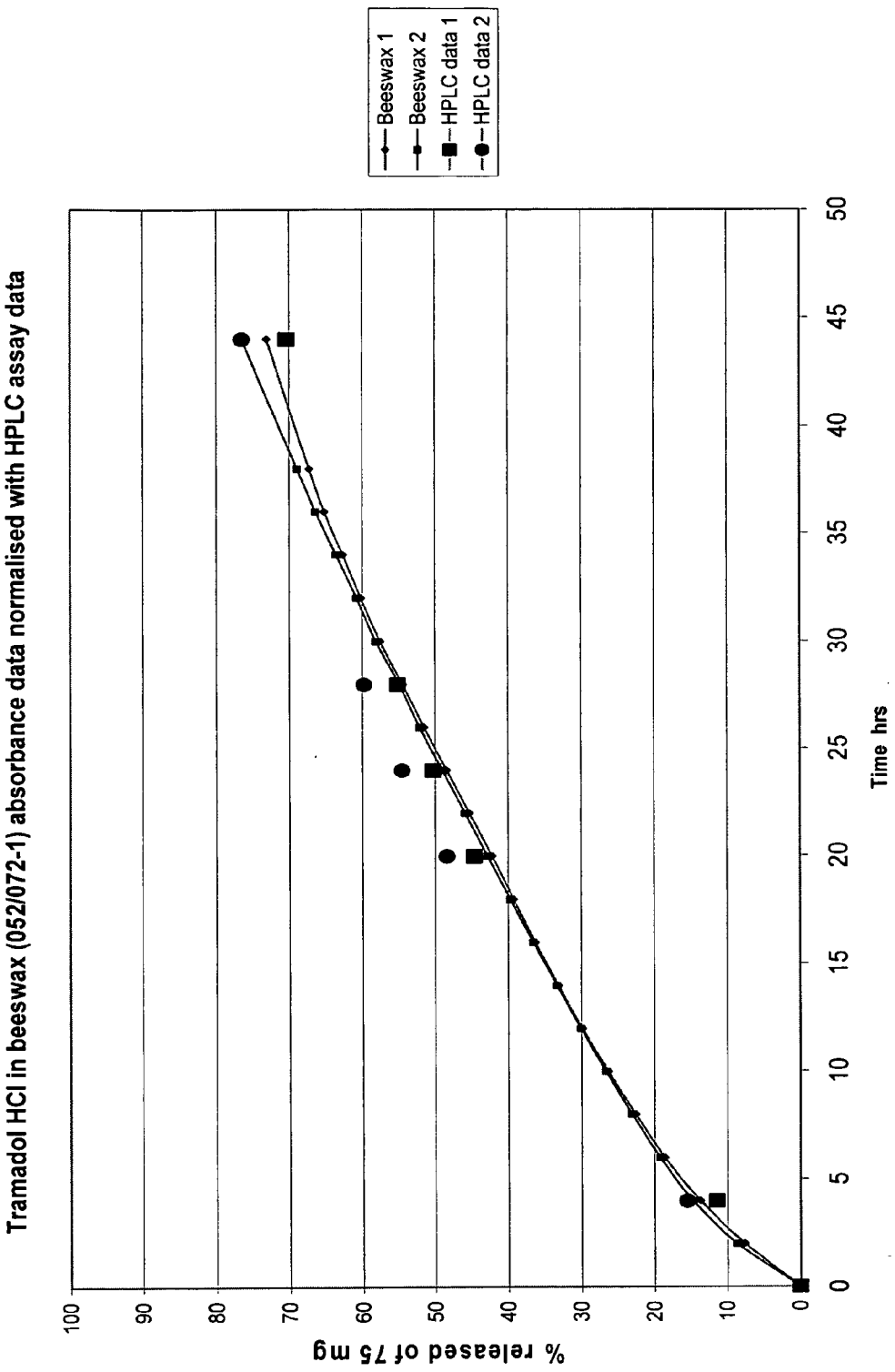
*Figure 29.* Tramadol HCL in beeswax dissolution profile normalised to HPLC assay data

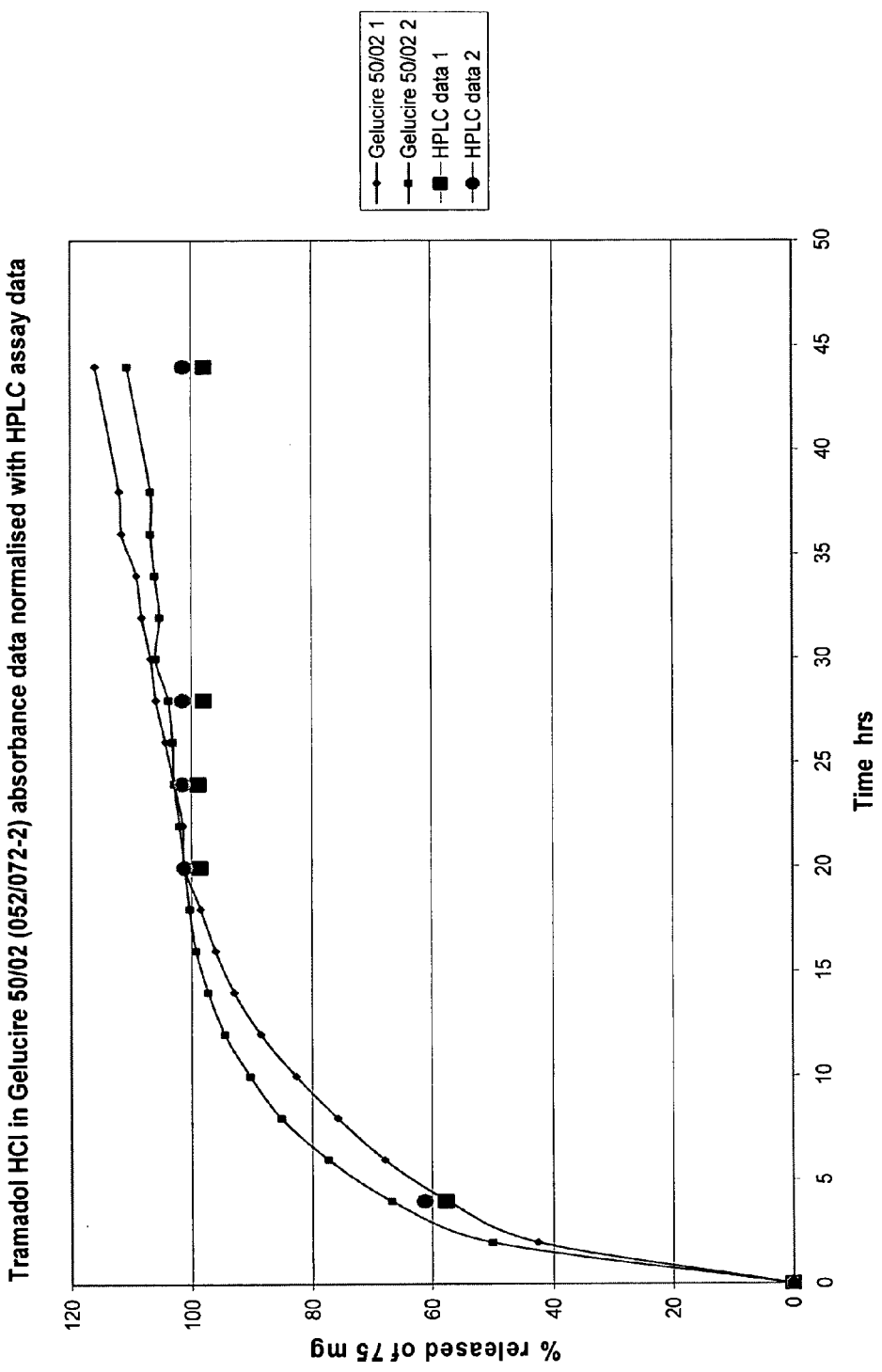
Figure 30. Tramadol HCL in Gelucire 50/02 dissolution profile normalised to HPLC assay data

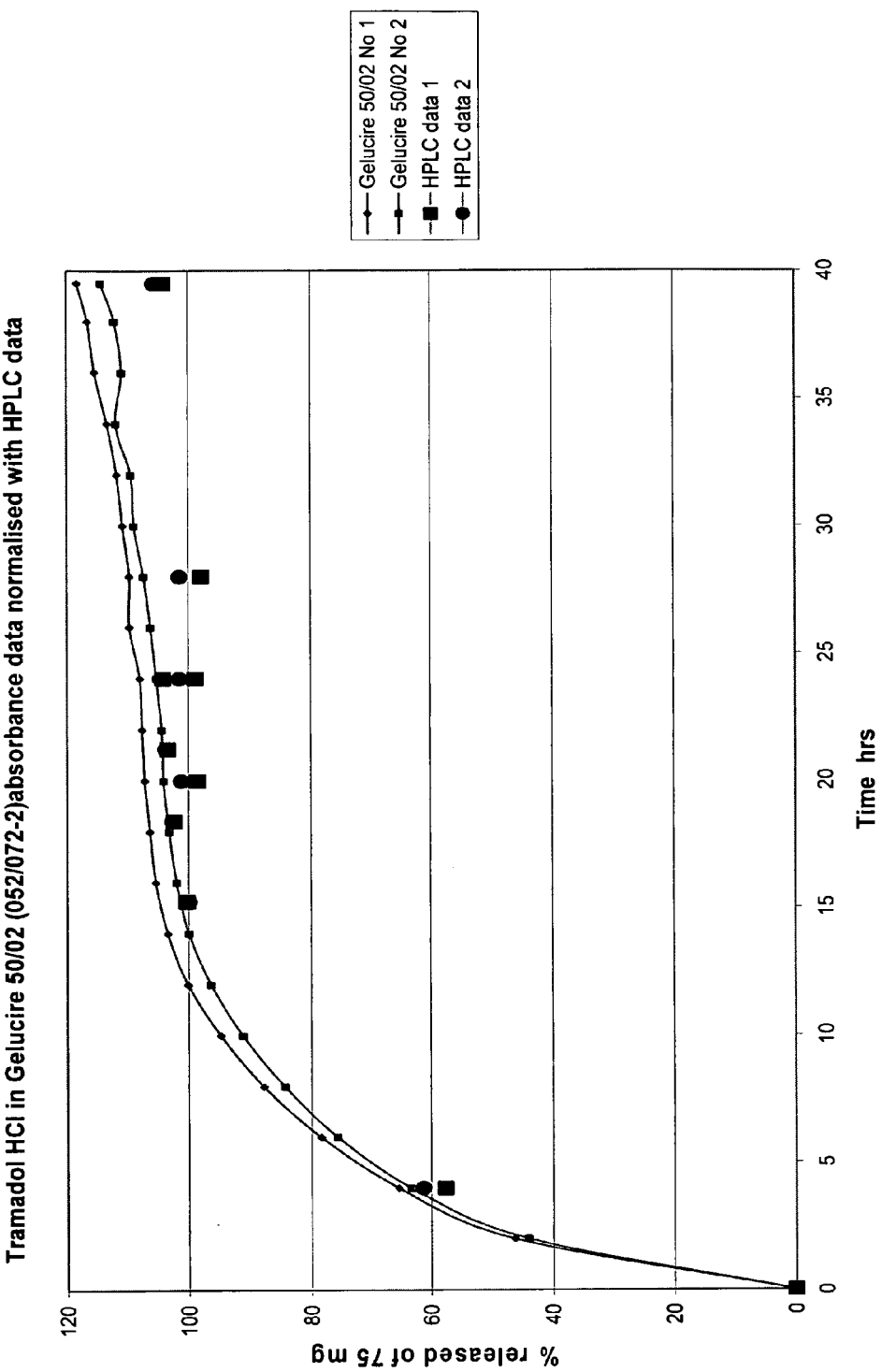
*Figure 31.* Tramadol HCL in Gelucire 50/02 repeat dissolution profile normalised to HPLC assay data

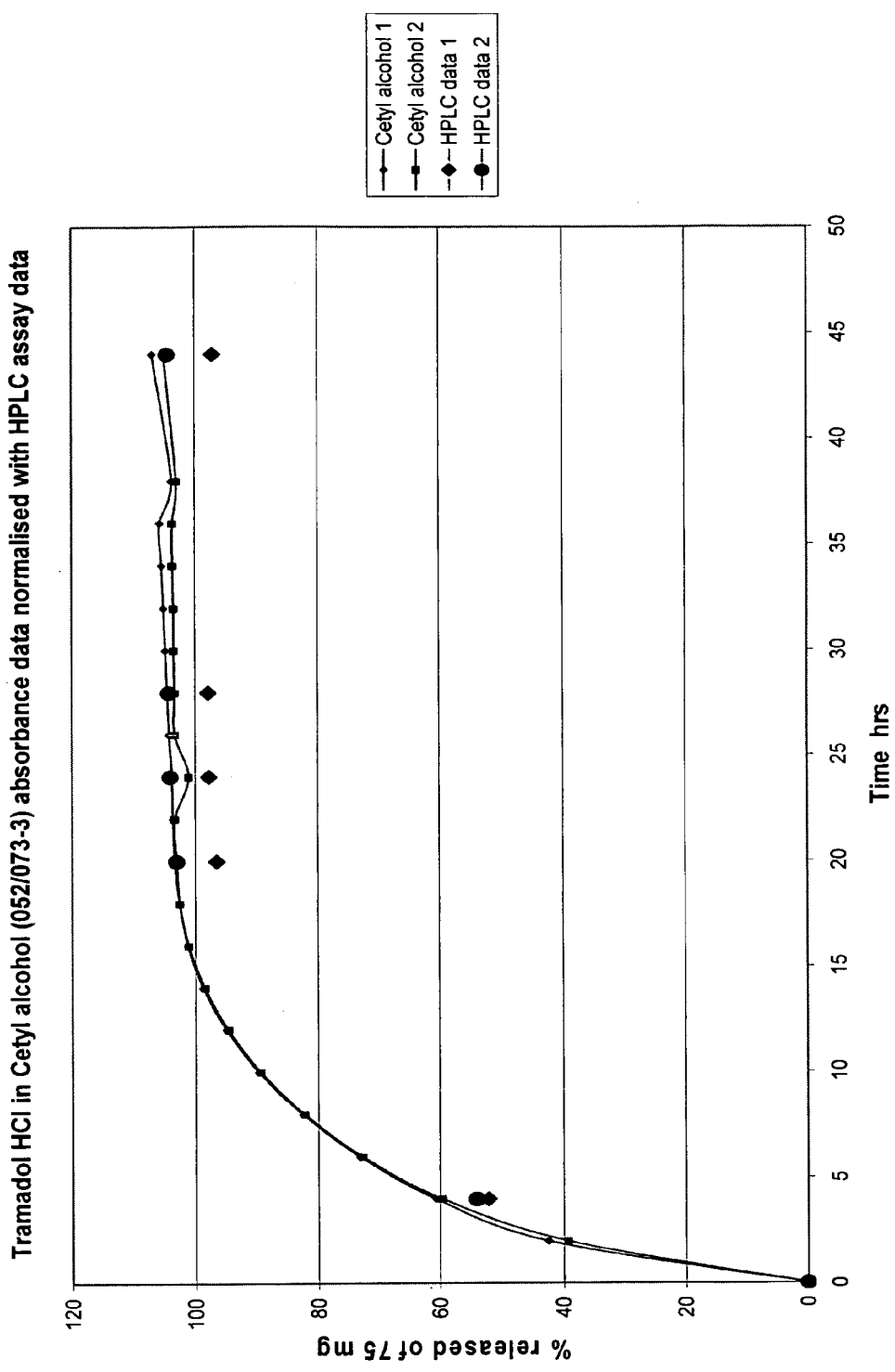
*Figure 32.* Tramadol HCL in cetyl alcohol dissolution profile normalised to HPLC assay data

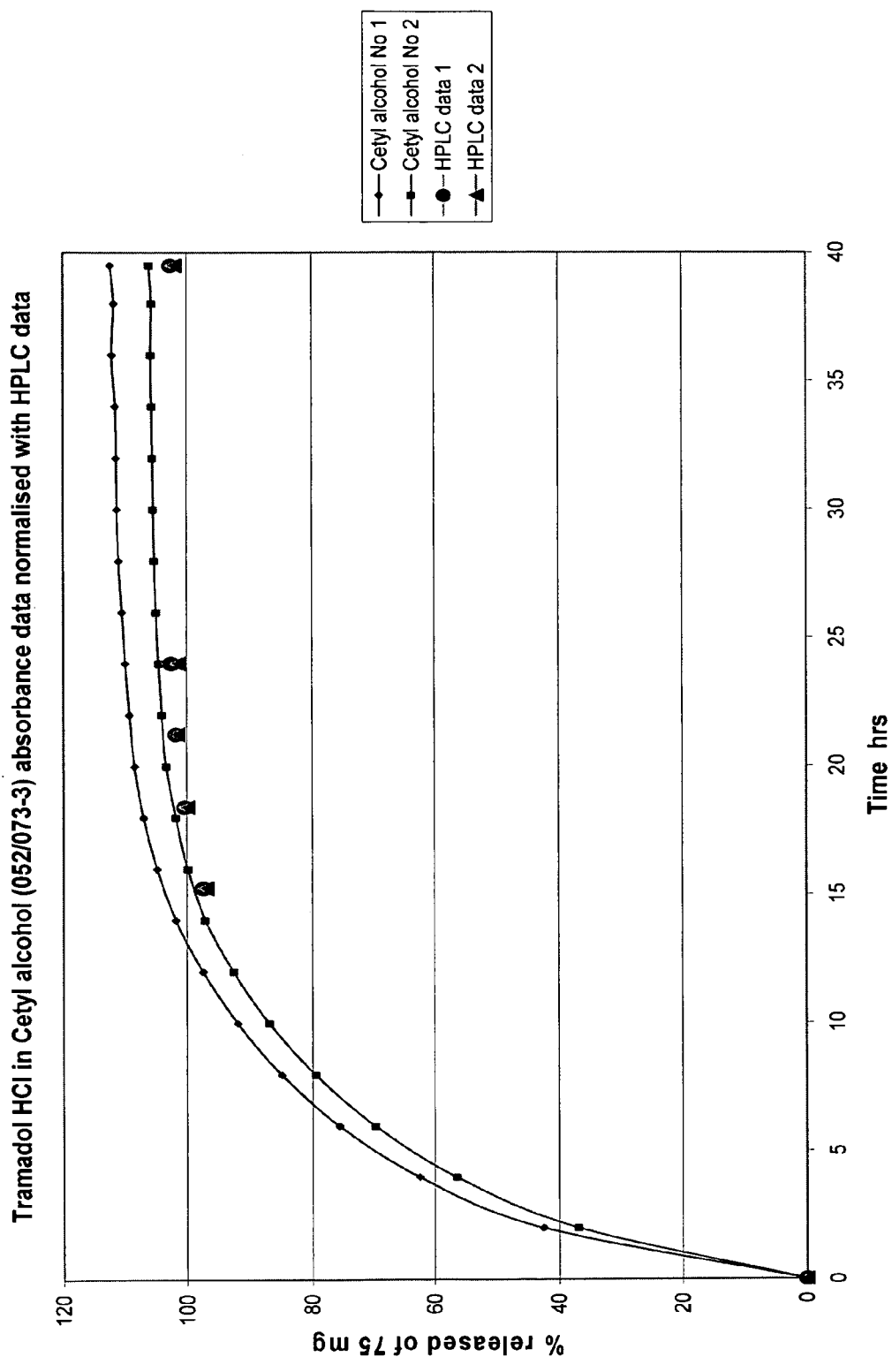
Figure 33. Tramadol HCL in cetyl alcohol repeat dissolution profile normalised to HPLC assay data

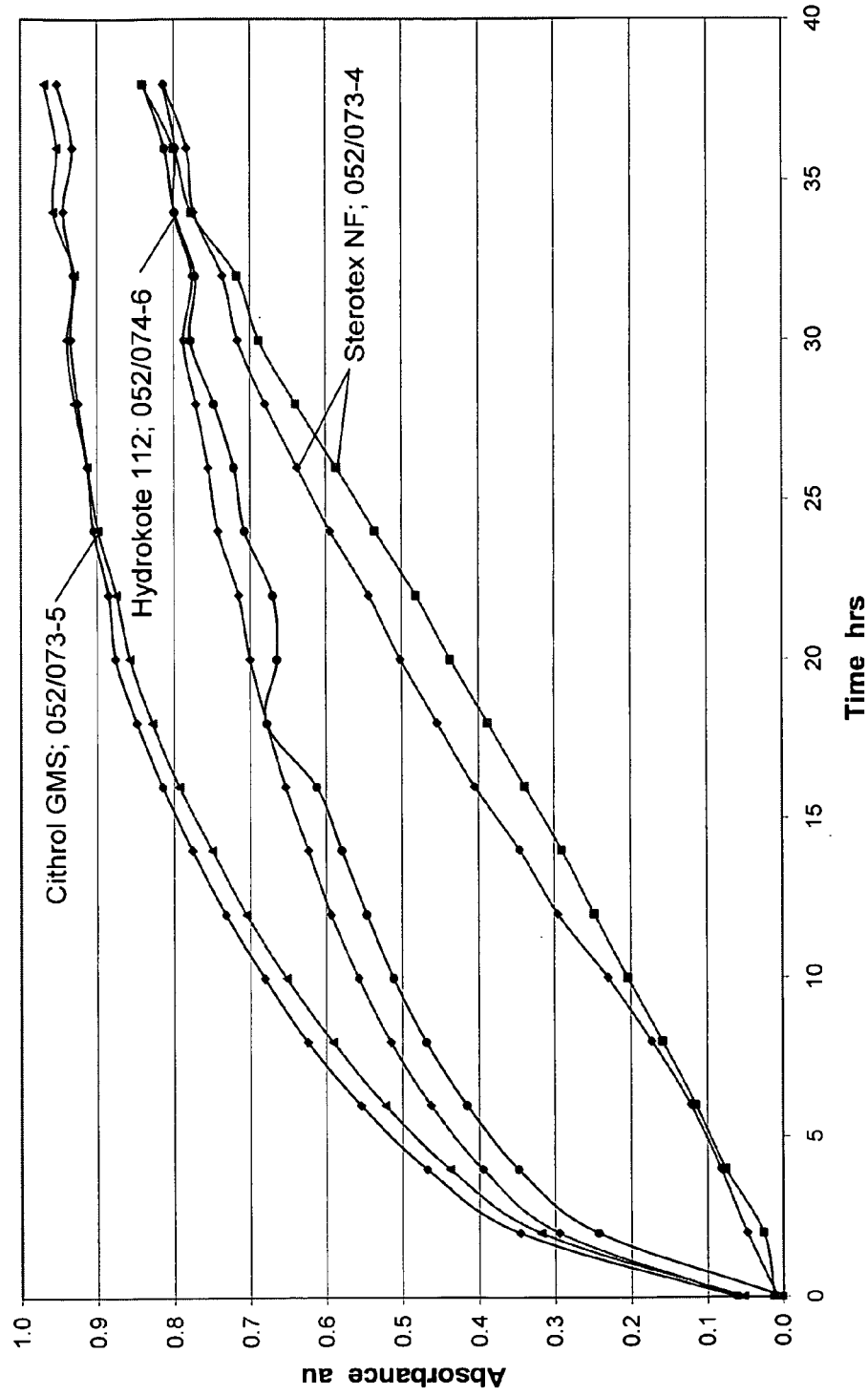
*Figure 34.* Combined dissolution profiles of second three Tramadol HCl formulations

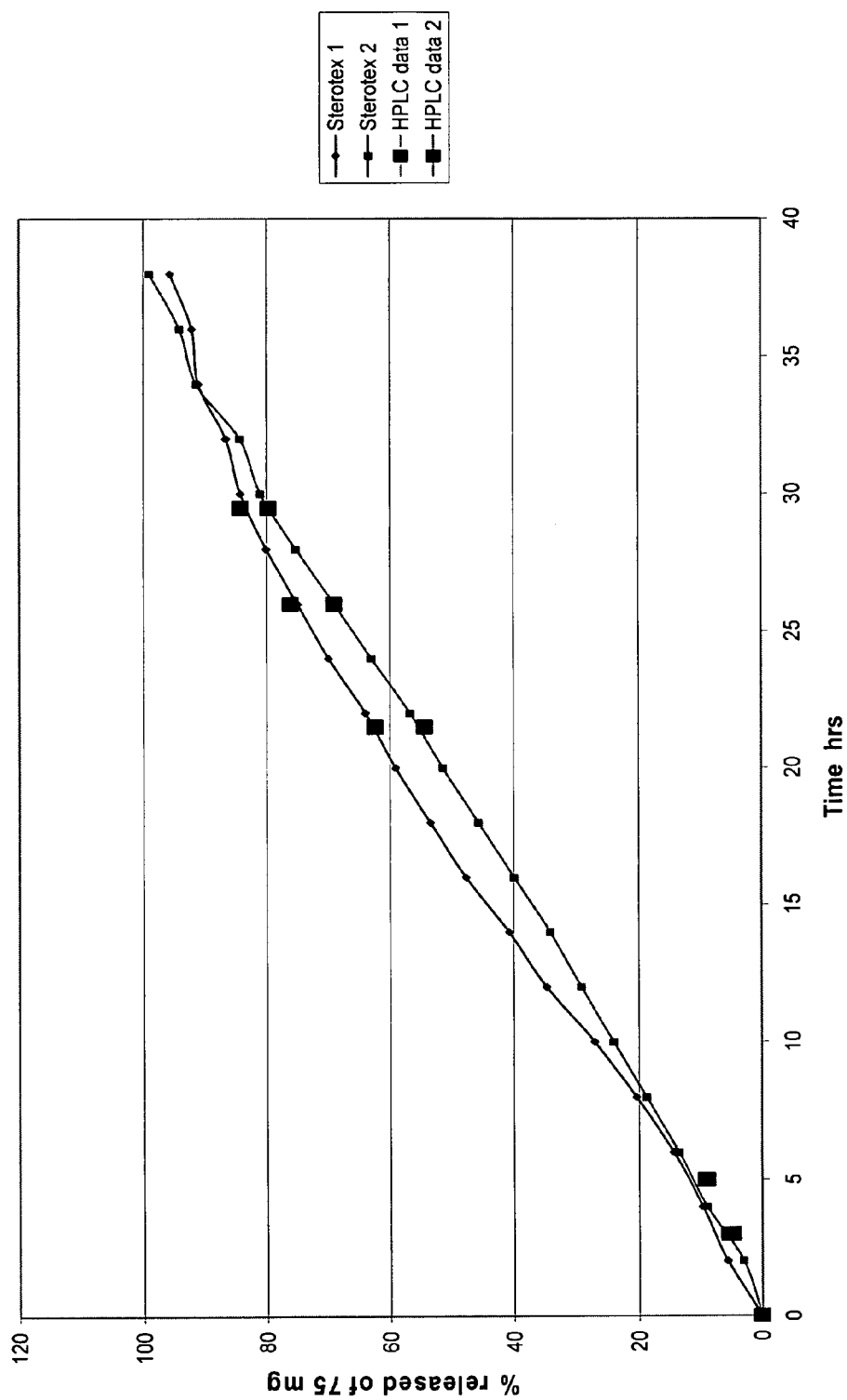
*Figure 35.* Tramadol HCL in Sterotex NF dissolution profile normalised to HPLC assay data

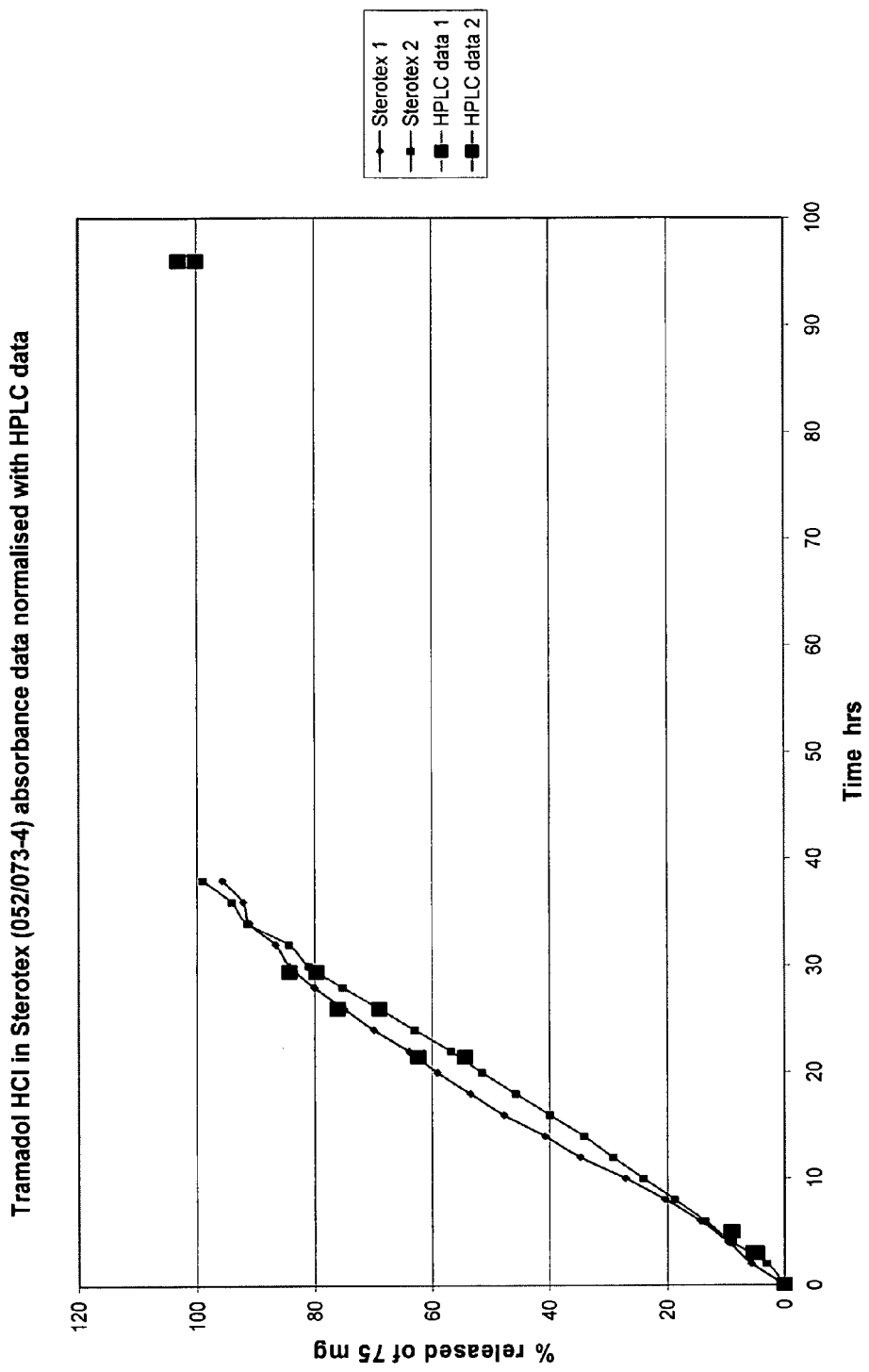
*Figure 36.* Tramadol HCL in Sterotex NF dissolution profile normalised to HPLC assay data with extended time scale

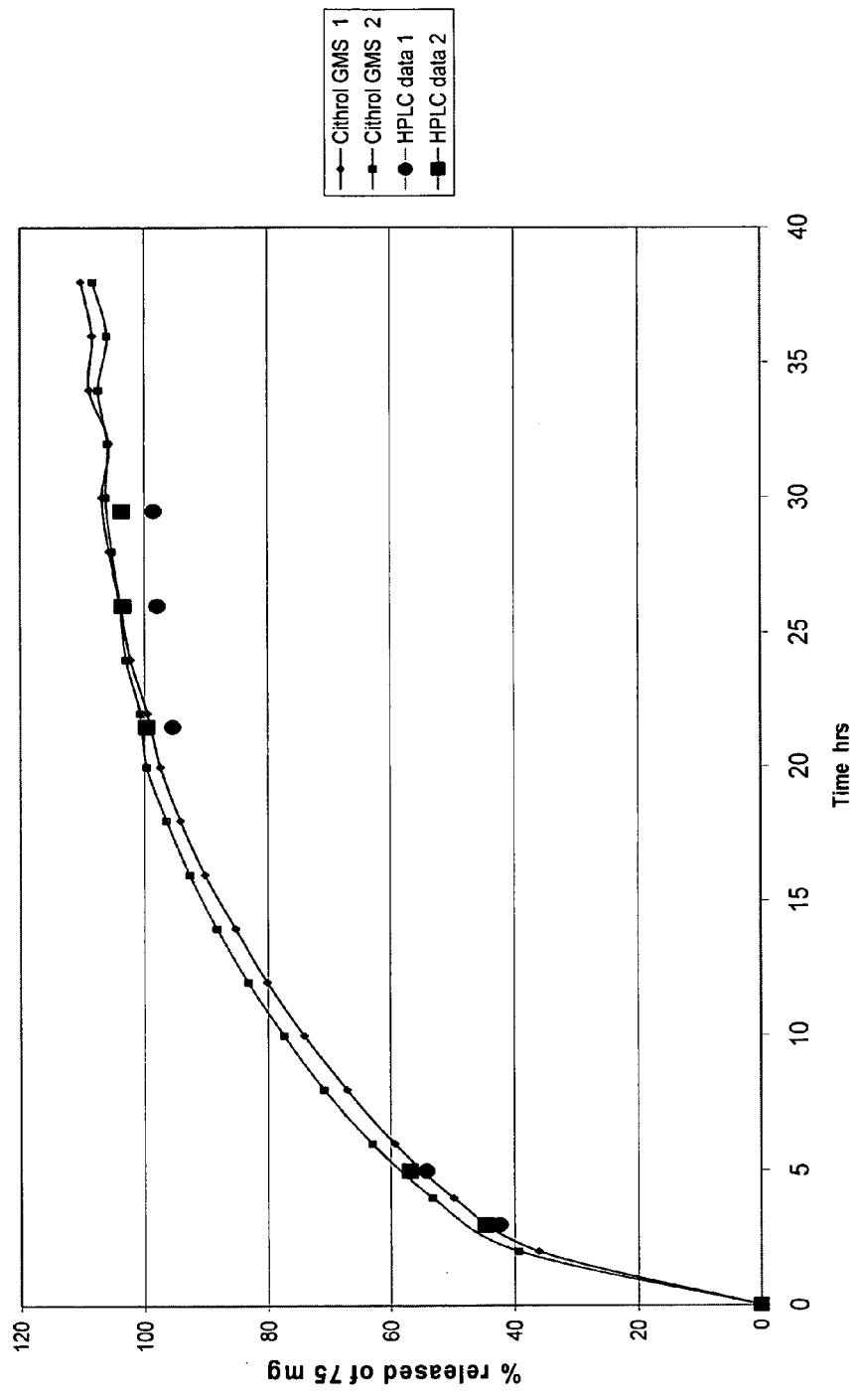
Figure 37. Tramadol HCL in Cithrol GMS dissolution profile normalised to HPLC assay data

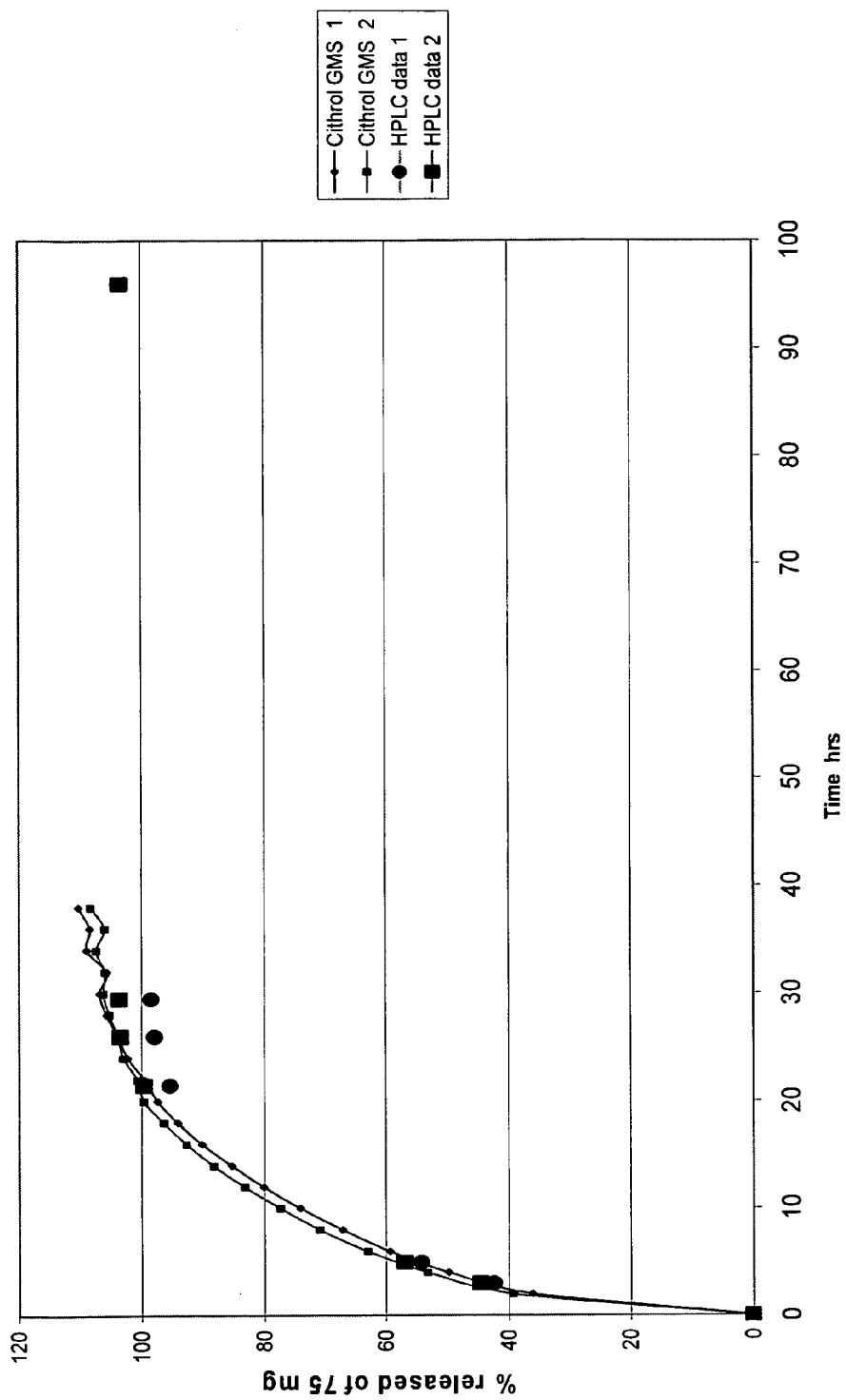
Figure 38. Tramadol HCL in Cithrol GMS dissolution profile normalised to HPLC assay data with extended time scale

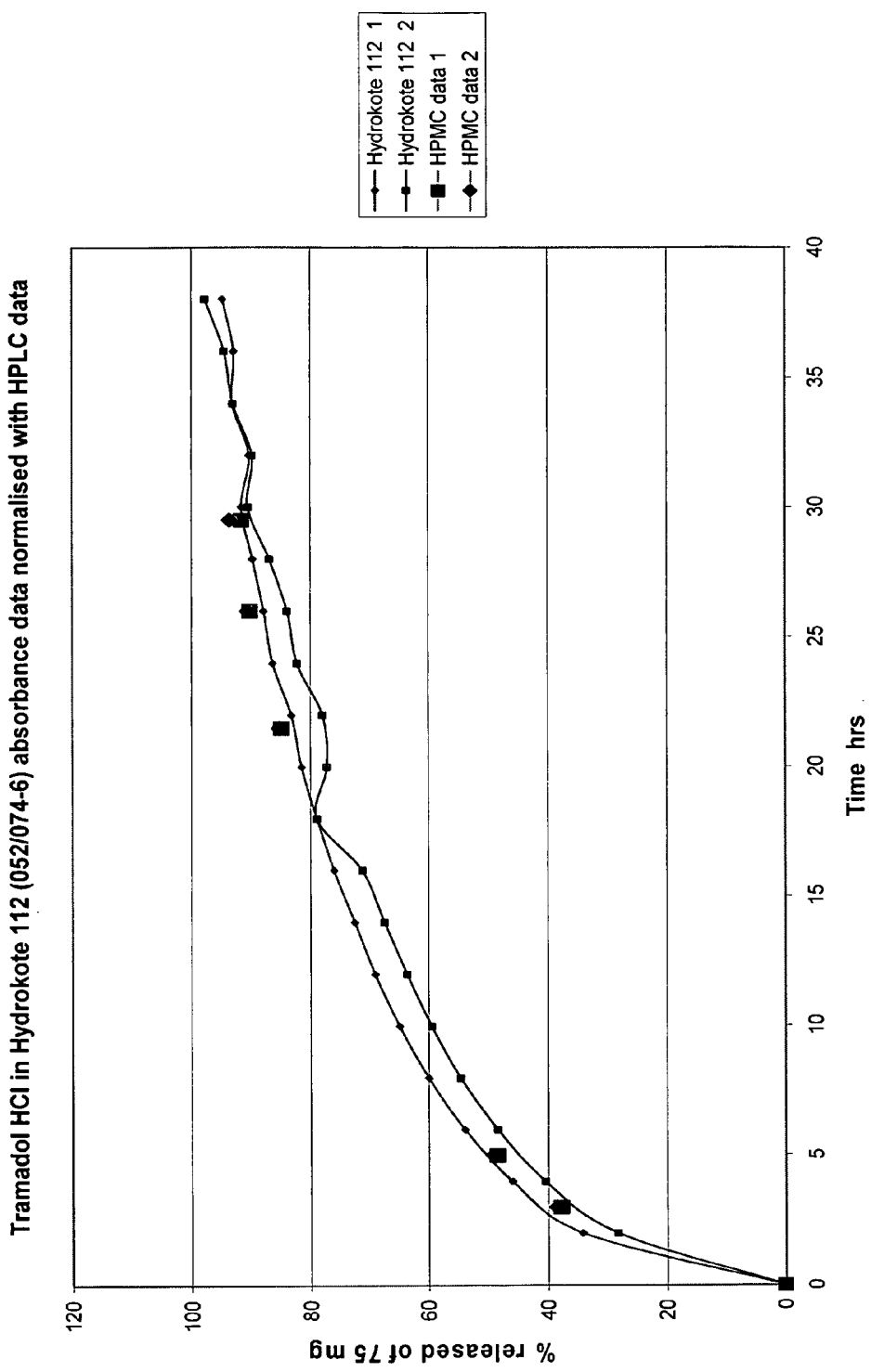
Figure 39. Tramadol HCL in Hydrokote 112 dissolution profile normalised to HPLC assay data

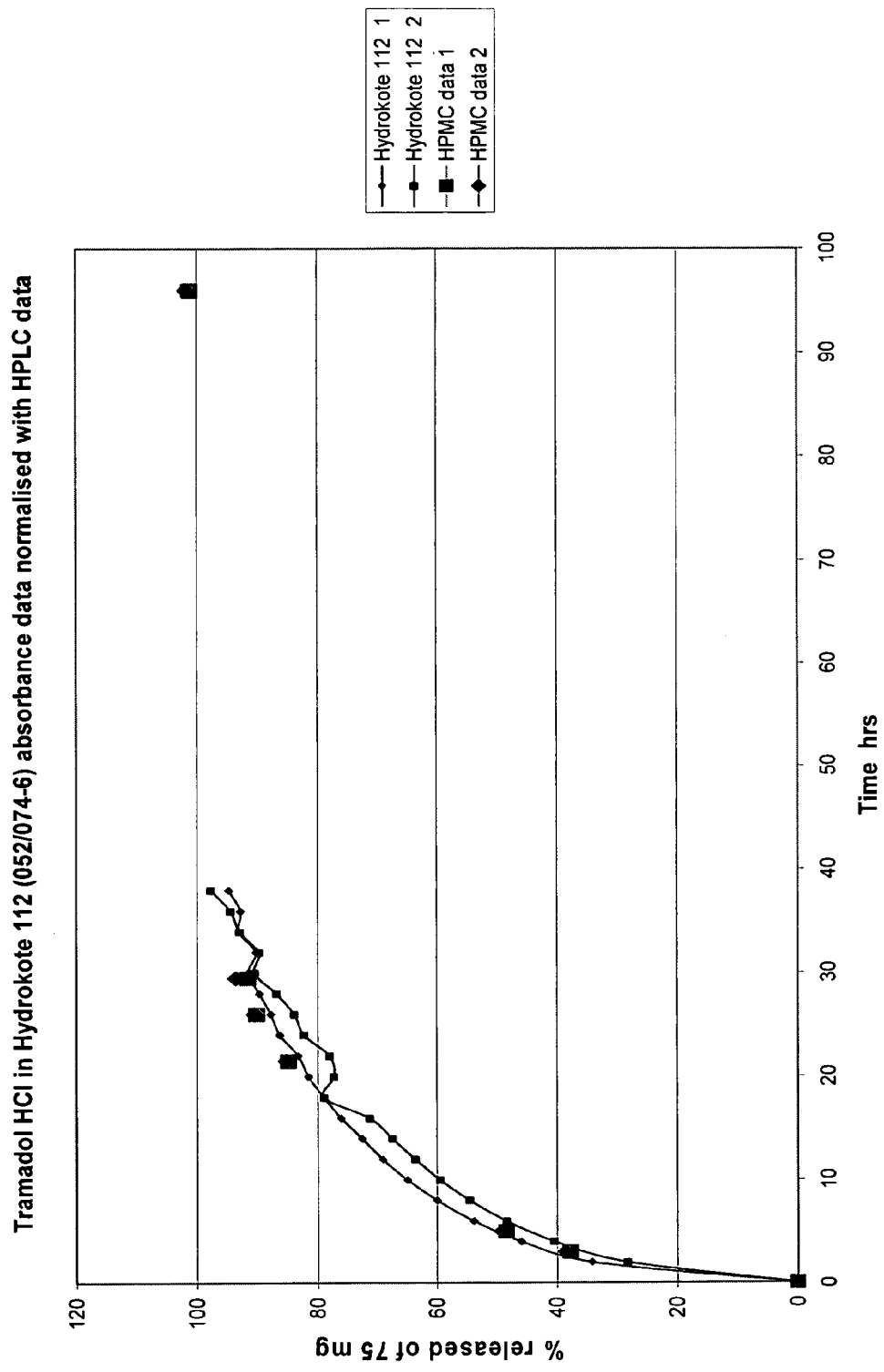
*Figure 40.* Tramadol HCL in Hydrokote 112 dissolution profile normalised to HPLC assay data with extended time scale

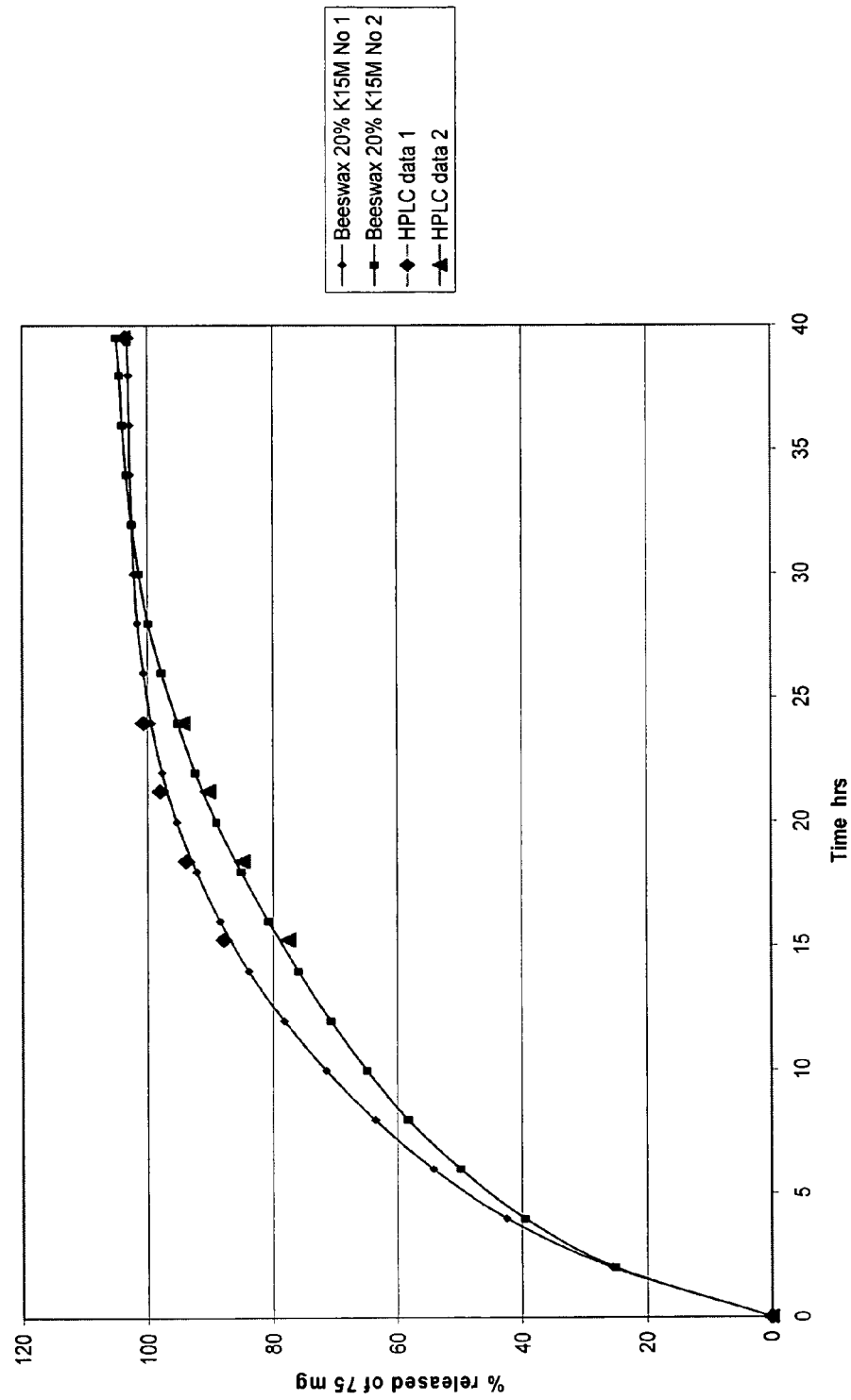
*Figure 41.* Tramadol HCL in beeswax dissolution profile normalised to HPLC assay data

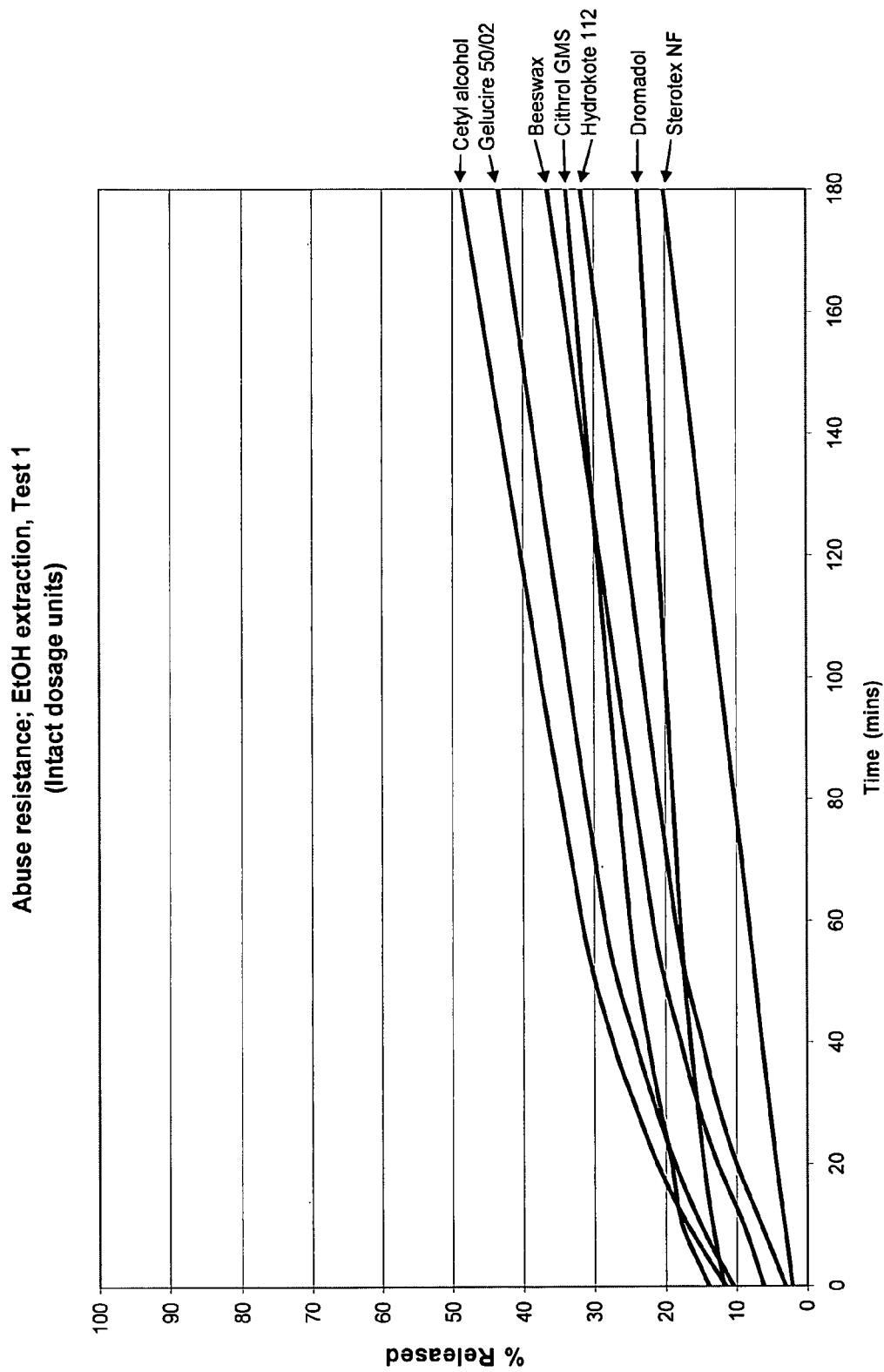
Figure 42. Abuse resistance testing, Test 1. Ethanol extraction on whole dosage units

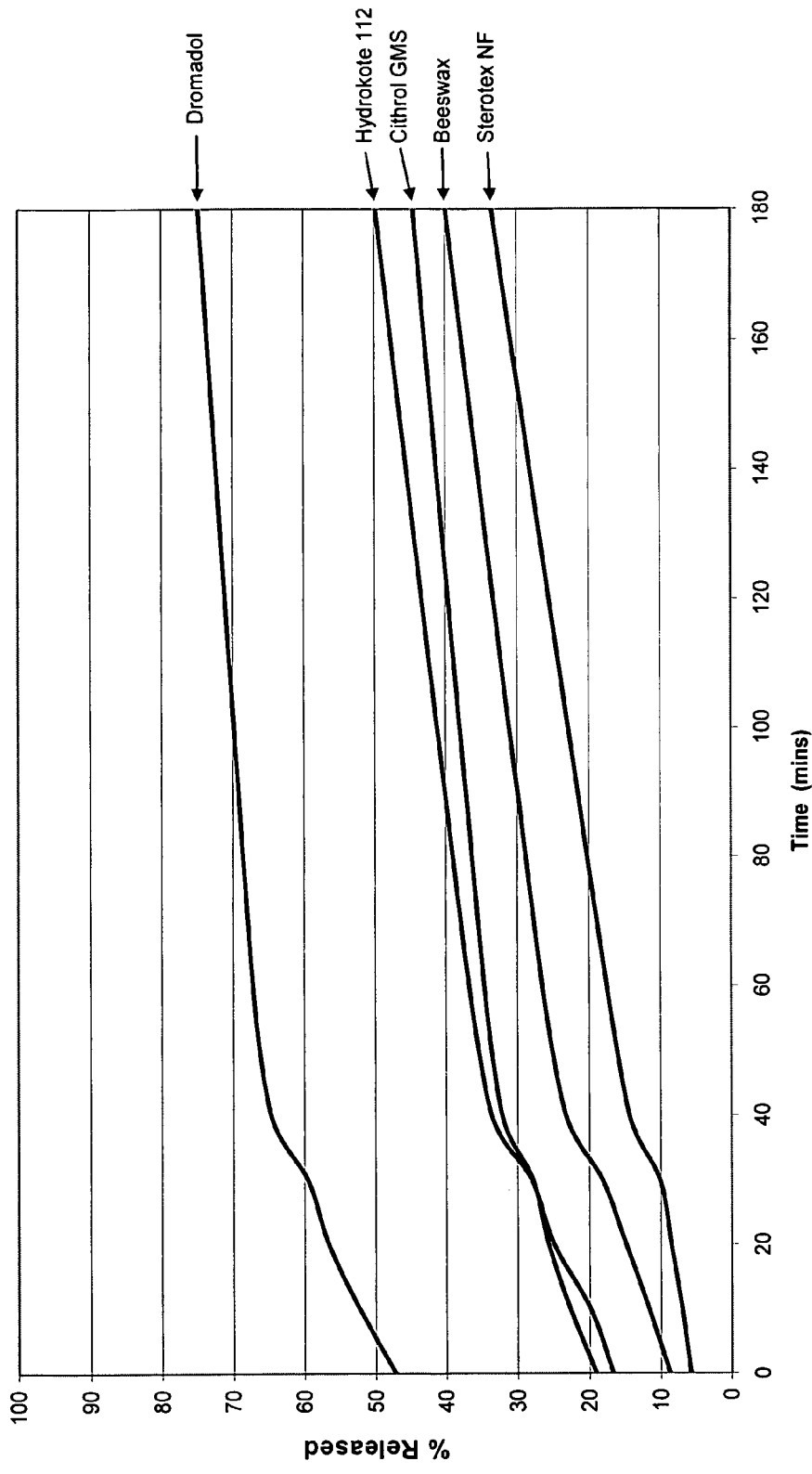
*Figure 43.* Abuse resistance testing, Test 1a. Ethanol extraction on cut or crushed dosage units

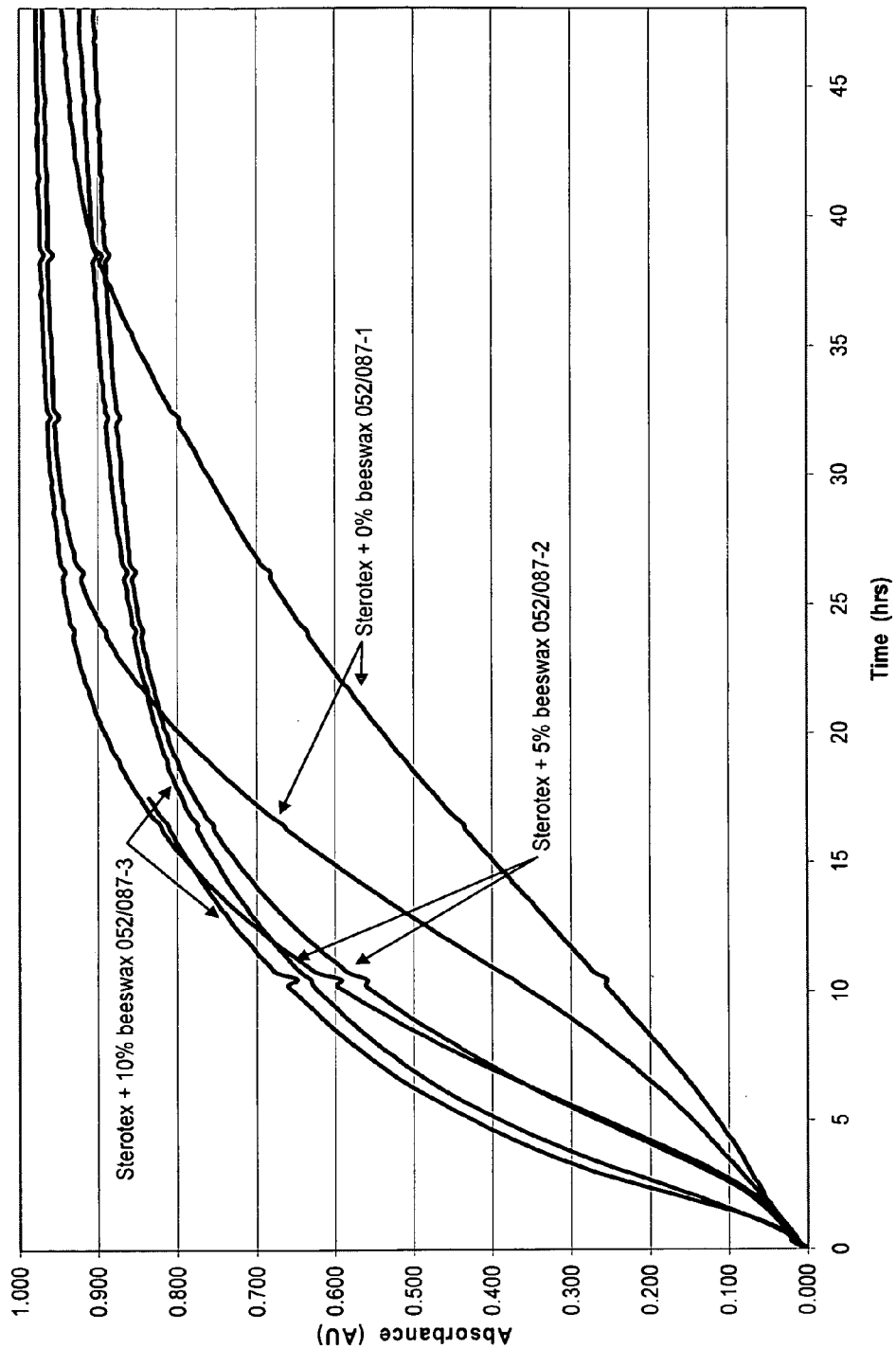
*Figure 44.* Dissolution profile of tramadol HCl in Sterotex NF formulations

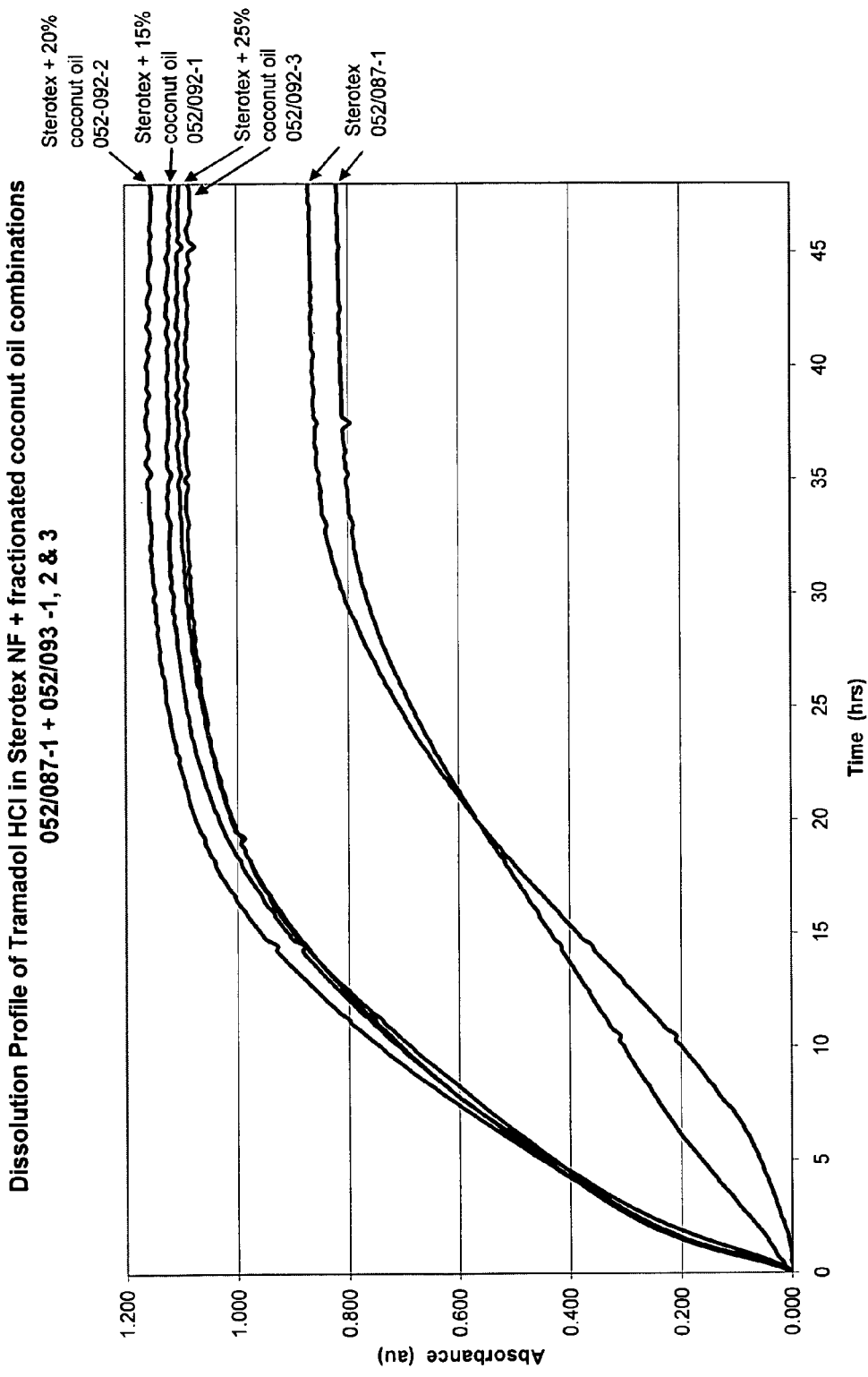
*Figure 45.* Dissolution profile of tramadol HCl in Sterotex NF formulations with and without fractionated coconut oil

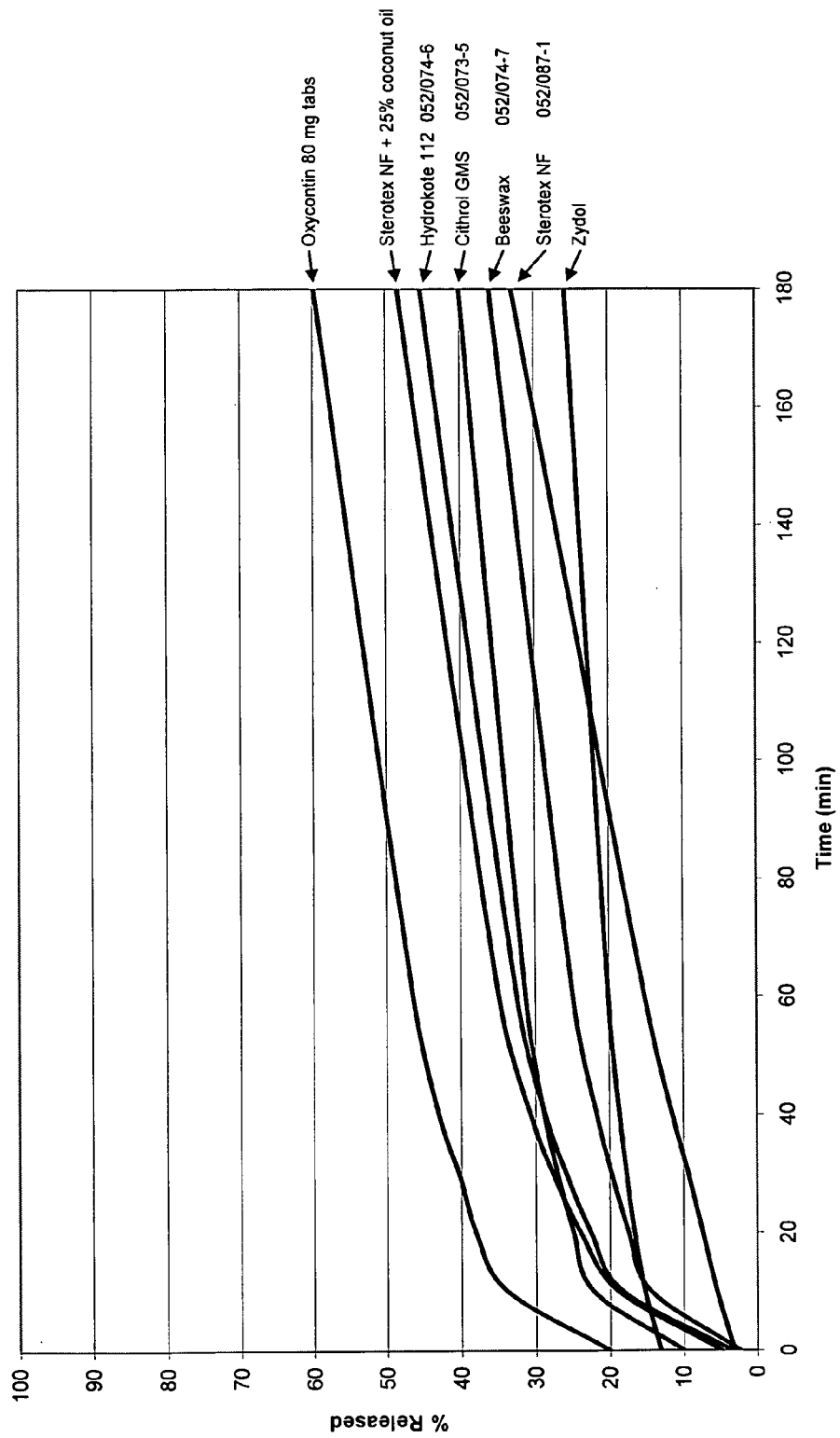
*Figure 46.* Abuse resistance testing, Test 1. Ethanol extraction on whole dosage units

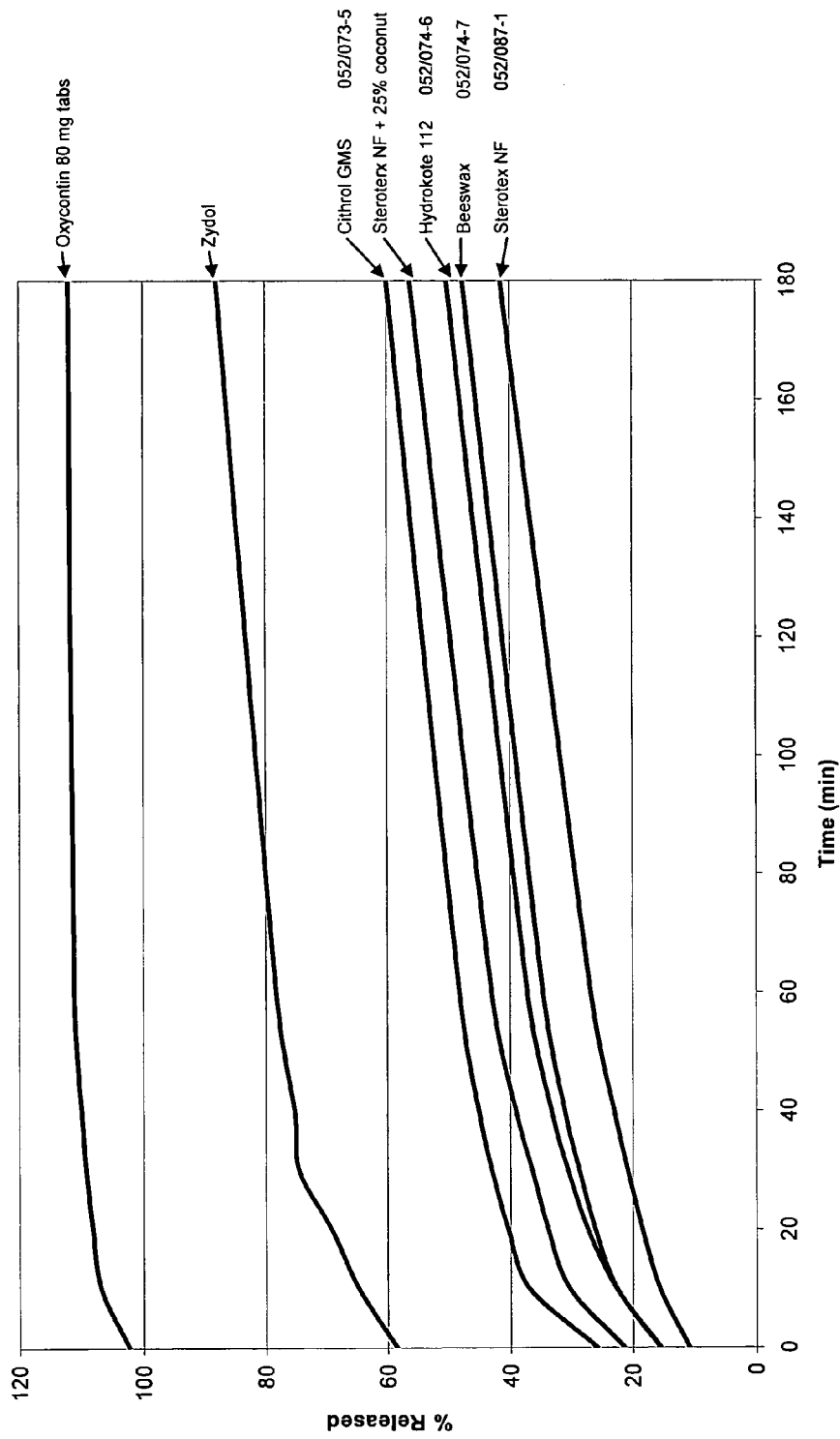
Figure 47. Abuse resistance testing, Test 1a. Ethanol extraction on crushed or cut dosage units

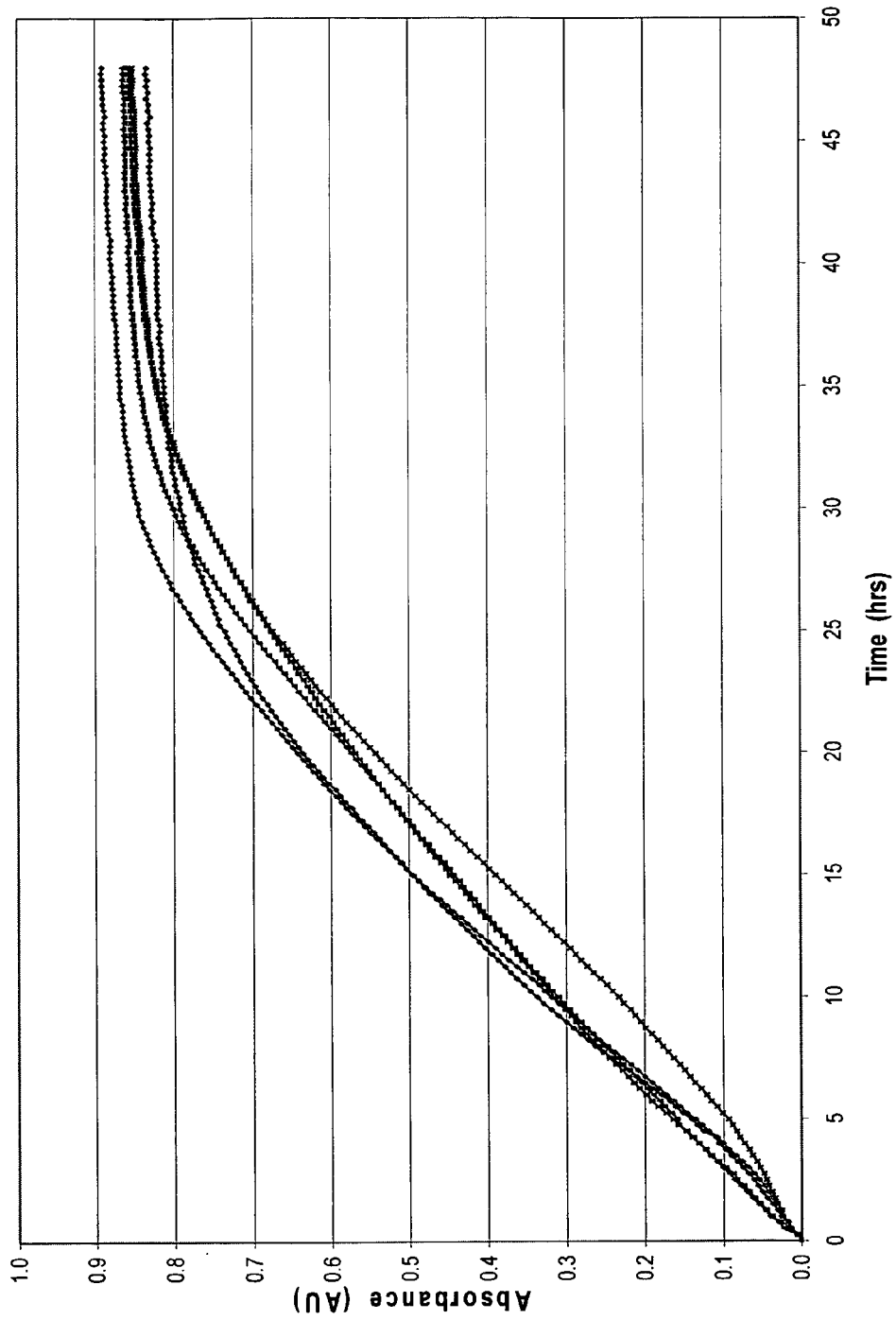
Figure 48. Dissolution profile of stored Sterotex NF formulation

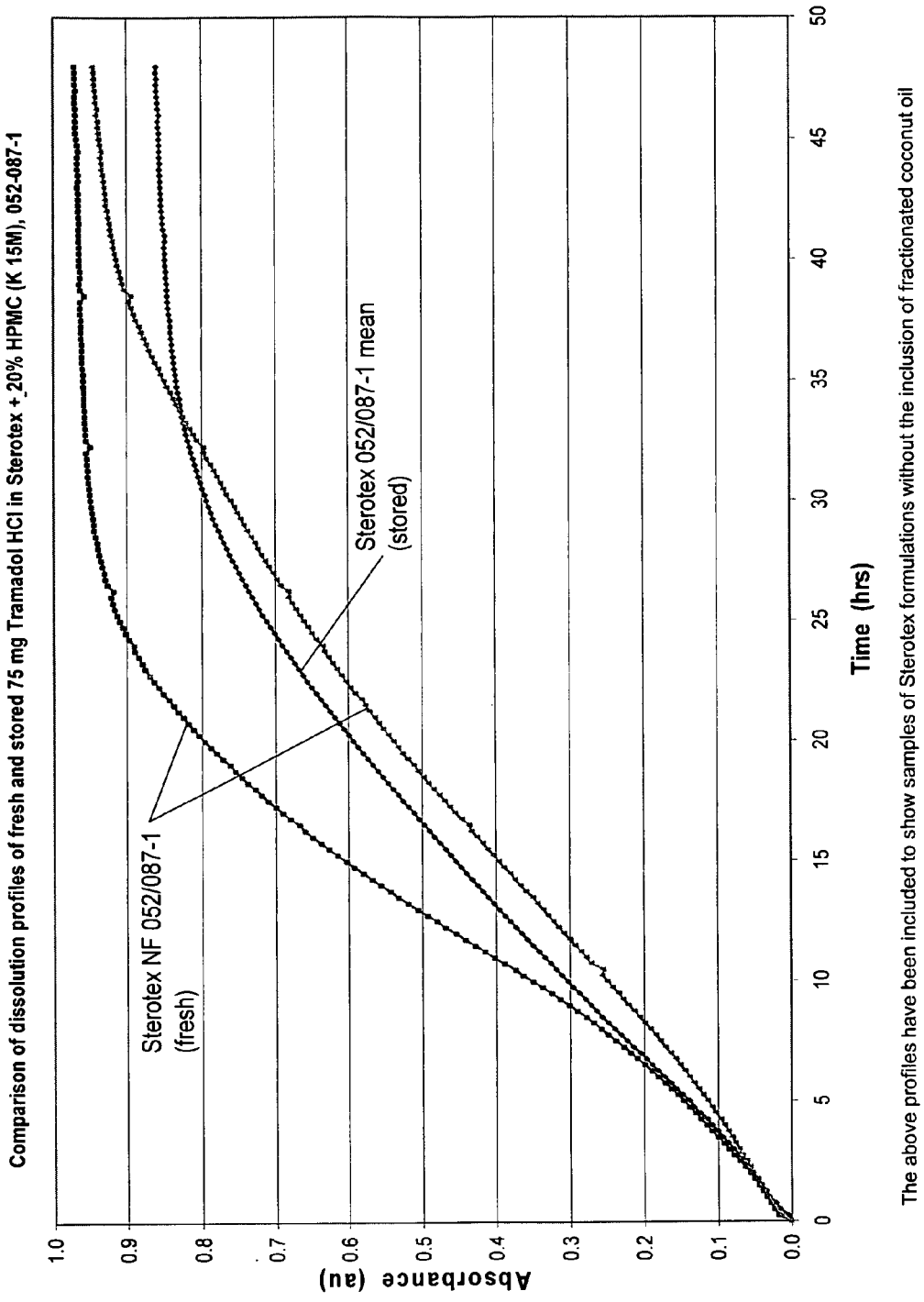
*Figure 49.* Comparison of Dissolution profiles of fresh and stored Sterotex NF formulation

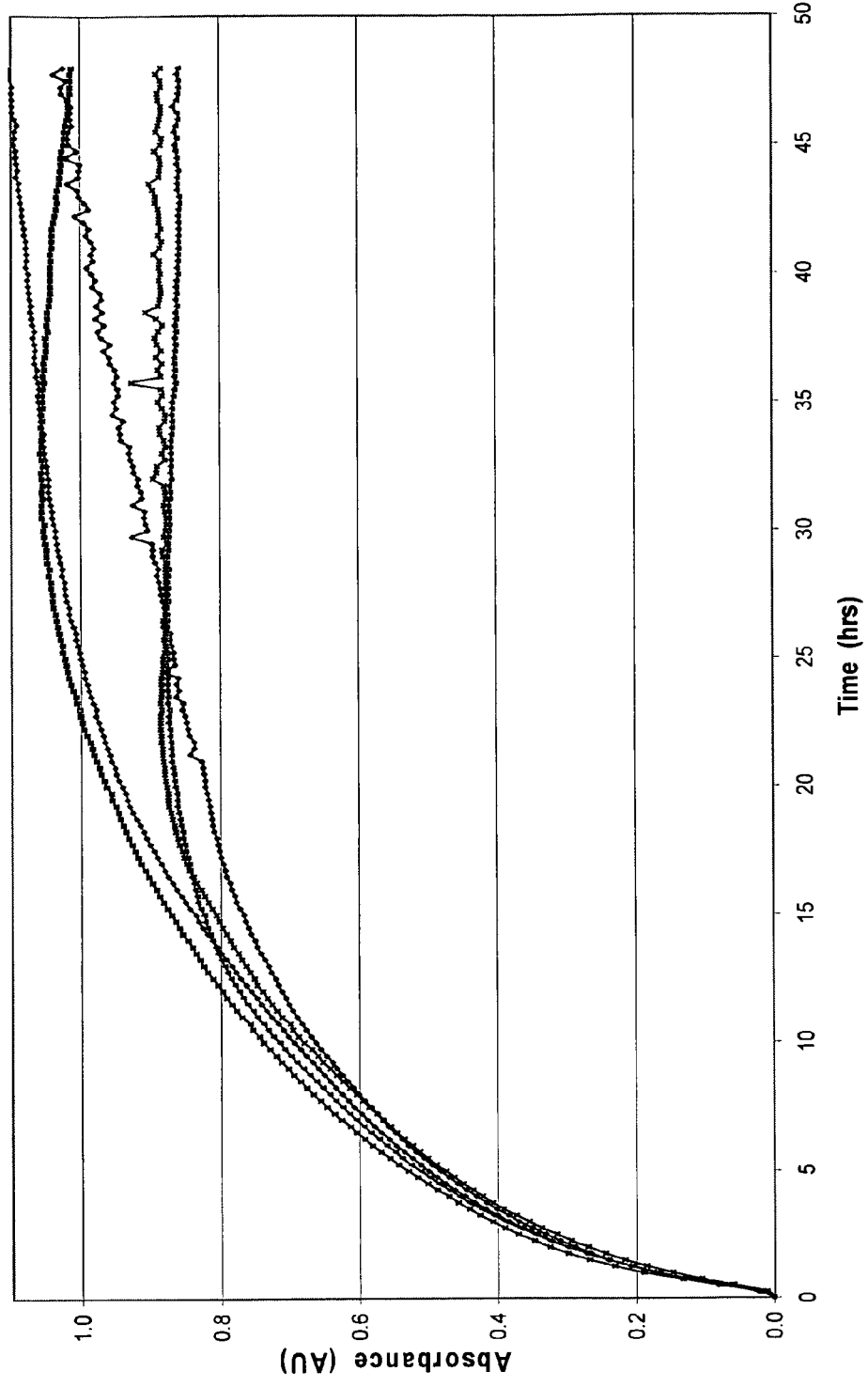
*Figure 50.* Dissolution profile of stored Sterotex NF formulation with 25% fractionated coconut oil

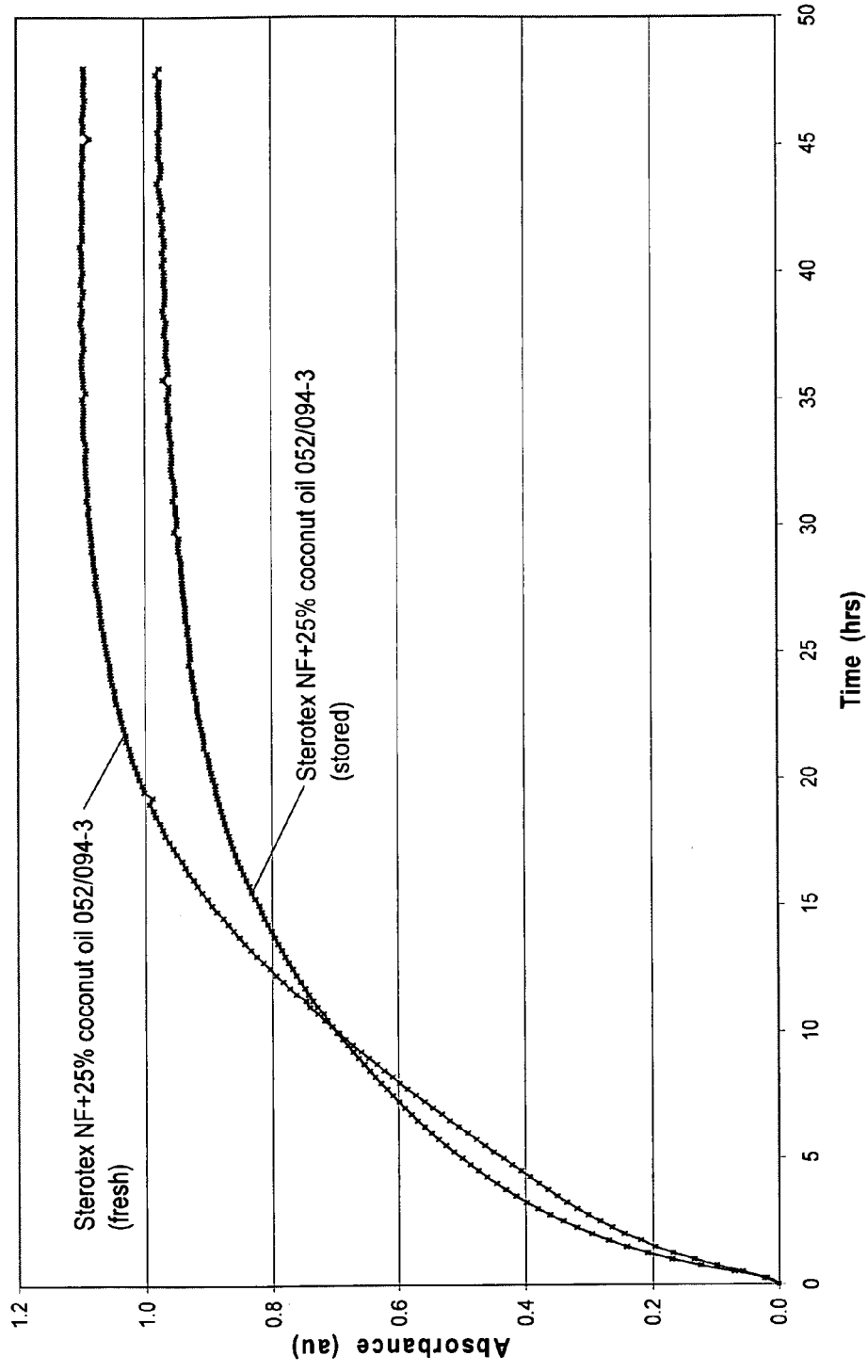
*Figure 51.* Comparison of Dissolution profiles of fresh and stored Sterotex NF formulation with 25% fractionated coconut oil

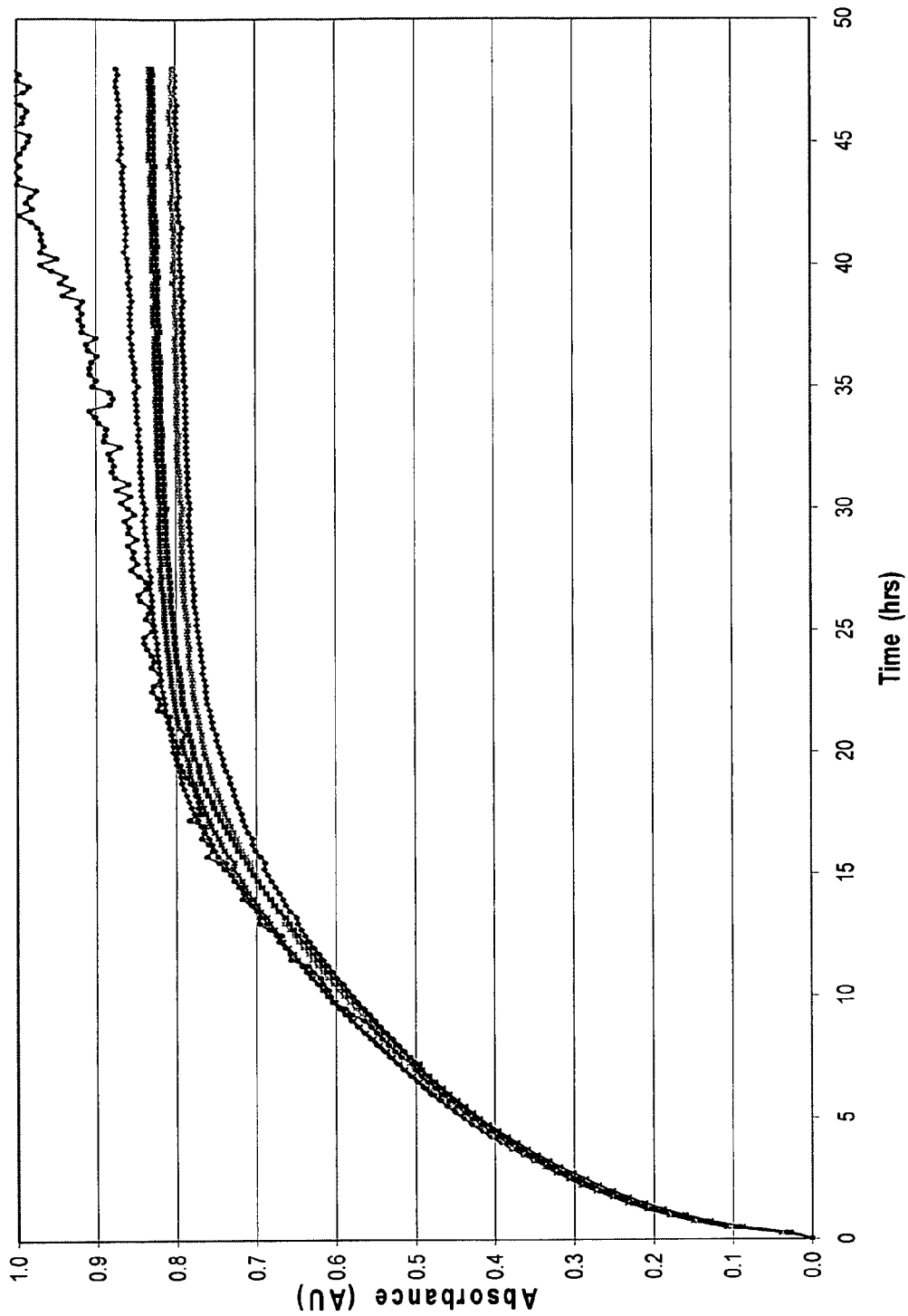
*Figure 52.* Dissolution profile of stored Cithrol GMS formulation

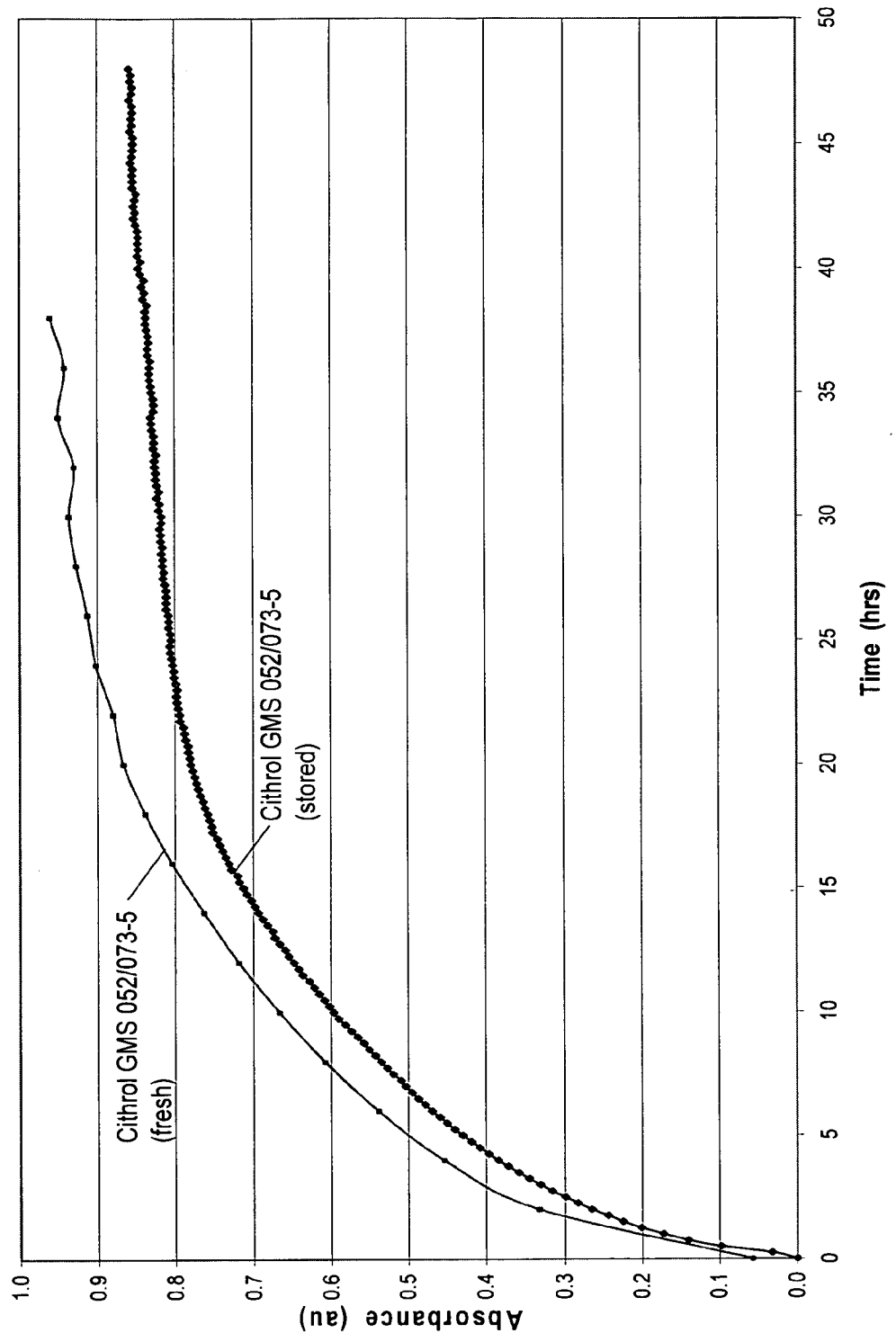
*Figure 53.* Comparison of Dissolution profiles of fresh and stored Cithrol GMS formulation

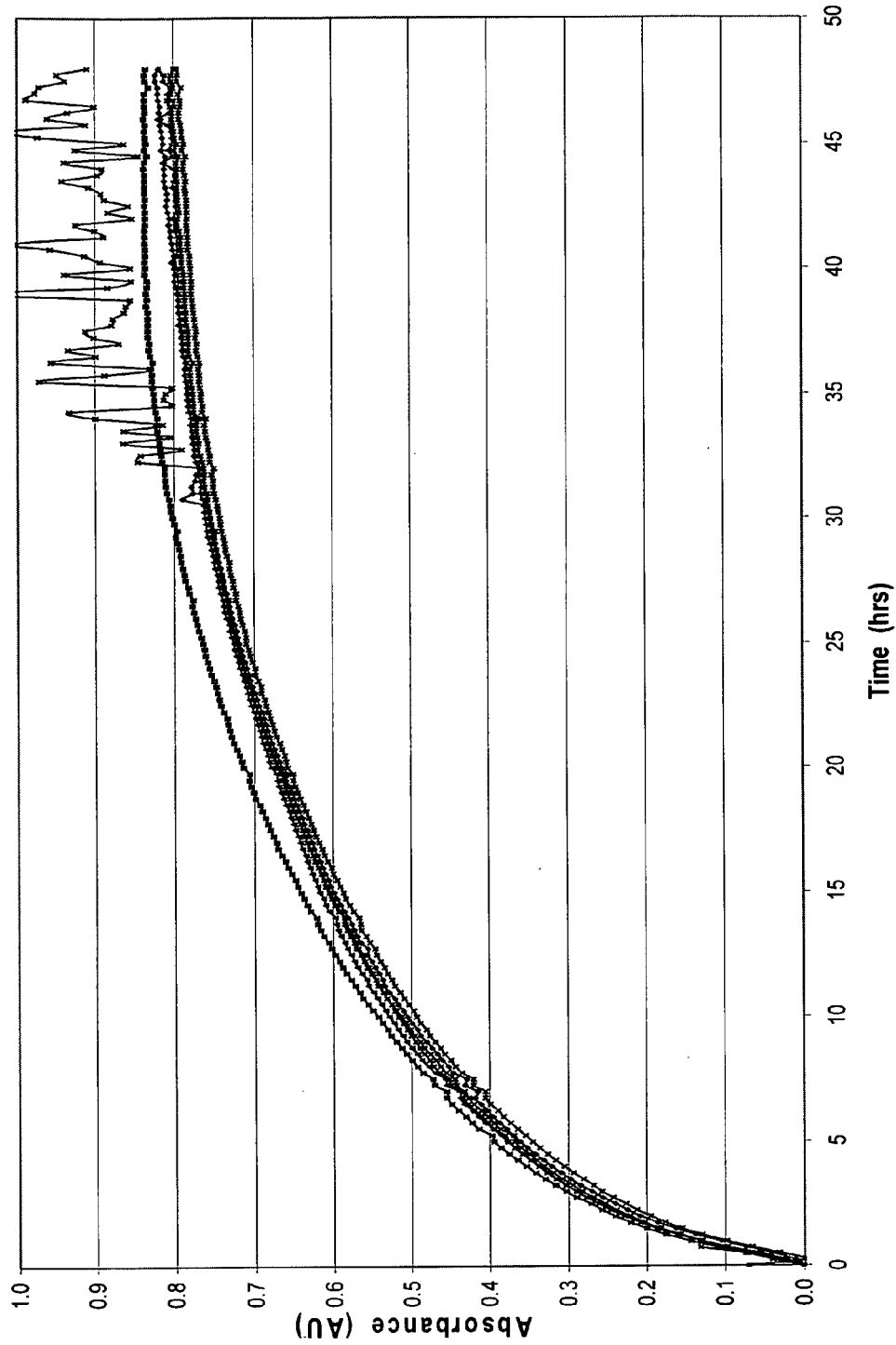
*Figure 54.* Dissolution profile of stored Hydrokote 112 formulation

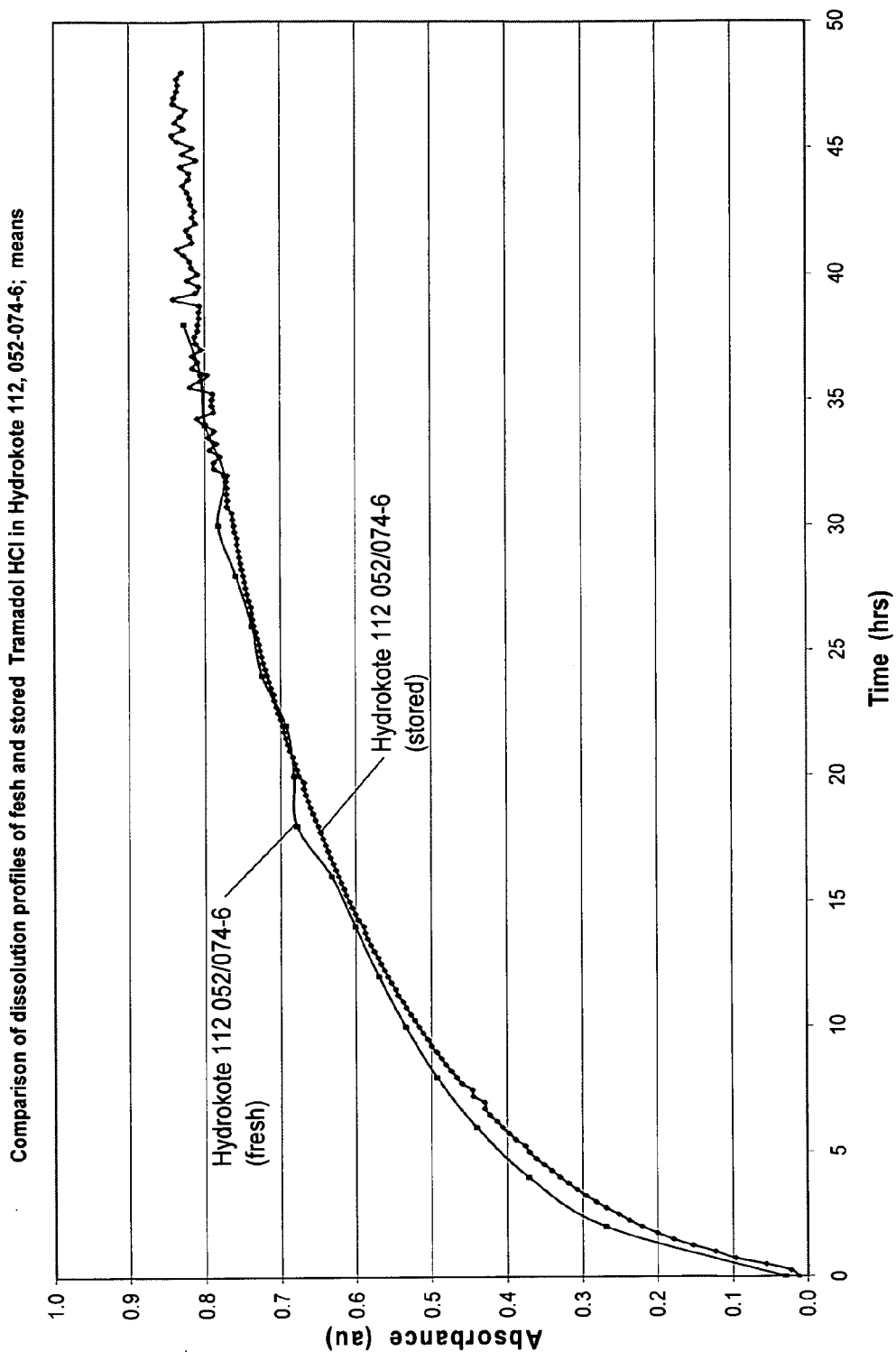
*Figure 55.* Comparison of Dissolution profiles of fresh and stored Hydrokote 112 formulation

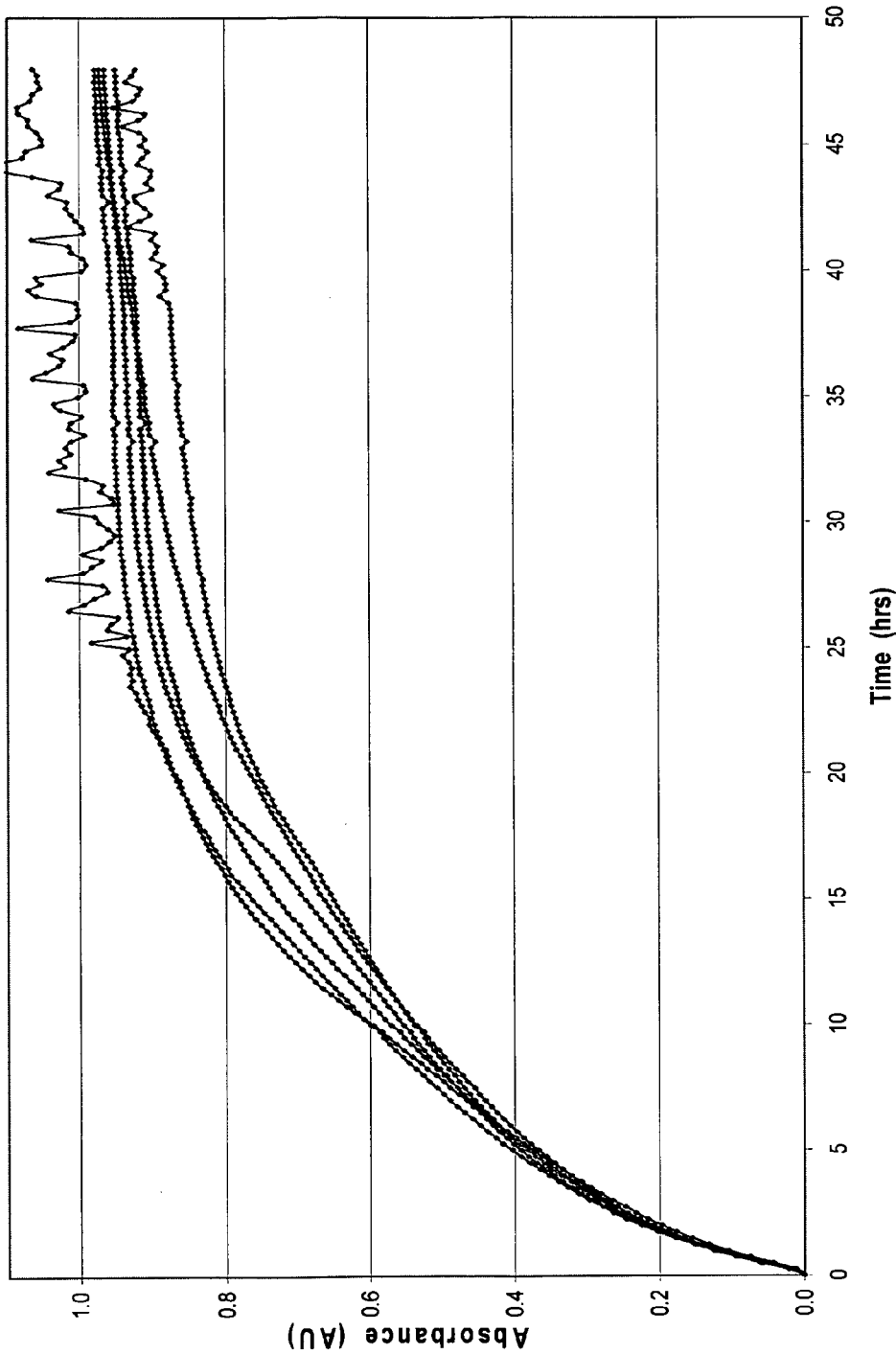
*Figure 56.* Dissolution profile of stored beeswax formulation

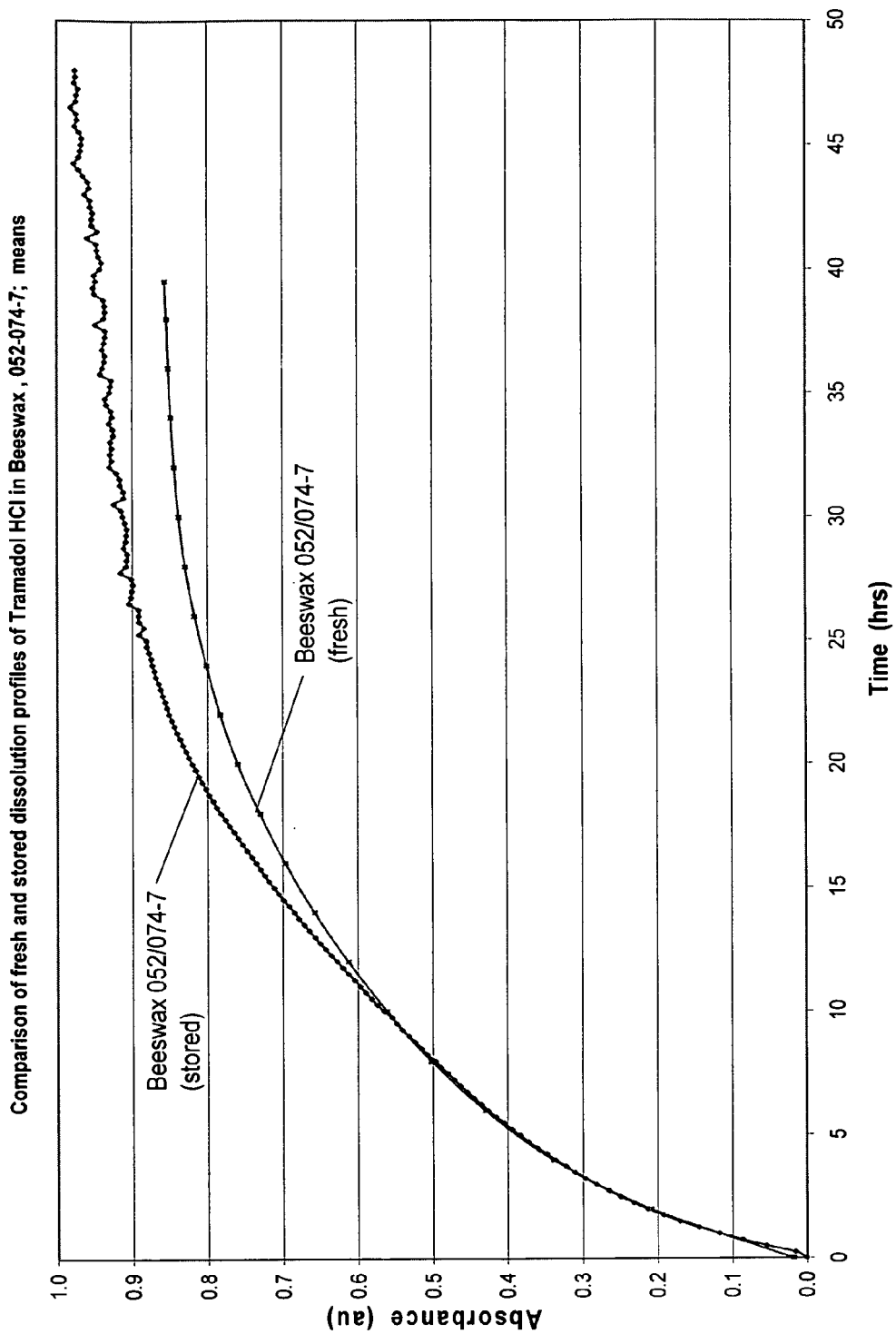
*Figure 57.* Comparison of Dissolution profiles of fresh and stored beeswax formulation

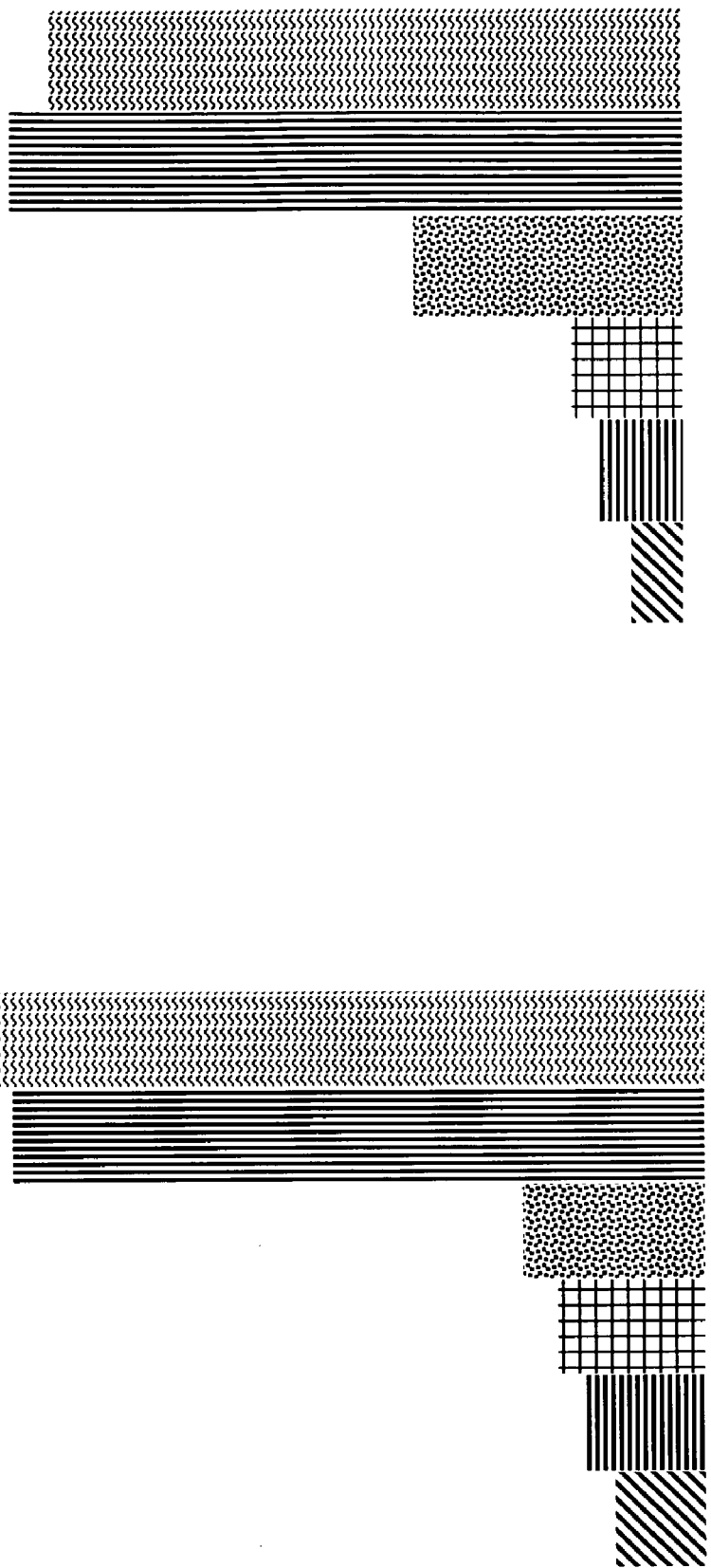
Figure 58. Crushing, Grinding, Water or Vinegar Solubilization and Filtration

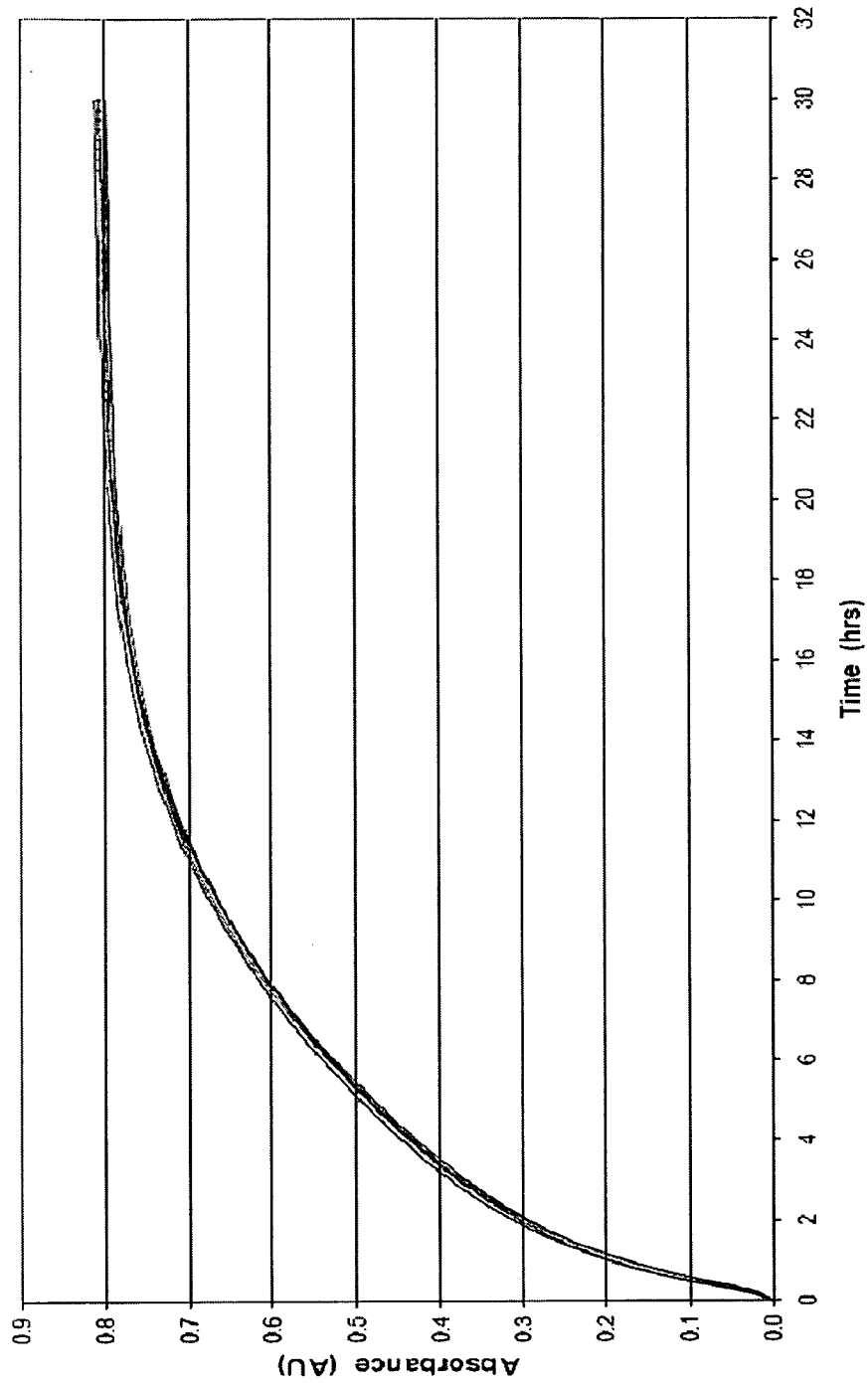
*Figure 59.* Dissolution Profiles of Tramadol HCl in Sterotex

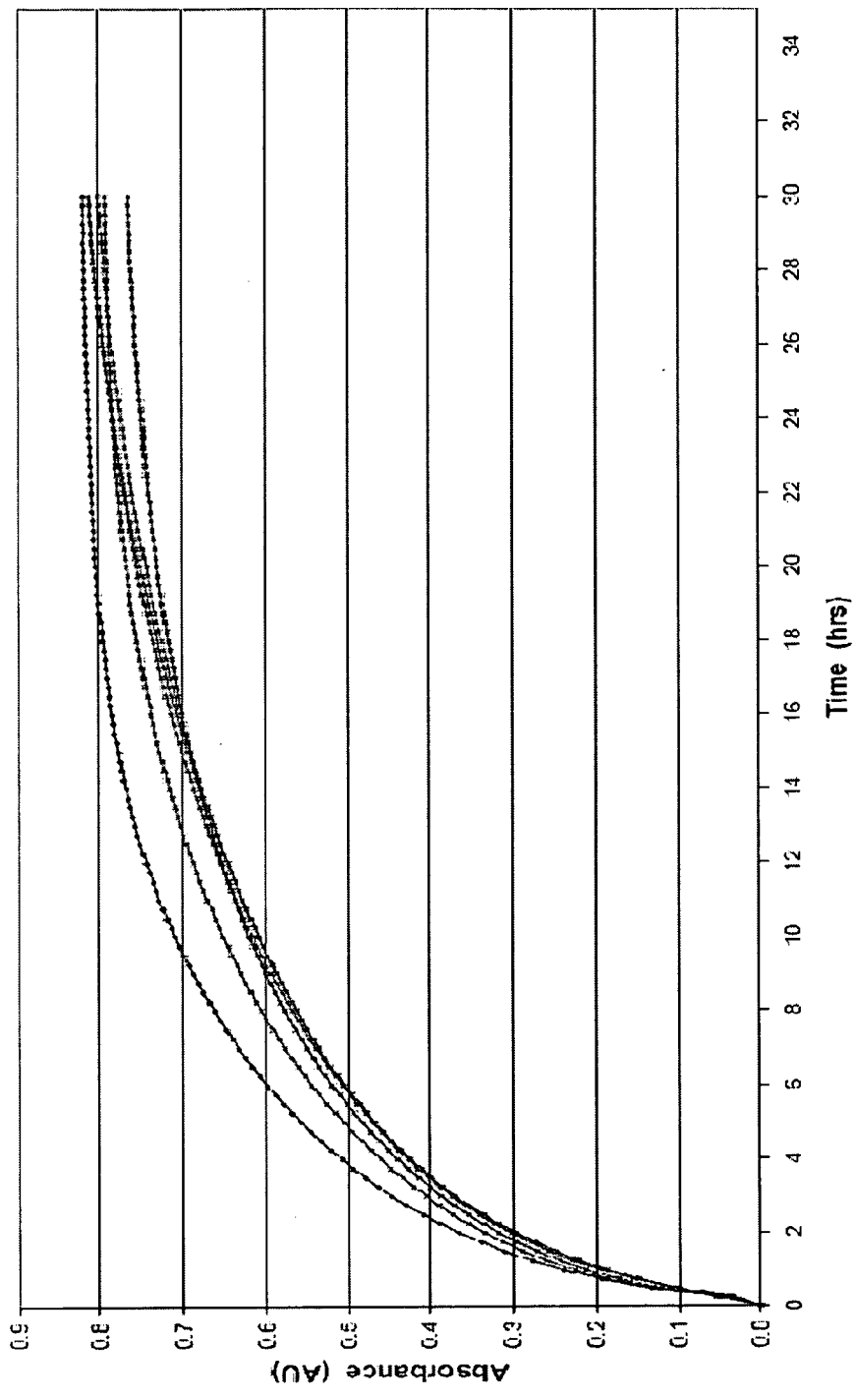
Figure 60. Dissolution Profiles of Tramadol HCl in Hydrocote 112

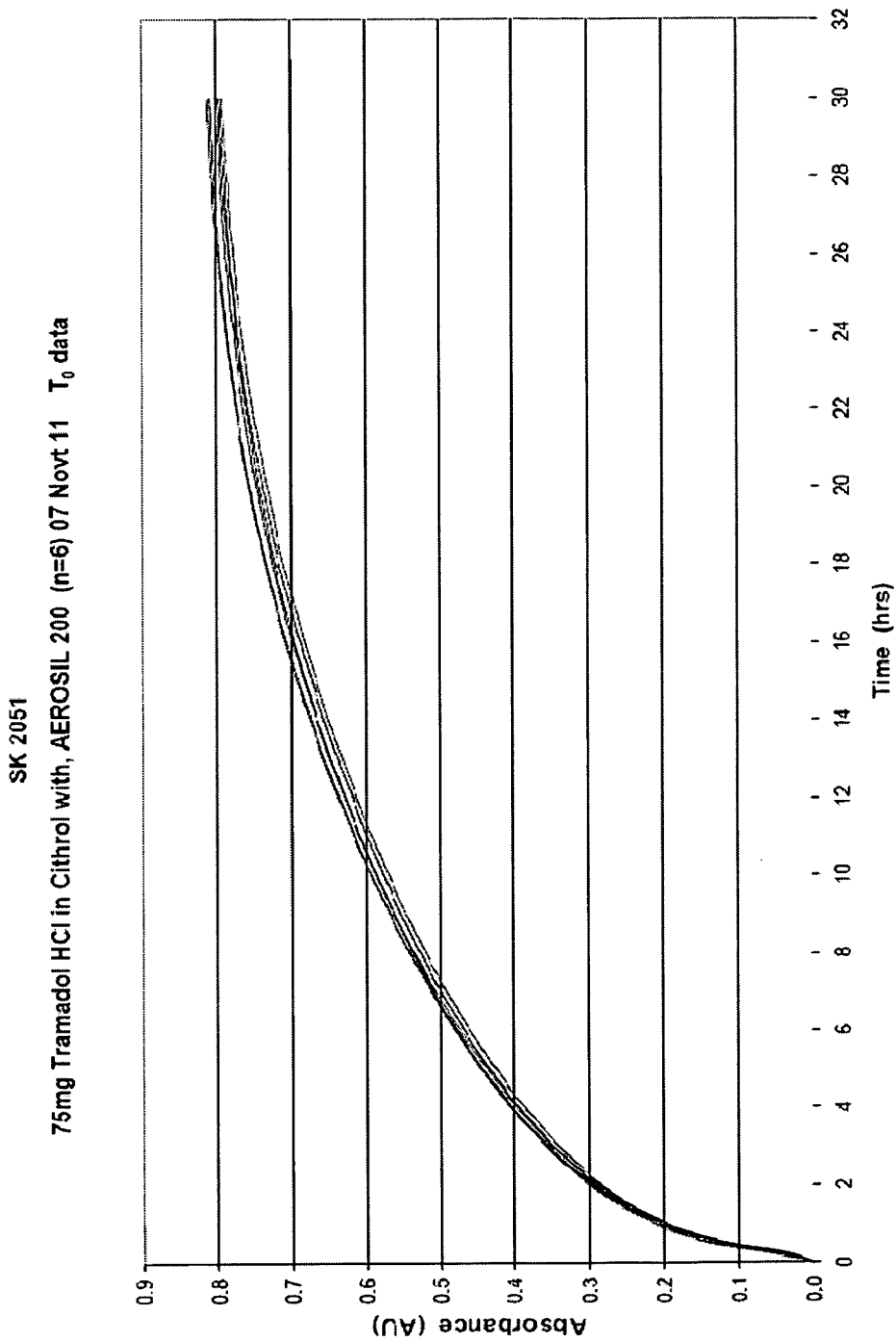
*Figure 61.* Dissolution Profiles of Tramadol HCl in Cithrol

*Figure 62.* Dissolution Profiles of Tramadol HCl in Beeswax
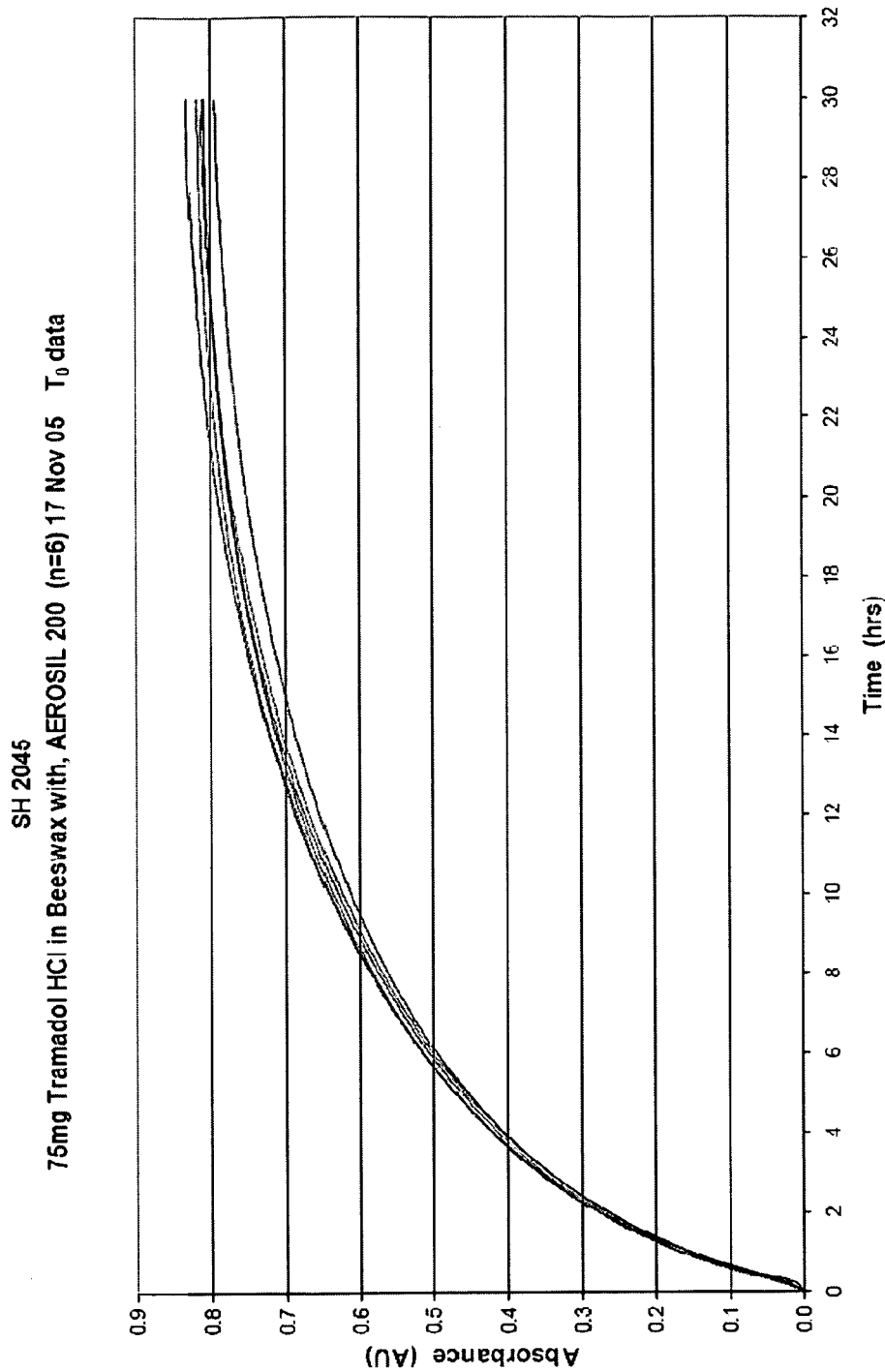

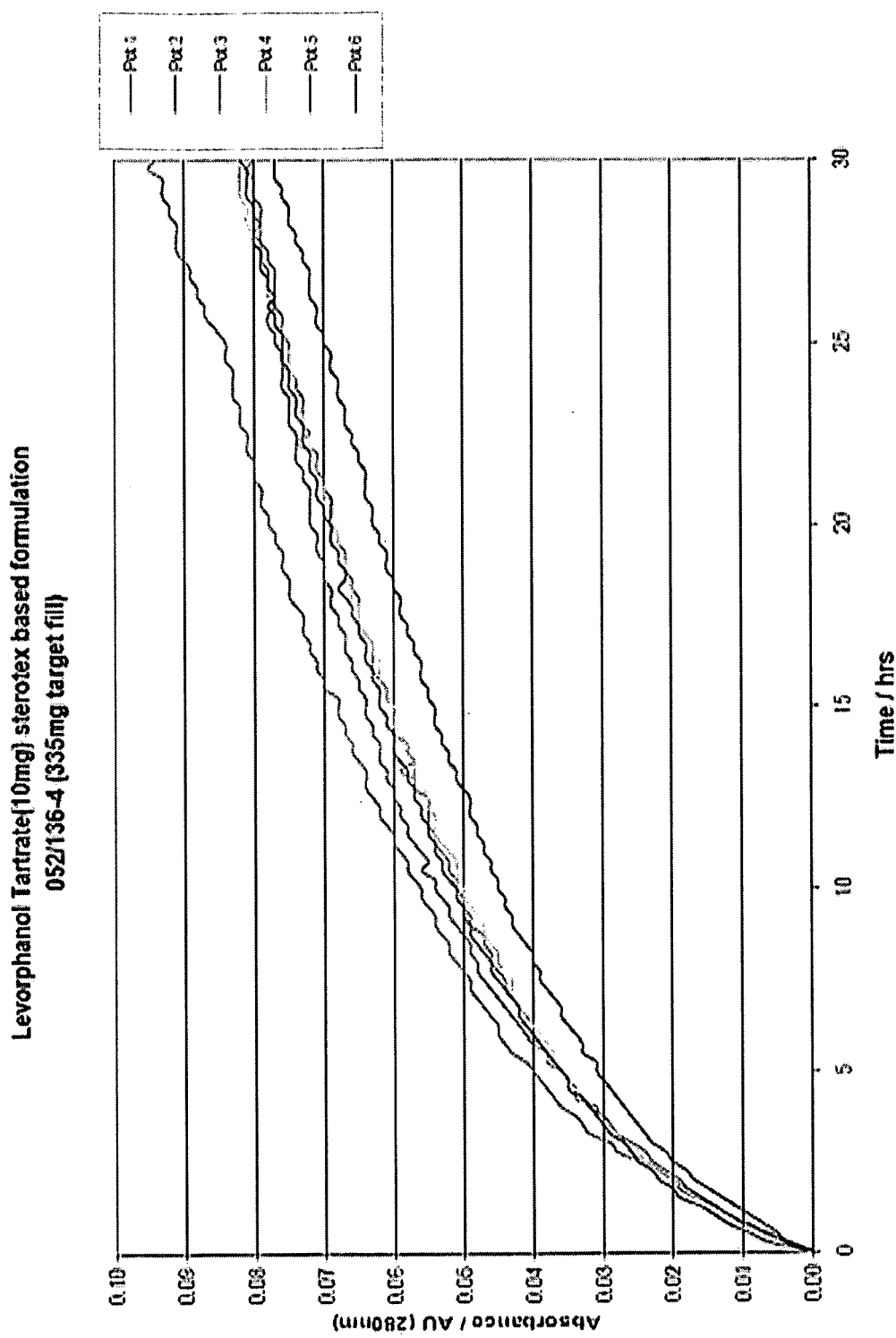
*Figure 63.* Dissolution Profiles of Levorphanol Tartrate in Sterotex

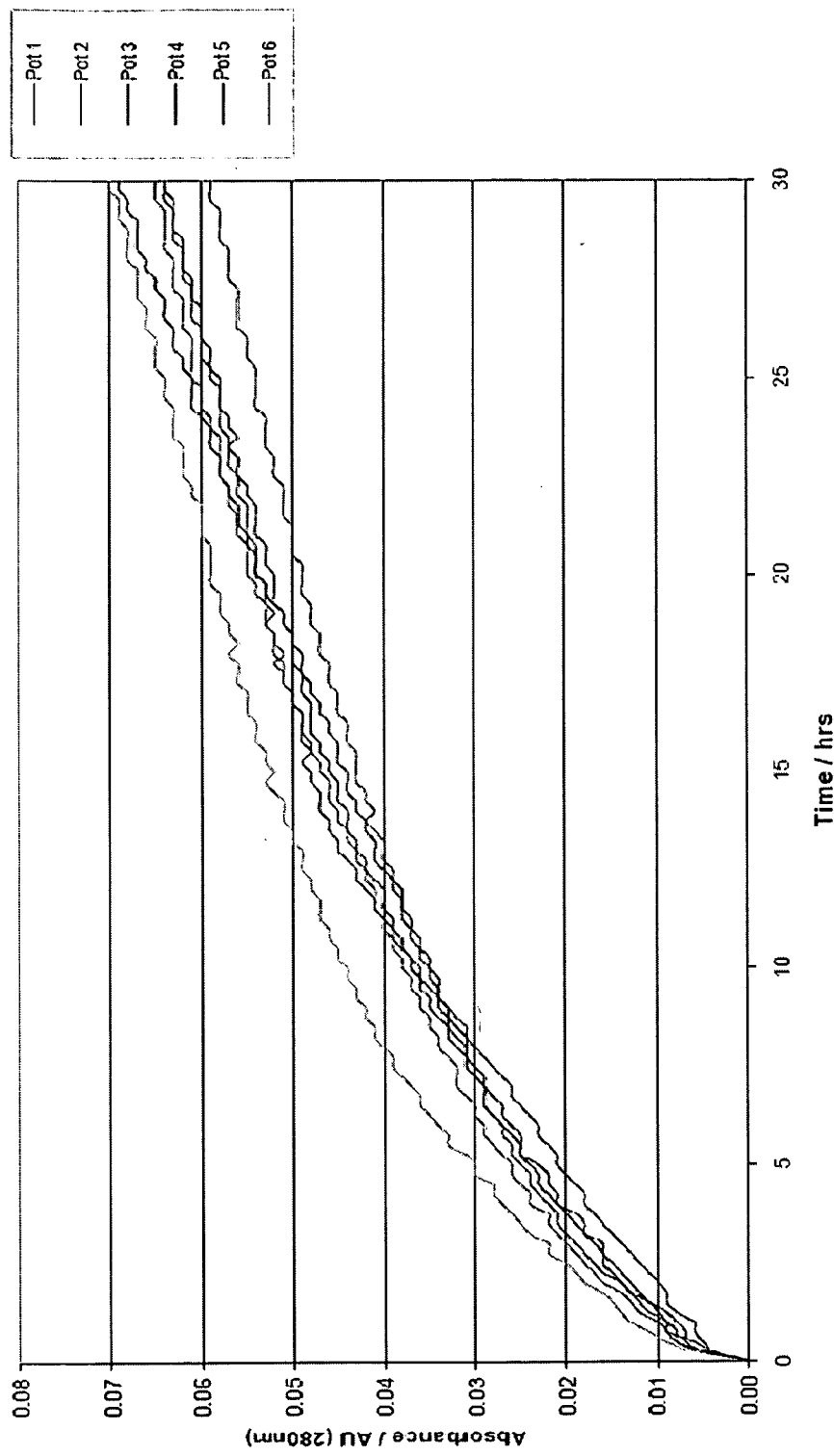
*Figure 64.* Dissolution Profiles of Levorphanol Tartrate in Hydrocote 122

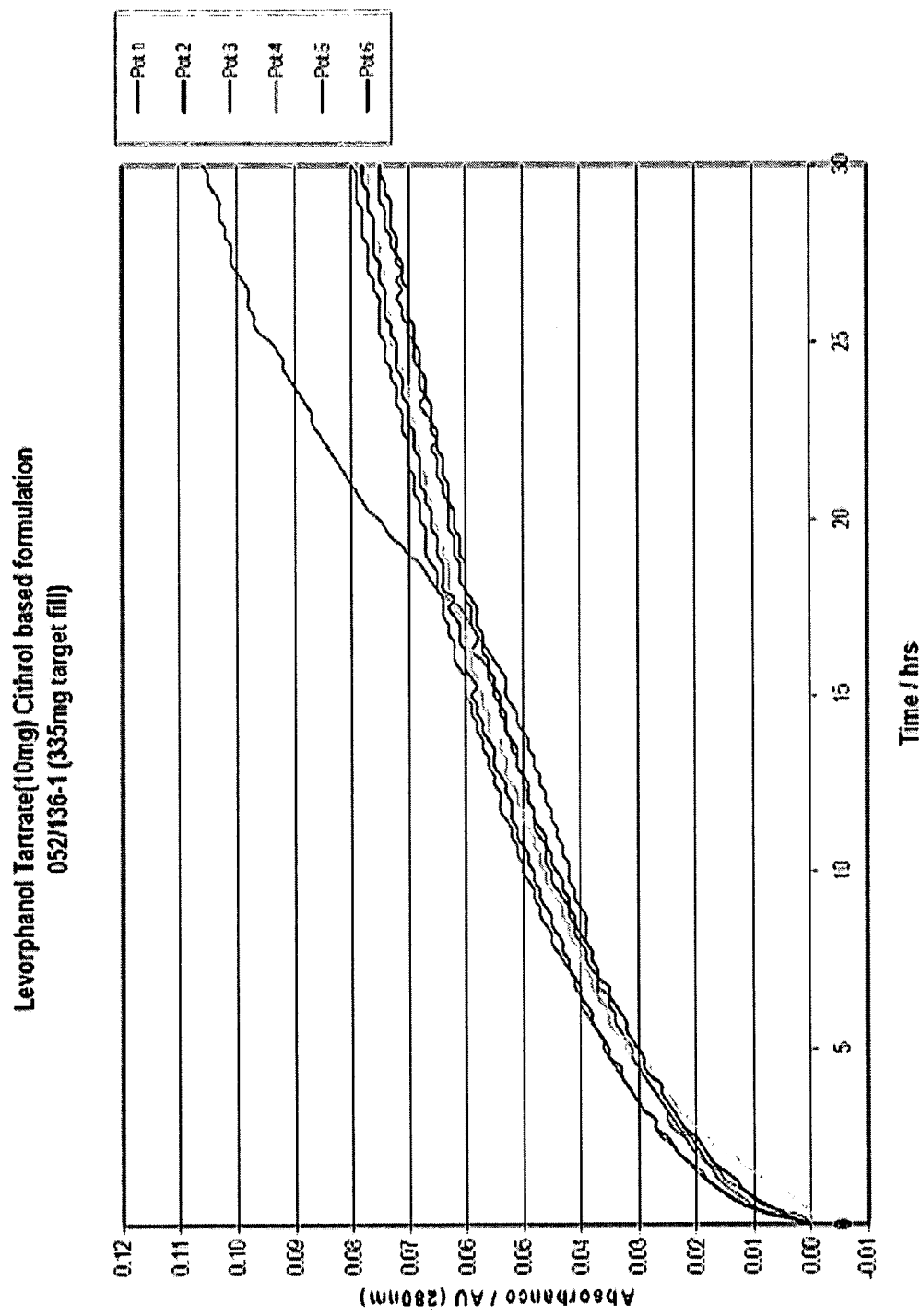
*Figure 65.* Dissolution Profiles of Levorphanol Tartrate in Cithrol

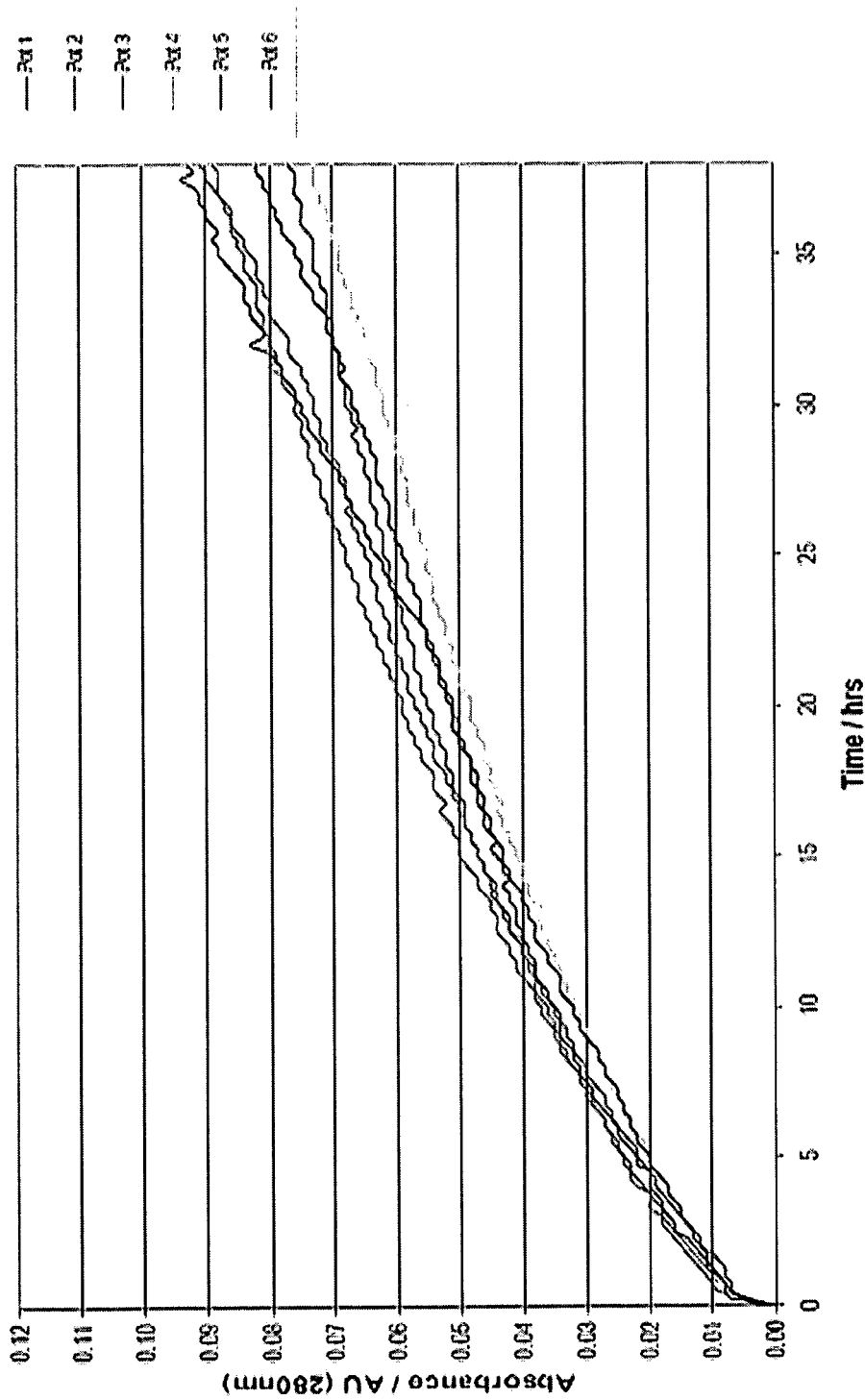
*Figure 66.* Dissolution Profiles of Levorphanol Tartrate in Beeswax

METHODS OF PREVENTING THE SEROTONIN SYNDROME AND COMPOSITIONS FOR USE THEREOF

This application is a continuation-in-part of U.S. application Ser. No. 12/223,987 filed Aug. 13, 2008, now abandoned which is a national phase filing under 35 U.S.C. §371 of international application PCT/US06/42962 filed 2 Nov. 2006, which international application is entitled to priority pursuant to 35 U.S.C. §119(e) to U.S. provisional application No. 60/732,121 (abandoned), which was filed on 2 Nov. 2005; this application is also entitled to priority pursuant to 35 U.S.C. §119(e) to U.S. provisional application No. 60/929,611 (abandoned), which was filed on 5 Jul. 2007.

FIELD OF THE INVENTION

The present invention is in the field of pharmaceutical compositions and the use thereof for preventing or minimizing the risk of the serotonin syndrome.

BACKGROUND ART

The serotonin syndrome is a potentially life-threatening adverse drug experience that results from therapeutic drug use, intentional self-poisoning or inadvertent interactions between drugs. The manifestations of the serotonin syndrome range from mild to fatal. (Boyer and Shannon, NEJM, 2005; Jones and Story, Anaesth Intensive Care, 2005; Sporer, Drug Safety, 1995). The serotonin syndrome is not to be confused with iatrogenic serotonergic side effects that usually manifest with the use of serotonin agonists or serotonergic drugs This syndrome is characterized by a constellation of symptoms. Patients with mild cases may be afebrile but have tachycardia, shivering, diaphoresis, or mydriasis. The neurologic examination may reveal intermittent tremor or myoclonus, as well as hyperreflexia. In moderate cases of the serotonin syndrome, patients may have tachycardia, hypertension, and hyperthermia. A core temperature of up to 40° C. is common in moderate intoxication. Common features include mydriasis, hyperreflexia, clonus, hyperactive bowel sounds, diaphoresis, mild agitation or hypervigilance, as well as pressured speech. Patients with severe cases of the serotonin syndrome may have severe hypertension and tachycardia that may progress to frank shock. Such patients may have delirium, muscular rigidity and hypertonicity. Although no laboratory tests confirm the diagnosis of the serotonin syndrome, lab abnormalities that occur in severe cases include metabolic acidosis, rhabdomyolysis, elevated levels of AST, ALT and creatinine, seizures, renal failure, and disseminated intravascular coagulopathy (DIC). (Boyer and Shannon, NEJM, 2005; Jones and Story, Anaesth Intensive Care, 2005; Sporer, Drug Safety, 1995).

The incidence of the serotonin syndrome appears to have increased with the widespread use of drugs that enhance the effects of serotonin, through serotonin reuptake inhibition, direct agonism at serotonin receptors or through unknown mechanisms, or through effects at receptors other than serotonin (proserotonergic agents). A wide variety of proserotonergic drugs, taken alone or in combination have been implicated in the causation of the serotonin syndrome (Boyer and Shannon, NEJM, 2005; Jones and Story, Anaesth Intensive Care, 2005; Sporer, Drug Safety, 1995). These include the now ubiquitous selective serotonin-reuptake inhibitors (SSRIs), e.g., citalopram, fluoxetine, fluvoxamine, paroxetine and sertaline; selective serotonin-norepinephrine reuptake inhibitors (SNRIs), e.g, venlafaxine, milnacipran; tricyclic and non-tricyclic antidepressants, e.g., buspirone, clomipramine, nefazodone, trazadone; monoamine oxidase (MAO) inhibitors, e.g., clorgiline, isocarboxazid, moclobemide, phenelzine and selegiline; antiepileptics, e.g., valproate; analgesics, e.g., fentanyl, meperidine, pentazocine and tramadol; antiemetic agents, e.g., granisetron, metoclopramide and ondansetron; antimigraine drugs, e.g., sumatriptan; bariatric medications, e.g., sibutramine; antibiotics, e.g., linezolide (a MAOI) and ritonavir (via CYP-450 3A4 inhibition); antitussives, e.g. dextromethorphan; dietary supplements and herbal products, e.g., tryptophan, Hypericum perforatum (St. John's wort), Panax ginseng (ginseng); and lithium. (Boyer and Shannon, NEJM, 2005; Jones and Story, Anaesth Intensive Care, 2005; Sporer, Drug Safety, 1995).

According to the Toxic Exposure Surveillance System (TESS), in 2002, there were 26,733 reported cases of exposure to selective serotonin-reuptake inhibitors (SSRIs) that caused serious toxic effects in 7,349 individuals and resulted in 93 fatalities (Isbister et al, J Toxicol Clin Toxicol 2004; Watson et al, Am J Emerg Med 2003).

The prevalence of the serotonin syndrome has relied on post-marketing surveillance reports, one of which identified an incidence of 0.4 per 1000 patient-months for patients who were taking the antidepressant nefazodone (Mackay et al, Br J Gen Pract 1999). The precise prevalence of the serotonin syndrome is difficult to assess; it is reported that approximately 85 percent of clinicians are unaware of the serotonin syndrome as a clinical diagnosis ((Mackay et al, Br J Gen Pract 1999). The serotonin syndrome occurs in approximately 14 to 16 percent of individuals who overdose on SSRIs (Isbister et al, J Toxicol Clin Toxicol 2004).

Clarkson et al (J Forensic Sci, 2004) reviewed a series of 66 deaths in Washington State between 1995-2000 in which tramadol was detected in the decedent's blood, in order to assess the role tramadol was determined to have played. Tramadol is an analgesic that exerts its effects through inhibition of reuptake of serotonin and norepinephrine, and through opioid agonism. Tramadol was consistently found together with other analgesic, muscle relaxant, and CNS depressant drugs. The investigators found that death was rarely attributable to tramadol alone. However, tramadol was a significant contributor to lethal intoxication when taken in excess with other drugs, via the potential interaction with serotonergic antidepressant medications (e.g., amitriptyline, nortriptyline, trazadone).

Serotonin syndrome can occur with the (i) initiation of therapy with a proserotonergic agent; (ii) the addition of a second proserotonergic agents; and (iii) intentional or accidental overdose with one or several proserotonergic agents. Proserotonergic agents are frequently used in patients with primary psychopathology (major depression, schizophrenia), in individuals who have chronic pain and those with chronic pain and comorbid depression or other affective disorders. Such populations are particularly predisposed to concomitant therapy with multiple proserotonergic drugs, other polypharmacy, drug and alcohol abuse and suicidal ideation. Consequently, patients receiving proserotonergic agents are at particular risk for accidental or intentional overdose with one or several prescribed or street drugs implicated in the serotonin syndrome.

Proserotonergic agents are also frequently used as primary therapy or in combination with conventional analgesics for the treatment of painful peripheral neuropathic pain (e.g., painful diabetic neuropathy, postherpetic neuralgia, etc) and central neuropathic pain (e.g, spinal cord injury pain, post-stroke pain, etc).

Over the past decade, there has been a growing appreciation of the value of extended release (also know as sustained release, controlled release and modified release) formulations in improving patient convenience and compliance for chronic conditions such as depression or chronic pain. Conventional (so called "immediate-release" or "short acting") medications provide short-lived plasma levels, thereby requiring frequent dosing during the day (e.g., 4, 6 or 8 hours) to maintain therapeutic plasma levels of drug. In contrast, extended release formulations are designed to maintain effective plasma levels throughout a 12 or 24-hour dosing interval. Extended release formulations result in fewer interruptions in sleep, reduced dependence on caregivers, improved compliance, enhanced quality of life outcomes, and increased control over the management of their disease. In addition, such formulations can provide more constant plasma concentrations and clinical effects, less frequent peak to trough fluctuations and fewer side effects, compared with short acting drugs (Sloan and Babul, Expert Opinion on Drug Delivery 2006; Babul et al. Journal of Pain and Symptom Management 2004; 28:59-71; Matsumoto et al., Pain Medicine 2005; 6:357-66; Dhaliwal et al., Journal of Pain Symptom Management 1995; 10:612-23; Hays et al., Cancer 1994; 74:1808-16; Arkinstall et al., Pain 1995; 64:169-78; Hagen et al., Journal of Clinical Pharmacology 1995; 35:38-45; Peloso et al., Journal of Rheumatology 2000; 27:764-71).

However, such medications are not without drawbacks. Commercially available immediate-release formulations are designed to release a small amount of drug into the systemic circulation over several hours. New, extended release formulations are designed to gradually release their much larger drug load over a 12 or 24-hour period. Experience with extended release formulations of the pain reliever, oxycodone (OxyContin®) has shown that intentional crushing, tampering or extraction of the active ingredient from the formulation by addicts and recreational drug users destroys the controlled-release mechanism and results in a rapid surge of drug into the bloodstream, with the entire 12 or 24-hour drug supply released immediately with potential for toxic effects.

In the case of proserotonergic drugs, accidental or intentional crushing or extraction or overdose will result in a surge of high blood levels (serotonin excess). Studies have demonstrated that serotonin excess, leading to the serotonin syndrome, may be a result of a single proserotonergic drug or more frequently, from the combined effect of multiple proserotonergic drugs (e.g., the analgesic tramadol with an SSRI). If not properly diagnosed and treated, serotonin syndrome can lead to life-threatening complications and death.

The onset of symptoms of the serotonin syndrome is usually rapid, with clinical manifestations frequently occurring within minutes after a change in medication or self-poisoning (Mason et al, Medicine, 2000). More than half the patients with the serotonin syndrome present within six hours after initial use, misuse or abuse of medication, an overdose, or a change in dosing. (Mason et al, Medicine, 2000). Patients with mild symptoms may present with subacute or chronic symptoms, while those with severe intoxication may progress rapidly to death. It is believed that the serotonin syndrome does not resolve spontaneously as long as precipitating agents continue to be administered.

Management of the serotonin syndrome involves the removal of the precipitating drugs, supportive care, control of agitation, administration of $5-HT_{2A}$ antagonists and control of autonomic instability and any hyperthermia. Many cases of the serotonin syndrome typically resolve within 24 hours after the initiation of therapy and the discontinuation of serotonergic drugs, but symptoms may persist in patients taking drugs with long elimination half-lives, active metabolites, or a protracted duration of action. (Boyer and Shannon, NEJM, 2005; Jones and Story, Anaesth Intensive Care, 2005; Sporer, Drug Safety, 1995).

According to a recent state of the art review Boyer and Shannon, NEJM, March 2005), the serotonin syndrome can be avoided by "a combination of pharmacogenomic research, the education of physicians, modifications in prescribing practices, and the use of technological advances. The application of pharmacogenomic principles can potentially protect patients at risk for the syndrome before the administration of serotonergic agents. Once toxicity occurs, consultation with a medical toxicologist, a clinical pharmacology service, or a poison-control center can identify proserotonergic agents and drug interactions, assist clinicians in anticipating adverse effects, and provide valuable clinical decision-making experience. The avoidance of multidrug regimens is critical to the prevention of the serotonin syndrome. If multiple agents are required, however, computer-based ordering systems and the use of personal digital assistants can detect drug interactions and decrease reliance on memory in drug ordering. Post-marketing surveillance linked to physician education has been proposed to improve awareness of the serotonin syndrome."

There is no prior art on pharmaceutical formulations of prosertonergic agents that have a reduced risk of producing the serotonin syndrome.

There is no prior art on pharmaceutical formulations of opioid agonist prosertonergic agents that have a reduced risk of producing the serotonin syndrome.

BRIEF SUMMARY OF THE INVENTION

The present invention is directed at pharmaceutical compositions and the use thereof for preventing or minimizing the risk of the serotonin syndrome. There are no methods in the literature directed at the development or use of pharmaceutical formulations that have a reduced risk of producing the serotonin syndrome.

The present invention is directed at pharmaceutical dosage forms that prevent or reduce the intensity of the serotonin syndrome by reducing the amount of proserotonergic agents accidentally or intentionally released into the systemic circulation.

Proserotonergic agents, including selective serotonin-reuptake inhibitors (SSRIs), e.g., citalopram, ecitalopram, fluoxetine, fluvoxamine, nefazodone, paroxetine, and sertaline; selective serotonin-norepinephrine reuptake inhibitors (SNRIs), e.g, bicifadine, venlafaxine, milnacipran, mirtazepine and nefazodone; tricyclic and non-tricyclic antidepressants, e.g., buspirone, clomipramine, trazadone; monoamine oxidase (MAO) inhibitors, e.g., clorgiline, isocarboxazid, moclobemide, phenelzine and selegiline; antiepileptics, e.g., valproate; analgesics, e.g., anileridine, dezocine, dihydrocodeine, hydrocodone, hydromorphone, fentanyl, levorphanol, meperidine, pentazocine, propiram, tramadol, other opioid analgesics; antiemetic agents, e.g., granisetron, metoclopramide and ondansetron; antimigraine drugs, e.g., sumatriptan; bariatric medications, e.g., sibutramine; antibiotics, e.g., linezolide (a MAOI) and ritonavir (via CYP-450 3A4 inhibition); antitussives, e.g. dextromethorphan; dietary supplements and herbal products, e.g., tryptophan, Hypericum perforatum (St. John's wort), Panax ginseng (ginseng); and lithium can be formulated and used with a reduced risk of the serotonin syndrome in the setting of accidental or intentional overdose and co-ingestion with other proserotonergic agents.

Both immediate release and extended release proserotonergic formulations can produce a serotonin surge when taken accidentally or intentionally in therapeutic, non-medical and overdose settings and when co-ingested with other proserotonergic agents.

Surprisingly, serotonin surge protector (SSP) formulations can reduce the incidence and severity of the serotonin syndrome.

As used herein, the term "serotonin surge protector", "SSP" or "SSP's" means pharmaceutical compositions that resist, deter or prevent crushing, shearing, grinding, chewing, dissolving, melting, needle aspiration, inhalation, insufflation or solvent extraction of the proserotonergic agent contained therein which is responsible for causing the serotonin syndrome through serotonin excess, thereby preventing or reducing the incidence and intensity of the serotonin syndrome when the SSP is combined in the same formulation with one or more proserotonergic agents. Preferred SSP's are selected from a group consisting of polymeric and/or nonpolymeric gel forming agents, viscosity enhancing agents, high viscosity liquids and high melting point waxes, hydrogenated Type I or Type II vegetable oils, polyoxyethylene stearates and distearates, glycerol monostearate, and non-polymeric, non-water soluble liquids, carbohydrate-based substances or poorly water soluble, high melting point (mp=40 to 100° C.) waxes and mixtures thereof. In some embodiments, SSP's include polyethylene oxides, polyvinyl alcohol, hydroxypropyl methyl cellulose, carbomers, ethylcellulose, cellulose acetate, cellulose acetate propionate, cellulose acetate butyrate, cellulose acetate phthalate and cellulose triacetate, cellulose ether, cellulose ester, cellulose ester ether, and cellulose, acrylic resins comprising copolymers synthesized from acrylic and methacrylic acid esters, the acrylic polymer may be selected from the group consisting of acrylic acid and methacrylic acid copolymers, methyl methacrylate copolymers, ethoxyetlryl methacrylates, cyanoetlryl methacrylate, poly(acrylic acid), poly(methaerylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), glycidyl methacrylate copolymers, microcrystalline cellulose with carboxymethylcellulose sodium, carboxymethylcellulose sodium, polyacrylic acid, locust bean flour, pectins, waxy corn starch, sodium alginate, guar flour, iota-carrageenan, karaya gum, gellan gum, galactomannan, tara stone flour, propylene glycol alginate, sodium hyaluronate, tragacanth, tara gum, fermented polysaccharide welan gum, xanthans, silicon dioxide, fumed silicon dioxide, coconut oil, hydrogenated palm kernel oil, hydrogenated cottonseed oil, hydrogenated palm kernel oil, hydrogenated palm oil, hydrogenated soybean oil and beeswax, and mixtures thereof. In some embodiments, SSP's include hydrophobic polymers, hydrophilic polymers, gums, protein derived materials, waxes, shellac, oils and mixtures thereof.

In some embodiments, the dosage form must include, in addition to at least one proserotonergic agent, at least two SSP's.

In some embodiments, the dosage form must include, in addition to at least one proserotonergic agent, at least two SSP's selected from the group comprising: (a) polymeric and/or nonpolymeric gel forming agents; (b) viscosity enhancing agents; (c) high viscosity liquids; and (d) high melting point waxes. In some preferred embodiments, to qualify as an "SSP" requires a mixture of two or more compounds, wherein the two or more compounds are selected from at least two of the foregoing groups [i.e., (a), (b), (c), and (d), for example one compound from (a) and one compound from (b) or one compound from (a) and two compounds from (b)]. In some preferred embodiments, to qualify as an "SSP" requires a mixture of three or more of the foregoing compounds. In some preferred embodiments, to qualify as an "SSP" requires a mixture of three or more of the foregoing compounds, wherein the three or more compounds are selected from at least two of the foregoing groups [i.e., (a), (b), (c), and (d), for example one compound from (a) and two compounds from (b)]. In some preferred embodiments, to qualify as an "SSP" requires a mixture of three or more of the foregoing compounds, wherein the three or more compounds are selected from at least three of the foregoing groups [i.e., (a), (b), (c), and (d), for example one compound from (a), one compounds from (b), and one compounds from (c)].

In some embodiments, the SSP refers to one or more compounds selected from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes, and mixtures thereof. In some preferred embodiments, the SSP is a mixture of two or more compounds from the forgoing group [i.e., (a) to (d)]. In some preferred embodiments, to qualify as an "SSP" requires a mixture of two or more compounds, wherein the two or more compounds are selected from at least two of the foregoing groups [i.e., (a), (b), (c), and (d), for example one compound from (a) and one compound from (b)].

In some preferred embodiments, to qualify as an "SSP" requires a mixture of three or more of the foregoing compounds. In some preferred embodiments, to qualify as an "SSP" requires a mixture of three or more of the foregoing compounds, wherein the three or more compounds are selected from at least two of the foregoing groups [i.e., (a), (b), (c), and (d), for example one compound from (a) and two compounds from (b)]. In some preferred embodiments, to qualify as an "SSP" requires a mixture of three or more of the foregoing compounds, wherein the three or more compounds are selected from at least three of the foregoing groups [i.e., (a), (b), (c), and (d), for example one compound from (a), one compounds from (b), and one compounds from (c)].

As used herein, the term "SSP" also includes glyceryl behenate (e.g., Comptirol™ 888 ATO), glyceryl palmitostearate (e.g., Precirol™ ATO 5), stearoyl macrogolglycerides (Gelucire™ 50/13), lauroyl macrogolglycerides (Labrafil™ M 2130 CS).

A first aspect of the present invention is directed to a novel method for reducing the peak concentration of proserotonergic agent, said method comprising administering a proserotonergic agent and a suitable amount of SSP.

A second aspect of the present invention is directed to a novel method for reducing the area under the plasma concentration time curve (AUC) of proserotonergic agent, said method comprising administering a proserotonergic agent and a suitable amount of SSP.

A third aspect of the present invention is directed to a novel method for reducing the average plasma concentration time (Cave) of proserotonergic agent, said method comprising administering a proserotonergic agent and a suitable amount of SSP.

A fourth aspect of the present invention is directed to a novel method for reducing the incidence of the serotonin syndrome, said method comprising administering a proserotonergic agent and a suitable amount of SSP.

A fifth aspect of the present invention is directed to a novel method for reducing the intensity of the serotonin syndrome, said method comprising administering a proserotonergic agent and a suitable amount of SSP.

A sixth aspect of the present invention is directed to a novel method for reducing the intensity or frequency of one or more symptoms of the serotonin syndrome, including hyperthermia, tachycardia, shivering, diaphoresis, mydriasis, tremor, myoclonus, hyperreflexia, hypertension, hyperactive bowel sounds, agitation, hypervigilance, pressured speech, delirium, muscular rigidity, hypertonicity, metabolic acidosis, rhabdomyolysis, elevated levels of AST, ALT and creatinine, seizures, renal failure, and disseminated intravascular coagulopathy (DIC), said method comprising administering a proserotonergic agent and a suitable amount of SSP.

A seventh aspect of the present invention is directed to novel pharmaceutical compositions of matter for use in reducing the peak concentration of proserotonergic agent, said method comprising administering a proserotonergic agent and a suitable amount of SSP.

An eighth aspect of the present invention is directed to novel pharmaceutical compositions of matter for reducing the area under the plasma concentration time curve (AUC) of proserotonergic agent, said method comprising administering a proserotonergic agent and a suitable amount of SSP.

A ninth aspect of the present invention is directed to novel pharmaceutical compositions of matter for reducing the average plasma concentration time (Cave) of proserotonergic agent, said method comprising administering a proserotonergic agent and a suitable amount of SSP.

A tenth aspect of the present invention is directed to novel pharmaceutical compositions of matter for reducing the incidence of the serotonin syndrome, said method comprising administering a proserotonergic agent and a suitable amount of SSP.

An eleventh aspect of the present invention is directed to novel pharmaceutical compositions of matter for reducing the intensity of the serotonin syndrome, said method comprising administering a proserotonergic agent and a suitable amount of SSP.

An twelfth aspect of the present invention is directed to novel pharmaceutical compositions of matter for reducing the intensity or frequency of one or more symptoms of the serotonin syndrome, including hyperthermia, tachycardia, shivering, diaphoresis, mydriasis, tremor, myoclonus, hyperreflexia, hypertension, hyperactive bowel sounds, agitation, hypervigilance, pressured speech, delirium, muscular rigidity, hypertonicity, metabolic acidosis, rhabdomyolysis, elevated levels of AST, ALT and creatinine, seizures, renal failure, and disseminated intravascular coagulopathy (DIC), said method comprising administering a proserotonergic agent and a suitable amount of SSP.

BRIEF SUMMARY OF THE SEVERAL VIEWS OF THE DRAWINGS

FIG. 1 shows the UV spectrum of tramadol HCI in water.
FIG. 2 shows the formulation 052/014 dissolution profile.
FIG. 3 shows the formulation 052/015 dissolution profile.
FIG. 4 shows the formulation 052/019 dissolution profile, Gelucire 50102 with Methocel K 100M.
FIG. 5 shows the formulation 052/024 dissolution profile.
FIG. 6 shows the formulation 052/024 dissolution profile in SIF containing pancreatin.
FIG. 7 shows the dissolution profile of propranolol HCl in Gelucire 50/02 in SIF without pancreatin.
FIG. 8 shows the dissolution profile of propranolol HCl in Gelucire 50/02 in SIF containing pancreatin.
FIG. 9 shows the combined averaged dissolution profiles of propranolol HCl in Gelucire 50/02 in SIF with and without pancreatin.
FIG. 10 shows the combined dissolution profiles of Zydol XL 150 and Dromadol SR tablets in SW.
FIG. 11 shows the combined dissolution profiles of seven different excipient formulations in SIF.
FIG. 12 shows the combined dissolution profiles of seven different excipient formulations, extended scale.
FIG. 13 shows the combined dissolution profiles of five base excipients in HPMC modified formulations.
FIG. 14 shows the dissolution profiles of five capsule sample of cetyl alcohol formulation with 10% HPMC.
FIG. 15 shows the dissolution profiles of modified Sterotex NF formulation.
FIG. 16 shows the average dissolution profiles of modified Sterotex NF formulation.
FIG. 17 shows the dissolution profiles of further modified Sterotex NF formulation.
FIG. 18 shows the average dissolution profiles of further modified Sterotex NF formulation.
FIG. 19 shows the dissolution profiles of Hydrokote formulations containing Methocel K 100M or Methocel K 15M.
FIG. 20 shows the averaged dissolution profiles of Hydrokote formulations containing Methocel K 100M or Methocel K 15M.
FIG. 21 shows the dissolution profiles of 250 mg Tramadol HCl in a 550 mg Sterotex NF based formulation.
FIG. 22 shows the averaged dissolution profiles of 250 mg Tramadol HCl in a 550 mg Sterotex NF based formulation.
FIG. 23 shows the dissolution profiles of 75 mg Tramadol HCl in beeswax with 20% HPMC based formulation.
FIG. 24 shows the averaged dissolution profiles of 75 mg Tramadol HCl in beeswax with 20% HPMC based formulation.
FIG. 25 shows the dissolution profiles of 75 mg Tramadol HCI in beeswax with 23% HPMC based formulation.
FIG. 26 shows the averaged dissolution profiles of 75 mg Tramadol HCl in beeswax with 23% HPMC based formulation.
FIG. 27 shows the comparison of averaged dissolution profiles of tramadol HCl in beeswax with 20% and 23% HPMC based formulation.
FIG. 28 shows the combined dissolution profiles of first three tramadol HCl formulations.
FIG. 29 shows the tramadol HCl in beeswax dissolution profile normalised to HPLC assay data.
FIG. 30 shows the tramadol HCl in Gelucire 50/02 dissolution profile normalised to HPLC assay data.
FIG. 31 shows the tramadol HCl in Gelucire 50/02 repeat dissolution profile normalised to HPLC assay data.
FIG. 32 shows the tramadol HCl in cetyl alcohol dissolution profile normalised to HPLC assay data.
FIG. 33 shows the tramadol HCl in cetyl alcohol repeat dissolution profile normalised to HPLC assay data.
FIG. 34 shows the combined dissolution profiles of second three Tramadol HCl formulations.
FIG. 35 shows the tramadol HCl in Sterotex NF dissolution profile normalised to HPLC assay data.
FIG. 36 shows the tramadol HCl in Sterotex NF dissolution profile normalised to HPLC assay data with extended time scale.
FIG. 37 shows the tramadol HCl in Cithrol GMS dissolution profile normalised to HPLC assay data.
FIG. 38 shows the tramadol HCl in Cithrol GMS dissolution profile normalised to HPLC assay data with extended time scale.
FIG. 39 shows the tramadol HCl in Hydrokote 112 dissolution profile normalised to HPLC assay data.

FIG. 40 shows the tramadol HCl in Hydrokote 112 dissolution profile normalised to HPLC assay data with extended time scale.

FIG. 41 shows the tramadol HCl in beeswax dissolution profile normalised to HPLC assay data.

FIG. 42 shows the abuse resistance testing, Test 1. Ethanol extraction on whole dosage units.

FIG. 43 shows the abuse resistance testing. Test 1a, Ethanol extraction on cut or crushed dosage units.

FIG. 44 shows the dissolution profile of tramadol HCl in Sterotex NF formulations.

FIG. 45 shows the dissolution profile of tramadol HCl in Sterotex NF formulations with and without fractionated coconut oil.

FIG. 46 shows the abuse resistance testing, Test 1. Ethanol extraction on whole dosage units.

FIG. 47 shows the abuse resistance testing. Test 1a. Ethanol extraction on crushed or cut dosage units.

FIG. 48 shows the dissolution profile of stored Sterotex NF formulation.

FIG. 49 shows the comparison of dissolution profiles of fresh and stored Sterotex NF formulation.

FIG. 50 shows the dissolution profile of stored Sterotex NF formulation with 25% fractionated coconut oil.

FIG. 51 shows the comparison of dissolution profiles of fresh and stored Sterotex NF formulation with 25% fractionated coconut oil.

FIG. 52 shows the dissolution profile of stored Cithrol GMS formulation.

FIG. 53 shows the comparison of dissolution profiles of fresh and stored Cithrol GMS formulation.

FIG. 54 shows the dissolution profile of stored Hydrokote 112 formulation.

FIG. 55 shows the comparison of dissolution profiles of fresh and stored Hydrokote 112 formulation.

FIG. 56 shows the dissolution profile of stored beeswax formulation.

FIG. 57 shows the comparison of dissolution profiles of fresh and stored beeswax formulation.

FIG. 58 shows the effects of crushing, grinding, water or vinegar solubilization and filtration.

FIG. 59 shows the dissolution profiles of tramadol HCl in Sterotex,

FIG. 60 shows the dissolution profiles of tramadol HCl in Hydrocote 112.

FIG. 61 shows the dissolution profiles of tramadol HCl in Cithrol.

FIG. 62 shows the dissolution profiles of tramadol HCl in Beeswax.

FIG. 63 shows the dissolution profiles of levorphanol tartrate in Sterotex.

FIG. 64 shows the dissolution profiles of levorphanol tartrate in Hydrocote 122.

FIG. 65 shows the dissolution profiles of levorphanol tartrate in Cithrol.

FIG. 66 shows the dissolution profiles of levorphanol tartrate in beeswax.

DETAILED DESCRIPTION OF THE INVENTION

The present invention relates to pharmaceutical compositions and the use thereof for preventing or minimizing the risk of the serotonin syndrome through the use of serotonin surge protectors (SSP).

SSP are pharmaceutical compositions which include one or more polymeric and/or nonpolymeric gel forming agents, viscosity increasing and/or high viscosity liquids, and optionally one or more excipients and inert carriers, that resist, deter or prevent crushing, shearing, grinding, chewing, dissolving, melting, needle aspiration, inhalation, insufflation or solvent extraction of the proserotonergic agent responsible for causing the serotonin syndrome through serotonin excess. SSP prevent or reduce the incidence and intensity of the serotonin syndrome when combined in the same formulation with one or more proserotonergic agents.

The present invention is related to pharmaceutical compositions comprising a proserotonergic agent alone or in combination with other therapeutic agents, one or more SSP, and optionally one or more excipients and inert carriers.

Compositions and methods of the present invention can form a viscous gel upon contact with a solvent such that the gel and proserotonergic agent cannot be easily drawn into a syringe, crushed to facilitate or enhance nasal delivery (snorting or nasal insufflation), inhalation or rapid oral delivery of a larger than planned delivery of the proserotonergic agent, such as to cause the serotonin syndrome.

In one embodiment of the invention, the SSP resists the release of all or substantially all of the proserotonergic contents of the unit dose. In another embodiment of the invention, the SSP resists the release of a portion of the proserotonergic contents of the unit dose. In yet another embodiment of the invention, the proserotonergic agent formulated with the SSP by a practitioner of the art resists the release the proserotonergic agent to a greater extent than when formulated without the SSP.

In some embodiments, the present invention is directed to oral dosage forms with an intended therapeutic effect of up to about 1 hour comprising (i) a prosertonergic agent and (ii) a serotonin surge protector.

In some embodiments, the present invention is directed to oral dosage forms with an intended therapeutic effect of up to about 2 hours comprising (i) a prosertonergic agent and (ii) a serotonin surge protector.

In some embodiments, the present invention is directed to oral dosage forms with an intended therapeutic effect of up to about 4 hours comprising (i) a prosertonergic agent and (ii) a serotonin surge protector.

In some embodiments, the present invention is directed to oral dosage forms with an intended therapeutic effect of up to about 6 hours comprising (i) a prosertonergic agent and (ii) a serotonin surge protector.

In some embodiments, the present invention is directed to oral dosage forms with an intended therapeutic effect of up to about 8 hours comprising (i) a prosertonergic agent and (ii) a serotonin surge protector.

In some embodiments, the present invention is directed to oral dosage forms with an intended therapeutic effect of up to about 12 hours comprising (i) a prosertonergic agent and (ii) a serotonin surge protector.

In some embodiments, the present invention is directed to oral dosage forms with an intended therapeutic effect of up to about 24 hours comprising (i) a prosertonergic agent and (ii) a serotonin surge protector.

In some preferred embodiments, the oral dosage form of the present invention is directed to an oral dosage form comprising (i) a proserotonergic agent and (ii) a serotonin surge protector, such that the ratio of the mean $C_{max}$ of the proserotonergic agent following single dose oral administration of the dosage form after intentional or inadvertent tampering to the mean $C_{max}$ of the proserotonergic agent after single dose oral administration of an intact dosage form is less than 10:1. In other embodiments of the invention, the mean $C_{max}$ ratio using the aforementioned test method is at less than 7:1, 5:1, 3:1, 2:1 or 1.5:1.

In some preferred embodiments, the oral dosage form of the present invention is directed to an oral dosage form comprising (i) a proserotonergic agent and (ii) a serotonin surge protector, such that the ratio of the mean $T_{max}$ of the proserotonergic agent following single dose oral administration of the dosage form after intentional or inadvertent tampering to the mean $T_{max}$ of the proserotonergic agent after single dose oral administration of an intact dosage form is less than 10:1. In other embodiments of the invention, the mean $T_{max}$ ratio using the aforementioned test method is at less than 7:1, 5:1, 3:1, 2:1 or 1.5:1.

In some preferred embodiments, the oral dosage form of the present invention is directed to an oral dosage form comprising (i) a proserotonergic agent and (ii) a serotonin surge protector, such that the ratio of the mean $AUC_{0-2}$ of the proserotonergic agent following single dose oral administration of the dosage form after intentional or inadvertent tampering to the mean $AUC_{0-2}$ of the proserotonergic agent after single dose oral administration of an intact dosage form is less than 10:1. In other embodiments of the invention, the mean $AUC_{0-2}$ ratio using the aforementioned test method is at less than 7:1, 5:1, 3:1, 2:1 or 1.5:1.

In some preferred embodiments, the oral dosage form of the present invention is directed to an oral dosage form comprising (i) a proserotonergic agent and (ii) a serotonin surge protector, wherein the amount of said proserotonergic agent released from the intact dosage form based on the dissolution at 1 hour of the dosage form in 900 mL of Simulated Gastric Fluid using a USP Type II (rotating paddle method) apparatus at 50 rpm at 37 degrees ° C. is 33% or less from the intact dosage form and 50% or less from the tampered dosage form. In other embodiments of the invention, the release rate using the aforementioned test method is 25% or less from the intact dosage form and 50% or less from the tampered dosage form, or 25% or less from the intact dosage form and 33% or less from the tampered dosage form or 20% or less from the intact dosage form and 33% or less from the tampered dosage form, or 15% or less from the intact dosage form and 25% or less from the tampered dosage form.

In one embodiment of the SSP, the therapeutic pharmaceutical composition can be formed into a unit dose including a proserotonergic agent and a gel forming polymer. In one embodiment, the polymer includes one or more of polyethylene oxide (e.g., having average molecular weight ranging form about 200,000 to about 5,000,000), polyvinyl alcohol (e.g., having a molecular weight of about 10,000 to 300,000) and hydroxypropyl methyl cellulose (e.g., having a molecular weight of about 10,000 to 1,700,000), and a carbomer (e.g., having a molecular weight ranging of about 600,000 to 4,000,000,000).

As described above, the present invention can include one or more gel forming agents. The total amount of gel forming agent is typically about 2 to about 80 percent, preferably 3 to 60 percent and more preferably 5 to 50 percent on a dry weight basis of the composition.

Suitable gel forming agents include compounds that, upon contact with a solvent (e.g., water), absorb the solvent and swell, thereby forming a viscous or semiviscous substance that significantly reduces and/or minimizes the amount of free solvent which can contain an amount of solubized drug. The gel can also reduce the overall amount of drug extractable with the solvent by entrapping the drug in a gel matrix. In one embodiment, typical gel forming agents include pharmaceutically acceptable polymers, typically hydrophilic polymers, such as hydrogels.

In some embodiments, the polymers exhibit a high degree of viscosity upon contact with a suitable solvent. The high viscosity can enhance the formation of highly viscous gels when attempts are made by to crush and dissolve the contents of a dosage form in an aqueous vehicle and inject it intravenously.

More specifically, in certain embodiments the polymeric material in the present invention provides viscosity to the dosage form when it is tampered. In such embodiments, when the composition is crushed and attempts are made to dissolve the dosage form in a solvent (e.g., water or saline), a viscous or semi-viscous gel is formed. The increase in the viscosity of the solution discourages injection of the gel by preventing the transfer of sufficient amounts of the solution to a syringe.

Suitable polymers include one or more pharmaceutically acceptable polymers selected from any pharmaceutical polymer that will undergo an increase in viscosity upon contact with a solvent. Preferred polymers include polyethylene oxide, polyvinyl alcohol, hydroxypropyl methyl cellulose and carbomers.

In some embodiments, the polymer includes polyethylene oxide. The polyethylene oxide can have an average molecular weight ranging from about 200,000 to about 5,000,000, more preferably from about 600,000 to about 5,000,000. In one embodiment, the polyethylene oxide includes a high molecular weight polyethylene oxide.

In one embodiment, the average particle size of the polyethylene oxide ranges from about 700 to about 2,000 microns. In another embodiment, the density of the polyethylene oxide can range from about 1.0 to about 1.35 g/mL. In another embodiment, the viscosity can range from about 8.00 to about 18,000 cps.

The polyethylene oxide used in a directly compressible formulation of the present invention is preferably a homopolymer having repeating oxyethylene groups, i.e., —(—O—CH$_2$.CH$_2$—)$_n$—, where n can range from about 2,000 to about 180,000. Preferably, the polyethylene oxide is a commercially available and pharmaceutically acceptable homopolymer having moisture content of no greater than about 1% by weight. Examples of suitable, commercially available polyethylene oxide polymers include Polyox®, WSRN-1105 and/or WSR-coagulant.

In some embodiments, the polyethylene oxide powdered polymers can contribute to a consistent particle size in a directly compressible formulation and eliminate the problems of lack of content uniformity and possible segregation.

In one embodiment, the gel forming agent includes polyvinyl alcohol. The polyvinyl alcohol can have a molecular weight ranging from about 10,000 to about 300,000. The specific gravity of the polyvinyl alcohol can range from about 1.10 to about 1.30 and the viscosity from about 3 to about 70 cps. The polyvinyl alcohol used in the formulation is preferably a water-soluble synthetic polymer represented by —(—C$_2$H$_4$O—)$_n$—, where n can range from about 400 to about 6,000. Examples of suitable, commercially available polyvinyl alcohol polymers include PVA.

In one embodiment, the gel forming agent includes hydroxypropyl methyl cellulose (Hypromellose). The hydroxypropyl methyl cellulose can have a molecular weight ranging from about 10,000 to about 1,700,000, and typically from about 4000 to about 12,000, i.e., a low molecular weight hydroxypropyl methyl cellulose polymer. The specific gravity of the hydroxypropyl methyl cellulose can range from about 1.10 to about 1.35, with an average specific gravity of about 1.25 and a viscosity of about 3500 to 6000. The hydroxypropyl methylcellulose used in the formulation can be a water-soluble synthetic polymer. Examples of suitable, commercially available hydroxypropyl methylcellulose polymers include Methocel K100LV and Methocel K4M.

In one embodiment, the present invention includes carbomers. The carbomers can have a molecular weight ranging from 600,000 to about 4,000,000,000. The viscosity of the polymer can range from about 3000 to about 40,000 cps. Examples of suitable, commercially available carbomers include carbopol 934P NF, carbopol 974P NF and carbopol 971P NF.

Following the teachings set forth herein, other suitable gel forming agents can include one or more of the following polymers: ethylcellulose, cellulose acetate, cellulose acetate propionate, cellulose acetate butyrate, cellulose acetate phthalate and cellulose triacetate, cellulose ether, cellulose ester, cellulose ester ether, and cellulose, acrylic resins comprising copolymers synthesized from acrylic and methacrylic acid esters, the acrylic polymer may be selected from the group consisting of acrylic acid and methacrylic acid copolymers, methyl methacrylate copolymers, ethoxyetlryl methacrylates, cyanoetlryl methacrylate, poly(acrylic acid), poly(methaerylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers.

Any of the above described polymers can be combined together or combined with other suitable polymers, and such combinations are within the scope of the present invention.

In some embodiments, SSP consists of hydrophobic polymers, hydrophilic polymers, gums, protein derived materials, waxes, shellac, oils and mixtures thereof.

In one embodiment, the SSP can prevent less than or equal to about 95%, 94%, 70%, 60%, 54%, 50%, 45%, 40%, 36%, 32%, 30%, 27%, 20%, 10%, 9%, 6%, 5% or 2% of the total amount of drug in a dosage form from being recovered from a solvent in contact with a dosage form of the present invention.

The above described gel forming agents can be further optimized as necessary or desired in terms of viscosity, molecular weight, etc.

The present invention can also optionally include other ingredients to enhance dosage form manufacture from a pharmaceutical composition of the present invention and/or alter the release profile of a dosage forming including a pharmaceutical composition of the present invention.

Some embodiments of the present invention include one or more pharmaceutically acceptable fillers/diluents. In one embodiment, Avicel PH (Microcrystalline cellulose) is a filler used in the formulation. The Avicel PH can have an average particle size ranging from 20 to about 200 μm, preferably about 100 μm. The density ranges from 1.5 to 1.7 g/cm$^3$. The Avicel PH should have molecular weight of about 36,000. Avicel PH effectiveness is optimal when it is present in an amount of from about 5 to 75 percent, by weight on a solid basis, of the formulation. Typical fillers can be present in amounts from 5 to 75 percent by weight on a dry weight basis. Other ingredients can include sugars and/or polyols.

Other ingredients can also include dibasic calcium phosphate having a particle size of about 60 to about 450 microns and a density of about 0.5 to about 1.5 g/ml, as well as calcium sulfate having a particle size of about 1 to about 200 microns and a density of about 0.6 to about 1.3 g/ml and mixtures thereof. Further, lactose having a particle size of about 20 to about 400 microns and a density of about 0.3 to about 0.9 g/ml can also be included.

In some embodiments of the invention, the fillers which can be present at about 5 to 85 percent by weight on a dry weight basis, also function as binders in that they not only impart cohesive properties to the material within the formulation, but can also increase the bulk weight of a directly compressible formulation (as described below) to achieve an acceptable formulation weight for direct compression. In some embodiments, additional fillers need not provide the same level of cohesive properties as the binders selected, but can be capable of contributing to formulation homogeneity and resist segregation from the formulation once blended. Further, preferred fillers do not have a detrimental effect on the flowability of the composition or dissolution profile of the formed tablets.

In one embodiment, the present invention can include one or more pharmaceutically acceptable disintegrants. Such disintegrants are known to those skilled in the art. In the present invention, disintegrants can include, but are not limited to, sodium starch glycolate having a particle size of about 100 microns and a density of about 0.75 g/mL, starch (e.g., Starch 21) having a particle size of about 2 to about 32 microns and a density of about 0.46 g/ml, Crospovidone® having a particle size of about 400 microns and a density of about 1.2 g/ml, and croscarmellose sodium (Ac-Di-Sol) having a particle size of about 37 to about 73.7 microns and a density of about 0.53 g/ml. The disintegrant selected should contribute to the compressibility, flowability and homogeneity of the formulation. Further the disintegrant can minimize segregation and provide an immediate release profile to the formulation. In some embodiments, the disintegrant(s) are present in an amount from about 2 to about 35 percent by weight on a solid basis of the directly compressible formulation.

In one embodiment, the present invention can include one or more pharmaceutically acceptable glidants, including but not limited to colloidal silicon dioxide. In one embodiment, colloidal silicon dioxide (Cab-O-Sil®) having a density of about 0.023 to about 0.040 g/ml can be used to improve the flow characteristics of the formulation. Such glidants can be provided in an amount of from about 0.1 to about 3 percent by weight of the formulation on a solid basis. It will be understood, based on this invention, however, that while colloidal silicon dioxide is one particular glidant, other glidants having similar properties which are known or to be developed could be used provided they are compatible with other excipients and the active ingredient in the formulation and which do not significantly affect the flowability, homogeneity and compressibility of the formulation.

In one embodiment, the present invention can include one or more pharmaceutically acceptable lubricants, including but not limited to magnesium stearate. In one embodiment, the magnesium stearate has a particle size of about 450 to about 550 microns and a density of about 1.0 to about 1.8 g/ml. In one embodiment, magnesium stearate can contribute to reducing friction between a die wall and a pharmaceutical composition of the present invention during compression and can ease the ejection of the tablets, thereby facilitating processing. In some embodiments, the lubricant resists adhesion to punches and dies and/or aid in the flow of the powder in a hopper and/or into a die. In an embodiment of the present invention, magnesium stearate having a particle size of from about 5 to about 50 microns and a density of from about 0.1 to about 1.1 g/ml is used in a pharmaceutical composition. In certain embodiments, a lubricant should make up from about 0.1 to about 2 percent by weight of the formulation on a solids basis. Suitable lubricants are stable and do not polymerize within the formulation once combined. Other lubricants known in the art or to be developed which exhibit acceptable or comparable properties include stearic acid, hydrogenated oils, sodium stearyl fumarate, polyethylene glycols, and Lubritab®.

In certain embodiments, the most important criteria for selection of the excipients are that the excipients should achieve good content uniformity and release the active ingredient as desired. The excipients, by having excellent binding properties, and homogeneity, as well as good compressibility, cohesiveness and flowability in blended form, minimize segregation of powders in the hopper during direct compression.

Compositions and methods of the SSP can also be selected from a group of viscosity-increasing agents selected from the group consisting of microcrystalline cellulose with 11 wt. % carboxymethylcellulose sodium (e.g., Avicel® RC 591), carboxymethylcellulose sodium (e.g., Blanose®, CMC-Na C3001P®, Frimulsion BLC-5®, Tylose C300 P®), polyacrylic acid (e.g., Carbopol® 980 NF, Carbopol® 981), locust bean flour (e.g., Cesagum® LA-200, Cesagum®(LID/150, Cesagum® LN-1), pectins, preferably from citrus fruits or apples (e.g., Cesapectin® HM Medium Rapid Set), waxy maize starch (e.g., C*Gel 04201®), sodium alginate (e.g., Frimulsion ALG (E401)®), guar flour (e.g., Frimulsion BM®, Polygum 2611-75®), iota-carrageenan (e.g., Frimulsion D021®), karaya gum, gellan gum (e.g., Kelcogel F®, Kelcogel LT1100®), galactomannan (e.g., Meyprogat 150), tara stone flour (e.g., Polygum 4311®), propylene glycol alginate (e.g., ProtanalEster SD-LB®), sodium hyaluronate, tragacanth, tara gum (e.g., Vidogum SP 200®), fermented polysaccharide welan gum (K1A96), xanthans such as xanthan gum (e.g., Xantural 180®). The names stated in brackets are the trade names by which the materials are known commercially. In general, a quantity of 0.1 to 90% w/w, preferably of 1 to 70% w/w, particularly preferably of 5 to 50% w/w of the viscosity-increasing agent, relative to the total formulation, is sufficient in order to meet the requirements of SSP.

Surprisingly, in one embodiment, due to the inventive selection of the SSP, it is possible to combine the proserotonergic agents and the viscosity-increasing agents in the dosage form according to the invention without spatial separation from one another.

In another embodiment, the viscosity-increasing agents and the proserotonergic agents are contained in the dosage form in a mutually spatially separated arrangement.

In yet another embodiment of the present invention, the orally administrable dosage form according to the invention assumes multiparticulate form containing in each case the complete mixture of active ingredient and viscosity-increasing agent, preferably in the form of microtablets, microcapsules, micropellets, granules, spheroids, beads or pellets, preferably packaged in capsules or press-molded into tablets The multiparticulate forms preferably have a size in the range from 0.1 to 3 mm, particularly preferably in the range from 0.5 to 2 mm.

Compositions and methods of the present SSP invention can also be selected from a group of viscosity-increasing, gel-forming and solvent extraction resistant agents selected from the group consisting of hydrogenated Type I or Type II vegetable oils, polyoxyethylene stearates and distearates, glycerol monostearate (e.g., Cithrol° GMS) and poorly water soluble, high melting point (mp=40 to 100° C.) waxes.

Hydrogenated vegetable oils of the present invention may include hydrogenated cottonseed oil (e.g., Akofine®; Lubritab®; Sterotex® NF), hydrogenated palm oil (Dynasan® P60; Softisan® 154), hydrogenated soybean oil (Hydrocote®; Lipovol HS-K®; Sterotex® HM) and hydrogenated palm kernel oil (e.g., Hydrokote® 112).

Polyoxyethylene stearates and distearates of the present invention include Polyoxyl 2, 4, 6, 8, 12, 20, 30, 40, 50, 100 and 150 stearates (e.g., Hodag® DGS; PEG-2 stearate; Acconon® 200-MS; Hodag® 20-S; PEG-4 stearate; Cerasynt® 616; Kessco® PEG 300 Monostearate; Acconon® 400-MS; Cerasynt® 660; Cithrol® 4MS; Hodag® 60-S; Kessco® PEG 600 Monostearate; Cerasynt® 840; Hodag 100-S; Myrj® 51; PEG-30 stearate; polyoxyethylene (30) stearate; Crodet® S40; E431; Emerest® 2672; Atlas G-2153; Crodet® S50) and polyoxyl 4, 8, 12, 32 and 150 distearates (e.g., Lipo-PEG® 100-S; Myrj® 59; Hodag® 600-S; Ritox® 59; Hodag® 22-S; PEG-4 distearate; Hodag® 42-S; Kessco® PEG 400 DS; Hodag® 62-S; Kessco® PEG 600 Distearate; Hodag® 154-S; Kessco® PEG 1540 Distearate; Lipo-PEG® 6000-DS; Protamate® 6000-DS).

In one preferred embodiment of the present invention, the proserotonergic agent is combined with beeswax, hydroxypropyl methyl cellulose (e.g, HPMC K15M), silicon dioxide (alone or in combination with $Al_2O_3$; e.g, Aerosil®, Aerosil® 200, Aerosil® COK84) as serotonin surge protectors.

In one preferred embodiment of the present invention, the proserotonergic agent is combined with hydrogenated cottonseed oil (e.g., Sterotex® NF), hydroxypropyl methyl cellulose (e.g, HPMC K15M), fractionated coconut oil and silicon dioxide (alone or in combination with $Al_2O_3$; e.g, Aerosil®, Aerosil® 200, Aerosil® COK84) as serotonin surge protectors.

In another preferred embodiment of the present invention, the proserotonergic agent is combined with glycerol monostearate (e.g., Cithrol® GMS), hydroxypropyl methyl cellulose (e.g, HPMC K100M) and silicon dioxide (alone or in combination with $Al_2O_3$; e.g, Aerosil®, Aerosil® 200, Aerosil® COK84) as serotonin surge protectors.

In yet another preferred embodiment of the present invention, the proserotonergic agent is combined with hydrogenated palm kernel oil (e.g., Hydrokote® 112), hydroxypropyl methyl cellulose (e.g, HPMC K15M) and silicon dioxide (alone or in combination with $Al_2O_3$; e.g, Aerosile, Aerosil® 200, Aerosil® COK84) as serotonin surge protectors.

In one embodiment of the present invention, release rate modifiers, including hydroxypropyl methyl cellulose (e.g, HPMC K15M) may incorporated. Release rate modifiers can also have additional useful properties that optimize the formulation. For example HPMC is soluble in cool/cold water and becomes insoluble over approximately 40° C. This resists the generation of injectable solutions, interferes with 'snorting' or 'dose dumping' (due to the viscous solutions produced) and resists extraction at elevated temperature. A range of HPMCs of differing molecular weights and viscosities may be used with the present invention.

A variety of agents may incorporated into the invention as thixotropes (e.g., fumed silicon dioxides, Aerosil, Aerosil COK84, Aerosil 200, etc.). Thixotropes enhance the pharmaceutical formulations of the invention by increasing the viscosity of solutions during attempted extraction, complementing the action of HPMCs. They may also provide a tamper resistance by helping to retain the structure of dosage units that have been heated to temperatures greater than the melting point of the base excipient (Aerosils are unaffected by heat).

The dosage form according to the invention may preferably also comprise one or more proserotonergic agents, blended with the viscosity-increasing, gel-forming, high melting point waxes and solvent extraction resistant agents, at least in part in delayed-release form, wherein delayed release may be achieved with the assistance of conventional materials and processes known to the person skilled in the art, for example by embedding the active ingredient in a delayed-release matrix or by applying one or more delayed-release coatings.

Delayed release of the active ingredient may preferably also be achieved by purposeful selection of one or more of the above-stated viscosity-increasing agents in suitable quantities as the matrix material. The person skilled in the art may determine the agents and the quantity thereof suitable for the particular desired release by simple preliminary testing, wherein it must, of course, be ensured that, as described above, gel formation occurs when the attempt is made to abuse the resultant dosage form.

If the dosage form according to the invention is intended for oral administration, it may also comprise a coating which is resistant to gastric juices and dissolves as a function of the pH value of the release environment.

By means of this coating, it is possible to ensure that, when correctly administered, the dosage form according to the invention passes through the stomach undissolved and the active ingredient is only released in the intestines.

In another embodiment of the present invention, the formulation may comprise one or more proserotonergic agents blended with one or more high viscosity liquids. High viscosity liquids refers to non-polymeric, non-water soluble liquids with a viscosity of at least 5,000 cP at 37° C. that do not crystallize neat under ambient or physiological conditions. High viscosity liquids may be carbohydrate-based, and may include one or more cyclic carbohydrates chemically combined with one or more carboxylic acids, such as sucrose acetate isobutyrate. High viscosity liquids also include non-polymeric esters or mixed esters of one or more carboxylic acids, having a viscosity of at least 5,000 cP at 37° C., that do not crystallize neat under ambient or physiological conditions, wherein when the ester contains an alcohol moiety (e.g., glycerol). The ester may, for example comprise from about 2 to about 20 hydroxy acid moieties.

The present invention may employ any high viscosity liquid, viscosity-enhancing compounds, gel-forming and solvent extraction resistant agents, not limited by any specifically described compounds.

In one embodiment of the invention, the formulation is ingested orally as a tablet or capsule, preferably as a capsule. In another embodiment of the invention, the formulation is administered bucally. In yet another embodiment of the invention, the formulation is administered sublingually.

In one embodiment of the invention, the dosage form includes a capsule within a capsule, each capsule containing a different drug or the same drug intended for a different purpose. In some embodiments, the outer capsule may be an enteric coated capsule or a capsule containing an immediate release formulation to provide rapid plasma concentrations or a rapid onset of effect or a loading dose and the inner capsule contains an extended release formulation. Up to 3 capsules within a capsule are contemplated as part of the invention in some embodiments. In one embodiment of the invention, the dosage form involves a tablet within a capsule, wherein the proserotonergic drug is either in the tablet and/or in one of the capsules.

In some preferred embodiments, pharmaceutical compositions and methods of the present invention provide protection against the serotonin syndrome; wherein the dosage form comprises one or more proserotonergic agents and one or more serotonin surge protectors.

In some preferred embodiments, pharmaceutical compositions and methods of the present invention provide both protection against the serotonin syndrome and abuse deterrence; wherein the dosage form comprises one or more abusable proserotonergic agents and one or more serotonin surge protectors.

In some preferred embodiments, pharmaceutical compositions and methods of the present invention provide both protection against the serotonin syndrome and abuse deterrence; wherein the dosage form comprises one or more abusable proserotonergic agents and one or more serotonin surge protectors; said protection against the serotonin syndrome and abuse deterrence achieved using substantially the same ingredients.

In some preferred embodiments, pharmaceutical compositions and methods of the present invention provide both protection against the serotonin syndrome and extended release; wherein the dosage form comprises one or more proserotonergic agents and one or more serotonin surge protectors.

In some preferred embodiments, pharmaceutical compositions and methods of the present invention provide both protection against the serotonin syndrome and extended release; wherein the dosage form comprises one or more proserotonergic agents and one or more serotonin surge protectors; said protection against the serotonin syndrome and said extended release achieved using substantially the same ingredients.

In some preferred embodiments, pharmaceutical compositions and methods of the present invention provide protection against the serotonin syndrome and abuse deterrence and further provides extended release; wherein the dosage form comprises one or more abusable proserotonergic agents and one or more serotonin surge protectors.

In some preferred embodiments, pharmaceutical compositions and methods of the present invention provide protection against the serotonin syndrome and abuse deterrence and further provides extended release; wherein the dosage form comprises one or more abusable proserotonergic agents and one or more serotonin surge protectors; said protection against the serotonin syndrome and said extended release achieved using substantially the same ingredients.

In some preferred embodiments, the dosage form of the present invention is directed to an oral dosage form comprising (i) a proserotonergic agent and (ii) a serotonin surge protector; said dosage form suitable for up to every 24 hour (once-a-day) administration to a human patient; said dosage form providing at least 60% of the steady state concentration of proserotonergic agent after administration of one dose at its intended dosing frequency. In other preferred embodiments, the dosage form provides at least about 62.5%, or at least about 65%, or at least about 67.5%, or at least about 70%, or at least about 72.5%, or at least about 75%, or at least about 77.5%, or at least about 80%, or at least about 82.5%, or at least about 85%, or at least about 87.5%, or at least about 90%, or at least about 92.5%, or at least about 95% or at least 98% of the steady state therapeutic concentration of proserotonergic agent after administration of one dose at its intended dosing frequency.

In some preferred embodiments, the oral dosage form of the present invention is directed to an oral dosage form comprising (i) a proserotonergic agent and (ii) a serotonin surge protector; said dosage form suitable for three times a day administration (TID) or about every eight hours administration (Q8H).

In some preferred embodiments, the TID or Q8H oral pharmaceutical composition of provides a therapeutic effect for about 8 hours. In some preferred embodiments, the TID or Q8H oral pharmaceutical composition of provides a $C_{max}$ of proserotonergic agents at about 1 to about 6 hours. In some preferred embodiments, the TID or Q8H oral pharmaceutical composition provide a $C_{min}$ of proserotonergic agents at about 6 to 10 hours. In some preferred embodiments, the TID or Q8H oral pharmaceutical composition provides a mean proserotonergic agents $C_8/C_{max}$ ratio of 0.25 to about 0.95. In some preferred embodiments, the TID or Q8H oral pharmaceutical composition provides a percent fluctuation of less than 400%. In some preferred embodiments, the TID or Q8H oral pharmaceutical composition provides a $W_{50}$ of 1.5 to about 6.5 hours. In some preferred embodiments, the TID or Q8H oral pharmaceutical composition provides an HVD of 2 to about 7 hours. In some preferred embodiments, the TID or Q8H oral pharmaceutical composition of provides an HVD of about 2 to about 7 hours. In some preferred embodiments, the TID or Q8H oral pharmaceutical composition of provides an AI of not more that 4.0.

In some preferred embodiments, the oral dosage form of the present invention is directed to an oral dosage form comprising (i) a proserotonergic agent and (ii) a serotonin surge protector; said dosage from providing a $C_{max}$ of proserotonergic agent occurring from a mean of about 0.25 to about 30 hours. In other preferred embodiments, the dosage form provides a $C_{max}$ of proserotonergic agent occurring from a mean of about 0.5 to about 30 hours, or from a mean of about 1 to about 30 hours, or about 1 to about 26 hours, or about 1 to about 24 hours, or about 1 to about 20 hours, or about 1 to about 18 hours, or about 1 to about 16 hours, or about 1 to about 14 hours, or about 1 to about 12 hours, or about 1 to about 10 hours, or about 1 to about 8 hours, or about 1 to about 6 hours, or about 1 to about 4 hours, or about 1 to about 3 hours, or about 2 to about 30 hours, or about 4 to about 30 hours, or about 4 to about 24 hours, or about 6 to about 24 hours, or about 8 to about 24 hours, or about 10 to about 20 hours, or about 12 to about 24 hours, or about 18 to about 24 hours, or about 2 to about 12 hours, or about 3 to about 12 hours, or about 3 to about 8 hours, or about 4 to about 10 hours, or about 4 to about 12 hours, or about 4 to about 9 hours, or about 5 to about 8 hours.

In some preferred embodiments, the oral dosage form of the present invention is directed to an oral dosage form comprising (i) a proserotonergic agent and (ii) a serotonin surge protector; said dosage from providing a $C_{min}$ of proserotonergic agent occurring from a mean of about 0.5 to about 28 hours, or about 1 to about 28 hours, or about 1 to 24 hours, or about 1 to about 20 hours, or about 1 to about 18 hours, or about 1 to about 16 hours, or about 1 to about 12 hours, or about 1 to 10 hours, or about 1 to about 8 hours, or about 1 to about 6 hours, or about 1 to about 4 hours, about 2 to about 24 hours, or about 3 to 24 hours, or about 4 to about 24 hours, or about 6 to about 24 hours, or about 8 to about 24 hours, about 2 to about 12 hours, or about 3 to 10 hours, or about 3 to about 8 hours, or about 4 to about 8 hours, or about 6 to about 10 hours.

In some preferred embodiments, the oral dosage form of the present invention is directed to an oral dosage form comprising (i) a proserotonergic agent and (ii) a serotonin surge protector; said dosage form providing a systemic exposure as assessed by the mean proserotonergic agent area under the plasma concentration time curve ($AUC_{0-t}$) after first administration which is at least about 40% of the area under the plasma drug concentration-time curve from time zero to infinity ($AUC_{0-\infty}$). In other preferred embodiments, the dosage from provides an $AUC_{0-t}$ which is at least about 45%, or which is at least about 50%, or which is at least about 55%, or at least about 60%, or which is at least about 65%, or at least about 70%, or which is at least about 75%, or at least about 80%, or at least about 85%, or at least about 88%, or at least about 90%, or at least about 92%, or at least about 94%, or at least about 96% or at least about 98% of the $AUC_{0-\infty}$.

In some preferred embodiments, the oral dosage form of the present invention is directed to an oral dosage form comprising (i) a proserotonergic agent and (ii) a serotonin surge protector; said dosage form providing at least 80% of the steady state therapeutic concentration of proserotonergic agent after administration of ≦three doses at their intended dosing frequency. In other preferred embodiments, said dosage form provides at least about 60%, or at least about 65%, or at least about 70%, or at least about 75%, or at least about 85%, or at least about 90%, or at least about 92%, or at least about 95%, or at least about 97%, or at least about 99% of the steady state therapeutic concentration of proserotonergic agent after administration of ≦three doses at their intended dosing frequency.

In some preferred embodiments, the oral dosage form of the present invention is directed to an oral dosage form comprising (i) a proserotonergic agent and (ii) a serotonin surge protector; said dosage form providing at least 80% of the steady state therapeutic concentration of proserotonergic agent after administration of ≦two doses at their intended dosing frequency. In other preferred embodiments, said dosage form provides at least about 60%, or at least about 65%, or at least about 70%, or at least about 75%, or at least about 85%, or at least about 90%, or at least about 92%, or at least about 95%, or at least about 97%, or at least about 99% of the steady state therapeutic concentration of proserotonergic agent after administration of ≦two doses at their intended dosing frequency.

In some preferred embodiments, the oral dosage form of the present invention is directed to an oral dosage form comprising (i) a proserotonergic agent and (ii) a serotonin surge protector; said dosage form providing at least 80% of the steady state therapeutic concentration of proserotonergic agent after administration of one dose at their intended dosing frequency. In other preferred embodiments, said dosage form provides at least about 60%, or at least about 65%, or at least about 70%, or at least about 75%, or at least about 85%, or at least about 90%, or at least about 92%, or at least about 95%, or at least about 97%, or at least about 99% of the steady state therapeutic concentration of proserotonergic agent after administration of one dose at their intended dosing frequency.

In some preferred embodiments, the oral dosage form of the present invention is directed to an oral dosage form comprising (i) a proserotonergic agent and (ii) a serotonin surge protector; said dosage form after administration to a human patient providing a $C_{min}/C_{max}$ ratio of proserotonergic agent of 0.1 to about 1.0. In other preferred embodiments, the dosage form provides a $C_{min}/C_{max}$ ratio of proserotonergic agent of about 0.1 to about 0.9, or about 0.1 to about 0.8, or about 0.1 to about 0.7, or about 0.1 to about 0.6, or about 0.1 to about 0.5, or about 0.1 to about 0.4, or about 0.1 to about 0.3, or about 0.2 to about 1.0, or about 0.25 to about 1.0, or about 0.4 to about 1.0, or about 0.5 to about 0.9, or about 0.5 to about 0.85, or about 0.5 to about 0.8, or about 0.5 to about 0.75, or about 0.5 to about 1.0, or about 0.65 to about 1.0, or about 0.75 to about 1.0, or about 0.2 to about 0.9, or about 0.3 to about 0.95, or about 0.3 to about 0.85, or about 0.3 to about 0.8, or about 03 to about 0.75, or about 0.3 to about 0.7, or about 0.3 to about 0.6, or about 0.4 to about 0.9, or about 0.4 to about 0.8, or about 0.4 to about 0.7, or about 0.4 to about 0.6, or about 0.8 to about 1, or about 0.8 to about 1.1.

In some preferred embodiments, the oral dosage form of the present invention is directed to an oral dosage form comprising (i) a proserotonergic agent and (ii) a serotonin surge protector; said dosage form after administration to a human patient providing a percent fluctuation of proserotonergic agent of less than 400%. In other preferred embodiments, the dosage form provides a percent fluctuation of proserotonergic agent of less than 350%, or less than 300%, or less than 250%, or less than 200%, or less than 150%, or less than 100%, or less than 75%, or less than 50%, or less than 25%.

In some preferred embodiments, the oral dosage form of the present invention is directed to an oral dosage form comprising (i) a proserotonergic agent and (ii) a serotonin surge protector; said dosage form after administration to a human patient providing a $W_{50}$ of proserotonergic agent of about 1 to about 6 hours for each 6 hour time period of intended dosing frequency and intended duration of action. In other preferred embodiments, the dosage form provides a $W_{50}$ of proserotonergic agent for each 6 hour time period of intended dosing frequency and intended duration of action of about 1 to about 5 hours, or about 1 to about 4 hours, or about 1 to about 3 hours, or about 1 to about 2 hours, or 2 to about 6 hours, or about 3 to about 6 hours, or about 4 to about 6 hours, or about 2 to about 4 hours.

In some preferred embodiments, the oral dosage form of the present invention is directed to an oral dosage form comprising (i) a proserotonergic agent and (ii) a serotonin surge protector; said dosage form after administration to a human patient providing an HVD of proserotonergic agent of about 1.5 to about 6 hours for each 6 hour time period of intended dosing frequency and intended duration of action. In other preferred embodiments, the dosage form provides a HVD of proserotonergic agent for each 6 hour time period of intended dosing frequency and intended duration of action of about 1.5 to about 5 hours, or about 1.5 to about 4 hours, or about 1.5 to about 3 hours, or about 1.5 to about 2 hours, or 2 to about 6 hours, or about 3 to about 6 hours, or about 4 to about 6 hours, or about 2 to about 4 hours.

In some preferred embodiments, the oral dosage form of the present invention is directed to an oral dosage form comprising (i) a proserotonergic agent and (ii) a serotonin surge protector; said dosage form after administration to a human patient providing an AI of proserotonergic agent of not more than 3.0. In other preferred embodiments, the dosage form provides an AI of proserotonergic agent of not more than about 2.5, or not more than about 2, or not more than about 1.75, or not more than about 1.5, or not more than about 1.25, or not more than about 1, or not more than about 0.75, or not more than about 0.5, or not more than about 0.25.

In some preferred embodiments, the oral dosage form of the present invention is directed to an oral dosage form comprising (i) a proserotonergic agent and (ii) a serotonin surge protector; said dosage form suitable for twice-a-day administration to a human patient; said dosage form providing a $C_{max}$ of proserotonergic agent at 2 to about 10 hours; and said dosage form providing a therapeutic effect for at least about 12 hours. In other preferred embodiments, the dosage form provides a $C_{max}$ of proserotonergic agent at about 2 to about 8 hour or about 2 to about 6 hours, or about 2 to about 5 hours, or about 2 to about 7 hours, or about 2 to about 4.5 hours, or about 2 to about 4 hours, or 2 to about 3.5 hours, or about 2 to about 3 hours, or about 3 to about 10 hours, or about 3.5 to about 10 hours, or about 4 to about 10 hours, or about 4.5 to about 10 hours, or about 5 to about 10 hours, or 5 to about 10 hours, or about 6 to about 10 hours, or about 3 to about 8 hours, or about 3 to about 7 hours, or about 3 to about 6 hours, or about 4 to about 8 hours, or about 4 to about 6.

In some preferred embodiments, the oral dosage form of the present invention is directed to an oral dosage form comprising (i) a proserotonergic agent and (ii) a serotonin surge protector; said dosage form suitable for twice-a-day administration to a human patient; said dosage form providing a $C_{12}/C_{max}$ ratio of proserotonergic agent of 0.1 to about 1; and said dosage form providing a therapeutic effect for at least about 12 hours. In other preferred embodiments, the dosage form provides a $C_{12}/C_{max}$ ratio of proserotonergic agent of about 0.25 to about 0.9, or about 0.25 to about 0.8, or about 0.25 to about 0.75, or about 0.25 to about 0.6, or about 0.25 to about 0.5, or about 0.25 to about 0.4, or about 0.25 to about 0.35, or about 0.3 to about 0.95, or about 0.4 to about 0.95, or about 0.5 to about 0.95, or about 0.65 to about 0.95, or about 0.75 to about 0.95, or about 0.3 to about 0.8, or about 0.4 to about 0.75, or about 0.5 to about 0.75, or about 0.1 to about 0.9, or about 0.1 to about 0.8, or about 0.1 to about 0.7, or about 0.1 to about 0.6, or about 0.1 to about 0.5, or about 0.1 to about 0.4, or about 0.1 to about 0.3, or about 0.2 to about 1.0, or about 0.25 to about 1.0, or about 0.4 to about 1.0, or about 0.5 to about 0.9, or about 0.5 to about 0.85, or about 0.5 to about 0.8, or about 0.5 to about 0.75, or about 0.5 to about 1.0, or about 0.65 to about 1.0, or about 0.75 to about 1.0, or about 0.2 to about 0.9, or about 0.3 to about 0.95, or about 0.3 to about 0.85, or about 0.3 to about 0.8, or about 03 to about 0.75, or about 0.3 to about 0.7, or about 0.3 to about 0.6, or about 0.4 to about 0.9, or about 0.4 to about 0.8, or about 0.4 to about 0.7, or about 0.4 to about 0.6, or about 0.8 to about 1, or about 0.8 to about 1.1.

In some preferred embodiments, the oral dosage form of the present invention is directed to an oral dosage form comprising (i) a proserotonergic agent and (ii) a serotonin surge protector; said dosage form suitable for twice-a-day administration to a human patient; said dosage form providing a percent fluctuation of proserotonergic agent of less than 400%; and said dosage form providing a therapeutic effect for at least about 12 hours. In other preferred embodiments, the dosage form provides a percent fluctuation of proserotonergic agent of less than about 375%, or less than about 350%, or less than about 325%, or less than about 300%, or less than about 275%, or less than about 250%, or less than about 225%, or less than about 200%, or less than about 175%, or less than about 150%, or less than about 125%, or less than about 100%, or less than about 75%, or less than about 50%, or less than about 25%.

In some preferred embodiments, the oral dosage form of the present invention is directed to an oral dosage form comprising (i) a proserotonergic agent and (ii) a serotonin surge protector; said dosage form suitable for twice-a-day administration to a human patient; said dosage form after administration to a human patient, providing a $W_{50}$ of proserotonergic agent of 2 to about 11 hours; and said dosage form providing a therapeutic effect for at least about 12 hours. In other preferred embodiments, the dosage form provides a $W_{50}$ of proserotonergic agent of about 2 to about 10 hours, or about 2 to about 9 hours, or about 2 to about 9 hours, or about 2 to about 8 hours, or 2 to about 7 hours, or about 2 to about 6 hours, or about 2 to about 5 hours, or about 2 to about 4 hours, or about 3 to about 10 hours, or about 4 to about 10 hours, or about 5 to about 10 hours, or about 6 to about 10 hours, or 7 to about 10 hours, or about 3 to about 8 hours, or about 4 to about 8 hours, or about 4 to about 7 hours, or about 3 to about 6 hours.

In some preferred embodiments, the oral dosage form of the present invention is directed to an oral dosage form comprising (i) a proserotonergic agent and (ii) a serotonin surge protector; said dosage form suitable for twice-a-day administration to a human patient; said dosage form after administration to a human patient, providing a HVD of proserotonergic agent of 1.5 to about 10 hours; and said dosage form providing a therapeutic effect for at least about 12 hours. In other preferred embodiments, the dosage form provides an HVD of proserotonergic agent of about 1.5 to about 9 hours, or about 1.5 to 8 hours, or about 1.5 to about 7 hours, or about 1.5 to 6 hours, or about 1.5 to about 5 hours, or about 1.5 to about 4 hours, or about 2 to about 10 hours, or about 3 to 10 hours, or about 4 to about 10 hours, or about 5 to 10 hours, or about 6 to about 10 hours, or about 8 to 10 hours, about 3 to about 8 hours, or about 4 to 8 hours, or about 5 to about 7 hours, or about 3 to 6 hours, or about 3 to about 8 hours, or about 5 to about 8 hours.

In some preferred embodiments, the oral dosage form of the present invention is directed to an oral dosage form comprising (i) a proserotonergic agent and (ii) a serotonin surge protector; said dosage form suitable for twice-a-day administration to a human patient; said dosage form after administration to a human patient, providing an AI of proserotonergic agent of not more that 4.0; and said dosage form providing a therapeutic effect for at least about 12 hours. In other preferred embodiments, the dosage form provides an AI of proserotonergic agent of not more than about 3.75, or not more than about 3.5, or not more than about 3.25, or not more than about 3, or not more than about 2.75, or not more than about 2.5, or not more than about 2, or not more than about 1.5, not more than about 1.25, or not more than about 1, or not more than about 0.75.

In some preferred embodiments, the oral dosage form of the present invention is directed to an oral dosage form comprising (i) a proserotonergic agent and (ii) a serotonin surge protector; said dosage form suitable for twice-a-day administration to a human patient; said dosage form providing an in-vitro release rate by weight of proserotonergic agent, when measured by the USP Basket and Paddle Methods at 100 rpm in 900 mL aqueous buffer at a pH of between 1.6 and 7.2 at 37° C. of from 0% to about 47.5% at 1 hour, from about 10% to about 65% at 2 hours, from about 15% to about 70% at 4 hours, from about 25% to about 77.5% at 6 hours, from about 35% to about 87.5% at 9 hours, and greater than about 65% at 12 hours. In other preferred embodiments, the dosage form provides said an in-vitro release rate of from 0% to about 40% at 1 hour, from about 5% to about 55% at 2 hours, from about 10% to about 60% at 4 hours, from about 15% to about 70% at 6 hours, from about 25% to about 80% at 9 hours, and greater than about 50% at 12 hours.

In some preferred embodiments, the oral dosage form of the present invention is directed to an oral dosage form comprising (i) a proserotonergic agent and (ii) a serotonin surge protector; said dosage form suitable for twice-a-day administration to a human patient; said dosage form providing an in-vitro release rate by weight of proserotonergic agent, when measured by the USP Basket and Paddle Methods at 100 rpm in 900 mL aqueous buffer at a pH of between 1.6 and 7.2 at 37° C. of from 0% to about 47.5% at 1 hour, from about 10% to about 65% at 2 hours, from about 15% to about 70% at 4 hours, from about 25% to about 77.5% at 6 hours, from about 35% to about 87.5% at 9 hours, and greater than about 65% at 12 hours; said dosage form providing a $C_{max}$ from a mean of about 2 to about 10 hours after first administration or at steady state.

In some preferred embodiments, the oral dosage form of the present invention is directed to an oral dosage form comprising (i) a proserotonergic agent and (ii) a serotonin surge protector; said dosage form suitable for twice-a-day administration to a human patient; said dosage form providing an in-vitro release rate by weight of proserotonergic agent, when measured by the USP Basket and Paddle Methods at 100 rpm in 900 mL aqueous buffer at a pH of between 1.6 and 7.2 at 37° C. of from 0% to about 47.5% at 1 hour, from about 10% to about 65% at 2 hours, from about 15% to about 70% at 4 hours, from about 25% to about 77.5% at 6 hours, from about 35% to about 87.5% at 9 hours, and greater than about 65% at 12 hours; said dosage form providing a $C_{min}$ occurring from a mean of about 10 to about 14 hours after first administration or at steady state.

In some preferred embodiments, the oral dosage form of the present invention is directed to an oral dosage form comprising (i) a proserotonergic agent and (ii) a serotonin surge protector; said dosage form suitable for twice-a-day administration to a human patient; said dosage form providing an in-vitro release rate by weight of proserotonergic agent, when measured by the USP Basket and Paddle Methods at 100 rpm in 900 mL aqueous buffer at a pH of between 1.6 and 7.2 at 37° C. of from 0% to about 47.5% at 1 hour, from about 10% to about 65% at 2 hours, from about 15% to about 70% at 4 hours, from about 25% to about 77.5% at 6 hours, from about 35% to about 87.5% at 9 hours, and greater than about 65% at 12 hours; said dosage form providing a mean proserotonergic agent $AUC_{0-\tau}/AUC_{0-\infty}$ ratio after first administration of about 0.4, or about 0.5, or about 0.6, or about 0.7, or about 0.75, or about 0.8, or about 0.85, or about 0.88, or about 0.90, or about 0.92, or about 0.95, or about 0.97 or about 0.99.

In some preferred embodiments, the oral dosage form of the present invention is directed to an oral dosage form comprising (i) a proserotonergic agent and (ii) a serotonin surge protector; said dosage form suitable for twice-a-day administration to a human patient; said dosage form providing an in-vitro release rate by weight of proserotonergic agent, when measured by the USP Basket and Paddle Methods at 100 rpm in 900 mL aqueous buffer at a pH of between 1.6 and 7.2 at 37° C. of from 0% to about 47.5% at 1 hour, from about 10% to about 65% at 2 hours, from about 15% to about 70% at 4 hours, from about 25% to about 77.5% at 6 hours, from about 35% to about 87.5% at 9 hours, and greater than about 65% at 12 hours; said in-vitro release rate being substantially independent of pH in that a difference, at any given time, between an amount of proserotonergic agent released at one pH and an amount released at any other pH, when measured in-vitro using the USP Basket and Paddle Methods of USP Drug Release test of U.S. Pharmacopeia (2003) at 100 rpm in 900 ml aqueous buffer, is no greater than 30%.

In some preferred embodiments, the oral dosage form of the present invention is directed to an oral dosage form comprising (i) a proserotonergic agent and (ii) a serotonin surge protector; said dosage form suitable for once-a-day administration to a human patient; said dosage form providing a $C_{max}$ of proserotonergic agent at about 3 to about 20 hours; and said dosage form providing a therapeutic effect for at least about 24 hours. In some preferred embodiments, the proserotonergic agents dosage forms provide a $C_{max}$ of proserotonergic agent at about 3 to about 18 hours, or about 3 to about 15 hours, or about 3 to about 12 hours, or at about 3 to about 10 hours, or at about 3 to about 8 hours, or at about 3 to about 7 hours, or at about 3 to about 7 hours, or about 4 to about 20 hours, or about 5 to about 20 hours, or about 6 to about 20 hours, or at about 8 to about 20 hours, or at about 10 to about 20 hours, or at about 12 to about 20 hours, or at about 14 to about 20 hours, or about 18 to about 20 hours, or about 4 to about 18 hours, or about 4 to about 16 hours, or at about 4 to about 12 hours, or at about 4 to about 8 hours, or at about 4 to about 10 hours, or at about 3 to about 6 hours.

In some preferred embodiments, the oral dosage form of the present invention is directed to an oral dosage form comprising (i) a proserotonergic agent and (ii) a serotonin surge protector; said dosage form suitable for once-a-day administration to a human patient; said dosage form providing a $C_{min}$ of proserotonergic agent at about 20 to about 28 hours; and said proserotonergic agents dosage forms providing a therapeutic effect for at least about 24 hours. In some preferred embodiments, the proserotonergic agents dosage forms provide a $C_{min}$ of proserotonergic agent at about 20 to about 26 hours, or about 20 to about 27 hours, or about 20 to about 25 hours, or about 20 to about 24 hours, or about 20 to about 23 hours, or about 21 to about 28 hours, or about 22 to about 28 hours, or about 23 to about 28 hours, or about 23.5 to about 28 hours, or about 22 to 26 hours.

In some preferred embodiments, the oral dosage form of the present invention is directed to an oral dosage form comprising (i) a proserotonergic agent and (ii) a serotonin surge protector; said dosage from providing a $C_{max}$ of proserotonergic agent from about 0.25 hours to about 30 hours.

In some preferred embodiments, the oral dosage form of the present invention is directed to an oral dosage form comprising (i) a proserotonergic agent and (ii) a serotonin surge protector; said dosage from providing a $C_{min}$ of proserotonergic agent from about 0.5 hour to about 30 hours.

In some preferred embodiments, the oral dosage form of the present invention is directed to an oral dosage form comprising (i) a proserotonergic agent and (ii) a serotonin surge protector; said dosage form suitable for once-a-day administration to a human patient; said dosage form providing a $C_{24}/C_{max}$ ratio of proserotonergic agent of 0.1 to about 1; and said dosage form providing a therapeutic effect for at least about 24 hours. In other preferred embodiments, the dosage form provides a $C_{24}/C_{max}$ ratio of proserotonergic agent of about 0.25 to about 0.9, or about 0.25 to about 0.8, or about 0.25 to about 0.75, or about 0.25 to about 0.6, or 0.25 to about 0.5, or about 0.25 to about 0.4, or about 0.25 to about 0.35, or about 0.3 to about 0.95, or about 0.4 to about 0.95, or about 0.5 to about 0.95, or about 0.65 to about 0.95, or about 0.75 to about 0.95, or about 0.3 to about 0.8, or about 0.4 to about 0.75, or about 0.5 to about 0.75, or about 0.1 to about 0.9, or about 0.1 to about 0.8, or about 0.1 to about 0.7, or about 0.1 to about 0.6, or about 0.1 to about 0.5, or about 0.1 to about 0.4, or about 0.1 to about 0.3, or about 0.2 to about 1.0, or about 0.25 to about 1.0, or about 0.4 to about 1.0, or about 0.5 to about 0.9, or about 0.5 to about 0.85, or about 0.5 to about 0.8, or about 0.5 to about 0.75, or about 0.5 to about 1.0, or about 0.65 to about 1.0, or about 0.75 to about 1.0, or about 0.2 to about 0.9, or about 0.3 to about 0.95, or about 0.3 to about 0.85, or about 0.3 to about 0.8, or about 03 to about 0.75, or about 0.3 to about 0.7, or about 0.3 to about 0.6, or about 0.4 to about 0.9, or about 0.4 to about 0.8, or about 0.4 to about 0.7, or about 0.4 to about 0.6, or about 0.8 to about 1, or about 0.8 to about 1.1.

In some preferred embodiments, the oral dosage form of the present invention is directed to an oral dosage form comprising (i) a proserotonergic agent and (ii) a serotonin surge protector; said dosage form suitable for once-a-day administration to a human patient; said dosage form providing a percent fluctuation of proserotonergic agent of less than 400%; and said dosage form providing a therapeutic effect for at least about 24 hours. In other preferred embodiments, the dosage form provides a percent fluctuation of proserotonergic agent of less than about 375%, or less than about 350%, or less than about 325%, or less than about 300%, or less than about 275%, or less than about 250%, or less than about 225%, or less than about 200%, or less than about 175%, or less than about 150%, or less than about 125%, or less than about 100%, or less than about 75%, or less than about 50%, or less than about 25%.

In some preferred embodiments, the oral dosage form of the present invention is directed to an oral dosage form comprising (i) a proserotonergic agent and (ii) a serotonin surge protector; said dosage form suitable for once-a-day administration to a human patient; said proserotonergic agents dosage form after administration to a human patient, providing a $W_{50}$ of proserotonergic agent of 4 to about 22 hours; and said dosage form providing a therapeutic effect for at least about 24 hours. In other preferred embodiments, the proserotonergic agents dosage from provides a $W_{50}$ of proserotonergic agent of about 4 to about 20 hours, or about 4 to about 19 hours, or about 4 to about 18 hours, or 4 to about 16 hours, or 4 to about 14 hours, or about 4 to about 12 hours, or about 4 to about 10 hours, or about 4 to about 8 hours, or about 6 to about 20 hours, or about 8 to about 20 hours, or about 10 to about 20 hours, or about 12 to about 20 hours, or 14 to about 20 hours, or about 6 to about 16 hours, or about 8 to about 16 hours, or about 8 to about 14 hours, or about 6 to about 12 hours.

I In some preferred embodiments, the oral dosage form of the present invention is directed to an oral dosage form comprising (i) a proserotonergic agent and (ii) a serotonin surge protector; said dosage form suitable for once-a-day administration to a human patient; said proserotonergic agents dosage form after administration to a human patient, providing a HVD of proserotonergic agent of 3 to about 20 hours; and said dosage form providing a therapeutic effect for at least about 24 hours. In other preferred embodiments, the proserotonergic agents dosage from provides an HVD of proserotonergic agent of about 3 to about 18 hours, or about 3 to 16 hours, or about 3 to about 14 hours, or about 3 to 12 hours, or about 3 to about 10 hours, or about 3 to about 8 hours, or about 4 to about 20 hours, or about 6 to 20 hours, or about 8 to about 20 hours, or about 10 to 20 hours, or about 12 to about 20 hours, or about 16 to 20 hours, about 6 to about 16 hours, or about 8 to 16 hours, or about 10 to about 14 hours, or about 6 to 12 hours, or about 6 to about 16 hours, or about 10 to about 16 hours.

In some preferred embodiments, the oral dosage form of the present invention is directed to an oral dosage form comprising (i) a proserotonergic agent and (ii) a serotonin surge protector; said dosage form suitable for once-a-day administration to a human patient; said dosage form after administration to a human patient, providing an AI of proserotonergic agent of not more that 4.0; and said proserotonergic agents dosage form providing a therapeutic effect for at least about 24 hours. In other preferred embodiments, the proserotonergic agents dosage from provides an AI of proserotonergic agent of not more than about 3.75, or not more than about 3.5, or not more than about 3.25, or not more than about 3, or not more than about 2.75, or not more than about 2.5, or not more than about 2, or not more than about 1.5, not more than about 1.25, or not more than about 1, or not more than about 0.75.

In some preferred embodiments, the oral dosage form of the present invention is directed to an oral dosage form comprising (i) a proserotonergic agent and (ii) a serotonin surge protector; said dosage form suitable for once-a-day administration to a human patient; said proserotonergic agents dosage form providing an in-vitro release rate by weight of proserotonergic agent, when measured by the USP Basket and Paddle Methods at 100 rpm in 900 mL aqueous buffer at a pH of between 1.6 and 7.2 at 37° C. of from 0% to about 30% at 1 hour, from about 10% to about 65% at 4 hours, from about 20% to about 70% at 8 hours, from about 25% to about 80% at 12 hours, from about 35% to about 95% at 18 hours, and greater than about 65% at 24 hours.

In some preferred embodiments, the oral dosage form of the present invention is directed to an oral dosage form comprising (i) a proserotonergic agent and (ii) a serotonin surge protector; said dosage form suitable for once-a-day administration to a human patient; said proserotonergic agents dosage form providing an in-vitro release rate by weight of proserotonergic agent, when measured by the USP Basket and Paddle Methods at 100 rpm in 900 mL aqueous buffer at a pH of between 1.6 and 7.2 at 37° C. of from 0% to about 30% at 1 hour, from about 10% to about 65% at 4 hours, from about 20% to about 70% at 8 hours, from about 25% to about 80% at 12 hours, from about 35% to about 95% at 18 hours, and greater than about 65% at 24 hours; said dosage form providing a $C_{max}$ from a mean of about 3 to about 20 hours after first administration or at steady state.

In some preferred embodiments, the oral dosage form of the present invention is directed to an oral dosage form comprising (i) a proserotonergic agent and (ii) a serotonin surge protector; said dosage form suitable for once-a-day administration to a human patient; said dosage form providing an in-vitro release rate by weight of proserotonergic agent, when measured by the USP Basket and Paddle Methods at 100 rpm in 900 mL aqueous buffer at a pH of between 1.6 and 7.2 at 37° C. of from 0% to about 30% at 1 hour, from about 10% to about 65% at 4 hours, from about 20% to about 70% at 8 hours, from about 25% to about 80% at 12 hours, from about 35% to about 95% at 18 hours, and greater than about 65% at 24 hours; said dosage form providing a $C_{min}$ of proserotonergic agent occurring from a mean of about 20 to about 28 hours after first administration or at steady state.

In some preferred embodiments, the oral dosage form of the present invention is directed to an oral dosage form comprising (i) a proserotonergic agent and (ii) a serotonin surge protector; said dosage form suitable for once-a-day administration to a human patient; said dosage form providing an in-vitro release rate by weight of proserotonergic agent, when measured by the USP Basket and Paddle Methods at 100 rpm in 900 mL aqueous buffer at a pH of between 1.6 and 7.2 at 37° C. of from 0% to about 30% at 1 hour, from about 10% to about 65% at 4 hours, from about 20% to about 70% at 8 hours, from about 25% to about 80% at 12 hours, from about 35% to about 95% at 18 hours, and greater than about 65% at 24 hours; said dosage form providing a mean proserotonergic agent $AUC_{0-t}/AUC_{0-\infty}$ ratio after first administration of about 0.4, or about 0.5, or about 0.6, or about 0.7, or about 0.75, or about 0.8, or about 0.85, or about 0.88, or about 0.90, or about 0.92, or about 0.95, or about 0.97 or about 0.99.

In some preferred embodiments, the oral dosage form of the present invention is directed to an oral dosage form comprising (i) a proserotonergic agent and (ii) a serotonin surge protector; said dosage form suitable for once-a-day administration to a human patient; said dosage form providing an in-vitro release rate by weight of proserotonergic agent, when measured by the USP Basket and Paddle Methods at 100 rpm in 900 mL aqueous buffer at a pH of between 1.6 and 7.2 at 37° C. of from 0% to about 30% at 1 hour, from about 10% to about 65% at 4 hours, from about 20% to about 70% at 8 hours, from about 25% to about 80% at 12 hours, from about 35% to about 95% at 18 hours, and greater than about 65% at 24 hours; said in-vitro release rate being substantially independent of pH in that a difference, at any given time, between an amount of proserotonergic agent released at one pH and an amount released at any other pH, when measured in-vitro using the USP Basket and Paddle Methods of USP Drug Release test of U.S. Pharmacopeia (2003) at 100 rpm in 900 ml aqueous buffer, is no greater than 30%.

In some preferred embodiments, the oral dosage form of the present invention is directed to an oral dosage form comprising (i) a proserotonergic agent and (ii) a serotonin surge protector; said dosage form after administration to a human patient providing a mean proserotonergic agent $C_{max}$ which is less than 65% of the $C_{max}$ of an equivalent dose of an oral immediate release proserotonergic agent solution or suspension; and said dosage form maintaining a mean proserotonergic agent plasma concentration within 50% of $C_{max}$ for about 1 to about 5.5 hours for each 6 hour time period of intended dosing frequency and intended duration of action.

In some preferred embodiments, the oral dosage form of the present invention is directed to an oral dosage form comprising (i) a proserotonergic agent and (ii) a serotonin surge protector; said dosage form providing an in-vitro release of from 0% to about 50% by weight of the proserotonergic agent or a pharmaceutically acceptable salt thereof from the dosage form at one hour when measured by the USP Basket and Paddle Methods at 100 rpm in 700 ml of Simulated Gastric Fluid (SGF) at 37° C. In other preferred embodiments, said in-vitro release rate by weight of the proserotonergic agent or a pharmaceutically acceptable salt thereof from said dosage form is from about 5% to about 45%, or about 10% to about 50%, or about 5% to about 60%, or about 5% to about 70%, or about 5% to about 80%, or about 5% to about 90%, or about 5% to about 100%, or about 10% to about 20%, or about 10% to about 35%, or about 10% to about 50%, or about 10% to about 60%, or about 10% to about 70%, or about 10% to about 80%, or about 10% to about 90%, or about 10% to about 100%, or about 20% to about 40%, or about 20% to about 50%, or about 20% to about 60%, or about 20% to about 70%, or about 20% to about 80%, or about 20% to about 90%, or about 20% to about 100%, or about 30% to about 50%, or about 30% to about 60%, or about 30% to about 70%, or about 30% to about 80%, or about 30% to about 90%, or about 40% to about 80%, or about 40% to about 90%, or about 60% to about 100%, or greater than about 5%, or greater than about 10%, or greater than about 15%, or greater than about 20%, or greater than about 30%, or greater than about 40%, or greater than about 50%, or greater than about 60%, or greater than about 80%, or greater than about 90%, or greater than about 95%, at one hour, when measured by the USP Basket and Paddle Methods at 100 rpm in 700 ml of Simulated Gastric Fluid (SGF) at 37° C.

In some preferred embodiments, the oral dosage form of the present invention is directed to an oral dosage form comprising (i) a proserotonergic agent and (ii) a serotonin surge protector; said dosage form providing a $C_{max}$ of proserotonergic agent which is less than 65% of the $C_{max}$ of an equivalent dose of an oral immediate release proserotonergic agent solution or suspension. In other preferred embodiments, said dosage form provides a $C_{max}$ which is less than about 85%, or less than about 75%, or less than about 60%, or less than about 55%, or less than about 50%, or less than about 45%, or less than about 40%, or less than about 30%, or less than about 20% of the $C_{max}$ of an equivalent dose of an oral immediate release proserotonergic agent solution or suspension.

In some preferred embodiments, the oral dosage form of the present invention is directed to an oral dosage form comprising (i) a proserotonergic agent and (ii) a serotonin surge protector; said dosage form providing a time to 75% mean $C_{max}$ of proserotonergic agent which is about 100% to about 2000% of the time to 75% mean $C_{max}$ of an oral immediate release proserotonergic agent solution or suspension.

In some preferred embodiments, the oral dosage form of the present invention is directed to an oral dosage form comprising (i) a proserotonergic agent and (ii) a serotonin surge protector; said dosage form providing a time to 30% mean $C_{max}$ of proserotonergic agent which is about 100% to about 2000% of the time to 30% mean $C_{max}$ of an oral immediate release proserotonergic agent solution or suspension.

In some preferred embodiments, the oral dosage form of the present invention is directed to an oral dosage form comprising (i) a proserotonergic agent and (ii) a serotonin surge protector; said dosage form maintaining a plasma proserotonergic agent concentration within 50% of $C_{max}$ for about 1 to about 9 hours during a 12 hour dosing interval. In other preferred embodiments, said dosage form maintains plasma proserotonergic agent concentration within 50% of $C_{max}$ for about 2 to about 9 hours, or about 3 to about 9 hours, or about 4 to about 9 hours, or about 5 to about 9 hours, or about 6 to about 9 hours, or about 1 to about 11 hours, or about 2 to about 11 hours, or about 3 to about 11 hours or about 4 to about 11 hours, or about 5 to about 11 hours, or about 6 to about 11 hours, or about 7 to about 11 hours, or about 8 to about 11 hours, or about 1 to about 10 hours, or about 2 to about 10 hours, or about 3 to about 10 hours or about 4 to about 10 hours, or about 5 to about 10 hours, or about 6 to about 10 hours, or about 7 to about 10 hours, or about 8 to about 10 hours, or about 1 to about 7 hours, or about 2 to about 7 hours, or about 3 to about 7 hours or about 4 to about 7 hours, or about 5 to about 7 hours, or about 6 to about 7 hours, or about 1 to about 4 hours, or about 1 to about 5 hours, during a 12 hour dosing interval.

In some preferred embodiments, the oral dosage form of the present invention is directed to an oral dosage form comprising (i) a proserotonergic agent and (ii) a serotonin surge protector; said dosage form maintains a plasma proserotonergic agent concentration within 30% of $C_{max}$ for about 1.5 to about 9 hours during a 12 hour dosing interval. In other preferred embodiments, said dosage form maintains plasma proserotonergic agent concentration within 30% of $C_{max}$ for about 2 to about 9 hours, or about 3 to about 9 hours, or about 4 to about 9 hours, or about 5 to about 9 hours, or about 6 to about 9 hours, or about 1 to about 11 hours, or about 2 to about 11 hours, or about 3 to about 11 hours or about 4 to about 11 hours, or about 5 to about 11 hours, or about 6 to about 11 hours, or about 7 to about 11 hours, or about 8 to about 11 hours, or about 1 to about 10 hours, or about 2 to about 10 hours, or about 3 to about 10 hours or about 4 to about 10 hours, or about 5 to about 10 hours, or about 6 to about 10 hours, or about 7 to about 10 hours, or about 8 to about 10 hours, or about 1 to about 7 hours, or about 2 to about 7 hours, or about 3 to about 7 hours or about 4 to about 7 hours, or about 5 to about 7 hours, or about 6 to about 7 hours, or about 1 to about 4 hours, or about 1 to about 5 hours, during a 12 hour dosing interval.

In some preferred embodiments, the oral dosage form of the present invention is directed to an oral dosage form comprising (i) a proserotonergic agent and (ii) a serotonin surge protector; said dosage form maintains a plasma proserotonergic agent concentration within 65% of $C_{max}$ for about 1 to about 9 hours during a 12 hour dosing interval. In other preferred embodiments, said dosage form maintains plasma proserotonergic agent concentration within 65% of $C_{max}$ for about 2 to about 9 hours, or about 3 to about 9 hours, or about 4 to about 9 hours, or about 5 to about 9 hours, or about 6 to about 9 hours, or about 1 to about 11 hours, or about 2 to about 11 hours, or about 3 to about 11 hours or about 4 to about 11 hours, or about 5 to about 11 hours, or about 6 to about 11 hours, or about 7 to about 11 hours, or about 8 to about 11 hours, or about 1 to about 10 hours, or about 2 to about 10 hours, or about 3 to about 10 hours or about 4 to about 10 hours, or about 5 to about 10 hours, or about 6 to about 10 hours, or about 7 to about 10 hours, or about 8 to about 10 hours, or about 1 to about 7 hours, or about 2 to about 7 hours, or about 3 to about 7 hours or about 4 to about 7 hours, or about 5 to about 7 hours, or about 6 to about 7 hours, or about 1 to about 4 hours, or about 1 to about 5 hours, during a 12 hour dosing interval.

In some preferred embodiments, the oral dosage form of the present invention is directed to an oral dosage form comprising (i) a proserotonergic agent and (ii) a serotonin surge protector; said dosage form maintains a plasma proserotonergic agent concentration within 55% of $C_{max}$ for about 3 to about 22 hours during a 24 hour dosing interval. In other preferred embodiments, said dosage form maintains plasma proserotonergic agent concentration within 50% of $C_{max}$ for about 1 to about 9 hours, or about 4 to about 9 hours, or about 6 to about 9 hours, or about 1 to about 20 hours, or about 2 to about 20 hours, or about 3 to about 20 hours, or about 1 to about 18 hours, or about 1 to about 16 hours or about 2 to about 18 hours, or about 2 to about 16 hours, or about 1 to about 14 hours, or about 1 to about 12 hours, or about 4 to about 16 hours, or about 4 to about 18 hours, or about 4 to about 20 hours, or about 3 to about 15 hours or about 6 to about 15 hours, or about 6 to about 12 hours, or about 6 to about 18 hours, or about 6 to about 20 hours, or about 5 to about 12 hours, or about 5 to about 14 hours, or about 3 to about 22 hours, or about 3 to about 9 hours or about 3 to about 12 hours, or about 1 to about 6 hours, or about 2 to about 8 hours, or about 2 to about 10 hours, or about 3 to about 16 hours, during a 24 hour dosing interval.

In some preferred embodiments, the oral dosage form of the present invention is directed to an oral dosage form comprising (i) a proserotonergic agent and (ii) a serotonin surge protector; said dosage form maintains a plasma proserotonergic agent concentration within 30% of $C_{max}$ for about 2 to about 22 hours during a 24 hour dosing interval. In other preferred embodiments, said dosage form maintains plasma proserotonergic agent concentration within 30% of $C_{max}$ for about 1 to about 9 hours, or about 4 to about 9 hours, or about 6 to about 9 hours, or about 1 to about 20 hours, or about 2 to about 20 hours, or about 3 to about 20 hours, or about 1 to about 18 hours, or about 1 to about 16 hours or about 2 to about 18 hours, or about 2 to about 16 hours, or about 1 to about 14 hours, or about 1 to about 12 hours, or about 4 to about 16 hours, or about 4 to about 18 hours, or about 4 to about 20 hours, or about 3 to about 15 hours or about 6 to about 15 hours, or about 6 to about 12 hours, or about 6 to about 18 hours, or about 6 to about 20 hours, or about 5 to about 12 hours, or about 5 to about 14 hours, or about 3 to about 22 hours, or about 3 to about 9 hours or about 3 to about 12 hours, or about 1 to about 6 hours, or about 2 to about 8 hours, or about 2 to about 10 hours, or about 3 to about 16 hours, during a 24 hour dosing interval.

In some preferred embodiments, the oral dosage form of the present invention is directed to an oral dosage form comprising (i) a proserotonergic agent and (ii) a serotonin surge protector; said dosage form maintains a plasma proserotonergic agent concentration within 65% of $C_{max}$ for about 2 to about 22 hours during a 24 hour dosing interval. In other preferred embodiments, said dosage form maintains plasma proserotonergic agent concentration within 65% of $C_{max}$ for about 1 to about 9 hours, or about 4 to about 9 hours, or about 6 to about 9 hours, or about 1 to about 20 hours, or about 2 to about 20 hours, or about 3 to about 20 hours, or about 1 to about 18 hours, or about 1 to about 16 hours or about 2 to about 18 hours, or about 2 to about 16 hours, or about 1 to about 14 hours, or about 1 to about 12 hours, or about 4 to about 16 hours, or about 4 to about 18 hours, or about 4 to about 20 hours, or about 3 to about 15 hours or about 6 to about 15 hours, or about 6 to about 12 hours, or about 6 to about 18 hours, or about 6 to about 20 hours, or about 5 to about 12 hours, or about 5 to about 14 hours, or about 3 to about 22 hours, or about 3 to about 9 hours or about 3 to about 12 hours, or about 1 to about 6 hours, or about 2 to about 8 hours, or about 2 to about 10 hours, or about 3 to about 16 hours, during a 24 hour dosing interval.

In some preferred embodiments, the oral dosage form of the present invention is directed to an oral dosage form comprising (i) a proserotonergic agent and (ii) a serotonin surge protector; said dosage form providing a $T_{max}$ of proserotonergic agent at a time point 1 to 18 times later than the $T_{max}$ provided by an equivalent dose of an oral immediate release proserotonergic agent solution or suspension. In the dosage form provides a $T_{max}$ at a time point about 1 to 15 times late, or about of 1 to 10 times later, or about of 1 to 7 times later, or about of 1 to 4 times later, or about of 3 to 20 times later, or about of 3 to 10 times later, or about of 3 to 5 times later, or about 1.5 to 15 times later, or about of 1.5 to 10 times later, or about of 1.5 to 7 times later, or about of 1.5 to 3 times later, or about of 2 to 20 times later, or about of 2 to 10 times later, or about of 2 to 5 times later, or about of 2 to 3 times later, or about of 2.5 to 20 times later, or about of 2.5 to 8 times later, or about of 2.5 to 5 times later, or about of 2.5 to 4 times later, or about of 3 to 20 times later, or about of 3 to 10 times later, or about of 3 to 5 times later.

In some preferred embodiments, the oral dosage form of the present invention is directed to an oral dosage form comprising (i) a proserotonergic agent and (ii) a serotonin surge protector; said dosage form providing a mean in vivo extent of absorption of proserotonergic agent from 0 to 4 hours which is at least 20% of the mean in vivo extent of absorption from to 0 to 12 hours, wherein the mean in vivo extent of absorption is the area under the plasma or serum proserotonergic agent concentration time curve from the time of drug administration to the specified time point. In other preferred embodiments, said in vivo extent of absorption from 0 to 4 hours is at least about 5%, or at least about 10%, or at least about 15%, or at least about 25%, or at least about 30%, or at least about 40%, or at least about 50%, or at least about 60%, or at least about 70%, or at least about 80%, at least about 90%, or about 100% of the mean in vivo extent of absorption from to 0 to 12 hours.

In some preferred embodiments, the oral dosage form of the present invention is directed to an oral dosage form comprising (i) a proserotonergic agent and (ii) a serotonin surge protector; said dosage form providing a mean in vivo extent of absorption of proserotonergic agent from 0 to 8 hours which is at least 20% of the mean in vivo extent of absorption from to 0 to 24 hours, wherein the mean in vivo extent of absorption is the area under the plasma or serum proserotonergic agent concentration time curve from the time of drug administration to the specified time point. In other preferred embodiments, said in vivo extent of absorption from 0 to 8 hours is at least about 5%, or at least about 10%, or at least about 15%, or at least about 25%, or at least about 30%, or at least about 40%, or at least about 50%, or at least about 60%, or at least about 70%, or at least about 80%, at least about 90%, or about 100% of the mean in vivo extent of absorption from to 0 to 24 hours.

In some preferred embodiments, the oral dosage form of the present invention is directed to an oral dosage form comprising (i) a proserotonergic agent and (ii) a serotonin surge protector; said dosage form providing a mean in vivo extent of absorption of proserotonergic agent from 0 to 12 hours which is at least 20% of the mean in vivo extent of absorption from to 0 to 24 hours, wherein the mean in vivo extent of absorption is the area under the plasma or serum proserotonergic agent concentration time curve from the time of drug administration to the specified time point. In other preferred embodiments, said in vivo extent of absorption from 0 to 12 hours is at least about 5%, or at least about 10%, or at least about 15%, or at least about 25%, or at least about 30%, or at least about 40%, or at least about 50%, or at least about 60%, or at least about 70%, or at least about 80%, at least about 90%, or about 100% of the mean in vivo extent of absorption from to 0 to 24 hours.

In some preferred embodiments, the oral dosage form of the present invention is directed to an oral dosage form comprising (i) a proserotonergic agent and (ii) a serotonin surge protector; said dosage form providing a mean in vivo extent of absorption of proserotonergic agent over the dosing interval, $AUC_{0-t}$ (e.g., from 0 to 8 hours, or from 0 to 12 hours or from 0 to 24 hours) which is at least 40% of the mean in vivo extent of absorption from to 0 to infinity ($AUC_{0-\infty}$). In other preferred embodiments, said $AUC_{0-t}$ is at least about 50%, or at least about 60%, or at least about 70%, or at least about 80%, or at least about 90% of the mean in vivo extent of absorption from to 0 to infinity ($AUC_{0-\infty}$).

In some preferred embodiments, the oral dosage form of the present invention is directed to an oral dosage form comprising (i) a proserotonergic agent and (ii) a serotonin surge protector; said proserotonergic agents dosage form providing an in-vitro release rate by weight of proserotonergic agent, when measured by the USP Basket and Paddle Methods at 100 rpm in 900 mL aqueous buffer at a pH of between 1.6 and 7.2 at 37° C. of between 0% to about 100% at 0.5 hours, and greater than about 60% at 1 hour.

In some preferred embodiments, the oral dosage form of the present invention is directed to an oral dosage form comprising (i) a proserotonergic agent and (ii) a serotonin surge protector; said proserotonergic agents dosage form providing an in-vitro release rate by weight of proserotonergic agent, when measured by the USP Basket and Paddle Methods at 100 rpm in 900 mL aqueous buffer at a pH of between 1.6 and 7.2 at 37° C. of between 0% to about 40% at 1 hour, from about 5% to about 60% at 2 hours, from about 10% to about 75% at 4 hours, from about 20% to about 75% at 6 hours, from about 30% to about 80% at 9 hours, and greater than about 70% at 12 hours.

In some preferred embodiments, the oral dosage form of the present invention is directed to an oral dosage form comprising (i) a proserotonergic agent and (ii) a serotonin surge protector; said proserotonergic agent dosage form providing an in-vitro release rate by weight of proserotonergic agent, when measured by the USP Basket and Paddle Methods at 100 rpm in 900 mL aqueous buffer at a pH of between 1.6 and 7.2 at 37° C. of between 1% and about 45% at 1 hour, between about 5% and about 70% at 2 hours, between about 10% and about 90% at 4 hours, between about 20% and about 90% at 8 hours, greater than about 60% at 12 hours, greater than about 80% at 18 hours, and greater than about 85% at 24 hours.

In some preferred embodiments, the oral dosage form of the present invention is directed to an oral dosage form comprising (i) a proserotonergic agent and (ii) a serotonin surge protector; said proserotonergic agent dosage form providing an in-vitro release rate by weight of proserotonergic agent, when measured by the USP Basket and Paddle Methods at 100 rpm in 900 mL aqueous buffer at a pH of between 1.6 and 7.2 at 37° C. of between 5% and about 60% at 1 hour, between about 12.5% and about 80% at 2 hours, between about 25% and about 95% at 4 hours, between about 45% and about 100% at 8 hours, greater than about 55% at 12 hours, greater than about 65% at 18 hours, and greater than about 70% at 24 hours.

In some preferred embodiments, the oral dosage form of the present invention is directed to an oral dosage form comprising (i) a proserotonergic agent and (ii) a serotonin surge protector; said proserotonergic agent dosage form providing an in-vitro release rate by weight of proserotonergic agent, when measured by the USP Basket and Paddle Methods at 100 rpm in 900 mL aqueous buffer at a pH of between 1.6 and 7.2 at 37° C. of between 0% and about 40% at 1 hour, between about 0% and about 70% at 2 hours, between about 5% and about 95% at 4 hours, between about 12.5% and about 100% at 8 hours, between about 20% and about 100% at 12 hours, between about 35% and about 100% at 16 hours, between about 55% and about 100% at 24 hours, and greater than about 75% at 36 hours.

In some preferred embodiments, the oral dosage form of the present invention is directed to an oral dosage form comprising (i) a proserotonergic agent and (ii) a serotonin surge protector; said proserotonergic agent dosage form providing an in-vitro release rate by weight of proserotonergic agent, when measured by the USP Basket and Paddle Methods at 100 rpm in 900 mL aqueous buffer at a pH of between 1.6 and 7.2 at 37° C. of between 0% and about 60% at 1 hour, between about 0% and about 75% at 2 hours, between about 5% and about 95% at 4 hours, between about 12.5% and about 100% at 8 hours, between about 15% and about 100% at 12 hours, between about 25% to about 100% at 16 hours, between about 30% and about 100% hours at 24 hours and greater than 60% at 36 hours.

In some preferred embodiments, the oral dosage form of the present invention is directed to an oral dosage form comprising (i) a proserotonergic agent and (ii) a serotonin surge protector; said proserotonergic agent dosage form providing an in-vitro release from the dosage form at one hour when measured by the USP Basket and Paddle Methods at 100 rpm in 700 ml of Simulated Gastric Fluid (SGF) at 37° C. of between 0% to about 50% by weight of the proserotonergic agent. In other preferred embodiments, said release rate is between 0% to about 1%, or 0% to about 3%, or 0% to about 5%, or 0% to about 10%, or 0% to about 15%, or 0% to about 20%, 0% to about 30%, or 0% to about 40%, or 0% to about 60%, or 0% to about 70%, or 0% to about 80%, or 0% to about 90%, 0% to about 100%.

In some preferred embodiments, the oral dosage form of the present invention is directed to an oral dosage form comprising (i) a proserotonergic agent and (ii) a serotonin surge protector; said proserotonergic agent dosage form providing an in-vitro release from the dosage form at one hour when measured by the USP Basket and Paddle Methods at 100 rpm in 900 mL aqueous buffer at a pH of between 1.6 and 7.2 at 37° C. of between 0% and about 60% at 1 hour, between about 0% and about 80% at 2 hours, between about 3% and about 95% at 4 hours and between about 10% and about 100% at 8 hours. In other preferred embodiments, said release rate is between 0% and about 10% at 1 hour, between about 0% and about 20% at 2 hours, between about 2% and about 80% at 4 hours and between about 5% and about 100% at 8 hours; or between 0% and about 20% at 1 hour, between about 0% and about 40% at 2 hours, between about 0% and about 80% at 4 hours and between about 2% and about 100% at 8 hours; or between 0% and about 40% at 1 hour, between about 0% and about 60% at 2 hours, between about 5% and about 85% at 4 hours and between about 5% and about 90% at 8 hours and greater than 20% at 12 hours; or between 0% and about 50% at 1 hour, between about 0% and about 50% at 2 hours, between about 10% and about 90% at 4 hours and between about 15% and about 90% at 8 hours and greater than 30% at 12 hours; or between 0% and about 70% at 1 hour, between about 0% and about 70% at 2 hours, between about 10% and about 75% at 4 hours and between about 15% and about 90% at 8 hours and greater than 30% at 12 hours.

In some preferred embodiments, the oral dosage form of the present invention is directed to an oral dosage form comprising (i) a proserotonergic agent and (ii) a serotonin surge protector; said proserotonergic agent dosage form providing an in-vitro release from the dosage form at one hour when measured by the USP Basket and Paddle Methods at 100 rpm in 900 mL aqueous buffer at a pH of between 1.6 and 7.2 at 37° C. of between 10% and about 65% at 1 hour, between about 20% and about 75% at 2 hours, between about 30% and about 95% at 4 hours and between about 40% and about 100% at 8 hours. In other preferred embodiments, said release rate is between 2% and about 70% at 1 hour, between about 5% and about 80% at 2 hours, between about 10% and about 90% at 4 hours and between about 20% and about 100% at 8 hours; or between 5% and about 60% at 1 hour, between about 10% and about 75% at 2 hours, between about 15% and about 85% at 4 hours and between about 30% and about 100% at 8 hours; or between 20% and about 70% at 1 hour, between about 20% and about 75% at 2 hours, between about 20% and about 90% at 4 hours and between about 40% and about 100% at 8 hours; or between 30% and about 80% at 1 hour, between about 40% and about 85% at 2 hours, between about 40% and about 90% at 4 hours and between about 60% and about 100% at 8 hours; or between 1% and about 20% at 1 hour, between about 5% and about 20% at 2 hours, between about 10% and about 40% at 4 hours and between about 20% and about 40% at 8 hours and greater than 40% at 12 hours.

In some preferred embodiments, the oral dosage form of the present invention is directed to an oral dosage form comprising (i) a proserotonergic agent and (ii) a serotonin surge protector; said proserotonergic agent dosage form providing an in-vitro release rate by weight of the proserotonergic agent, when measured by the USP Basket and Paddle Methods at 100 rpm in 900 mL aqueous buffer at a pH of between 1.6 and 7.2 at 37° C. of between 0% to about 47.5% at 1 hour, from about 10% to about 65% at 2 hours, from about 15% to about 70% at 4 hours, from about 25% to about 77.5% at 6 hours, from about 35% to about 87.5% at 9 hours, and greater than about 65% at 12 hours. In other preferred embodiments, said release rate is between 0% to about 30% at 1 hour, from about 5% to about 45% at 2 hours, from about 10% to about 60% at 4 hours, from about 15% to about 70% at 6 hours, from about 25% to about 80% at 9 hours, and greater than about 50% at 12 hours; or between 0% to about 20% at 1 hour, from about 2% to about 35% at 2 hours, from about 5% to about 50% at 4 hours, from about 10% to about 60% at 6 hours, from about 15% to about 70% at 9 hours, and greater than about 40% at 12 hours; or between 0% to about 10% at 1 hour, from about 1% to about 30% at 2 hours, from about 5% to about 40% at 4 hours, from about 10% to about 60% at 6 hours, from about 15% to about 70% at 9 hours, and greater than about 40% at 12 hours; or between 0% to about 5% at 1 hour, from about 0% to about 10% at 2 hours, from about 2% to about 20% at 4 hours, from about 5% to about 30% at 6 hours, from about 10% to about 40% at 9 hours, and greater than about 30% at 12 hours; or between 0% to about 50% at 1 hour, from about 15% to about 70% at 2 hours, from about 20% to about 75% at 4 hours, from about 30% to about 80% at 6 hours, from about 30% to about 90% at 9 hours, and greater than about 70% at 12 hours; or between 0% to about 60% at 1 hour, from about 15% to about 80% at 2 hours, from about 25% to about 85% at 4 hours, from about 35% to about 90% at 6 hours, from about 40% to about 90% at 9 hours, and greater than about 80% at 12 hours; or between 0% to about 70% at 1 hour, from about 20% to about 80% at 2 hours, from about 25% to about 80% at 4 hours, from about 35% to about 80% at 6 hours, from about 40% to about 80% at 9 hours, and greater than about 60% at 12 hours; or between 0% to about 75% at 1 hour, from about 30% to about 80% at 2 hours, from about 35% to about 90% at 4 hours, from about 50% to about 90% at 6 hours, from about 55% to about 95% at 9 hours, and greater than about 70% at 12 hours.

In some preferred embodiments, the oral dosage form of the present invention is directed to an oral dosage form comprising (i) a proserotonergic agent and (ii) a serotonin surge protector; said proserotonergic agent dosage form providing an in-vitro release rate by weight of the proserotonergic agent, when measured by the USP Basket and Paddle Methods at 100 rpm in 900 mL aqueous buffer at a pH of between 1.6 and 7.2 at 37° C. of between 5% and about 50% at 1 hour, between about 10% and about 75% at 2 hours, between about 20% and about 95% at 4 hours, between about 40% and about 100% at 8 hours, greater than about 50% at 12 hours, greater than about 70% at 18 hours, and greater than about 80% at 24 hours. In other preferred embodiments, said release rate is between 2% and about 50% at 1 hour, between about 5% and about 75% at 2 hours, between about 15% and about 75% at 4 hours, between about 30% and about 90% at 8 hours, greater than about 40% at 12 hours, greater than about 60% at 18 hours, and greater than about 70% at 24 hours; or between 1% and about 40% at 1 hour, between about 2% and about 60% at 2 hours, between about 10% and about 65% at 4 hours, between about 20% and about 80% at 8 hours, greater than about 30% at 12 hours, greater than about 40% at 18 hours, and greater than about 60% at 24 hours; or between 5% and about 60% at 1 hour, between about 15% and about 80% at 2 hours, between about 25% and about 95% at 4 hours, between about 45% and about 100% at 8 hours, greater than about 60% at 12 hours, greater than about 80% at 18 hours, and greater than about 90% at 24 hours; or between 10% and about 65% at 1 hour, between about 20% and about 85% at 2 hours, between about 30% and about 100% at 4 hours, between about 60% and about 100% at 8 hours, greater than about 70% at 12 hours, greater than about 90% at 18 hours, and greater than about 95% at 24 hours.

In some preferred embodiments, the oral dosage form of the present invention is directed to an oral dosage form comprising (i) a proserotonergic agent and (ii) a serotonin surge protector; said proserotonergic agent dosage form providing an in-vitro release rate by weight of the proserotonergic agent, when measured by the USP Basket and Paddle Methods at 100 rpm in 900 mL aqueous buffer at a pH of between 1.6 and 7.2 at 37° C. of between 0% to about 30% at 1 hour, from about 10% to about 65% at 4 hours, from about 20% to about 70% at 8 hours, from about 25% to about 80% at 12 hours, from about 35% to about 95% at 18 hours, and greater than about 65% at 24 hours. In other preferred embodiments, said release rate is between 0% to about 20% at 1 hour, from about 5% to about 50% at 4 hours, from about 10% to about 60% at 8 hours, from about 15% to about 70% at 12 hours, from about 25% to about 90% at 18 hours, and greater than about 55% at 24 hours; or between 0% to about 10% at 1 hour, from about 5% to about 40% at 4 hours, from about 8% to about 50% at 8 hours, from about 10% to about 60% at 12 hours, from about 22% to about 80% at 18 hours, and greater than about 45% at 24 hours; or between 0% to about 35% at 1 hour, from about 15% to about 70% at 4 hours, from about 25% to about 75% at 8 hours, from about 30% to about 85% at 12 hours, from about 40% to about 100% at 18 hours, and greater than about 75% at 24 hours; or between 0% to about 40% at 1 hour, from about 20% to about 70% at 4 hours, from about 30% to about 80% at 8 hours, from about 35% to about 90% at 12 hours, from about 45% to about 100% at 18 hours, and greater than about 80% at 24 hours; or between 0% to about 45% at 1 hour, from about 25% to about 75% at 4 hours, from about 35% to about 85% at 8 hours, from about 40% to about 90% at 12 hours, from about 50% to about 100% at 18 hours, and greater than about 90% at 24 hours; or between 0% to about 50% at 1 hour, from about 30% to about 80% at 4 hours, from about 40% to about 90% at 8 hours, from about 45% to about 95% at 12 hours, from about 60% to about 100% at 18 hours, and greater than about 95% at 24 hours; or between 0% to about 60% at 1 hour, from about 40% to about 80% at 4 hours, from about 45% to about 90% at 8 hours, from about 50% to about 100% at 12 hours, from about 70% to about 100% at 18 hours, and greater than about 80% at 24 hours.

In some preferred embodiments, the oral dosage form of the present invention is directed to an oral dosage form comprising (i) a proserotonergic agent and (ii) a serotonin surge protector; said proserotonergic agent dosage form providing an in-vitro release rate by weight of the proserotonergic agent, when measured by the USP Basket and Paddle Methods at 100 rpm in 900 mL aqueous buffer at a pH of between 1.6 and 7.2 at 37° C. of between 0% and about 50% at 1 hour, between about 0% and about 75% at 2 hours, between about 3% and about 95% at 4 hours, between about 10% and about 100% at 8 hours, between about 25% and about 100% at 12 hours, between about 30% and about 100% at 16 hours, between about 50% and about 100% at 24 hours, and greater than about 80% at 36 hours. In other preferred embodiments, said release rate is between 0% and about 40% at 1 hour, between about 0% and about 65% at 2 hours, between about 2% and about 85% at 4 hours, between about 8% and about 90% at 8 hours, between about 20% and about 95% at 12 hours, between about 25% and about 95% at 16 hours, between about 40% and about 90% at 24 hours, and greater than about 70% at 36 hours; or between 0% and about 30% at 1 hour, between about 0% and about 50% at 2 hours, between about 1% and about 75% at 4 hours, between about 5% and about 80% at 8 hours, between about 10% and about 85% at 12 hours, between about 15% and about 90% at 16 hours, between about 30% and about 80% at 24 hours, and greater than about 70% at 36 hours; or between 0% and about 60% at 1 hour, between about 0% and about 80% at 2 hours, between about 5% and about 100% at 4 hours, between about 15% and about 100% at 8 hours, between about 35% and about 100% at 12 hours, between about 40% and about 100% at 16 hours, between about 60% and about 100% at 24 hours, and greater than about 85% at 36 hours; or between 0% and about 65% at 1 hour, between about 0% and about 85% at 2 hours, between about 10% and about 100% at 4 hours, between about 20% and about 100% at 8 hours, between about 40% and about 100% at 12 hours, between about 50% and about 100% at 16 hours, between about 70% and about 100% at 24 hours, and greater than about 90% at 36 hours; or between 0% and about 70% at 1 hour, between about 0% and about 90% at 2 hours, between about 20% and about 100% at 4 hours, between about 30% and about 100% at 8 hours, between about 50% and about 100% at 12 hours, between about 60% and about 100% at 16 hours, between about 80% and about 100% at 24 hours, and greater than about 95% at 36 hours.

In some preferred embodiments, the oral dosage form of the present invention is directed to an oral dosage form comprising (i) a proserotonergic agent and (ii) a serotonin surge protector; said proserotonergic agent dosage form providing an in-vitro release rate by weight of the proserotonergic agent, when measured by the USP Basket and Paddle Methods at 100 rpm in 900 mL aqueous buffer at a pH of between 1.6 and 7.2 at 37° C. of between 20% and about 50% at 1 hour, between about 40% and about 75% at 2 hours, between about 60% and about 95% at 4 hours, between about 80% and about 100% at 8 hours and between about 90% and about 100% at 12 hours. In other preferred embodiments, said release rate is between 15% and about 45% at 1 hour, between about 35% and about 70% at 2 hours, between about 55% and about 90% at 4 hours, between about 75% and about 90% at 8 hours and between about 80% and about 95% at 12 hours; or between 10% and about 40% at 1 hour, between about 30% and about 65% at 2 hours, between about 50% and about 85% at 4 hours, between about 70% and about 85% at 8 hours and between about 75% and about 90% at 12 hours; or between 5% and about 35% at 1 hour, between about 25% and about 60% at 2 hours, between about 45% and about 80% at 4 hours, between about 65% and about 80% at 8 hours and between about 70% and about 85% at 12 hours; or between 25% and about 55% at 1 hour, between about 45% and about 80% at 2 hours, between about 65% and about 95% at 4 hours, between about 85% and about 100% at 8 hours and between about 95% and about 100% at 12 hours; or between 30% and about 60% at 1 hour, between about 50% and about 80% at 2 hours, between about 70% and about 95% at 4 hours, between about 90% and about 100% at 8 hours and between about 95% and about 100% at 12 hours; or between 35% and about 60% at 1 hour, between about 50% and about 80% at 2 hours, between about 80% and about 95% at 4 hours, between about 90% and about 100% at 8 hours and between about 95% and about 100% at 12 hours; or between 20% and about 40% at 1 hour, between about 40% and about 65% at 2 hours, between about 60% and about 85% at 4 hours, between about 70% and about 90% at 8 hours and between about 80% and about 100% at 12 hours.

In some preferred embodiments, the oral dosage form of the present invention is directed to an oral dosage form comprising (i) a proserotonergic agent and (ii) a serotonin surge protector; said proserotonergic agent dosage form providing an in-vitro release rate by weight of the proserotonergic agent, when measured by the USP Basket and Paddle Methods at 100 rpm in 900 mL aqueous buffer at a pH of between 1.6 and 7.2 at 37° C. of between 0% and about 50% at 1 hour, between about 0% and about 75% at 2 hours, between about 10% and about 95% at 4 hours, between about 35% and about 100% at 8 hours, between about 55% and about 100% at 12 hours, between about 70% to about 100% at 16 hours, and greater than about 90% at 24 hours. In other preferred embodiments, said release rate is between 0% and about 40% at 1 hour, between about 0% and about 65% at 2 hours, between about 8% and about 85% at 4 hours, between about 30% and about 90% at 8 hours, between about 45% and about 100% at 12 hours, between about 60% to about 100% at 16 hours, and greater than about 80% at 24 hours; or between 0% and about 30% at 1 hour, between about 0% and about 55% at 2 hours, between about 5% and about 75% at 4 hours, between about 20% and about 80% at 8 hours, between about 35% and about 100% at 12 hours, between about 50% to about 100% at 16 hours, and greater than about 70% at 24 hours; or between 0% and about 20% at 1 hour, between about 0% and about 45% at 2 hours, between about 5% and about 65% at 4 hours, between about 10% and about 70% at 8 hours, between about 25% and about 80% at 12 hours, between about 40% to about 100% at 16 hours, and greater than about 60% at 24 hours; or between 0% and about 60% at 1 hour, between about 0% and about 80% at 2 hours, between about 15% and about 95% at 4 hours, between about 40% and about 100% at 8 hours, between about 60% and about 100% at 12 hours, between about 75% to about 100% at 16 hours, and greater than about 90% at 24 hours; or between 0% and about 65% at 1 hour, between about 0% and about 85% at 2 hours, between about 20% and about 90% at 4 hours, between about 45% and about 100% at 8 hours, between about 65% and about 100% at 12 hours, between about 80% to about 100% at 16 hours, and greater than about 90% at 24 hours; or between 0% and about 40% at 1 hour, between about 0% and about 50% at 2 hours, between about 10% and about 80% at 4 hours, between about 25% and about 70% at 8 hours, between about 40% and about 80% at 12 hours, between about 60% to about 100% at 16 hours, and greater than about 90% at 24 hours.

In some preferred embodiments, the oral dosage form of the present invention is directed to an oral dosage form comprising (i) a proserotonergic agent and (ii) a serotonin surge protector; said proserotonergic agent dosage form providing an in-vitro release rate by weight of the proserotonergic agent, when measured by the USP Basket and Paddle Methods at 100 rpm in 900 mL aqueous buffer at a pH of between 1.6 and 7.2 at 37° C. of between 0% and about 30% at 1 hour, between about 0% and about 45% at 2 hours, between about 3% and about 55% at 4 hours, between about 10% and about 65% at 8 hours, between about 20% and about 75% at 12 hours, between about 30% to about 88% at 16 hours, between about 50% and about 100% hours at 24 hours and greater than 80% at 36 hours. In other preferred embodiments, said release rate is between 0% and about 25% at 1 hour, between about 0% and about 40% at 2 hours, between about 2% and about 50% at 4 hours, between about 8% and about 60% at 8 hours, between about 10% and about 70% at 12 hours, between about 25% to about 80% at 16 hours, between about 45% and about 100% hours at 24 hours and greater than 75% at 36 hours; or between 0% and about 20% at 1 hour, between about 0% and about 35% at 2 hours, between about 1% and about 45% at 4 hours, between about 5% and about 55% at 8 hours, between about 8% and about 65% at 12 hours, between about 20% to about 75% at 16 hours, between about 40% and about 100% hours at 24 hours and greater than 70% at 36 hours; or between 0% and about 15% at 1 hour, between about 0% and about 30% at 2 hours, between about 0% and about 40% at 4 hours, between about 5% and about 50% at 8 hours, between about 8% and about 60% at 12 hours, between about 15% to about 70% at 16 hours, between about 35% and about 100% hours at 24 hours and greater than 60% at 36 hours; or between 0% and about 10% at 1 hour, between about 0% and about 25% at 2 hours, between about 0% and about 35% at 4 hours, between about 5% and about 45% at 8 hours, between about 10% and about 50% at 12 hours, between about 10% to about 60% at 16 hours, between about 30% and about 90% hours at 24 hours and greater than 70% at 36 hours; or between 0% and about 35% at 1 hour, between about 0% and about 50% at 2 hours, between about 5% and about 60% at 4 hours, between about 15% and about 70% at 8 hours, between about 25% and about 80% at 12 hours, between about 35% to about 90% at 16 hours, between about 55% and about 100% hours at 24 hours and greater than 85% at 36 hours; or between 0% and about 40% at 1 hour, between about 0% and about 55% at 2 hours, between about 10% and about 65% at 4 hours, between about 20% and about 75% at 8 hours, between about 30% and about 85% at 12 hours, between about 40% to about 100% at 16 hours, between about 55% and about 100% hours at 24 hours and greater than 90% at 36 hours; or between 0% and about 45% at 1 hour, between about 0% and about 60% at 2 hours, between about 15% and about 70% at 4 hours, between about 25% and about 80% at 8 hours, between about 35% and about 90% at 12 hours, between about 45% to about 100% at 16 hours, between about 60% and about 100% hours at 24 hours and greater than 60% at 36 hours; or between 0% and about 50% at 1 hour, between about 5% and about 65% at 2 hours, between about 20% and about 75% at 4 hours, between about 30% and about 85% at 8 hours, between about 40% and about 95% at 12 hours, between about 50% to about 100% at 16 hours, between about 70% and about 100% hours at 24 hours and greater than 70% at 36 hours; or between 0% and about 30% at 1 hour, between about 5% and about 40% at 2 hours, between about 10% and about 60% at 4 hours, between about 20% and about 70% at 8 hours, between about 30% and about 100% at 12 hours, between about 40% to about 100% at 16 hours, between about 60% and about 100% hours at 24 hours and greater than 90% at 36 hours; or between 0% and about 30% at 1 hour, between about 0% and about 30% at 2 hours, between about 0% and about 30% at 4 hours, between about 5% and about 70% at 8 hours, between about 10% and about 80% at 12 hours, between about 20% to about 100% at 16 hours, between about 40% and about 100% hours at 24 hours and greater than 50% at 36 hours; or between 0% and about 20% at 1 hour, between about 0% and about 20% at 2 hours, between about 0% and about 20% at 4 hours, between about 0% and about 20% at 8 hours, between about 5% and about 40% at 12 hours, between about 10% to about 80% at 16 hours, between about 40% and about 100% hours at 24 hours and greater than 60% at 36 hours; or between 0% and about 10% at 1 hour, between about 0% and about 20% at 2 hours, between about 0% and about 40% at 4 hours, between about 5% and about 60% at 8 hours, between about 10% and about 80% at 12 hours, between about 20% to about 100% at 16 hours, between about 40% and about 100% hours at 24 hours and greater than 50% at 36 hours.

In some preferred embodiments, the oral dosage form of the present invention is directed to an oral dosage form comprising (i) a proserotonergic agent and (ii) a serotonin surge protector; said proserotonergic agent dosage form providing an in-vitro release rate by weight of the proserotonergic agent, when measured by the USP Basket and Paddle Methods at 100 rpm in 900 mL aqueous buffer at a pH of between 1.6 and 7.2 at 37° C. of between 0% and about 50% at 1 hour, between about 0% and about 75% at 2 hours, between about 3% and about 95% at 4 hours, between about 10% and about 100% at 8 hours, between about 20% and about 100% at 12 hours, between about 30% to about 100% at 16 hours, between about 50% and about 100% hours at 24 hours and greater than 80% at 36 hours. In other preferred embodiments, said release rate is between 0% and about 45% at 1 hour, between about 0% and about 70% at 2 hours, between about 3% and about 90% at 4 hours, between about 8% and about 100% at 8 hours, between about 15% and about 100% at 12 hours, between about 25% to about 100% at 16 hours, between about 45% and about 100% hours at 24 hours and greater than 80% at 36 hours; or between 0% and about 40% at 1 hour, between about 0% and about 65% at 2 hours, between about 0% and about 80% at 4 hours, between about 5% and about 80% at 8 hours, between about 10% and about 90% at 12 hours, between about 20% to about 100% at 16 hours, between about 40% and about 100% hours at 24 hours and greater than 70% at 36 hours; or between 0% and about 35% at 1 hour, between about 0% and about 60% at 2 hours, between about 0% and about 70% at 4 hours, between about 3% and about 70% at 8 hours, between about 5% and about 80% at 12 hours, between about 15% to about 100% at 16 hours, between about 30% and about 100% hours at 24 hours and greater than 40% at 36 hours; or between 0% and about 60% at 1 hour, between about 0% and about 80% at 2 hours, between about 5% and about 100% at 4 hours, between about 15% and about 100% at 8 hours, between about 30% and about 100% at 12 hours, between about 40% to about 100% at 16 hours, between about 60% and about 100% hours at 24 hours and greater than 70% at 36 hours; or between 0% and about 50% at 1 hour, between about 0% and about 75% at 2 hours, between about 5% and about 95% at 4 hours, between about 25% and about 80% at 8 hours, between about 30% and about 100% at 12 hours, between about 40% to about 100% at 16 hours, between about 60% and about 100% hours at 24 hours and greater than 60% at 36 hours; or between 0% and about 60% at 1 hour, between about 0% and about 85% at 2 hours, between about 5% and about 100% at 4 hours, between about 10% and about 100% at 8 hours, between about 20% and about 100% at 12 hours, between about 30% to about 100% at 16 hours, between about 50% and about 100% hours at 24 hours and greater than 80% at 36 hours.

In some preferred embodiments, the oral dosage form of the present invention is directed to an oral dosage form comprising (i) a proserotonergic agent and (ii) a serotonin surge protector; said proserotonergic agent dosage form providing an in-vitro release rate by weight of the proserotonergic agent, when measured by the USP Basket and Paddle Methods at 100 rpm in 900 mL aqueous buffer at a pH of between 1.6 and 7.2 at 37° C. of between 15% and about 25% at 1 hour, between about 25% and about 35% at 2 hours, between about 30% and about 45% at 4 hours, between about 40% and about 60% at 8 hours, between about 55% and about 70% at 12 hours and between about 60% to about 75% at 16 hours. In other preferred embodiments, said release rate is between 10% and about 20% at 1 hour, between about 20% and about 30% at 2 hours, between about 25% and about 40% at 4 hours, between about 30% and about 50% at 8 hours, between about 50% and about 65% at 12 hours and between about 55% to about 65% at 16 hours; or between 5% and about 15% at 1 hour, between about 15% and about 25% at 2 hours, between about 20% and about 35% at 4 hours, between about 25% and about 45% at 8 hours, between about 45% and about 60% at 12 hours and between about 50% to about 60% at 16 hours; or between 15% and about 30% at 1 hour, between about 20% and about 40% at 2 hours, between about 20% and about 50% at 4 hours, between about 30% and about 70% at 8 hours, between about 60% and about 80% at 12 hours and between about 70% to about 90% at 16 hours; or between 0% and about 50% at 1 hour, between about 5% and about 50% at 2 hours, between about 5% and about 70% at 4 hours, between about 10% and about 80% at 8 hours, between about 20% and about 100% at 12 hours and between about 40% to about 100% at 16 hours; or between 15% and about 40% at 1 hour, between about 15% and about 45% at 2 hours, between about 20% and about 60% at 4 hours, between about 20% and about 80% at 8 hours, between about 30% and about 90% at 12 hours and between about 40% to about 100% at 16 hours.

In some preferred embodiments, the oral dosage form of the present invention is directed to an oral dosage form comprising (i) a proserotonergic agent and (ii) a serotonin surge protector; said proserotonergic agent dosage form providing an in-vitro release rate which is substantially independent of pH in that a difference, at any given time, between an amount of proserotonergic agent released at one pH and an amount released at any other pH, when measured in-vitro using the USP Basket and Paddle Methods of USP Drug Release test of U.S. Pharmacopeia (2003) at 100 rpm in 900 ml aqueous buffer, is no greater than 30%. In other preferred embodiments, the difference, at any given time, between an amount of proserotonergic agent released at one pH and an amount released at any other pH using the aforementioned methods is no greater than 50%, or no greater than 40%, or no greater than 35%, or no greater than 25%, or no greater than 20%, or no greater than 15%, or no greater than 10%, or no greater than 5%.

In some preferred embodiments, the oral dosage form of the present invention is directed to an oral dosage form comprising (i) a proserotonergic agent and (ii) a serotonin surge protector; said proserotonergic agent dosage form providing in-vitro release rates by weight of between 0% to about 50% by weight of the proserotonergic agent from the dosage form at one hour when measured by the USP Basket and Paddle Methods at 100 rpm in 700 ml of Simulated Gastric Fluid (SGF) at 37° C. In other preferred embodiments, said release rate at one hour is between 0% to about 10% by weight, or 0% to about 20% by weight, or is between 0% to about 30% by weight, or 0% to about 40% by weight, or between 0% to about 60% by weight, or 0% to about 70% by weight, or 0% to about 80% by weight, or 0% to about 90% by weight, or 10% to about 50% by weight, or 10% to about 60% by weight, or 10% to about 70% by weight, or 10% to about 90% by weight, or 10% to about 100% by weight, or 30% to about 100% by weight, or 50% to about 100% by weight.

In some preferred embodiments, the oral dosage form of the present invention is directed to an oral dosage form comprising (i) a proserotonergic agent and (ii) a serotonin surge protector; said proserotonergic agent dosage form providing in-vitro release rate by weight of proserotonergic agent, when measured by the USP Basket and Paddle Methods at 100 rpm in 900 mL aqueous buffer at a pH of between 1.6 and 7.2 at 37° C. of between 0% to about 80% at 0.5 hours, and greater than about 40% at 1 hour. In other preferred embodiments, said release rate is between 0% to about 40% at 0.5 hours, and greater than about 60% at 1 hour; or between 0% to about 20% at 0.5 hours, and greater than about 40% at 1 hour; or between 0% to about 20% at 0.5 hours, and greater than about 20% at 1 hour; or between 0% to about 90% at 0.5 hours, and greater than about 60% at 1 hour; or between 0% to about 100% at 0.5 hours, and greater than about 60% at 1 hour; or between 0% to about 90% at 1 hour, and greater than about 40% at 2 hours; or between 0% to about 100% at 1 hour, and greater than about 60% at 2 hours; or between 0% to about 60% at 1 hour, and greater than about 40% at 2 hours; or between 0% to about 40% at 1 hour, and greater than about 30% at 2 hours; or between 0% to about 50% at 1 hour, and greater than about 40% at 2 hours; or between 0% to about 30% at 1 hour, and greater than about 20% at 2 hours; or between 0% and about 50% at 1 hour, between about 0% and about 80% at 2 hours, between about 5% and about 100% at 4 hours and between about 10% and about 100% at 8 hours; or between 10% and about 60% at 1 hour, between about 15% and about 75% at 2 hours, between about 20% and about 95% at 4 hours and between about 30% and about 100% at 8 hours.

In some preferred embodiments, the oral dosage form of the present invention is directed to an oral dosage form comprising (i) a proserotonergic agent and (ii) a serotonin surge protector, such that the ratio of the mean $C_{max}$ of the proserotonergic agent after single dose oral administration of the dosage form after tampering to the mean $C_{max}$ of proserotonergic agent after single dose oral administration of an intact dosage form is not more than about 20:1. In other embodiments of the invention, the mean $C_{max}$ ratio using the aforementioned test method is not more than about 15:1, or about 10:1, or about 7.5:1, or about 6:1, or about 5:1, or about 4:1, or about 3:1, or about 2:1, or about 1.5:1, or about 1.25:1.

In some preferred embodiments, the oral dosage form of the present invention is directed to an oral dosage form comprising (i) a proserotonergic agent and (ii) a serotonin surge protector, such that the ratio of the mean $C_{max}$ of the proserotonergic agent after single dose oral administration of an immediate release reference product containing an equivalent amount of proserotonergic agent to the mean $C_{max}$ of proserotonergic agent after single dose oral administration of an intact dosage form of the invention is at least about 1.25:1. In other embodiments of the invention, the mean $C_{max}$ ratio using the aforementioned test method is at least about 1.5:1, or about 2:1, or about 3:1, or about 4:1, or about 5:1, or about 6:1, or about 10:1, or about 15:1 or about 20:1.

In some preferred embodiments, the oral dosage form of the present invention is directed to an oral dosage form comprising (i) a proserotonergic agent and (ii) a serotonin surge protector, such that the ratio of the mean $AUC_{0-2}$ of the proserotonergic agent after single dose oral administration of the dosage form after tampering to the mean $AUC_{0-2}$ of proserotonergic agent after single dose oral administration of an intact dosage form is not more than about 20:1. In other embodiments, the mean AUC ratio using the aforementioned test method is measured from time 0 to up to 1, 2.5, 3, 4, 5 or 6 hours post dose (i.e., $AUC_{0-1}$, $AUC_{0-2.5}$, $AUC_{0-3}$, $AUC_{0-4}$, $AUC_{0-5}$ and $AUC_{0-6}$, respectively). In other embodiments of the invention, the mean $AUC_{0-1}$, $AUC_{0-2}$, $AUC_{0-2.5}$, $AUC_{0-3}$, $AUC_{0-4}$, $AUC_{0-5}$ and $AUC_{0-6}$ ratios using the aforementioned test method are not more than about 15:1, or about 10:1, or about 7.5:1, or about 6:1, or about 5:1, or about 4:1, or about 3:1, or about 2:1 or about 1.5:1.

In some preferred embodiments, the oral dosage form of the present invention is directed to an oral dosage form comprising (i) a proserotonergic agent and (ii) a serotonin surge protector, such that the ratio of the mean $AUC_{0-2}$ of the proserotonergic agent after single dose oral administration of an immediate release reference product containing an equivalent amount of proserotonergic agent to the mean $AUC_{0-2}$ of proserotonergic agent after single dose oral administration of an intact dosage form of the invention is at least about 1.25:1. In other embodiments, the mean AUC ratio using the aforementioned test method is measured from time 0 to up to 1, 2.5, 3, 4, 5 or 6 hours post dose (i.e., $AUC_{0-1}$, $AUC_{0-2.5}$, $AUC_{0-3}$, $AUC_{0-4}$, $AUC_{0-5}$ and $AUC_{0-6}$, respectively). In other embodiments of the invention, the mean $AUC_{0-1}$, $AUC_{0-2}$, $AUC_{0-2.5}$, $AUC_{0-3}$, $AUC_{0-4}$, $AUC_{0-5}$ and $AUC_{0-6}$ ratios using the aforementioned test method are not more than about 15:1, or about 10:1, or about 7.5:1, or about 6:1, or about or about 5:1, or about 4:1, or about 3:1, or about 2:1 or about 1.5:1.

In some preferred embodiments, the oral dosage form of the present invention is directed to an oral dosage form comprising (i) a proserotonergic agent and (ii) a serotonin surge protector, such that the ratio of the mean $T_{max}$ of the proserotonergic agent after single dose oral administration of the intact dosage form to the mean $T_{max}$ of proserotonergic agent after single dose oral administration of an dosage form after tampering is not more than about 20:1. In other embodiments of the invention, the mean $T_{max}$ ratio using the aforementioned test method is not more than about 15:1, or not more than about 10:1, or not more than about 7.5:1, or not more than about 6:1, or not more than about 5:1, or not more than about 4:1, or not more than about 3:1, or not more than about 2:1, or not more than about 1.5:1, or not more than about 1.25:1.

In some preferred embodiments, the oral dosage form of the present invention is directed to an oral dosage form comprising (i) a proserotonergic agent and (ii) a serotonin surge protector, such that the ratio of the mean $T_{max}$ of the proserotonergic agent after single dose oral administration of an immediate release reference product containing an equivalent amount of proserotonergic agent to the mean $T_{max}$ of proserotonergic agent after single dose oral administration of an intact dosage form of the invention is at least about 1.25:1. In other embodiments of the invention, the mean $T_{max}$ ratio using the aforementioned test method is at least about 1.5:1, or at least about 2:1, or at least about 3:1, or at least about 4:1, or at least about 5:1, or at least about 6:1, or at least about 10:1, or at least about 15:1 or at least about 20:1.

In some preferred embodiments, the oral dosage form of the present invention is directed to an oral dosage form comprising (i) a proserotonergic agent and (ii) a serotonin surge protector, such that less than 70% of the proserotonergic agent is released from the intact dosage form after 1 hour based on the in-vitro dissolution of the dosage form in 900 mL of 40% ethanol in water using the USP Basket and Paddle Methods at 50 rpm and 37° C. In other embodiments of the invention, the release rate of the proserotonergic agent from the intact dosage form by the aforementioned USP basket method at 1 hours is 60% or less, 50% or less, 45% or less, 40% or less, 35% or less, 33% or less, 30% or less, 25% or less, 20% or less or 15% or less.

In certain preferred embodiments of the invention, the mean ratio of the amount of proserotonergic agent released from the dosage form after mechanical tampering (e.g., after crushing with a single crush of a spatula or in the case of a capsule containing a solid, cutting into two pieces) to the amount of proserotonergic agent released from the intact dosage form based on the dissolution at 0.5 hours of the dosage form in 900 mL of Simulated Gastric Fluid using the USP Basket and Paddle Methods at 50 rpm at 37 degrees ° C. is less than 20:1. In other embodiments of the invention, the mean ratio by the aforementioned USP basket method at 0.5 hours is 15:1 or less, 10:1 or less, 7.5:1 or less, 5:1 or less. 3:1 or less, 2:1 or less, 1.5:1 or less.

In certain preferred embodiments of the invention, the mean ratio of the amount of proserotonergic agent released from the dosage form after mechanical tampering (e.g., after crushing with a single crush of a spatula or in the case of a capsule containing a solid, cutting into two pieces) to the amount of proserotonergic agent released from the intact dosage form based on the dissolution at 1 hour of the dosage form in 900 mL of Simulated Gastric Fluid using the USP Basket and Paddle Methods at 50 rpm at 37 degrees ° C. is less than 20:1. In other embodiments of the invention, the mean ratio by the aforementioned USP basket method at 1 hour is 15:1 or less, 10:1 or less, 7.5:1 or less, 5:1 or less. 3:1 or less, 2:1 or less, 1.5:1 or less.

In certain preferred embodiments of the invention, the mean ratio of the amount of proserotonergic agent released from the dosage form after mechanical tampering (e.g., after crushing with a single crush of a spatula or in the case of a capsule containing a solid, cutting into two pieces) to the amount of proserotonergic agent released from the intact dosage form based on the dissolution at 2 hours of the dosage form in 900 mL of Simulated Gastric Fluid using the USP Basket and Paddle Methods at 50 rpm at 37 degrees ° C. is less than 20:1. In other embodiments of the invention, the mean ratio by the aforementioned USP basket method at 2 hours is 15:1 or less, 10:1 or less, 7.5:1 or less, 5:1 or less. 3:1 or less, 2:1 or less, 1.5:1 or less.

In some preferred embodiments, the oral dosage form of the present invention is directed to an oral dosage form comprising (i) a proserotonergic agent and (ii) a serotonin surge protector, such that the ratio of the mean $C_{max}$ of the proserotonergic agent after single dose oral administration of the dosage form after tampering to the mean $C_{max}$ of proserotonergic agent after single dose oral administration of an intact dosage form is less than about 20:1. In other embodiments of the invention, said mean ratio using the aforementioned test method is less than about 15:1 or less than about 10:1, or less than about 7:1, or less than about 5:1, or less than about 4:1, or less than about 3:1, or less than about 2.5:1, or less than about 2:1, or less than about 1.75:1, or less than about 1.5:1, or less than about 1.25:1 or less than about 1.25:1

In some preferred embodiments, the oral dosage form of the present invention is directed to an oral dosage form comprising (i) a proserotonergic agent and (ii) a serotonin surge protector, such that the ratio of the mean $AUC_{0-2}$ of the proserotonergic agent after single dose oral administration of an immediate release dosage form containing an equivalent amount of proserotonergic agent to the mean $AUC_{0-2}$ of proserotonergic agent after single dose oral administration of an intact dosage form of the invention is at least 1.25:1. In other embodiments of the invention, the mean $AUC_{0-2}$ ratio using the aforementioned test method is at least about 1.5:1, or at least about 1.75:1, or at least about 2:1, or at least about 2.5:1, or at least about 3:1, or at least about 3.5:1, or at least about 4:1, or at least about 5:1, or at least about 6:1, or at least about 10:1 or at least about 15:1 or at least about 20:1.

The invention is also directed to methods of preventing or reducing the serotonin syndrome utilizing the dosage forms disclosed herein. The method can in some embodiments, comprise providing the proserotonergic agent and one or more serotonin surge protectors, in an oral dosage form wherein the proserotonergic agent is present in a form which is partially or substantially resistant to serotonin excess upon deliberate or inadvertent tampering.

In certain preferred embodiments of the invention, the release for the proserotonergic agent component of the formulation is expressed in terms of a ratio of the release achieved after tampering, relative to the amount released from the intact formulation. The ratio is therefore expressed as [Crushed]/[Whole], and it is desired that this ratio have a numerical range of not more than 20:1 (crushed release in 1 hour/intact release in 1 hour), based on in-vitro dissolution of the dosage form in 900 ml of Simulated Gastric Fluid using the USP Basket and Paddle Methods at 50 rpm and 37° C. In other embodiments of the invention, the mean ratio using the aforementioned test method is less than about 15:1, or less than about 10:1, or less than about 7:1, or less than about 5:1, or less than about 3:1, or less than about 2:1, or less than about 1.5:1, or less than about 1.25:1.

In some embodiments, the proserotonergic agent dosage form of the invention is bioequivalent when taken under fed and fasted conditions.

In some embodiments, the proserotonergic agent dosage form of the invention upon administration provides a mean fed to fasted proserotonergic agent $AUC_{0-\infty}$ difference of less than about 50%, or less than about 45%, or less than about 40%, or less than about 35%, or less than about 30%, or less than about 27%, or less than about 25%, or less than about 22%, or less than about 20% or less than about 18%, or less than about 15%, or less than about 12%, or less than about 10%, or less than about 8%, or less than about 6%, or less than about 5%, or less than about 3%.

In some embodiments, the proserotonergic agent dosage form of the invention upon administration provides a mean fed to fasted proserotonergic agent $C_{max}$ difference of less than about 50%, or less than about 45%, or less than about 40%, or less than about 35%, or less than about 30%, or less than about 27%, or less than about 25%, or less than about 22%, or less than about 20% or less than about 18%, or less than about 15%, or less than about 12%, or less than about 10%, or less than about 8%, or less than about 6%, or less than about 5%, or less than about 3%.

In some preferred embodiments, the oral dosage form contains a proserotonergic agent, in an amount ranging from about 0.00001 mg to about 3000 mg, or about 0.00001 mg to about 2000 mg, or about 0.001 mg to about 3000 mg, or about 0.01 mg to about 1500 mg, or about 0.1 mg to about 1500 mg, or about 0.1 mg to about 1400 mg, or about 0.1 mg to about 1300 mg, or about 0.1 mg to about 1200 mg, or about 0.1 mg to about 1100 mg, or about 0.1 mg to about 1000 mg, or about 0.1 mg to about 900 mg, or about 0.1 mg to about 800 mg, or about 0.1 mg to about 700 mg, or about 0.1 mg to about 600 mg, or about 0.1 mg to about 500 mg, or about 0.1 mg to about 400 mg, or about 0.1 mg to about 300 mg, or about 0.1 mg to about 200 mg, or about 0.01 mg to about 1000 mg, or about 1 mg to about 800 mg, or about 1 mg to about 600 mg, or about 5 mg to about 1000 mg, or about 10 mg to about 1000 mg, or about 25 mg to about 1000 mg, or about 50 mg to about 1000 mg.

In some preferred embodiments, the oral dosage form contains a serotonin surge protector, in an amount ranging from about 1 mg to about 3000 mg, or about 5 mg to about 3000 mg, or about 10 mg to about 3000 mg, or about 25 mg to about 3000 mg, or about 50 mg to about 3000 mg, or about 100 mg to about 3000 mg, or about 150 mg to about 3000 mg, or about 1 mg to about 2000 mg, or about 5 mg to about 2000 mg, or about 10 mg to about 2000 mg, or about 25 mg to about 2000 mg, or about 50 mg to about 2000 mg, or about 100 mg to about 2000 mg, or about 150 mg to about 2000 mg, or about 1 mg to about 1000 mg, or about 5 mg to about 1000 mg, or about 10 mg to about 1000 mg, or about 25 mg to about 1000 mg, or about 50 mg to about 1000 mg, or about 100 mg to about 1000 mg, or about 150 mg to about 1000 mg.

In certain preferred embodiments of the invention comprising (i) a proserotonergic agent and (ii) a serotonin surge protector, wherein the proserotonergic agent is an analgesic, the mean ratio of the time to confirmed perceptible pain relief after administration of the intact dosage form to the time to confirmed perceptible pain relief after administration of the tampered dosage form is less than 20:1. In other embodiments of the invention, the mean ratio using the aforementioned test method is less than about 15:1, or less than about 10:1, or less than about 7:1, or less than about 5:1, or less than about 3:1, or less than about 2:1, or less than about 1.5:1, or less than about 1.25:1.

In certain preferred embodiments of the invention comprising (i) a proserotonergic agent and (ii) a serotonin surge protector, wherein the proserotonergic agent is an analgesic, the mean ratio of the time to meaningful pain relief after administration of the intact dosage form to the time to meaningful pain relief after administration of the tampered dosage form is less than 20:1. In other embodiments of the invention, the mean ratio using the aforementioned test method is less than about 15:1, or less than about 10:1, or less than about 7:1, or less than about 5:1, or less than about 3:1, or less than about 2:1, or less than about 1.5:1, or less than about 1.25:1.

In certain preferred embodiments of the invention comprising (i) a proserotonergic agent and (ii) a serotonin surge protector, wherein the proserotonergic agent is an analgesic, the mean ratio of the peak pain intensity difference score after administration of the tampered dosage form to the peak pain intensity difference score after administration of the intact dosage form is less than 10:1. In other embodiments of the invention, the mean ratio using the aforementioned test method is less than about 8:1, or less than about 7:1, or less than about 5:1, or less than about 3:1, or less than about 2:1, or less than about 1.5:1, or less than about 1.25:1.

In certain preferred embodiments of the invention comprising (i) a proserotonergic agent and (ii) a serotonin surge protector, wherein the proserotonergic agent is an analgesic, the mean ratio of the peak pain relief score after administration of the tampered dosage form to the peak pain relief score after administration of the intact dosage form is less than 10:1. In other embodiments of the invention, the mean ratio using the aforementioned test method is less than about 8:1, or less than about 7:1, or less than about 5:1, or less than about 3:1, or less than about 2:1, or less than about 1.5:1, or less than about 1.25:1.

In certain preferred embodiments of the invention comprising (i) a proserotonergic agent and (ii) a serotonin surge protector, wherein the proserotonergic agent is an analgesic, the mean ratio of change from baseline to two hours post-dose in pain intensity score after administration of the tampered dosage form to the change from baseline to two hours post-dose in pain intensity score after administration of the intact dosage form is less than 20:1. In other embodiments of the invention, the mean ratio using the aforementioned test method is less than about 15:1, or less than about 10:1, or less than about 7:1, or less than about 5:1, or less than about 3:1, or less than about 2:1, or less than about 1.5:1, or less than about 1.25:1.

In certain preferred embodiments of the invention comprising (i) a proserotonergic agent and (ii) a serotonin surge protector, wherein the proserotonergic agent is an analgesic, the mean ratio of the number of patients with pain who need to be treated to obtain ≧50% pain relief in one patient (i.e., number needed to treat or NNT) after administration of the tampered dosage form to the NNT after administration of the intact dosage form is less than 20:1. In other embodiments of the invention, the mean ratio using the aforementioned test method is less than about 15:1, or less than about 10:1, or less than about 7:1, or less than about 5:1, or less than about 3:1, or less than about 2:1, or less than about 1.5:1, or less than about 1.25:1. Preferably, the aforementioned at NNT is measured at 0.5, 1, 1.5, 2, 3, 4, 5 or 6 hours post-dose.

In certain preferred embodiments of the invention comprising (i) a proserotonergic agent and (ii) a serotonin surge protector, wherein the proserotonergic agent produces nausea, the mean ratio of the number needed to harm (referred to hereinafter as "NNH") due to moderate or severe nausea in healthy subjects (naïve to said analgesic) after administration of the tampered dosage form to the NNH after administration of the intact dosage form is less than 20:1. In other embodiments of the invention, the mean ratio using the aforementioned test method is less than about 15:1, or less than about 10:1, or less than about 7:1, or less than about 5:1, or less than about 3:1, or less than about 2:1, or less than about 1.5:1, or less than about 1.25:1. Preferably, the aforementioned at NNH is measured at 0.5, 1, 1.5, 2, 3, 4, 5 or 6 hours post-dose.

In certain preferred embodiments of the invention comprising (i) a proserotonergic agent and (ii) a serotonin surge protector, wherein the proserotonergic agent produces nausea on administration to naïve (i.e., proserotonergic agent naïve) healthy subjects, the mean ratio of the NNH due to moderate or severe nausea in naïve healthy subjects after administration of the tampered dosage form to the NNH after administration of the intact dosage form is less than 20:1. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1. Preferably, the aforementioned at NNH is measured at 0.5, 1, 1.5, 2, 3, 4, 5 or 6 hours post-dose.

In certain preferred embodiments of the invention comprising (i) a proserotonergic agent and (ii) a serotonin surge protector, wherein the proserotonergic agent produces sedation, the mean ratio of the NNH due to moderate or severe sedation or drowsiness in healthy subjects (naïve to said analgesic) after administration of the tampered dosage form to the NNH after administration of the intact dosage form is less than 20:1. In other embodiments of the invention, the mean ratio using the aforementioned test method is less than about 15:1, or less than about 10:1, or less than about 7:1, or less than about 5:1, or less than about 3:1, or less than about 2:1, or less than about 1.5:1, or less than about 1.25:1. Preferably, the aforementioned at NNH is measured at 0.5, 1, 1.5, 2, 3, 4, 5 or 6 hours post-dose.

In certain preferred embodiments of the invention comprising (i) a proserotonergic agent and (ii) a serotonin surge protector, wherein the proserotonergic agent produces sedation is an analgesic, the mean ratio of the NNH due to moderate or severe sedation or drowsiness in healthy subjects who are naïve to said proserotonergic agent and who are occasional or light consumers of alcohol after administration of the tampered dosage form to the NNH after administration of the intact dosage form is less than 20:1, said NNH measured 2.5 to 6 hours after administration of the dosage form, said dosage form administration followed about 1.5 hours later by alcohol (ethanol) administration sufficient to maintain a blood alcohol concentration of 0.04% to 0.08%. In other embodiments of the invention, the mean ratio using the aforementioned test method is less than about 15:1, or less than about 10:1, or less than about 7:1, or less than about 5:1, or less than about 3:1, or less than about 2:1, or less than about 1.5:1, or less than about 1.25:1.

In certain preferred embodiments of the invention comprising (i) a proserotonergic agent and (ii) a serotonin surge protector, wherein the proserotonergic agent produces sedation or drowsiness on administration to naïve (i.e., proserotonergic agent naïve) healthy subjects, the mean ratio of the NNH due to moderate or severe sedation or drowsiness in healthy subjects who are naïve to said proserotonergic agent and who are occasional or light consumers of alcohol, after administration of the tampered dosage form to the NNH after administration of the intact dosage form is less than 20:1, said NNH measured 2.5 to 6 hours after administration of the dosage form, said dosage form administration followed about 1.5 hours later by alcohol (ethanol) administration sufficient to maintain a blood alcohol concentration of 0.04% to 0.08%. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1.

In certain preferred embodiments of the invention comprising (i) a proserotonergic agent and (ii) a serotonin surge protector, wherein patients have the medical condition for which the proserotonergic agent is medically used, the mean ratio of the number of patients who need to be treated (NNT) to obtain ≧50% reduction in the cardinal sign or symptom of the medical condition (e.g., pain relief when the medical condition is pain, depression rating score when the medical condition is depression, etc.) after administration of the tampered dosage form to the NNT after administration of the intact dosage form is less than 20:1. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1. Preferably, the aforementioned at NNT is measured at 0.5, 1, 1.5, 2, 3, 4, 5 or 6 hours post-dose.

In certain preferred embodiments of the invention comprising (i) a proserotonergic agent and (ii) a serotonin surge protector, upon administration of proserotonergic agent that produces dizziness to naïve (i.e., proserotonergic agent naïve) healthy subjects, the mean ratio of the NNH due to the incidence of dizziness in naïve healthy subjects after administration of the tampered dosage form to the NNH after administration of the intact dosage form is less than 20:1. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1. Preferably, the aforementioned at NNH is measured at 0.5, 1, 1.5, 2, 3, 4, 5 or 6 hours post-dose.

In certain preferred embodiments of the invention comprising (i) a proserotonergic agent and (ii) a serotonin surge protector, upon administration of proserotonergic agent that produces lightheadedness to naïve (i.e., proserotonergic agent naïve) healthy subjects, the mean ratio of the NNH due to the incidence of lightheadedness in naïve healthy subjects after administration of the tampered dosage form to the NNH after administration of the intact dosage form is less than 20:1. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less, than about 2:1, less than about 1.75:1, or less than about 15:1, or less than about 1.25:1, or less than about 1.1:1. Preferably, the aforementioned at NNH is measured at 0.5, 1, 1.5, 2, 3, 4, 5 or 6 hours post-dose.

In certain preferred embodiments of the invention comprising (i) a proserotonergic agent and (ii) a serotonin surge protector, upon administration of proserotonergic agent that produces dry mouth to naïve (i.e., proserotonergic agent naïve) healthy subjects, the mean ratio of the NNH due to the incidence of dry mouth in naïve healthy subjects after administration of the tampered dosage form to the NNH after administration of the intact dosage form is less than 20:1. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, or less than about 3:1, or less than about 2.5:1, or less than about 2:1, less than about 1.75:1, or less than about 15:1, or less than about 1.25:1, or less than about 1.1:1. Preferably, the aforementioned at NNH is measured at 0.5, 1, 1.5, 2, 3, 4, 5 or 6 hours post-dose.

In certain preferred embodiments of the invention comprising (i) a proserotonergic agent and (ii) a serotonin surge protector, upon administration of an abusable proserotonergic agent to drug abusers and recreational drug users, the mean ratio of the drug liking score after administration of the tampered dosage form to the mean ratio of the drug liking score after administration of the intact dosage form is less than 20:1. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1. Preferably, the aforementioned ratio is measured at 0.5, 1, 1.5, 2, 3, 4, 5 or 6 hours post-dose In certain preferred embodiments of the invention comprising (i) a proserotonergic agent and (ii) a serotonin surge protector, upon administration of abusable proserotonergic agent to drug abusers and recreational drug users, the mean ratio of the drug effect score after administration of the tampered dosage form to the mean ratio of the drug effect score after administration of the intact dosage form is less than 20:1. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1. Preferably, the aforementioned ratio is measured at 0.5, 1, 1.5, 2, 3, 4, 5 or 6 hours post-dose.

In certain preferred embodiments of the invention comprising (i) a proserotonergic agent and (ii) a serotonin surge protector, upon administration of abusable proserotonergic agent to drug abusers and recreational drug users, the mean ratio of the score on the "take again" questionnaire after administration of the tampered dosage form to the mean ratio of the score on the "take again" questionnaire after administration of the intact dosage form is less than 20:1. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1. Preferably, the aforementioned ratio is measured at 0.5, 1, 1.5, 2, 3, 4, 5 or 6 hours post-dose.

In certain preferred embodiments of the invention comprising (i) a proserotonergic agent and (ii) a serotonin surge protector, upon administration of abusable proserotonergic agent to drug abusers and recreational drug users, the mean ratio of the score on the "coasting" questionnaire after administration of the tampered dosage form to the mean ratio of the score on the "coasting" questionnaire after administration of the intact dosage form is less than 20:1. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1. Preferably, the aforementioned ratio is measured at 0.5, 1, 1.5, 2, 3, 4, 5 or 6 hours post-dose.

In certain preferred embodiments of the invention comprising (i) a proserotonergic agent and (ii) a serotonin surge protector, wherein the proserotonergic agent produces sedation or drowsiness on administration to naïve (i.e., proserotonergic agent naïve) healthy subjects, the mean ratio of impairment on the "critical tracking task" driving skills test in naïve healthy subjects after administration of the tampered dosage form to the impairment after administration of the intact dosage form is less than 20:1. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1. Preferably, the aforementioned ratio is measured at 0.5, 1, 1.5, 2, 3, 4, 5 or 6 hours post-dose.

In certain preferred embodiments of the invention comprising (i) a proserotonergic agent and (ii) a serotonin surge protector, wherein the proserotonergic agent produces sedation or drowsiness on administration to healthy subjects who are naïve to said proserotonergic agent and who are occasional or light consumers of alcohol, the mean ratio of impairment on the "critical tracking task" driving skills test score in naïve healthy subjects after administration of the tampered dosage form to the impairment after administration of the intact dosage form is less than 20:1, said "critical tracking task" driving skills test score measured 2.5 to 6 hours after administration of the dosage form, said dosage form administration followed about 1.5 hours later by alcohol (ethanol) administration sufficient to maintain a blood alcohol concentration of 0.04% to 0.08%. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1.

In certain preferred embodiments of the invention comprising (i) a proserotonergic agent and (ii) a serotonin surge protector, wherein the proserotonergic agent produces sedation or drowsiness on administration to naïve (i.e., proserotonergic agent naïve) healthy subjects, the mean ratio of impairment on the "stop signal task" driving skills test in naïve healthy subjects after administration of the tampered dosage form to the impairment after administration of the intact dosage form is less than 20:1. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1. Preferably, the aforementioned ratio is measured at 0.5, 1, 1.5, 2, 3, 4, 5 or 6 hours post-dose.

In certain preferred embodiments of the invention comprising (i) a proserotonergic agent and (ii) a serotonin surge protector, wherein the proserotonergic agent produces sedation or drowsiness on administration to healthy subjects who are naïve to said proserotonergic agent and who are occasional or light consumers of alcohol, the mean ratio of impairment on the "stop signal task" driving skills test score in naïve healthy subjects after administration of the tampered dosage form to the impairment after administration of the intact dosage form is less than 20:1, said "stop signal task" driving skills test score measured 2.5 to 6 hours after administration of the dosage form, said dosage form administration followed about 1.5 hours later by alcohol (ethanol) administration sufficient to maintain a blood alcohol concentration of 0.04% to 0.08%. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1.

In certain preferred embodiments of the invention comprising (i) a proserotonergic agent and (ii) a serotonin surge protector, wherein the proserotonergic agent produces sedation or drowsiness on administration to naïve (i.e., proserotonergic agent naïve) healthy subjects, the mean ratio of impairment on the "Tower of London" driving skills test score in naïve healthy subjects after administration of the tampered dosage form to the impairment after administration of the intact dosage form is less than 20:1. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1. Preferably, the aforementioned ratio is measured at 0.5, 1, 1.5, 2, 3, 4, 5 or 6 hours post-dose.

In certain preferred embodiments of the invention comprising (i) a proserotonergic agent and (ii) a serotonin surge protector, wherein the proserotonergic agent produces sedation or drowsiness on administration to healthy subjects who are naïve to said proserotonergic agent and who are occasional or light consumers of alcohol, the mean ratio of impairment on the "Tower of London" driving skills test score in naïve healthy subjects after administration of the tampered dosage form to the impairment after administration of the intact dosage form is less than 20:1 said "Tower of London" driving skills test score measured 2.5 to 6 hours after administration of the dosage form, said dosage form administration followed about 1.5 hours later by alcohol (ethanol) administration sufficient to maintain a blood alcohol concentration of 0.04% to 0.08%. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1.

The invention is also directed to a method of treating or preventing diseases and disorders amenable to treatment with proserotonergic agents. The method can comprise providing an oral dosage form containing a proserotonergic agent and a serotonin surge protector; said dosage form having a reduced propensity for causing the serotonin syndrome; said dosage form in immediate release form, or extended release form or a both immediate release and extended release from.

The oral dosage form containing an proserotonergic agent in combination with a serotonin surge protector includes, but is not limited to tablets or capsules. The dosage forms of the present invention may include any desired pharmaceutical excipients known to those skilled in the art. The oral dosage forms may further provide an immediate release of the proserotonergic agent. In certain preferred embodiments, the oral dosage forms of the present invention provide a sustained release of the proserotonergic agent contained therein. Oral dosage forms providing sustained release of the proserotonergic agent may be prepared in accordance with formulations/methods of manufacture known to those skilled in the art of pharmaceutical formulation.

In certain preferred embodiments, a combination of two proserotonergic agent is included in the formulation with the serotonin surge protector. In further embodiments, one or more proserotonergic agent and one or more serotonin surge protectors are included. In yet other embodiments, one or more proserotonergic agent and one or more serotonin surge protectors are included, and a further non-proserotonergic agent is also included for the treatment of the same medical condition as the proserotonergic agent or for the treatment of a different medical condition.

Another embodiment of the invention is directed to a method of preventing or treating pain, addiction disorders, spasticity, musculoskeletal disorders, depression, epilepsy, neuropathy, smoking cessation, nausea or vomiting, migraine, cough, insomnia, excessive sleepiness, daytime sleepiness, sleep disorders, anxiety disorders, panic attacks, agoraphobia, obsessive-compulsive disorders, Parkinson's disease, infectious diseases, psychiatric disorders, neurologic disorders, excess weight, obesity and other medical maladies responsive to treatment with the proserotonergic agents with the disclosed dosage forms. In certain preferred embodiments, the method of treating the aforementioned disorders in patients with a dosage form having a reduced frequency or intensity of signs and/or symptoms of the serotonin syndrome comprises providing an oral dosage form containing one or more proserotonergic agents and one or more serotonin surge protectors; and orally administering the dosage form to provide a plasma level of proserotonergic agent greater than the minimum therapeutic or minimum effective concentration of the proserotonergic agent.

The invention is also directed to methods of preparing the dosage forms disclosed herein.

In some embodiments of the invention, when the extended release dosage form of the invention is tampered, the amount of proserotonergic agent released in immediate release form is reduced, which in turn reduces the toxicity of the proserotonergic agent from the serotonin syndrome.

When the dosage form of the present invention is orally administered as intended to humans, the proserotonergic agents is released into systemic circulation as intended and is therefore available for absorption into the body. However, if the dosage forms of the present invention is tampered (e.g., chemical, solvent, thermal or mechanical extraction, followed by administration into the body) the serotonin surge protector of the invention would reduce the amount of proserotonergic agents available in immediate release form. Additionally, the dosage form of the invention substantially reduces the efficiency of drug aspiration into syringes, drug filtration after solvent extraction and drug extraction after attempts at chemical, mechanical or thermal extraction from both immediate and sustained release dosage form of the invention. These characteristic decrease the potential for toxicity of the proserotonergic agent from the serotonin syndrome.

The term "tampering" or "tamper" means any manipulation by mechanical, thermal and/or chemical means which changes the physical or chemical properties of the dosage form, e.g., to liberate the proserotonergic agents for immediate release if it is in sustained release form, or to make the proserotonergic agents available for inappropriate use such as administration by an alternate route, e.g., parenterally. The tampering can be, e.g., by means of crushing, shearing, grinding, mechanical extraction, solvent extraction, solvent immersion, combustion, heating or any combination thereof.

The term "tamper resistant", "deters tampering" and the like are used interchangeably in the context of the present invention and include pharmaceutical compositions and methods that resist, deter, discourage, diminish, delay and/or frustrate: (i) the intentional, unintentional or accidental physical or chemical manipulation or tampering of the dosage form (e.g., crushing, shearing, grinding, chewing, dissolving, melting, needle aspiration, inhalation, insufflation, extraction by mechanical, thermal and chemical means, and/or filtration); (ii) the intentional, unintentional or accidental use or misuse of the dosage form outside the scope of specific instructions for use provided by a qualified medical professional, or outside the supervision of a qualified medical professional and outside the approved instructions on proper use provided by the drug's legal manufacturer (e.g., intravenous use, intranasal use, inhalational use and oral ingestion to provide high peak concentrations); (iii) the intentional, unintentional or accidental conversion of an extended release dosage form of the invention into a more immediate release form; (iv) in the case of abusable proserotonergic agents, the intentional and iatrogenic increase in physical and psychic effects sought by recreational drug users, addicts, and patients with pain who have an addiction disorder; (v) attempts at surreptitious administration of the dosage form to a third party (e.g., in a beverage); (vi) attempts to procure the dosage form by manipulation of the medical system and from non-medical sources; (vii) the sale or diversion of the dosage form into the non-medical supply chain and for medically unapproved or unintended mood altering purposes; (viii) the intentional, unintentional or accidental attempts at otherwise changing the physical, pharmaceutical, pharmacological and/or medical properties of the dosage form from what was intended by the manufacturer.

As used herein, the term "aversive agents", "aversion producing agents" and "aversive compounds" means to compounds contained within the dosage form that produce an aversive, undesirable, repugnant, distasteful, unpleasant, unacceptable physiologic or unacceptable psychic effects, or that pharmacologically block or reduce one or more of the following effects: mood alterations; euphoria, pleasure; a feeling of high; a feeling of drug liking; anxiolysis; mental stimulation; increased mental arousal; sedation; calmness; a state of relaxation; psychotomimesis; hallucinations; alterations in perception, cognition and mental focus; insomnia; hypersomnia; increased wakefulness or alertness; memory improvement; increased sexual gratification; increased sexual arousal; increased sexual desire and sexual anticipation; increased socialization; reduced social anxiety; psychologically reinforcement; and psychologically rewarding.

In some embodiments, the intention of the aversive agent is deter or further deter the misuse, abuse, tampering or diversion of the drug. Preferably the aversive agent produces aversive effects only when the dosage form of the proserotonergic agent of the invention is abused. Preferably the aversive agent is contained within the dosage form at a dose or in a form that does not produce aversive effects when the dosage form of the proserotonergic agent of the invention is taken as medically directed or in a manner that is consistent with the manufacturer's prescribing information, but which when abused or tampered with, produces an aversive effect. For example, in some embodiments, the dosage form of the proserotonergic agent of the invention contains one or more aversive agents in a non-releasable form (i.e., sequestered) form, said aversive agent partially or substantially released upon tampering the dosage form (e.g., mechanical, thermal, chemical, solvent tampering, ingestion in ways not recommended, and the like). For example, in some other embodiments, the dosage form of the proserotonergic agent of the invention contains one or more aversive agents in releasable or partially releasable form, said dosage form not aversive when taken at medically approved doses or at doses consistent with the manufacturers prescribing information, said dosage form producing an aversive effect when taken in excess of medically approved doses or the manufacturers prescribing information. For example, in yet other embodiments, the dosage form of the proserotonergic agent of the invention contains one or more aversive agents in a non-releasable form (i.e., sequestered) form, said aversive agent partially or substantially released upon tampering the dosage form (e.g., mechanical, thermal, chemical, solvent tampering, ingestion in ways not recommended, and the like), and said aversive agent pharmacologically blocking the effects of the proserotonergic agent and/or the effects of a co-abused drug, said co-abused drug not part of the dosage form of the invention.

In some embodiments, the "serotonin surge protector" is one or more compounds selected from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes, and mixtures thereof. In some preferred embodiments, serotonin surge protector is a mixture of two or more compounds from the forgoing group [i.e., (a) to (d)]. In some preferred embodiments, to qualify as an "serotonin surge protector" requires a mixture of two or more compounds from the form the foregoing group [i.e., (a) to (d)]. In some preferred embodiments, to qualify as an "serotonin surge protector" requires a mixture of two or more compounds selected from at least two categories[i.e., (a) to (d)].

In some preferred embodiments, the present invention refers to pharmaceutical compositions, dosage forms, methods, processes and other innovations that comprise (i) one or more proserotonergic agents, in unsalified form or their pharmaceutically acceptable salts, prodrugs, esters, analogs, derivatives, solvates, complexes, polymorphs, hydrates and metabolites, as racemates or an individual diastereoisomers or enantiomeric isomers thereof or mixtures thereof, (ii) one or more compounds selected serotonin surge protectors selected from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes, and mixtures thereof, said compounds also referred to as serotonin surge protector; and optionally [(iii) and/or (iv)], (iii) other non-proserotonergic agents for the treatment of the same or a different medical condition; and/or (iv) pharmaceutical excipients, adjuvants and auxiliary agents including binders, disintegrants, fillers, diluents, anti-adherents or glidants, lubricants, stabilizers, wetting agents, pharmaceutically compatible carriers and dissolution rate modifiers, and channel and pore formers.

In some preferred embodiments, the present invention refers to pharmaceutical compositions, dosage forms, methods, processes and other innovations that comprise (i) one or more proserotonergic agents, in unsalified form or their pharmaceutically acceptable salts, prodrugs, esters, analogs, derivatives, solvates, complexes, polymorphs, hydrates and metabolites, as racemates or an individual diastereoisomers or enantiomeric isomers thereof or mixtures thereof; (ii) two or more serotonin surge protectors selected from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes, and mixtures thereof, said compounds also referred to as serotonin surge protector; and optionally [(iii) and/or (iv)], (iii) other abusable or non-proserotonergic agents for the treatment of the same or a different medical condition; and/or (iv) pharmaceutical excipients, adjuvants and auxiliary agents including binders, disintegrants, fillers, diluents, anti-adherents or glidants, lubricants, stabilizers, wetting agents, pharmaceutically compatible carriers and dissolution rate modifiers, and channel and pore formers.

In some preferred embodiments, the dosage form may optionally also contain serotonin surge protectors selected from the group comprising hydrophobic polymers, hydrophilic, polymers, gums, protein derived materials, other waxes, shellac, other oils and mixtures thereof.

In some preferred embodiments, the dosage form may optionally also contain hydrophobic polymers, hydrophilic polymers, gums, protein derived materials, other waxes, shellac, other oils and mixtures thereof.

In some preferred embodiments, the invention is directed at a proserotonergic agent dosage form, said dosage form having a non-toxic bittering agent to deter surreptitious attempts at intoxication of another subject (e.g., in an alcoholic or non-alcoholic beverage).

In some preferred embodiments, the invention is directed at a proserotonergic agent dosage form, said dosage form having a non-toxic bittering agent to deter oral or nasal ingestion of the dosage form.

In some preferred embodiments, the in vivo pharmacokinetic parameters of the specifications and claims are derived or determined from first administration. In other preferred embodiments, the in vivo pharmacokinetic parameters are derived or determined from steady state administration.

In some preferred embodiments, the in vivo pharmacokinetic parameters of the specifications and claims are derived or determined under fed conditions. In other preferred embodiments, the in vivo pharmacokinetic parameters are derived or determined under fasted conditions.

In some preferred embodiments, the in vivo pharmacokinetic parameters of the specifications and claims are derived or determined from an individual subject. In other preferred embodiments, the in vivo pharmacokinetic parameters are derived or determined from a population of subjects.

In some preferred embodiments, the in vivo pharmacokinetic parameters of the specifications and claims are derived or determined in subjects having a Body Mass Index (BMI) between 18 and 26 kg/m$^2$, inclusive (BMI=[weight in kg/height in m$^2$]×10,000). In some preferred embodiments, the in vivo pharmacokinetic parameters of the specifications and claims are derived or determined in subjects having a Body Mass Index (BMI)$\geq$38 kg/m$^2$.

When the proserotonergic agent is an analgesic or a drug which can prevent or treat pain, all pain states are contemplated by this invention, regardless of etiology, mechanisms, duration, prior treatment response and anatomic location, including acute pain, inflammatory pain, chronic pain, cancer pain, visceral pain and neuropathic pain.

Also disclosed are methods of providing relief in a human patient suffering from neuropathic and chronic pain comprising a therapeutically effective amount of oral proserotonergic agent which possesses analgesic properties or pharmaceutically acceptable salts thereof or mixtures thereof. In some preferred embodiments, the dosage form of the invention is intended for the treatment of neuropathic pain, peripheral neuropathic pain, central neuropathic pain, chronic pain, osteoarthritis, back pain, cancer pain, fibromyalgia, and chronic inflammatory pain.

The amount of proserotonergic agent in the oral dosage form will vary depending on variety of physiologic, pharmacologic, pharmacokinetic, pharmaceutical and physicochemical factors, including: (i) the choice of proserotonergic agent as the unsalified form, pharmaceutically acceptable salt or mixtures thereof; (ii) the nature of the oral dosage form (e.g, immediate release or extended release); (iii) the intensity and intractability of the medical condition; (iv) the absorption, metabolism, distribution and excretion of orally administered proserotonergic agent in healthy subjects and in patients with various diseases and disorders, including renal and hepatic impairment; (v) the presence of comorbid pathology; (vi) the patient's risk of iatrogenic side effects; (vii) the tolerability of the dose, including the patient's propensity for proserotonergic agent associated side effects; (viii) use of other drugs to treat the same medical condition; (ix) the efficiency of the dosage form; (x) the physicochemical properties of the proserotonergic agent, including its solubility and hydrophilicity.

The invention is also directed to methods of preparing the dosage forms disclosed herein.

The term "first administration" means administration of a dose of the present invention at the initiation of therapy to an individual patient or a patient population.

The term "steady state" means that the amount of the drug reaching the system is approximately the same as the amount of the drug leaving the system. Thus, at "steady-state", the patient's body eliminates the drug at approximately the same rate that the drug becomes available to the patient's system through absorption into the blood stream.

As used herein the terms: (i) "$AUC_{0-t}$" means area under the plasma drug concentration-time curve from time zero to the "t", where t is the time point of the maximum intended dosing frequency of the dosage form (e.g., 4 hours, 6 hours, 8 hours, 12 hours or 24 hours for dosage forms intended to be administered every 4 hours, every 6 hours, every 8 hours, every 12 hours and every 24 hours, respectively, thereby providing an $AUC_{0-t}$ time interval of 0 to 4 hours, 0 to 6 hours, 0 to 8 hours, 0 to 12 hours and 0 to 24 hours, respectively); (ii) "$AUC_{0-\infty}$" means area under the plasma drug concentration-time curve from time zero to infinity; (iii) "$AUC_{0-8}$" means area under the plasma drug concentration-time curve from time zero to 8 hours after dosing; (iv) "$AUC_{0-12}$" means area under the plasma drug concentration-time curve from time zero to 12 hours after dosing; (v) "$AUC_{0-24}$" means area under the plasma drug concentration-time curve from time zero to 24 hours after dosing; (vi) "$C_{max}$" means the maximum observed plasma drug concentration; (vii) "$C_8$" means the plasma drug concentration at 8 hours after dosing; (viii) "$C_{12}$" means the plasma drug concentration at 12 hours after dosing; (ix) "$C_{24}$" means the plasma drug concentration at 24 hours after dosing; (x) "$t_{max}$" or "$T_{max}$" means the time of the observed maximum drug concentration (also known as the time at which $C_{max}$ occurs); (xi) "$C_{min}$" means the minimum observed drug concentration following the maximum plasma concentration or the concentration at the end of the intended dosing interval; (xii) "time at which $C_{min}$ occurs" means the time at when the minimum observed drug concentration occurs; (xiii) "half value duration" or "HVD" means the duration over the dosing interval during which plasma concentration of drug are greater than or equal to one-half of $C_{max}$, obtained by calculating the time interval beginning when the interpolated concentration first equals or exceeds one-half of $C_{max}$ and ending at the first time point for which the interpolated concentration falls below one-half of $C_{max}$; (xiv) "$W_{50}$" means the duration of the dosing interval over which the plasma concentrations are equal to or greater than 50% of the peak concentration; (xv) "steady state" is a state of equilibrium wherein the amount of the drug reaching the system is approximately the same as the amount of the drug leaving the system or put another way, the patient's body eliminates the drug at approximately the same rate that the drug becomes available to the patient's system through absorption into the blood stream, said "time to steady state" measured by calculating the $C_{min}$ after each sequential dosing of drug administered at the intended dosing frequency until two consecutive $C_{min}$'s are not statistically different at a 10% significance level (p=0.10); (xvi) "percent fluctuation" means the variation in plasma concentrations of the drug computed as: (a) $(C_{max}-C_{min})/C_{min} \times 100$ (for an individual patient) and (mean $C_{max}$-mean $C_{min}$)/mean $C_{min} \times 100$ (for a population); or (b) $(C_{max}-C_{min})/C_{av} \times 100$ (for an individual patient) and (mean $C_{max}$-mean $C_{min}$)/mean $C_{av} \times 100$ (for a population); (xvii) "accumulation index" or "AI" means the ratio of the plasma concentration of the drug at the end of the intended dosing interval (i.e., 8 hours for a Q8H dosage form, 12 hours for a Q12H dosage form, and 24 hours for a Q24H dosage form) after administration, determined at steady-state ($C_{ssmin}$) to the plasma concentration of the drug at the end of the intended dosing interval determined at first administration (i.e., after the first dose); (xviii) "$AUC_{0-2}$" means area under the drug concentration-time curve from time zero to two hours post-dose.

Pharmacokinetic parameters of the invention are be computed from first administration and steady state pharmacokinetic studies conducted in an individual subject or in a population of subjects in the fasted or fed states. The AI and percent of steady state computations requires both first administration and steady state pharmacokinetic assessment.

In certain preferred embodiments of the present invention, an effective amount of proserotonergic agent in immediate release form is included in the controlled release unit dose proserotonergic agent formulation to be administered. The immediate release form of the proserotonergic agent is preferably included in an amount which is effective to shorten the time to $C_{max}$ or increase the magnitude of the $C_{max}$ of the proserotonergic agent in the blood (e.g., plasma). In such embodiments, an effective amount of the proserotonergic agent in immediate release form may be coated onto the substrates of the present invention. For example, where the extended release proserotonergic agent from the formulation is due to a controlled release coating, the immediate release layer would be overcoated on top of the controlled release coating. On the other hand, the immediate release layer maybe coated onto the surface of substrates wherein the proserotonergic agent is incorporated in a controlled release matrix. Where a plurality of the sustained release substrates comprising an effective unit dose of the proserotonergic agent are incorporated into a hard gelatin capsule, the immediate release portion of the proserotonergic agent dose may be incorporated into the gelatin capsule via inclusion of the sufficient amount of immediate release proserotonergic agent as a powder or granulate within the capsule. Alternatively, the gelatin capsule itself may be coated with an immediate release layer of the proserotonergic agent. In some other embodiments, the immediate release proserotonergic agent is in liquid form, for example as a capsule within a capsule or as a liquid in contact with an extended release dosage form within a capsule. One skilled in the art would recognize still other alternative manners of incorporating the immediate release proserotonergic agent into the unit dose. Such alternatives are deemed to be encompassed by the appended claims. By including such an effective amount of immediate release proserotonergic agent in the unit dose, they may experience of relatively higher levels of symptom relief or faster symptom relief.

In certain preferred embodiments, any one or all of the above in-vivo parameters are achieved after a first administration of the dosage form to a human patient or a population of human patients.

In certain alternative embodiments, any one or all of the above in-vivo parameters are achieved after steady state administration of the dosage form to a human patient or a population of human patients.

Perceptible Pain Relief, Confirmed Perceptible Pain Relief and Meaningful Pain Relief are assessed and defined as follows: At the time of dosing with the study medication, a trained member of study staff starts two stopwatches for each patient. The patient is instructed to stop the first stopwatch at the time of perceptible pain relief and the second stopwatch at the time when they first experience meaningful pain relief. The usual definitions of the perceptible and meaningful pain relief are as follows: Perceptible Pain Relief is when the patient begins to feel any pain relieving effect from the drug. The patient is typically instructed as follows: "I would like you to stop the first stopwatch when you first feel any pain relief whatsoever. This does not mean you feel completely better, although you might, but when you first feel any difference in the pain that you have had". Meaningful Pain Relief is when the patient feels their pain relief is meaningful to them. The patient is typically instructed as follows: "I would like you to stop the second stopwatch when you have meaningful pain relief. That is, when the relief from the pain is meaningful to you". Confirmed Perceptible Pain Relief is Perceptible Pain Relief in those patients who go on to also have Meaningful Pain Relief.

As used herein, "NNT" or "the number needed to treat" is the number of patients who need to be treated in order for one patient to obtain ≧50% reduction in signs or symptoms (e.g., ≧50% reduction in pain intensity or ≧50% reduction in depression rating score).

The "NNH" or "number needed to harm" is a measure that indicates how many patients would require a specific treatment to cause harm in one patient. As used herein, the "NNH or "number needed to harm" is a measure that indicates: (i) how many proserotonergic agent naïve healthy subjects would require treatment to cause moderate or severe sedation (or drowsiness) in one subject, where moderate to severe sedation or drowsiness is defined as a VAS score of ≧50 mm on a 100 mm scale bounded on the left by "no sedation or drowsiness" and on the right by "extreme sedation or drowsiness"; (ii) how many proserotonergic agent naïve healthy subjects would require treatment to cause moderate or severe nausea in one subject, where moderate to severe nausea is defined as a VAS score of ≧50 mm on a 100 mm scale bounded on the left by "no nausea" and on the right by "extreme nausea"; (iii) how many proserotonergic agent naïve healthy subjects would require treatment to cause dizziness in one subject, where dizziness is defined as unsteadiness, imbalance, lightheadedness, spinning sensation or sensation that one is falling; (iv) how many proserotonergic agent naïve healthy subjects would require treatment to cause a sensation of dry mouth in one subject, where dry mouth is defined as abnormal dryness of the mouth associated with decreased secretion of saliva.

The "drug effects" questionnaire assesses the extent to which subjects currently felt a drug effect, on a scale of 1 to 5 (1="I feel no effect from it at all"; 2="I think I feel a mild effect, but I'm not sure"; 3="I feel an effect, but it is not real strong"; 4="I feel a strong effect"; 5="I feel a very strong effect"). This questionnaire can be used to examine the overall drug effects of proserotonergic agents given intact and upon tampering, preferably in drug abusers and recreational drug users without the medical condition for which the drug is effective.

The "drug liking" questionnaire assesses the extent to which subjects currently like the effects of the drug on a 100-mm VAS, bounded on the left by "0=dislike a lot", bounded on the right by "100=like a lot". This questionnaire can be used to examine the overall drug liking of proserotonergic agents given intact and upon tampering, preferably in drug abusers and recreational drug users without the medical condition for which the drug is effective.

The "take again" questionnaire assesses whether subjects would take the proserotonergic agent again if given the opportunity. The patient is asked "If given an opportunity, would you take this drug again? (circle one: YES or NO). This questionnaire can be used to examine the overall desirability of the drug experience with the proserotonergic agents taken intact and taken after tampering, preferably in drug abusers and recreational drug users without the medical condition for which the drug is effective.

On the "coasting" questionnaire the patient is asked to put a mark on a horizontal line that best describes their response to the question: "Do you feel like you are coasting or spaced out? The horizontal line is a visual analog scale (VAS) bounded on the left by "not at all" and on the right by "extremely". This questionnaire can be used to examine the degree to which subjects feel like they are coasting or spaced out with the proserotonergic agents taken intact and taken after tampering, preferably in drug abusers and recreational drug users without the medical condition for which the drug is effective.

Three performance tasks may be employed for measuring skills related to driving as noted below.

The "critical tracking task" measures the patient's ability to control a displayed error signal in a first-order compensatory tracking task. The error is displayed as a horizontal deviation of a cursor from the midpoint on a horizontal, linear scale. Compensatory joystick movements correct the error by returning the cursor to the midpoint. The frequency at which the patient loses the control is the critical frequency. The critical tracking task measures the psychomotor control during a closed loop operation. It is a laboratory analog to on-the-road tracking performance.

The "stop signal task" measures motor impulsivity, which is defined as the inability to inhibit an activated or pre-cued response leading to errors of commission. The task requires patients to make quick key responses to visual go signals, i.e. the letters ABCD presented one at a time in the middle of the screen, and to inhibit any response when a visual stop signal, i.e. "*" in one of the four corners of the screen, is presented at predefined delays. The main dependent variable is the stop reaction time on stop signal trials that represents the estimated mean time required to inhibit a response.

The Tower of London (TOL) is a decision-making task that measures executive function and planning. The task consists of computer generated images of begin- and end-arrangements of three colored balls on three sticks. The subject's task is to determine as quickly as possible, whether the end-arrangement can be accomplished by "moving" the balls in two to five steps from the beginning arrangement by pushing the corresponding number coded button. The total number of correct decisions is the main performance measure.

For the purposes of in vivo testing, unless specified otherwise, pain intensity is measured on a VAS or categorical scale. On the categorical scale, the patient is asked "My pain at this time is: None=0, Mild=1, Moderate=2, Severe=3. On the VAS, the patient is asked "My pain at this time is" (with VAS anchors: "No Pain" and "Extreme Pain").

For the purposes of in vivo testing, unless specified otherwise, pain relief is measured on a categorical scale. The patient is asked "My relief from starting pain is: None=0, A little=1, Some=2, A lot=3, Complete=4.

In certain preferred embodiments of the present invention, the ratio of the proserotonergic agent and the serotonin surge protector is about 1:10,000 to about 10,000:1 by weight, preferably about 1:1000 to about 1000:1 by weight, more preferably 1:250 to 250:1.

The term "USP Basket and Paddle Methods" is the Basket and Paddle Method described, e.g., in specified in the United States Pharmacopeia, USP-28 NF-23 (2005), published by the United States Pharmacopeial Convention, Inc, and herein incorporated by reference.

The term "pH-dependent" for purposes of the present invention is defined as having characteristics (e.g., dissolution) which vary according to environmental pH.

The term "pH-independent" for purposes of the present invention is defined as having characteristics (e.g., dissolution) which are substantially unaffected by pH.

The term "bioavailability" is defined for purposes of the present invention as the rate and extent to which the drug (e.g., the proserotonergic agent) is absorbed from the unit dosage forms.

As used herein with respect to the proserotonergic agent dosage forms of the invention, the term "oral", "oral dosage", "oral dosage form", "oral pharmaceutical dosage form", "oral administration", and "oral route", refers to any method of administration involving contact with the mouth and oral mucosa, including the ingestion of intact drugs (e.g., capsules, tablets, liquids swallowed whole), lingual, sublingual administration, buccal administration and transmucosal administration. Particularly preferred embodiments involve oral ingestion of intact drugs (e.g., capsules, tablets, liquids swallowed whole).

All oral pharmaceutical dosage forms of the invention are contemplated, including oral suspensions, tablets, capsules, lozenges, effervescent tablets, effervescent powders, powders, solutions, powders for reconstitution, transmucosal films, buccal products, oral mucoretentive products, oral gastroretentive tablets and capsules, orally disintegrating tablets, fast dissolving tablets, fast dispersing tablets, fast disintegrating dosage forms, administered as immediate release, delayed release, modified release, enteric coated, sustained release, controlled release, pulsatile release and extended release dosage form.

As used herein, "controlled release" is interchangeable with "extended release", "sustained release", "modified release", "delayed release" and the like. Such products provide a longer duration of action than conventional immediate release formulations of the same drugs and are usually administered about every 6, 8, 12 or 24 hours, more usually every 12 or 24 hours.

Controlled release dosage forms of the present invention release proserotonergic agent from the oral dosage form at slower rate than immediate release formulations. In some preferred embodiments, controlled release dosage forms release proserotonergic agent at such a rate that blood (e.g., plasma) concentrations (levels) or therapeutic effects are maintained within the therapeutic range (above the minimum effective therapeutic concentration) but below toxic levels for intended duration (e.g., over a period of 1 to 24 hours, preferably over a period of time indicative of Q4, Q6, Q8, Q12 or Q24H administration). Notwithstanding the foregoing, in some preferred embodiments, the controlled release formulations of the present invention provide therapeutic effects for a duration that is longer or substantially longer than the duration of meaningful or detectable plasma concentrations of proserotonergic agent. Controlled release dosage forms may be administered around the clock on a scheduled or time contingent basis, or on an as needed or PRN basis, e.g., Q3 PRN, Q4 PRN, Q6 PRN, Q8 PRN, Q12 PRN or Q24H PRN administration.

The term "immediate release proserotonergic agent" for purposes of the present invention is proserotonergic agent for oral administration in a dosage form which is formulated to release the active drug from the dosage form immediately (i.e., without an attempt to delay or prolong the release of the active drug from the dosage form as is the case for extended release dosage forms). In the absence of a commercially available oral immediate release proserotonergic agent product, an available parenteral formulation of proserotonergic agent or a salt thereof may be used orally or a solution of proserotonergic agent or a salt thereof may be prepared for the purpose of in vivo testing requiring immediate release proserotonergic agent.

For purposes of the invention, the controlled release formulations disclosed herein and the immediate release control formulations are dose proportional. In such formulations, the pharmacokinetic parameters (e.g., AUC and $C_{max}$) increase linearly from one dosage strength to another. Therefore the pharmacokinetic parameters of a particular dose can be inferred from the parameters of a different dose of the same formulation.

The phrase "cardinal sign or symptom" and "cardinal sign or symptom of said medical condition" when referring to the use of the proserotonergic agent of the present invention means the major sign or symptom of the medical condition for which the proserotonergic agent is approved or commonly used, said sign or symptom commonly used as the primary endpoint in clinical trials published in peer-review journals and for approval of the drug by the U.S. FDA and other major drug regulatory authorities (e.g., the EMEA, National regulatory authorities of member countries of the European Union and the TPD in Canada).

The term "abuse", "drug abuse", "proserotonergic drug abuse", "opioid abuse", and "abusable proserotonergic agent" in the context of the present invention includes intermittent use, recreational use and chronic use of proserotonergic agents alone or in conjunction with other drugs: (i) in quantities or by methods and routes of administration that do not conform to standard medical practice; (ii) outside the scope of specific instructions for use provided by a qualified medical professional; (iii) outside the supervision of a qualified medical professional; (iv) outside the approved instructions on proper use provided by the drug's legal manufacturer; (v) which is not in specifically approved dosage forms for medical use as pharmaceutical agents; (vi) where there is an intense desire for and efforts to procure same; (vii) with evidence of compulsive use; (viii) through acquisition by manipulation of the medical system, including falsification of medical history, symptom intensity, disease severity, patient identity, doctor shopping, prescription forgeries; (ix) where there is impaired control over use; (x) despite harm; (xi) by procurement from non-medical sources; (xii) by others through sale or diversion by the individual into the non-medical supply chain; (xiii) for medically unapproved or unintended mood altering purposes.

As used herein, "abusable proserotonergic agents", "proserotonergic agent that can be abused" are proserotonergic agents which (i) have medical applications for the prevention or treatment of diseases and disorders (i.e., "therapeutically active agents") and (ii) have the potential for being abused by drug abusers, recreational drug users and individuals with an addiction disorder for intermittent use, recreational use or chronic use, wherein the proserotonergic agent is being abused for one or more of the following effects: mood alterations; euphoria, pleasure; a feeling of high; a feeling of drug liking; anxiolysis; sedation; calmness; a state of relaxation; hallucinations; alterations in perception, cognition and mental focus; insomnia; hypersomnia; increased wakefulness or alertness; memory improvement; increased sexual gratification; increased sexual arousal; increased sexual desire and sexual anticipation; increased socialization; reduced social anxiety; psychological reinforcement; and psychologically rewarding. It reasons that various abusable proserotonergic agents of the invention will have different abusable characteristics being sought after by the drug addict or recreational drug user.

The singular forms "a", "an" and "the" include plural references unless the context clearly dictates otherwise. Thus, for example, reference to "serotonin surge protector" includes a serotonin surge protector compound as well as a mixture of two or more different serotonin surge protector compounds, reference to "proserotonergic agent" includes a proserotonergic agent as well as two or more different proserotonergic agents in combination, and the like.

As used herein, the term "analgesic" includes pharmacologic agents intended for or effective in the prevention and/or treatment of pain.

In some embodiments, in addition to preventing or treating pain, analgesics provide salutary effects on signs and symptoms associated with pain. For example, opioid analgesics, in addition to relieving pain in patients with osteoarthritis, relieve stiffness, improve physical function, sleep and quality of life (Babul et al. Journal of Pain and Symptom Management 2004; 28:59-71; Matsumoto et al., Pain Medicine 2005; 6:357-66; Dhaliwal et al., Journal of Pain Symptom Management 1995; 10:612-23; Hays et al., Cancer 1994; 74:1808-16; Arkinstall et al., Pain 1995; 62:169-78; Hagen et al., Journal of Clinical Pharmacology 1995; 35:38-45; Peloso et al., Journal of Rheumatology 2000; 27:764-71). For example, opioid analgesics, in addition to relieving pain in patients with neuropathic pain, reduce diasability (Watson and Babul, Neurology 1998; 50:1837-41).

As used herein, the term "pain" includes: (i) peripheral neuropathic pain, e.g., acute and chronic inflammatory demeyelinating polyradiculopathy, alcoholic polyneuropathy, chemotherapy-induced polyneuropathy, complex regional pain syndrome (CRPS) Type I and Type II, entrapment neuropathies (e.g., carpal tunnel syndrome), HIV sensory neuropathy, iatrogenic neuralgias (e.g., postthoracotomy pain, postmastectomy pain), idiopathic sensory neuropathy, painful diabetic neuropathy, phantom limb pain, postherpetic neuralgia, trigeminal neuralgia, radiculopathy (e.g., cervical thoracic, lumbosacral), sciatica, acute herpes zoster pain, temporomandibular joint disorder pain and postradiation plexopathy; and (ii) central neuropathic pain, e.g., compressive myelopathy from spinal stenosis, HIV myelopathy, multiple sclerosis pain, Parkinson's disease pain, postischemic myelopathy, post postradiation myelopathy, poststroke pain, posttraumatic spinal cord injury and syringomyelia; and (iii) cancer associated neuropathic pain, e.g., chemotherapy induced polyneuropathy, neuropathy secondary to tumor infiltration or nerve compression, phantom breast pain, postmastectomy pain, postradiation plexopathy and myelopathy; (iv) chronic pain, e.g., back pain, rheumatoid arthritis, osteoarthritis, inflammatory pain, non-inflammatory pain, myofascial pain, fibromyalgia, cancer pain, visceral pain, somatic pain, pelvic pain, musculoskeletal pain, post-traumatic pain, bone pain and idiopathic pain; (v) acute pain, e.g, acute postsurgical pain (including laparoscopic, laparatomy, gynecologic, urologic, cardiothoracic, arthroscopic, gastrointestinal, neurologic, orthopedic, oncologic, maxillofacial, ophthalmic, otolaryngologic, soft tissue, plastic, cosmetic, vascular and podiatric surgery, including abdominal surgery, abdominoplasty, adenoidectomy, amputation, angioplasty, appendectomy, arthrodesis, arthroplasty, arthroscopy, bilateral cingulotomy, biopsy, brain surgery, breast biopsy, cauterization, cesarean section, cholecystectomy, circumcision, commissurotomy, cordotomy, corneal transplantation, cricothoracotomy, discectomy, diverticulectomy, episiotomy, endarterectomy, endoscopic thoracic sympathectomy, foreskin restoration, fistulotomy, frenectomy, frontalis lift, fundectomy, gastrectomy, grafting, heart transplantation, hemicorporectomy, hemorrhoidectomy, hepatectomy, hernia repair, hypnosurgery, hysterectomy, kidney transplantation, laminectomy, laparoscopy, laparotomy, laryngectomy, lithotripsy, lobotomy, lumpectomy, lung transplantation, mammectomy, mammoplasty, mastectomy, mastoidectomy, mentoplasty, myotomy, mryingotomy, nephrectomy, nissen fundoplication, oophorectomy, orchidectomy, parathyroidectomy, penectomy, phalloplasty, pneumotomy, pneumonectomy, prostatectomy, psychosurgery, radiosurgery, ritidoplasty, rotationplasty, sigmoidostomy, sphincterotomy, splenectomy, stapedectomy, thoracotomy, thrombectomy, thymectomy, thyroidectomy, tonsillectomy, tracheotomy, tracheostomy, tubal ligation, ulnar collateral ligament reconstruction, ureterosigmoidostomy, vaginectomy, vasectomy, vulvectomy; renal colic; incisional pain; inflammatory incisional pain; nociceptive incisional pain; acute neuropathic incisional pain following surgery), renal colic, trauma, acute back pain, burn pain, burn dressing change pain, migraine pain, tension headache pain, acute musculoskeletal pain, acute exacerbation or flare of chronic back pain, acute exacerbation or flare of osteoarthritis, acute exacerbation or flare of chronic pain, breakthrough chronic non-cancer pain, breakthrough cancer pain, acute exacerbation or flare of fibromylagia, acute exacerbation or flare of rheumatoid arthritis, acute exacerbation or flare of myofacsial pain, acute exacerbation or flare of chronic idiopathic pain, acute exacerbation or flare of neuropathic pain, procedure related pain (e.g., arthroscopy, laparoscopy, endoscopy, intubation, bone marrow biopsy, soft tissue biopsy, catheterization), and other self-limiting pain states.

As used herein, the term "acute pain" refers to self-limiting pain that subsides over time and usually lasting less that about 30 days and more preferably lasting less than about 21 days. Acute pain does not include chronic conditions such as chronic neuropathy, chronic neuropathic pain and chronic cancer and non-cancer pain.

As used herein, "neuropathic pain" is pain initiated or caused by a primary lesion or dysfunction of the nervous system and includes (i) peripheral neuropathic pain and (ii) central neuropathic pain.

As used herein, the term "chronic pain" includes all non-neuropathic pain lasting more than 30 days, including inflammatory pain, non-inflammatory pain, muscle pain, joint pain, fascia pain, visceral pain, bone pain and idiopathic pain.

As used herein, "neurologic disorders" are disorders that affect the central nervous system (brain and spinal cord), the peripheral nervous system (peripheral nerves—cranial nerves included), or the autonomic nervous system (parts of which are located in both central and peripheral nervous system). See Adams & Victor's Principles of Neurology (McGraw-Hill Professional; 7 edition, 2000); Merritt's Textbook of Neurology (9th ed. Edited by Lewis P. Rowland. Baltimore: Williams and Wilkins, 1995); and Guide to Clinical Neurology (Mohr and Gautier, eds, New York, Churchill Livingstone, 1995).

The term "psychiatric disorders" and "mental illness" are used interchangeably. A mental illness is an abnormal mental condition or disorder expressing symptoms that cause significant distress and/or dysfunction. This can involve cognitive, emotional, behavioral and interpersonal impairments. As used herein, psychiatric disorders are disorders described in the Diagnostic and Statistical Manual of Mental Disorders (DSM), 1994, as revised in 2000 (DSM-IV-TR).

The term "analgesic effectiveness" is defined for purposes of the present invention as a satisfactory prevention, reduction in or elimination of pain, along with a tolerable level of side effects, as determined by the human patient.

The term "effective amount" means the quantity of a compound according to the invention necessary to prevent, to cure, or at least partially arrest a sign or symptom for which the compound (e.g., proserotonergic agent) has been prescribed to a subject.

The term "tamper resistant" and "tamper deterrent" are used interchangeably and include pharmaceutical compositions and methods to resist intentional, unintentional or accidental physical, mechanical, chemical or thermal manipulation or tampering of the dosage form (e.g., crushing, shearing, grinding, pulverizing, chewing, dissolving, melting, needle aspiration, syringe aspiration, syringe injection, solvent extraction, inhalation, insufflation, extraction by mechanical, thermal and chemical means, and/or filtration). The term "tamper resistant" and "tamper deterrent" also includes pharmaceutical compositions and methods to resist intentional, unintentional or accidental use or misuse of the dosage form: (i) in quantities or by methods and routes of administration that do not conform to standard medical practice; (ii) outside the scope of specific instructions for use provided by a qualified medical professional; (iii) outside the supervision of a qualified medical professional; (iv) outside the approved instructions on proper use provided by the drug's legal manufacturer; (v) in unapproved dosage forms; (vi) for compulsive use; (vii) through acquisition by manipulation of the medical system; (viii) for medically unapproved or unintended mood altering purposes.

The term "subject" for purposes of treatment is used interchangeably with "patient", "male", "female", and includes any human subject.

As used herein, "bioequivalent" and "bioequivalence" means that the 90% Confidence Interval (CI) of the relative mean $C_{max}$, $AUC_{(0-t)}$ and $AUC_{(0-\infty)}$ of the drug under test and reference conditions (e.g., generic vs. brand name, or fed versus fasted, or with and without concurrent alcohol) is within 80% to 125%, when tested in accordance with U.S. FDA guidelines (see "Guidance for Industry: Bioavailability and Bioequivalence Studies for Orally Administered Drug Products—General Considerations", Department of Health and Human Services, Food and Drug Administration, Center for Drug Evaluation and Research, July 2002 and "Guidance for Industry: Food-Effect Bioavailability and Fed Bioequivalence Studies Study Design, Data Analysis and Labeling", Department of Health and Human Services, Food and Drug Administration, Center for Drug Evaluation and Research, October, 2001, which are hereby incorporated by reference).

"Pharmaceutically or therapeutically acceptable excipient or carrier" or "excipient" refers to a substance which does not interfere with the effectiveness or the biological activity of the active ingredients and which is not toxic to the subject. In some preferred embodiments of the present invention, pharmaceutically or therapeutically acceptable excipients or carriers may play a role in imparting or optimizing the rate and extent of absorption of opioid or additional drugs in the pharmaceutical composition. In some preferred embodiments of the present invention, pharmaceutically or therapeutically acceptable excipients or carriers may play a role in stabilizing the opioids or additional drugs in the pharmaceutical composition.

In certain preferred embodiments of the present invention, the dosage form may include, in addition to opioids or a pharmaceutically acceptable salt thereof and serotonin surge protector, other tamper resistant substances, process or technologies known in the art, including one or more aversive agents. All kinds of aversive agents are contemplated, including, without limitation, antagonists of proserotonergic agents, laxatives, cutaneous vasodilators, headache producing agents, emetics, emetogenic compound, nausea producing compounds, bittering agents, drugs that cause burning on irritation when in contact with tissue or mucous membranes (e.g., naso-mucosal irritants, oro-mucosal irritants, respiratory irritants), tissue irritants, gastrointestinal irritants, drugs that precipitate withdrawal effects, tissue dyes, lakes and colorants, beverage dyes, lakes and colorants, non-tissue staining beverage dyes, lakes and colorants (i.e, that do not stain or discolor the skin upon ingestion), fecal discolorants, urine discolorants, malodorous agents, opioid antagonists, benzodiazepine antagonists (e.g., flumazenil), cannabinoid antagonists and pharmacologic antagonists to co-abused drugs not contained in the dosage form. Such aversive agents may be in the dosage form in a releasable, partially releasable or a non-releasable form (i.e., sequestered), the latter being released on tampering the dosage form (e.g., mechanical, thermal, chemical, solvent tampering, ingestion in ways not recommended, and the like). Further, in some embodiments, such aversive agents may be in the dosage form in an amount that does not produce an aversive effect or aversion in any, many or substantially all patients when taken in accordance with the prescribing information or the manufacturer's instructions (for example, in small quantities), but which produce an aversive effect when taken in excess (e.g., higher dose or more frequently).

In some embodiments, one or more aversive agents may be added to the formulation in an aversive agent amount of less than about 80% by weight, preferably less than about 60% by weight, more preferably less than about 40% by weight of the dosage form, even more preferably less than about 20% by weight of the dosage form, and most preferably less than about 10 by weight of the dosage form (e.g., 0.000000000000001% to 1%, or 0.000000001% to 3%, or 0.0001% to 10%, or 0.001% to 5%, or 1% to 10%, or 0.001% to 2%, or 1% or 10%, or 2% to 7%) depending on the particular aversive agent used.

In some embodiments, the aversive agent in the dosage form may be about 0.00000000001 mg to about 2000 mg, or about 0.0000001 mg to about 1500 mg, or about 0.000001 mg to about 1000 mg, or about 0.0001 mg to about 1000 mg, or about 0.001 mg to about 1000 mg, or about 0.01 mg to about 1000 mg, or about 0.1 mg to about 1500 mg, or 1 mg to about 800 mg, or about 1 mg to about 500 mg, or about 1 mg to about 300 mg, or about 1 mg to about 150 mg, or about 5 mg to about 400 mg, or about 5 mg to about 200 mg, or about 0.00000000001 mg to about 200 mg, or about 0.00000000001 mg to about 100 mg, or about 0.00000000001 mg to about 50 mg, or about 0.0000001 mg to about 200 mg, or about 0.0000001 mg to about 100 mg, or about 0.00001 mg to about 400 mg, or about 0.0001 mg to about 300 mg.

As described above, the present invention can include one or more aversive agents, selected from the group including, without limitation antagonists of proserotonergic agents, laxatives, cutaneous vasodilators headache producing agents, emetics, emetogenic compound, nausea producing compounds, bittering agents, drugs that cause burning on irritation when in contact with tissue or mucous membranes (e.g., naso-mucosal irritants, oro-mucosal irritants, respiratory irritants), tissue irritants, gastrointestinal irritants, drugs that precipitate withdrawal effects, tissue dyes, lakes and colorants, beverage dyes, lakes and colorants, non-tissue staining beverage dyes, lakes and colorants, fecal discolorants, urine discolorants, malodorous agents, pharmacologic antagonists to proserotonergic agents. Preferably, the aversive agent is a pharmaceutically acceptable agent that produces an aversive effect only when the dosage form of the invention containing the aversive agent is abused, for example, when taken in excess of medically approved doses, taken in excess of approved doses in the manufacturer's prescribing information, taken after tampering of the dosage form (e.g., mechanical, thermal, chemical, solvent tampering), ingestion in ways not medically recommended, administration by routes not approved for the dosage form (e.g., intranasal, inhalation, intravenous) or in a manner inconsistent with the manufacturer's prescribing information.

In some embodiments, the amount of aversive agent in the dosage form of the present invention can be a fixed ratio in relation to the amount of proserotonergic agent in the dosage form. By appropriately selecting the quantity of the aversive agent in the dosage form, aversive effects can be avoided under conditions of proper medical use (e.g., manufacturers prescribing directions). However, under some conditions of abuse, for example excessive intake of the dosage form of the invention, the quantity of aversive agent consumed will exceed the "no effect" or "minimum effect" threshold, thereby producing one or more aversive effects, for example, e.g., nausea, emesis, diarrhea, Taxation, cutaneous vasodilation, headache, bitter taste, naso-mucosal irritation, oro-mucosal irritation, precipitation of abstinence from the proserotonergic agent of the dosage form, precipitation of abstinence from a co-abused drug which is not part of the dosage form, reduction of the pleasurable, mood altering, rewarding, reinforcing, stimulant, depressant or other psychic and physiologic effects of the proserotonergic agent or a co-abused drug, etc.).

In some embodiments, the "no effect" or "minimum effect" threshold amount of aversive agent can be exceeded when the dosage form of the invention is taken in excess of the manufacturer's recommendation by a factor of about 1.5, or about 2, or about 2.5, or about 3, or about 4, or about 5, or about 6, or about 7, or about 8, or about 10, or more than 10. In some embodiments, the production of an aversive effect can reduce or stop further abuse of the dosage form, thereby reducing the harm or toxicity of the drug in the subject who is tampering, misusing or abusing the dosage form, e.g., addicts, drug abusers and recreational drug users.

Aversive agents may include compounds found on the FDA EAFUS database (http://vm.cfsan.fda.gov/~dms/eafus.html); FDA Food Additives Status List (http://www.cfsan.fda.gov/~dms/opa-appa.html); FDAGRAS list and database; FDA Color Additive Status List (http://www.cfsan.fda.gov/~dms/opa-appc.html); FDA Inactive Ingredients Database (http://www.accessdata.fda.gov/scripts/cder/iig/index.cfm); Rowe, Sheskey and Owen, Handbook of Pharmaceutical Excipients, APhA Publications; 5th edition (2006); Goodman & Gilman's The Pharmacological Basis of Therapeutics (Brunton, Lazo and Parker, eds, 11th ed., McGraw Hill (2005); Remington: The Science and Practice of Pharmacy, 21st ed, Lippincott Williams & Wilkins (2005); Martindale: The Complete Drug Reference, 35th Edition, Pharmaceutical Press (2007); United States Pharmacopeia—National Formulary (USP-NF), (USP 30—NF 25, 2007), the International Programme on Chemical Safety (http://www.inchem.org/); Pharmaceutical Additives Electronic Handbook, Third Edition, Michael Ash (compiler), Synapse Information Resources, Inc.; 3 Cdr edition (Feb. 19, 2007); and Health Canada's List of Acceptable Non-medicinal Ingredients (http://www.hc-sc.gc.ca/dhp-mps/prodnatur/legislation/docs/nmi-imn_list1_e.html), all hereby incorporated by reference in their entirety.

It should be noted that the above mentioned aversive agents may, in some embodiments be used in the dosage form of the invention for purposes other than as aversive agents, or for both aversive and non-aversive purposes. Such non-aversive uses can include, without limitation, pharmaceutical purposes and pharmacologic purposes. For example, in some embodiments, the laxative agent may be used to counteract the constipating effects of the abusable dosage form of the invention. In some embodiments, zinc and pharmaceutically acceptable salts of zinc and niacin may be used for pharmaceutical purposes (e.g., pharmaceutical optimization, drug release and drug stability).

Additional serotonin surge protectors that may be used to formulate oral dosage forms of the present invention include compounds found in the FDA EAFUS database (http://vm.cfsan.fda.gov/~dms/eafus.html); FDA Food Additives Status List (http://www.cfsan.fda.gov/~dms/opa-appa.html); FDAGRAS list and database; FDA Color Additive Status List (http://www.cfsan.fda.gov/~dms/opa-appc.html); FDA Inactive Ingredients Database (http://www.accessdata.fda.gov/scripts/cder/iig/index.cfm); Rowe, Sheskey and Owen, Handbook of Pharmaceutical Excipients, APhA Publications; 5th edition (2006); Goodman & Gilman's The Pharmacological Basis of Therapeutics (Brunton, Lazo and Parker, eds, 11th ed., McGraw Hill (2005); Remington: The Science and Practice of Pharmacy, 21st ed, Lippincott Williams & Wilkins (2005); Martindale: The Complete Drug Reference, 35th Edition, Pharmaceutical Press (2007); United States Pharmacopeia—National Formulary (USP-NF), (USP 30—NF 25, 2007), the International Programme on Chemical Safety (http://www.inchem.org/); Pharmaceutical Additives Electronic Handbook, Third Edition, Michael Ash (compiler), Synapse Information Resources, Inc.; 3 Cdr edition (Feb. 19, 2007); and Health Canada's List of Acceptable Non-medicinal Ingredients (http://www.hc-sc.gc.ca/dhp-mps/prodnatur/legislation/docs/nmi-imn_list1_e.html), all hereby incorporated by reference in their entirety.

In one preferred embodiment of the invention, the dosage form includes a capsule within a capsule, each capsule containing a different drug or the same drug intended for treating the same or a different medical condition. In some preferred embodiments, the outer capsule may be an enteric coated capsule or a capsule containing an immediate release formulation to provide rapid plasma concentrations or a rapid onset of effect or a loading dose and the inner capsule contains an extended release formulation.

In one preferred embodiment of the invention, the formulation is ingested orally as a tablet or capsule, preferably as a capsule. In another preferred embodiment of the invention, the formulation is administered bucally. In yet another preferred embodiment of the invention, the formulation is administered sublingually.

The term "pharmaceutically acceptable salt" as used herein refers to a salt which is toxicologically safe for human and animal administration. Nonlimiting examples of salts include hydrochlorides, hydrobromides, hydroiodides, sulfates, bisulfates, nitrates, citrates, tartrates, bitartrates, phosphates, malates, maleates, napsylates, fumarates, succinates, acetates, terephlhalates, pamoates and pectinates.

In some embodiments, the proserotonergic agent pharmaceutical composition is a salt or complex of inorganic cation salts, organic salts such primary, secondary, tertiary and quaternary amines include substituted amines In some embodiments, examples of suitable pharmaceutically acceptable salts of proserotonergic agents include any of the inorganic cation salts such as sodium, potassium, lithium, magnesium, calcium, cesium, ammonia, ferrous, zinc, manganous, aluminum, ferric, and manganic; organic salts with primary, secondary, tertiary and quaternary amines, or mixtures thereof. Examples of such primary, secondary, tertiary and quaternary amines include substituted amines including but not limited to naturally occurring substituted amines, cyclic amines, basic ion exchange resins, and mixtures thereof. More specifically, suitable amines include but are not limited to tromethamine, triethylamine, tripropylamine, dropopizine, 2-dimethylaminoethanol, 2-diethylaminoethanol, lysine, arginine, ornithine, histidine, caffeine, procaine, N-ethylpiperidine, hydrabamine, choline, betaine, ethylenediamine, glucosamine, tris-(hydroxymethyl)aminomethane, N-methylglucamine, methylglycamine, theobromine, piperazine, piperidine, polyamine resins and the like, and mixtures thereof.

In some embodiments, examples of suitable pharmaceutically acceptable salts of proserotonergic agents include aminoalcohols chosen from the group consisting of ethanolamine, 3-amino-1-propanol, (R)-1-amino-2-propanol, (S)-1-amino-2-propanol, 2-amino-1,3-propandiol, N-(2-hydroxyethyl)pyrrolidine, D-glucamine and L-prolinol, D-glucosamine, and N-methylglucosamine.

In some embodiments, examples of suitable pharmaceutically acceptable salts of proserotonergic agents include alkali and alkaline earth metals and salts of an organic nature, such as the salts of basic amino acids.

It is contemplated that the present invention may be used alone or in combination with other drugs to provide additive, complementary, or synergistic therapeutic effects or for the treatment of entirely different medical conditions.

Other pharmaceutically active ingredients from various therapeutic classes may also be used in combination with the present invention. They include, but are not limited to decongestants, analgesics, analgesic adjuvants, antidepressants, antipsychotics, anxiolytics, hypnotics, sedatives, anti-ADHD drugs, psychostimulants, drugs to treat urinary incontinence, antihistamines, expectorants, antitussives, diuretics, anti-inflammatory agents, antipyretics, antirheumatics, antioxidants, laxatives, local anesthetics, proton pump inhibitors, motility modifying agents, vasodilators, inotropes, beta blockers, beta adrenergic agonists, drugs to treat asthma and COPD, antiinfectives, anti-migraine agents, antihypertensives, antianginal agents, gastric acid reducing agents, anti-ulcer agents, anticoagulants, lipid and cholesterol lowering drugs, anti-diabetic drugs, anti-epileptics, hormones, smooth muscle relaxants, skeletal muscle relaxants, bronchodilators, vitamins, trace minerals, amino acids, biological peptides and drugs to treat various infectious, immunologic disorders, cardiovascular, pulmonary, gastrointestinal, hepatic, biliary, nutritional, metabolic, endocrine, hematologic, oncologic, musculoskeletal, neurologic, psychiatric, genitourinary, gynecologic, obstetric, pediatric, otolaryngogologic, ophthalmic, dermatologic, dental, oral, and genetic disorders, diseases and maladies. The drug being used in combination therapy with the present invention can be administered by any route, including parenterally, orally, topically, transdermally, sublingually, and the like.

In some preferred embodiments, the oral proserotonergic agent is intended to prevent or treat pain. A co-administered drug (in the same or different dosage form, by any route of administration) may be used to provide additive, complementary, superadditive or synergistic therapeutic analgesic effects, including analgesics-linked to nitric oxide donors, NSAIDs, NO-NSAIDs, COX-2 selective inhibitors, acetaminophen, alpha-2 agonists, bradykinin antagonists, cannabinoid agonists, beta adrenergic agonists, conopeptides, nitroparacetamol, purinergic P2 receptor antagonists, antidepressants, tricyclic antidepressants, tetracyclic antidepressants, SSRI's, SNRI's, tramadol, tapentadol, local anesthetics, antidepressants, beta adrenergic agonists, alpha-2 agonists, prostanoid receptor antagonists, cannabinoid agonists, opioid receptor agonists, NO-opioid receptor agonists, NMDA antagonists, NMDA receptor antagonists, gabapentin, pregabalin, gabapentinoids, ligands of alpha(2)delta subunits of voltage-gated calcium channels, neuronal nicotinic receptor agonists, nitric oxide donors, calcium channel antagonists, N-type voltage-sensitive calcium channels antagonists, T-type calcium channels antagonists, sodium channel blockers, superoxide dismutase mimetics, p38 MAP kinase inhibitors, TRPV1 agonists, dextromethorphan, dextrorphan, ketamine, glycine receptor antagonists, antiepileptics, ziconotide corticosteroids, and any other drugs that can be shown by a person proficient in the art to prevent or treat pain, as well as their pharmaceutically acceptable salts, prodrugs, esters, analogs, derivatives, solvates, complexes, polymorphs, hydrates and metabolites, as racemates or an individual diastereoisomers or enantiomeric isomers thereof or mixture thereof. and.

In other preferred embodiments, particularly preferred combinations include proserotonergic agents with acetaminophen.

In other preferred embodiments, particularly preferred combinations include proserotonergic agents with an NSAID. Nonsteroidal anti-inflammatory drugs typically have analgesic, anti-inflammatory, and antipyretic properties. Their mode of action appears to involve inhibition of cyclooxygenases (COX-1 and COX-2), leukotriene biosynthesis, and antibradykinin activity. NSAIDs may be non-selective (inhibit COX-1 and COX-2 isozymes) or COX-2 selective (preferentially inhibit the COX-2 isozymes). Non-limiting examples of NSAIDs or COX-2 selective inhibitor include aceclofenac, acemetacin, acetylsalicylic acid, aminoprofen, bucloxic acid, bufexamac, burnadizone, carprofen, celecoxib, clidanac, dexketoprofen, diclofenac, diflunisal, droxicam, eltenac, epirizole, etodolac, etofenamate, etoricoxib, felbinac, fenbufen, fenoprofen, fentiazac, flufenamic acid, fentiazac, fepradinol, feprazone, floctafenine, flufenamic acid, flunixine, flunoxaprofen, flurbiprofen, flubufen, flufenisal, flurprofen, glafenine, glucametacin, ibuprofen, indobufen, indoprofen, indomethacin, isonixin, isoxicam, ketorolac, ketoprofen, lornoxicam, loxoprofen, lumiracoxib, meclofenamic acid, mefenamic acid, meloxicam, mofebutazone, muroprofen, nabumetone, naproxen, nifenazone, niflumic acid, nimesulide, oxaprozin, oxpinac, piketoprofen, piroxicam, pirprofen, pranoprofen, pramoprofen, proquazone, rofecoxib, salicylic acid, salsalate, sudoxicam, sulindac, suprofen, tenidap, tetridamine, tiaprofenic acid, tiopinac, trioxaprofen, tenoxicam, tolfenamic acid, tolmetin, valdecoxib, zaltoprofen and zidometacin, and as well as their pharmaceutically acceptable salts, prodrugs, esters, analogs, derivatives, solvates, complexes, polymorphs, hydrates and metabolites, as racemates or an individual diastereoisomers or enantiomeric isomers thereof or mixture thereof.

In other preferred embodiments, particularly preferred combinations include proserotonergic agents with NMDA antagonists.

In other preferred embodiments, particularly preferred combinations include proserotonergic agent with antiepileptics. Non-limiting examples of anti-epileptic compounds include gabapentin, pregabalin, carbamazepine, oxcarbazepine, lamotrigine, phenyloin, fosphenyloin, valproate, valproic acid, tiagabine, topiramate, divalproex, harkoseride, and levetiracetam, in unsalified form or as pharmaceutically acceptable salts, prodrugs, esters, analogs, derivatives, solvates, complexes, polymorphs, hydrates and metabolites, as racemates or an individual diastereoisomers or enantiomeric isomers thereof or mixture thereof.

In other preferred embodiments, particularly preferred combinations include proserotonergic agents with antidepressants. Antidepressants are well known in the art. Non-limiting examples of antidepressants include drugs from the following classes: tricyclic antidepressants, tetaracyclic antidepressants, SRI's, SSRI's, SNRI's and NSRI's. Non-limiting examples of specific antidepressants include amitriptyline, bupropion, citalopram, protriptyline, nortriptyline, desipramine, doxepin, imipramine, clomipramine, fluoxetine, paroxetine, sertraline, venlafaxine, duloxetine, trazodone, nefazodone, maprotiline and mirtazpine in unsalified form or as pharmaceutically acceptable salts, prodrugs, esters, analogs, derivatives, solvates, complexes, polymorphs, hydrates and metabolites, as racemates or an individual diastereoisomers or enantiomeric isomers thereof or mixture thereof.

In other preferred embodiments, particularly preferred combinations include proserotonergic agents with calcium channel blockers.

In other preferred embodiments, particularly preferred combinations include proserotonergic agents with sodium channel modulators.

In some preferred embodiments, the serotonin surge protector of the invention is selected from among hydrogenated Type I or Type II vegetable oils.

In some preferred embodiments, the serotonin surge protector of the invention is selected from among polyoxyethylene stearates.

In some preferred embodiments, the serotonin surge protector of the invention is selected from among polyoxyethylene distearates.

In some preferred embodiments, the serotonin surge protector of the invention is selected from among polyoxyethylene stearates or distearates.

In some preferred embodiments, the serotonin surge protector of the invention is selected from among poorly water soluble, high melting point (mp=45 to 100° C.) waxes.

In some preferred embodiments, the serotonin surge protector of the invention is selected from among hydrogenated Type I or Type II vegetable oils; said invention also including an aversive agent.

In some preferred embodiments, the serotonin surge protector of the invention is selected from among polyoxyethylene stearates; said invention also including an aversive agent.

In some preferred embodiments, the serotonin surge protector of the invention is selected from among polyoxyethylene distearates; said invention also including an aversive agent.

In some preferred embodiments, the serotonin surge protector of the invention is selected from among polyoxyethylene stearates or distearates; said invention also including an aversive agent.

In some preferred embodiments, the serotonin surge protector of the invention is selected from among poorly water soluble, high melting point (mp=45 to 100° C.) waxes; said invention also including an aversive agent.

In some preferred embodiments, the serotonin surge protector of the invention excludes hydrogenated Type I vegetable oils.

In some preferred embodiments, the serotonin surge protector of the invention excludes hydrogenated Type II vegetable oils.

In some preferred embodiments, the serotonin surge protector of the invention excludes hydrogenated Type I or Type II vegetable oils.

In some preferred embodiments, the serotonin surge protector of the invention excludes polyoxyethylene stearates.

In some preferred embodiments, the serotonin surge protector of the invention excludes polyoxyethylene distearates.

In some preferred embodiments, the serotonin surge protector of the invention excludes polyoxyethylene stearates or distearates.

In some preferred embodiments, the serotonin surge protector of the invention excludes poorly water soluble, high melting point (mp=45 to 100° C.) waxes.

In some preferred embodiments, the serotonin surge protector of the invention excludes poorly water soluble, high melting point (mp=50 to 100° C.) waxes.

In some preferred embodiments, the serotonin surge protector of the invention excludes poorly water soluble, high melting point (mp=60 to 100° C.) waxes.

In some preferred embodiments, the serotonin surge protector of the invention excludes poorly water soluble, high melting point (mp=70 to 100° C.) waxes.

In a particularly preferred embodiment of the invention, the dosage form includes two or more serotonin surge protector selected from the categories [(i) to (iv)] from the group consisting of: (i) hydrogenated Type I or Type II vegetable oils; (ii) polyoxyethylene stearates and distearates; (iii) glycerol monostearate; (iv) poorly water soluble, high melting point (mp=45 to 100° C.) waxes.

In a most preferred embodiment of the invention, the dosage form includes two or more serotonin surge protector selected from at least two categories [(i) to (iv)] from the group consisting of: (i) hydrogenated Type I or Type II vegetable oils; (ii) polyoxyethylene stearates and distearates; (iii) glycerol monostearate; (iv) poorly water soluble, high melting point (mp=45 to 100° C.) waxes.

In some preferred embodiments, the dosage form includes hydrogenated Type I or Type II vegetable oils as serotonin surge protectors in an amount that is less than about 1200 mg, or less than about 100 mg, or less than about 900 mg, or less than about 800 mg, or less than about 700 mg, or less than about 600 mg, or less than about 550 mg, or less than about 500 mg, or less than about 400 mg, or less than about 375 mg, or less than about 350 mg, or less than about 325 mg, or less than about 300 mg, or less than about 275 mg, or less than about 250 mg, or less than about 225 mg, or less than about 200 mg, or less than about 175 mg, or less than about 150 mg, or less than about 125 mg, or less than about 100 mg, or less than about 90 mg, or less than about 80 mg, or less than about 70 mg, or less than about 60 mg, or less than about 50 mg, or less than about 40 mg, or less than about 30 mg, or less than about 20 mg, or less than about 10 mg.

In some preferred embodiments, the dosage form includes polyoxyethylene stearates as serotonin surge protectors in an amount that is less than about 1200 mg, or less than about 100 mg, or less than about 900 mg, or less than about 800 mg, or less than about 700 mg, or less than about 600 mg, or less than about 550 mg, or less than about 500 mg, or less than about 400 mg, or less than about 375 mg, or less than about 350 mg, or less than about 325 mg, or less than about 300 mg, or less than about 275 mg, or less than about 250 mg, or less than about 225 mg, or less than about 200 mg, or less than about 175 mg, or less than about 150 mg, or less than about 125 mg, or less than about 100 mg, or less than about 90 mg, or less than about 80 mg, or less than about 70 mg, or less than about 60 mg, or less than about 50 mg, or less than about 40 mg, or less than about 30 mg, or less than about 20 mg, or less than about 10 mg.

In some preferred embodiments, the dosage form includes polyoxyethylene distearates as serotonin surge protectors in an amount that is less than about 1200 mg, or less than about 100 mg, or less than about 900 mg, or less than about 800 mg, or less than about 700 mg, or less than about 600 mg, or less than about 550 mg, or less than about 500 mg, or less than about 400 mg, or less than about 375 mg, or less than about 350 mg, or less than about 325 mg, or less than about 300 mg, or less than about 275 mg, or less than about 250 mg, or less than about 225 mg, or less than about 200 mg, or less than about 175 mg, or less than about 150 mg, or less than about 125 mg, or less than about 100 mg, or less than about 90 mg, or less than about 80 mg, or less than about 70 mg, or less than about 60 mg, or less than about 50 mg, or less than about 40 mg, or less than about 30 mg, or less than about 20 mg, or less than about 10 mg.

In some preferred embodiments, the dosage form includes glycerol monostearate as serotonin surge protectors in an amount that is less than about 1200 mg, or less than about 100 mg, or less than about 900 mg, or less than about 800 mg, or less than about 700 mg, or less than about 600 mg, or less than about 550 mg, or less than about 500 mg, or less than about 400 mg, or less than about 375 mg, or less than about 350 mg, or less than about 325 mg, or less than about 300 mg, or less than about 275 mg, or less than about 250 mg, or less than about 225 mg, or less than about 200 mg, or less than about 175 mg, or less than about 150 mg, or less than about 125 mg, or less than about 100 mg, or less than about 90 mg, or less than about 80 mg, or less than about 70 mg, or less than about 60 mg, or less than about 50 mg, or less than about 40 mg, or less than about 30 mg, or less than about 20 mg, or less than about 10 mg.

In some preferred embodiments, the dosage form includes poorly water soluble, high melting point (mp=45 to 100° C.) waxes as serotonin surge protectors in an amount that is less than about 1200 mg, or less than about 100 mg, or less than about 900 mg, or less than about 800 mg, or less than about 700 mg, or less than about 600 mg, or less than about 550 mg, or less than about 500 mg, or less than about 400 mg, or less than about 375 mg, or less than about 350 mg, or less than about 325 mg, or less than about 300 mg, or less than about 275 mg, or less than about 250 mg, or less than about 225 mg, or less than about 200 mg, or less than about 175 mg, or less than about 150 mg, or less than about 125 mg, or less than about 100 mg, or less than about 90 mg, or less than about 80 mg, or less than about 70 mg, or less than about 60 mg, or less than about 50 mg, or less than about 40 mg, or less than about 30 mg, or less than about 20 mg, or less than about 10 mg.

In some preferred embodiments, the dosage form includes two or more as serotonin surge protectors selected from the categories [(i) to (iv)] from the group consisting of: (i) hydrogenated Type I or Type II vegetable oils; (ii) polyoxyethylene stearates and distearates; (iii) glycerol monostearate; (iv) poorly water soluble, high melting point (mp=45 to 100° C.) waxes in total (i.e. cumulative) amount that is less than about 1200 mg, or less than about 100 mg, or less than about 900 mg, or less than about 800 mg, or less than about 700 mg, or less than about 600 mg, or less than about 550 mg, or less than about 500 mg, or less than about 400 mg, or less than about 375 mg, or less than about 350 mg, or less than about 325 mg, or less than about 300 mg, or less than about 275 mg, or less than about 250 mg, or less than about 225 mg, or less than about 200 mg, or less than about 175 mg, or less than about 150 mg, or less than about 125 mg, or less than about 100 mg, or less than about 90 mg, or less than about 80 mg, or less than about 70 mg, or less than about 60 mg, or less than about 50 mg, or less than about 40 mg, or less than about 30 mg, or less than about 20 mg, or less than about 10 mg.

In some preferred embodiments, the dosage form includes the dosage form includes two or more as serotonin surge protectors selected from the categories [(i) to (iv)] from the group consisting of: (i) hydrogenated Type I or Type II vegetable oils; (ii) polyoxyethylene stearates and distearates; (iii) glycerol monostearate; (iv) poorly water soluble, high melting point (mp=45 to 100° C.) waxes in total (i.e. cumulative) amount that is less than about 1200 mg, or less than about 100 mg, or less than about 900 mg, or less than about 800 mg, or less than about 700 mg, or less than about 600 mg, or less than about 550 mg, or less than about 500 mg, or less than about 400 mg, or less than about 375 mg, or less than about 350 mg, or less than about 325 mg, or less than about 300 mg, or less than about 275 mg, or less than about 250 mg, or less than about 225 mg, or less than about 200 mg, or less than about 175 mg, or less than about 150 mg, or less than about 125 mg, or less than about 100 mg, or less than about 90 mg, or less than about 80 mg, or less than about 70 mg, or less than about 60 mg, or less than about 50 mg, or less than about 40 mg, or less than about 30 mg, or less than about 20 mg, or less than about 10 mg.

Representative examples of hydrogenated vegetable oils as serotonin surge protectors of the present invention include, without limitation, hydrogenated cottonseed oil (e.g., Akofine®; Lubritab®; Sterotex® NF), hydrogenated palm oil (Dynasan® P60; Softisan® 154), hydrogenated soybean oil (Hydrocote®; Lipovol HS-K®; Sterotex® HM) and hydrogenated palm kernel oil (e.g., Hydrokote® 112).

Representative examples of polyoxyethylene stearates and distearates as serotonin surge protectors of the present invention include, without limitation, Polyoxyl 2, 4, 6, 8, 12, 20, 30, 40, 50, 100 and 150 stearates (e.g., Hodag® DGS; PEG-2 stearate; Acconon® 200-MS; Hodag® 20-S; PEG-4 stearate; Cerasynt® 616; Kessco® PEG 300 Monostearate; Acconon® 400-MS; Cerasynt® 660; Cithrol® 4MS; Hodag® 60-S; Kessco® PEG 600 Monostearate; Cerasynt® 840; Hodag 100-S; Myrj® 51; PEG-30 stearate; polyoxyethylene (30) stearate; Crodet® S40; E431; Emerest® 2672; Atlas G-2153; Crodet® S50) and polyoxyl 4, 8, 12, 32 and 150 distearates (e.g, Lipo-PEG® 100-S; Mydj® 59; Hodag® 600-S; Ritox® 59; Hodag® 22-S; PEG-4 distearate; Hodag® 42-S; Kessco® PEG 400 DS; Hodag® 62-S; Kessco® PEG 600 Distearate; Hodag® 154-S; Kessco® PEG 1540 Distearate; Lipo-PEG® 6000-DS; Protamate® 6000-DS).

Representative examples of poorly water soluble, high melting point (mp=45 to 100° C.) waxes as serotonin surge protectors of the present invention include, without limitation: (i) animal waxes; (ii) insect waxes; (iii) vegetable waxes; (iv) mineral waxes; (v) petroleum waxes; (vi) synthetic waxes; (vi) nonionic emulsifying waxes or cetomacrogol emulsifying wax (e.g., Collone NI™; Crodex N™; Emulgade 1000NI™; Permulgin D™; Polawax™; Ritachol 2000; T-Wax™); (vii) anionic emulsifying wax (e.g., Collone HV™; Crodex A™; Cyclonette wax; Lanette wax SX™ BP); (viii) carnauba wax (also known as Brazil wax; caranda wax; E903); (ix) microcrystalline wax (also known as amorphous wax; E907; petroleum ceresin; petroleum wax (microcrystalline)); (x) yellow wax (e.g., yellow beeswax; Apifil™; E901; refined wax]; (xi) white wax (bleached wax; E901); (xii) cetyl esters wax (e.g., cera cetyla; Crodamol SS™; Cutina CP™; Liponate SPS™; Protachem MST™; Ritaceti™; Ritachol SS™; spermaceti wax replacement; Starfol wax CG™; Synaceti 116™; synthetic spermaceti); (xiii) hydrogenated castor oil (e.g., Castorwax™; Castorwax MP 70™; Castorwax MP 80™; Croduret™; Cutina HR™; Fancol™; Simulsol 1293™); (xiv) lanolin alcohols (e.g., Cholesterol; lanolin; lanolin, hydrous; petrolatum and lanolin alcohols; mineral oils); (xv) lanolin (e.g., cera lanae; E913; lanolina; lanolin anhydrous; Protalan anhydrous; purified lanolin; refined wool fat); (xvi) glyceryl palmitostearate; (xvii) cetostearyl alcohol (e.g., cetearyl alcohol; Crodacol CS90™; Lanette O™; Tego Alkanol 1618™; Tego Alkanol 6855™); (xviii) beeswax.

In some embodiments, the dosage form is devoid of animal waxes. In other embodiments, the dosage form is devoid of insect waxes. In other embodiments, the dosage form is devoid of vegetable waxes. In other embodiments, the dosage form is devoid of mineral waxes. In other embodiments, the dosage form is devoid of petroleum waxes. In other embodiments, the dosage form is devoid of synthetic waxes. In other embodiments, the dosage form is devoid of nonionic emulsifying waxes or cetomacrogol emulsifying wax. In other embodiments, the dosage form is devoid of anionic emulsifying wax. In other embodiments, the dosage form is devoid of carnauba wax. In other embodiments, the dosage form is devoid of microcrystalline wax. In other embodiments, the dosage form is devoid of yellow wax. In other embodiments, the dosage form is devoid of white wax. In other embodiments, the dosage form is devoid of cetyl esters wax. In other embodiments, the dosage form is devoid of hydrogenated castor oil. In other embodiments, the dosage form is devoid of lanolin alcohols. In other embodiments, the dosage form is devoid of lanolin. In other embodiments, the dosage form is devoid of glyceryl palmitostearate. In other embodiments, the dosage form is devoid of cetostearyl alcohol. In other embodiments, the dosage form is devoid of beeswax.

In one preferred embodiment of the present invention, release rate modifiers may be incorporated. Release rate modifiers can also have additional useful properties that optimize the formulation.

In one preferred embodiment of the present invention, also included are cellulose and cellulose derivatives including, without limitation cellulose acetate, microcrystalline cellulose, powdered cellulose, cellulose acetate phthalate, hydroxyethyl cellulose, silicified microcrystalline cellulose, hydroxypropyl cellulose, hydroxyethylmethyl cellulose, low-substituted hydroxypropyl cellulose, carboxymethylcellulose, carboxymethylcellulose calcium, hypromellose acetate succinate, hypromellose phthalate and ethylcellulose as additional excipients or as part of the serotonin surge protector.

In one preferred embodiment of the present invention, also included are coconut oil products as serotonin surge protectors, including without limitation, coconut oil, fractionated coconut oil, cetyl alcohol, lauric acid and medium chain triglycerides (e.g., Bergabest; caprylic/capric triglyceride; Captex 300; Captex 355; Crodamol GTC/C; glyceryl tricaprylate/caprate; Labrafac CC; MCT oil; Miglyol 810™; Miglyol 812™; Myritol; Neobee M5™; Nesatol™; oleum neutrale; oleum vegetable tenue; thin vegetable oil; Waglinol 3/9280™). In a most preferred embodiment, the coconut oil is fractionated coconut oil.

In one preferred embodiment of the present invention, hydroxypropyl methyl cellulose (e.g, HPMC K15M) may be incorporated as serotonin surge protectors.

A variety of agents may be incorporated into the serotonin surge protector invention as thixotropes (e.g., fumed silicon dioxides, Aerosil®, Aerosil® COK84, Aerosil® 200, etc.). Thixotropes enhance the pharmaceutical formulations of the invention by increasing the viscosity of solutions during attempted extraction, complementing the action of HPMCs. They may also provide a tamper resistance by helping to retain the structure of dosage units that have been heated to temperatures greater than the melting point of the base excipient (Aerosils are unaffected by heat). Thus thixotropes may be included as part of serotonin surge protectors or as pharmaceutical excipeints.

As described above, the present invention can include one or more serotonin surge protectors. Any amount of serotonin surge protector may be used. In some embodiments, the total amount of serotonin surge protector is about 5 to about 98 percent, preferably 7 to 90 percent and more preferably 10 to 85 percent on a dry weight basis of the composition.

In one preferred embodiment, the serotonin surge protector can prevent less than or equal to about 98%, 90%, 80% 75%, 60%, 50%, 45%, 40%, 33%, 30%, 25%, 15%, 10%, 8%, 5%, or 2% of the total amount of drug in a dosage form from being recovered from a solvent in contact with a dosage form of the present invention.

In some preferred embodiments, the dosage form is devoid of hydrogenated Type I vegetable oils. In other embodiments, the dosage form is devoid of hydrogenated Type II vegetable oils. In other embodiments, the dosage form is devoid of polyoxyethylene stearates. In other embodiments, the dosage form is substantially of polyoxyethylene distearates; in other embodiments, the dosage form is substantially of glycerol monostearate. In other embodiments, the dosage form is substantially of poorly water soluble, high melting point (mp=45 to 100° C.) waxes.

The present invention can also optionally include other ingredients to enhance dosage form manufacture from a pharmaceutical composition of the present invention and/or alter the release profile of a dosage form including a pharmaceutical composition of the present invention.

Some embodiments of the present invention include one or more pharmaceutically acceptable fillers, diluents, glidants and lubricants of various particle sizes and molecular weights.

The dosage form according to the invention may also comprise a coating which is resistant to gastric juices and dissolves as a function of the pH value of the release environment. By means of this coating, it is possible to ensure that, when correctly administered, the dosage form according to the invention passes through the stomach undissolved and the active ingredient is only released in the intestines.

In some preferred embodiments, the dosage form may include a surfactant ingredient to impart suitable formulation characteristics to the composition. Surfactants may be hydrophilic preferably selected from the group consisting of non-ionic hydrophilic surfactants and anionic hydrophilic surfactants or the surfactant may have hydrophobic properties. Examples of non-ionic hydrophilic surfactants are polyoxyethylene sorbitan esters, cremophores and poloxamers. Examples of anionic surfactants are sodium lauryl sarcosinate, docusate and pharmaceutically acceptable docusate salts. Also a mixture of these surfactants can be used.

The formulation optionally comprises auxiliary materials. Examples of these auxiliary materials (or pharmaceutically acceptable excipients) are (i) Binders such as acacia, alginic acid and salts thereof, cellulose derivatives, methylcellulose, hydroxyethyl cellulose, hydroxypropyl cellulose, magnesium aluminum silicate, polyethylene glycol, gums, polysaccharide acids, bentonites, hydroxypropyl methylcellulose, gelatin, polyvinylpyrrolidone, polyvinylpyrrolidone/vinyl acetate copolymer, crospovidone, povidone, polymethacrylates, hydroxypropylmethylcellulose, hydroxypropylcellulose, starch, pregelatinized starch, ethylcellulose, tragacanth, dextrin, microcrystalline cellulose, sucrose, or glucose, and the like; (ii) Disintegrants such as starches, pregelatinized corn starch, pregelatinized starch, celluloses, cross-linked carboxymethylcellulose, crospovidone, cross-linked polyvinylpyrrolidone, a calcium or a sodium alginate complex, clays, alginates, gums, or sodium starch glycolate, and any disintegration agents used in tablet preparations; (iii) Filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like; (iv) Stabilizers such as any antioxidation agents, reducing agents, buffers, or acids, sodium citrate, ascorbyl palmitate, propyl gallate, ascorbic acid, vitamin E, sodium bisulfite, butylhydroxyl toluene, BHA, acetylcysteine, monothioglycerol, phenyl-alpha-nathylamine, lecithin, EDTA, and the like; (v) Lubricants such as magnesium stearate, calcium hydroxide, talc, colloidal silicon dioxide, sodium stearyl fumarate, hydrogenated vegetable oil, stearic acid, glyceryl behenate, magnesium, calcium and sodium stearates, stearic acid, talc, waxes, Stearowet, boric acid, sodium benzoate, sodium acetate, sodium chloride, DL-leucine, polyethylene glycols, sodium oleate, or sodium lauryl sulfate, and the like; (vi) Wetting agents such as oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, or sodium lauryl sulfate, and the like; (vii) Diluents such lactose, starch, mannitol, sorbitol, dextrose, microcrystalline cellulose, dibasic calcium phosphate, sucrose-based diluents, confectioner's sugar, monobasic calcium sulfate monohydrate, calcium sulfate dihydrate, calcium lactate trihydrate, dextrates, inositol, hydrolyzed cereal solids, amylose, powdered cellulose, calcium carbonate, glycine, or bentonite, and the like; (viii) Anti-adherents or glidants such as talc, corn starch, DL-leucine, sodium lauryl sulfate, and magnesium, calcium, or sodium stearates, and the like; (ix) Pharmaceutically compatible carriers such as acacia, gelatin, colloidal silicon dioxide, calcium glycerophosphate, calcium lactate, maltodextrin, glycerin, magnesium silicate, sodium caseinate, soy lecithin, sodium chloride, tricalcium phosphate, dipotassium phosphate, sodium stearoyl lactylate, carrageenan, monoglyceride, diglyceride, or pregelatinized starch, and the like; (x) Other pharmaceutical excipients including polymers, hydrogels, silicon dioxide, ion exchange resins, cellulose acetate butyrate, carbohydrate polymers, organic acids of carbohydrate polymers caprylic/capric triglyceride, isopropyl myristate, ethyl oleate, triethyl citrate, dimethyl phthalate, and benzyl benzoate.

The pharmaceutical compositions and dosage form of the invention may further contain one or more pharmaceutically acceptable excipients. When used in the present invention, pharmaceutically acceptable excipients can play a small or significant role in the behavior of the dosage form, depending on the choice of excipient, quantity of excipient and interaction with other constituents of the dosage form and the gastrointestinal tract. Pharmaceutically acceptable excipients are well known in the art and include, without limitation, excipients referenced in the FDA EAFUS database (http://vm.cfsan.fda.gov/~dms/eafus.html); FDA Food Additives Status List (http://www.cfsan.fda.gov/~dms/opa-appa.html); FDA-GRAS list and database; FDA Color Additive Status List (http://www.cfsan.fda.gov/~dms/opa-appc.html); FDA Inactive Ingredients Database (http://www.accessdata.fda.gov/scripts/cder/iig/index.cfm); Rowe, Sheskey and Owen, Handbook of Pharmaceutical Excipients, APhA Publications; 5th edition (2006); Goodman & Gilman's The Pharmacological Basis of Therapeutics (Brunton, Lazo and Parker, eds, 11th ed., McGraw Hill (2005); Remington: The Science and Practice of Pharmacy, 21st ed, Lippincott Williams & Wilkins (2005); Martindale: The Complete Drug Reference, 35th Edition, Pharmaceutical Press (2007); United States Pharmacopeia—National Formulary (USP-NF), (USP 30—NF 25, 2007), the International Programme on Chemical Safety (http://www.inchem.org/); Pharmaceutical Additives Electronic Handbook, Third Edition, Michael Ash (compiler), Synapse Information Resources, Inc.; 3 Cdr edition (Feb. 19, 2007); and Health Canada's List of Acceptable Non-medicinal Ingredients (http://www.hc-sc.gc.ca/dhp-mps/prodnatur/legislation/docs/nmi-imn_list1_e.html), all hereby incorporated by reference in their entirety.

The dosage form according to the invention may also comprise a coating which is resistant to gastric juices and dissolves as a function of the pH value of the release environment. By means of this coating, it is possible to ensure that, when correctly administered, the dosage form according to the invention passes through the stomach undissolved and the active ingredient is only released in the intestines.

Although opioids agonists are used primarily to treat pain of various etiologies, intensities and duration, opioids can also be used for non-painful conditions such as restless leg syndrome and urinary incontinence. The present invention contemplates all medical uses of opioids by the oral route of administration, preferably the oral route.

In one preferred embodiment, the formulation is used to treat restless leg syndrome. In another preferred embodiment of the invention, the formulation is used to treat urinary incontinence. In another preferred embodiment of the invention, the formulation is used to addiction disorders.

In one preferred embodiment, the invention provides for methods and pharmaceutical compositions to simultaneously provide serotonin surge protection and extended release for proserotonergic agents.

In one preferred embodiment, the invention provides for methods and pharmaceutical compositions to simultaneously provide serotonin surge protection and extended release for proserotonergic agents using substantially the same ingredients.

In one preferred embodiment, the invention provides for methods and pharmaceutical compositions to simultaneously provide serotonin surge protection and abuse deterrence for abusable proserotonergic agents.

In one preferred embodiment, the invention provides for methods and pharmaceutical compositions to simultaneously provide serotonin surge protection and abuse deterrence for abusable proserotonergic agents using substantially the same ingredients.

In one preferred embodiment, the invention provides for methods and pharmaceutical compositions to simultaneously provide serotonin surge protection, abuse deterrence and extended release for abusable proserotonergic agents.

In one preferred embodiment, the invention provides for methods and pharmaceutical compositions to simultaneously provide serotonin surge protection, abuse deterrence and extended release for abusable proserotonergic agents using substantially the same ingredients.

It is understood that each of the various embodiments of methods and pharmaceutical compositions described herein may be used alone or in conjunction with one or more or all of the various embodiments described herein.

Additionally, it is understood that each of the various embodiments of the pharmaceutical compositions described herein may be used with each of the various embodiments of the described method of the present invention as described herein.

Determination of Biologic Effects in Humans

The pharmacologic effects of the pharmaceutical compositions of the present invention can be evaluated using methods well established in the art. The pharmacologic effects of the proserotonergic analgesic pharmaceutical compositions of the present invention can be evaluated using methods well established in the art. A wide variety of pain states and study designs may be used to evaluate the therapeutic effects of intact and tampered dosage forms of the invention. This invention therefore contemplates the use of test methods other than those specifically disclosed herein, including those which may hereafter become known to the art to be capable of performing the necessary functions. Sample sizes in the studies are sufficient to demonstrate the objectives of the testing. A non-limiting list of methods to evaluate the analgesic and other effects of the invention is provided below:

Third Molar Extraction Model

Male and female patients with acute postsurgical pain following the removal of one or more bony impacted third molars are participants. Within 4 to 6 hours after completion of surgery, patients who are experiencing moderate or severe pain, as measured by a visual analog pain intensity scale (VAS≧50 mm) and by a categorical pain intensity scale (moderate or severe pain descriptor), and who meet all other inclusion/exclusion criteria are admitted to the study. Patients are randomly assigned to receive the dosage form of the invention given intact or placebo, in some preferred embodiments, and the dosage form of the invention given intact or dosage form of the invention given in tampered form in other embodiments. Both single and multiple (repeated) dose studies may be conducted. Pain intensity (VAS and categorical), pain relief (categorical) and whether pain is half-gone is recorded by the patient under the supervision of the investigator study coordinator at the various time points: Baseline (0 hour—pain intensity only), 15, 30 and 45 minutes, and at 1, 1.5, 2, 3, 4, 5, 6, 7, 8 and 12 hours after administration of study medication, and immediately prior to the first rescue dose. Sedation and nausea may be evaluated using VAS or categorical scales. Time to onset of perceptible and meaningful pain relief is evaluated using the two stopwatch method. Patients record their global evaluation of study medication at the completion of the 8-hour assessment or at the time of first rescue medication use. Efficacy endpoints include Total Pain Relief (TOTPAR), Sum of Pain Intensity Difference (SPID) and Sum of Pain Relief Intensity Difference (SPRID) at various time points, Time to First Rescue, Time Specific Pain Intensity Difference (PID), Time Specific Pain Relief (PR), Peak Pain Intensity Difference (PPID), Peak Pain Relief (PPR), Time to Confirmed Perceptible Pain Relief (stopwatch), Time to Meaningful Pain Relief (stopwatch), Patient Global Evaluation, Time to Change in Categorical PID$\geq$1, Percent Change in Pain Intensity Score from Baseline, Mean Change in Pain Intensity Score From Baseline, Percent Change in Pain Relief Score from Baseline, Mean Change in Pain Relief Score From Baseline, Percent of Responders, Number of Patients Needed to Treat to Obtain One Patient with $\geq$50% Response (NNT).

Bunionectomy Surgery

Male or female patients requiring primary unilateral first metatarsal bunionectomy surgery alone or with ipsilateral hammertoe repair (without additional collateral procedures) under regional anesthesia (Mayo block) are participants.

Patients who experience moderate or severe pain on a categorical scale (moderate or severe descriptor) and on a visual analog pain intensity scale (VAS; $\geq$50 mm) within 6 hours following completion of bunionectomy surgery are randomly assigned to receive the dosage form of the invention given intact or placebo In some preferred embodiments, and the dosage form of the invention given intact or dosage form of the invention given in tampered form in other embodiments. Both single and multiple (repeated) dose studies may be conducted. Patients are encouraged to wait at least 60 minutes before requesting remedication for pain. At the completion of the single-dose phase (8 hours) or at first request for remedication (whichever is earlier), patients enter into a multiple-dose phase lasting approximately 72 hours. During the multiple dose phase patients receive study medication or placebo at a fixed dose interval (e.g., every 8, 12 or 24 hours). Once the multiple dose phase of the study has begun, patients experiencing pain between scheduled doses of study medication are provided access to supplemental open-label (rescue) analgesia. Patients whose pain cannot be adequately managed on a combination of study medication and rescue medication or who develop unacceptable side effects during the study are discontinued from further study participation and their pain managed conventionally.

Pain intensity (VAS and categorical), pain relief (categorical) and whether pain is half-gone is recorded by the patient under the supervision of the investigator study coordinator at representative time points, e.g., Baseline (pain intensity only), 15, 30 and 45 minutes and 1, 1.5, 2, 3, 4, 5, 6, 7 and 8 hours after administration of study medication and immediately prior to the first remedication. Sedation and nausea may be evaluated using VAS or categorical scales. Time to onset of perceptible and meaningful pain relief is evaluated using the double-stopwatch method. Patients complete a global evaluation of study medication at the completion of the 8-hour assessment or just prior to the first remedication. Following completion of the single-dose phase (8 hours or just prior to first remedication, if $\leq$8 hours), patients begin the multiple dose phase of the study. During the multiple dose phase, patients record their overall pain intensity since the previous scheduled dose, their current pain intensity and a patient global, immediately prior to each scheduled dose of study medication and at early termination.

Measures of efficacy in the single-dose phase include Sum of Pain Intensity Difference (SPID), Total Pain Relief (TOTPAR), Sum of Pain Relief Intensity Difference (SPRID), Time to First Remedication, Time Specific Pain Intensity Difference (PID), Time Specific Pain Relief (PR), Peak Pain Intensity Difference (PPID), Peak Pain Relief (PPR), Time to Confirmed Perceptible Pain Relief (stopwatch), Time to Meaningful Pain Relief (stopwatch), Patient Global Evaluation, Time to Change in Categorical PID$\geq$1, Percent Change in Pain Intensity Score from Baseline, Mean Change in Pain Intensity Score From Baseline, Percent Change in Pain Relief Score from Baseline, Mean Change in Pain Relief Score From Baseline, Percent of Responders, Number of Patients Needed to Treat to Obtain One Patient with $\geq$50% Response (NNT).

Measures of efficacy in the multiple-dose phase include the time specific overall pain intensity, current pain intensity and patient global at the time of scheduled remedication, the average of overall pain intensity, current pain intensity and patient global over 0-24, 24-48 and 48-72 and number of doses of rescue analgesic over 0-24, 24-48 and 48-72 and 0-72 hours.

Chronic Pain of Osteoarthritis

The analgesic efficacy of the invention may be demonstrated in single or repeated dose randomized double-blind, controlled studies. Patients are randomized to receive the dosage form of the invention given intact or placebo, in some preferred embodiments, and the dosage form of the invention given intact or dosage form of the invention given in tampered form in other embodiments. In repeated dose studies, typically, patients who meet the American College of Rheumatology criteria for knee and/or hip OA are washed off their analgesics for 2 to 7 days to allow for pain of moderate to severe intensity to return. Once a stable baseline pain score is established, patients are randomized to treatment, usually for a period of 1 to 12 weeks. Pain, joint stiffness and physical function can be measured with a multidimensional instrument, such as the WOMAC, quality of life with the SF-12 or SF-36 and adverse events with a non-directed questionnaire at baseline and at post-baseline return visits. Response to pain, stiffness, physical function, quality of life and adverse events are calculated as change from baseline and compared between treatments. Sedation and nausea may be evaluated using VAS or categorical scales.

Migraine

The analgesic efficacy of the invention may be demonstrated in single or repeated dose randomized double-blind, controlled studies. Patients are randomized to receive the dosage form of the invention given intact or placebo, in some preferred embodiments, and the dosage form of the invention given intact or dosage form of the invention given in tampered form in other embodiments. Patients with migraine headaches are typically evaluated in prospective, randomized, double-blind, parallel group, single-dose studies. Crossover studies are also possible. The study population consists of male and non-pregnant female subjects, 18 to 65 years of age with a primary headache diagnosis of either migraine attack without aura or migraine attack with aura, as diagnosed according to the International Classification of Headache Disorders-2 criteria. To qualify, the subject must typically have a history, on average, of at least one migraine attack per month, but an average of no more than 6 migraine attacks each month during the past year. Using a headache diary subjects are instructed to treat and evaluate the headache pain and symptoms associated with one eligible migraine attack, with or without aura, with at least moderate headache pain intensity. Eligible subjects are randomly assigned to receive the drug to treat one migraine attack, with or without aura, with headache pain of at least moderate pain intensity as determined by them migraine questionnaire they are asked to take a single dose of study drug, according to their randomized treatment assignment. Headache pain intensity, nausea, photophobia, phonophobia, vomiting, and ability to function are assessed at baseline, 0.25, 0.5, 0.75, 1, 1.5, 2, 2.5, 3, 4, 8, 16 and 24 hours post-dose. In addition, the recurrence of pain and use of any rescue mediation is documented. Primary efficacy variables typically consist of the percent of subjects who are without: (i) pain; (ii) nausea; (iii) photophobia and, (iv) phonophobia, each at 2 hours post-dosing. Secondary efficacy variables typically consist of headache pain intensity and associated symptoms at each evaluation time point, incidence of vomiting, patient function, sum of pain intensity difference at each evaluation time (SPID), percent of subjects who experience headache recurrence up to 24 hours, and the median time to recurrence. Sedation may be evaluated using VAS or categorical scales. Recurrence is defined as the reduction in pain from moderate or severe pain to none at 2 hours after taking study drug, followed by: (i) an increase to mild, moderate or severe pain within 24 hours after taking the study drug, or (ii) consuming a rescue medication within 24 hours after taking the study drug.

Postherpetic Neuralgia

The analgesic efficacy of the invention may be demonstrated in repeated dose randomized double-blind, controlled studies. Patients are randomized to receive the dosage form of the invention given intact or placebo, in some preferred embodiments, and the dosage form of the invention given intact or dosage form of the invention given in tampered form in other embodiments. Patients with a history of postherpetic neuralgia ≧3 months and pain of at least moderate intensity are enrolled in the study. Patients with hypersensitivity to study medications, a history of drug or alcohol abuse and significant pain of alternate etiology are generally excluded. Patients meeting study eligibility criteria are "washed off" their analgesics in some embodiments, generally for 2 to 7 days to allow for pain of moderate to severe intensity to return. Once a stable baseline pain score is established, patients are randomized to treatment, usually for a period of 4 to 12 weeks. Pain intensity is assessed one to several times a day and in some cases only once weekly using VAS, categorical or numerical rating scales. Various dimensions of neuropathic pain may be assessed, including steady pain (ongoing pain), brief pain (paroxysmal pain) and skin pain (allodynia). Pain may also be assessed at scheduled clinic study visits. Pain may also be assessed using standardized pain scales such as the Neuropathic Pain Scale (Galer et al., Neurology 1997; 48:332-8), the Neuropathic Pain Symptom Inventory (Bouhassira et al., Pain 2004; 108:248-57), interference measures of the Brief Pain Inventory (Cleeland, CRC Press, 1991:293-305 and Ann Acad Med Singapore 1994; 23:129-38) or the McGill Pain Questionnaire Short-Form (Melzack, Pain 1987; 30:191-7). Patient global assessment may be measured using a number of available tools, for example Patient Global Impression of Change (Farrar et al., Pain 2001; 94:149-580). Quality of life may similarly be assessed using number of available tools, for example the SF-36, SF-12 or SF-8. Examples of randomized, placebo or active studies conducted in postherpetic neuralgia are known in the art (e.g., Watson and Babul, Neurology 1998; 50:1837-41; Sabatowski et al., Pain. 2004; 109:26-35; Rowbotham et al., JAMA. 1998; 280: 1837-42). Adverse events may be assessed using a non-directed questionnaire, a symptom checklist or specific queries on adverse signs and symptoms. Response to pain, function, quality of life and adverse events are calculated as change from baseline and compared between treatments. Sedation and nausea may be evaluated using VAS or categorical scales.

The preparation of oral immediate release dosage forms is well known in the art—see Remington: the science of Pharmacy Practice, 21$^{st}$ Edition, 2006, Lippincott, Williams & Wilkins, Baltimore, Md.; Pharmaceutical Preformulation and Formulation: A Practical Guide from Candidate Drug Selection to Commercial Dosage Form. Gibson, M (ed). CRC Press, 2001; Niazi, S. Handbook of Pharmaceutical Manufacturing Formulations: Uncompressed Solid Products (Volume 2 of 6), CRC Press, 2004; Niazi, S. Handbook of Pharmaceutical Manufacturing Formulations: Compressed Solid Products (Volume 1 of 6), CRC Press, 2004; Mollet, H, Grubenmann A, Payne H. Formulation Technology Emulsions, Suspensions, Solid Forms, Wiley-VCH, 2001; Niazi S and Niazi S K, Pharmaceutical Capsules, 2$^{nd}$ Ed., Podczeck, F and Jones B E (eds)., Pharmaceutical Press, 2004, London (all of which are hereby incorporated by reference). A majority of oral dosage forms commercially available world wide are formulated as immediate release products.

Evaluating Effects Fed and Fasted State on Oral Bioavailability

The effects of fed and fasted state of the invention, and in particular, their effects on $C_{max}$, $AUC_{0-t}$ and $AUC_{0-\infty}$, can be evaluated using methods well know in the art. More specifically, the invention relies on the methods contained in the document entitled: "Guidance for Industry: Food-Effect Bioavailability and Fed Bioequivalence Studies Study Design, Data Analysis and Labeling", Department of Health and Human Services, Food and Drug Administration, Center for Drug Evaluation and Research, October, 2001, which is here incorporated by reference. Additional guidance on the conduct of bioavailability studies is found in "Guidance for Industry: Bioavailability and Bioequivalence Studies for Orally Administered Drug Products—General Considerations", Department of Health and Human Services, Food and Drug Administration, Center for Drug Evaluation and Research, July 2002, which is here incorporated by reference.

Tamper Resistance and Tamper Deterrence Testing

The popularity of immediate release formulations of abusable proserotonergic agents among drug addicts and recreational drug users is in part due to the mood altering and reinforcing effects of the drug. The popularity of extended release formulations of abusable proserotonergic agents among drug addicts and recreational drug users is in part due to the pharmacologic properties of the drug therein (e.g., mood altering and reinforcing effects) and in part due to the large amount of drug per tablet or capsule (e.g., a 12 or 24 hour supply). For example commercially available immediate release abusable proserotonergic tablets and capsules are usually administered every 4 to 6 hours and they release their dose into the systemic circulation over one to two hours. New, extended release formulations are designed to gradually release their much larger proserotonergic content over a 12 or 24-hour period. Most recreational drug users and addicts have a unit of use which is one tablet or capsule. The 12 or 24-hour supply of a proserotonergic agents typically contained in one extended release tablet or capsule, instead of in 4 to 6 tablets or capsules means that there is a greater risk that such formulations may be highly sought by drug addicts and recreational drug users alike, for non-medical use. Intentional or inadvertent tampering from extended release formulations will rapidly deliver a massive dose and produce profound pharmacologic effects.

Addicts and recreational drug users commonly use abusable proserotonergic agents by a variety of routes of administration. Commonly used methods include 1) parenteral (e.g., intravenous injection, where the drug is crushed and extracted or melted and the contents of a dosage unit then injected), 2) intranasal (e.g., snorting, where the drug is inhaled as powdered dosage unit), and 3) episodic or repeated oral ingestion of crushed product, where the drug is chewed to increase the surface area and permit rapid release of drug substance. All of these strategies are intended to more efficiently get the abusable proserotonergic agent into the CNS, both in terms of total amount of drug, peak concentration of drug and time to peak concentration of drug.

One mode of abuse involves the extraction of the drug component from the dosage form by first mixing the tablet or capsule with a suitable solvent (e.g., water or alcohol), and then filtering and/or extracting the drug component from the mixture for intravenous injection. Another mode of abuse of extended release drugs involves dissolving the drug in water, alcohol or another "recreational solvent" to hasten its release and to ingest the contents orally, in order to provide high peak concentrations and maximum euphoriant effects.

It is necessary to be able to measure resistance or deterrence to the likely routes of tampering in a meaningful and relevant way. The in vitro tests below are provided for illustration of some testing methods and are intended to be non-limiting examples. This invention therefore contemplates the use of test methods other than those specifically disclosed herein, including those which may hereafter become known to the art to be capable of performing the necessary functions.

Extraction with Alcohol on Whole Dosage Unit

Method: Place a whole dosage unit in 18 mL of 0.1N HCl in a 60 mL amber bottle and shake at 240 rpm on an orbital shaker for 30 min. After 30 min add 12 mL of ethanol (95-96%) to each bottle. Swirl by hand and remove a 1 mL sample from each bottle ($T_0$). Place the solutions back in the orbital shaker for further shaking at 240 rpm. Take 1 mL samples after 10, 20, 30, 40, 60 and 180 min of further shaking for each bottle. Analyze and graph the results on a linear scale of cumulative release (%) vs. time (min).

Extraction with Alcohol on a Crushed or Cut Dosage Unit

Extension of the above test. Method: Place a tablet (after crushing with a single crush with a spatula) or a capsule (cut in half) in 18 mL of 0.1N HCl in a 60 mL amber bottle and shake at 240 rpm on an orbital shaker for 30 min. Continue the test as in 1) above.

Extraction into Water

Method: Crush with a mortar and pestle and grind in 5 mL of water for 5 minutes. The resulting suspension is filtered through a 0.45 micron filter into a flask and diluted to 50 mL with water. Quantify drug concentration by HPLC.

Freeze and Crush

Method: Freeze the dosage unit in a domestic freezer for 24 hr, then grind with a mortar and pestle for five minutes. Sieve through a suitable sieve (ca 600 micron) and, by weighing, measure the percentage passing the sieve.

Taste of Base Excipient Mix (Organoleptic Test)

Method: Chew a placebo mix for five minutes and rate the taste on a 0-10 scale with 0 as bland to repulsive at 10. This method is relevant only to dosage units containing taste modifiers.

Extraction into Acid

Method: Crush with a mortar and pestle and heat to boiling in 5 mL of vinegar. The resulting suspension is filtered through a 0.45 micron filter into a flask and diluted to 50 mL with water. Quantify drug concentration by HPLC.

Application of Heat (Melting Temperature≧50° C. or 55° C.)

Method: Heat the squashed contents of a dosage unit on a hot plate until melted. Determine the temperature of melting and test whether the mix becomes sufficiently fluid to be drawn up into a syringe via a 1.2 mm needle then expelled.

"Drug", "pharmacological agent", "pharmaceutical agent", "active agent," and "agent" are used interchangeably and are intended to have their broadest interpretation as to any therapeutically active substance which is delivered to a living organism to produce a desired, usually beneficial effect. In general, this includes therapeutic agents in all of the major therapeutic areas, also including proteins, peptides, oligonucleotides, and carbohydrates as well as inorganic ions, such as calcium ion, lanthanum ion, potassium ion, magnesium ion, phosphate ion, and chloride ion.

"Pharmaceutically or therapeutically acceptable excipient or carrier" refers to a substance which does not interfere with the effectiveness or the biological activity of the active ingredients and which is not toxic to the hosts, which may be either humans or animals, to which it is administered. In some embodiments of the present invention, pharmaceutically or therapeutically acceptable excipients or carriers may play a role imparting or optimizing the SSP characteristics to the pharmaceutical composition.

"Therapeutically effective amount" refers to the amount of an active agent sufficient to induce a desired biological result. That result may be alleviation of the signs, symptoms, or causes of a disease, or any other desired alteration of a biological system.

The phrase "therapeutically-effective" is intended to qualify the amount of each agent which will achieve the goal of improvement in disease severity and the frequency of incidence over treatment of each agent by itself, while avoiding adverse side effects typically associated with alternative therapies.

The term "effective amount" means the quantity of a compound according to the invention necessary to prevent, to cure, or at least partially arrest a symptom for which the proserotonergic agent has been prescribed to a subject. A subject is any animal, preferably any mammal, more preferably a human.

The term "agonist" means a ligand that binds to a receptor and alters the receptor state resulting in a biological response. Conventional agonists increase receptor activity, whereas inverse agonists reduce it (See Neubig et al, IUPHAR Committee on Receptor Nomenclature and Classification, Pharmacol Rev, 2003; Howlett et al., Mol Pharmacol, 1988).

An "antagonist" is a drug or ligand that reduces the action of another drug or ligand, generally an agonist. Many antagonists act at the same receptor macromolecule as the agonist. (See Neubig et al, IUPHAR Committee on Receptor Nomenclature and Classification, Pharmacol Rev, 2003; Howlett et al., Mol Pharmacol, 1988).

The term "receptor" means a molecule within a cell, on a cell surface, on a membrane, in tissue, in fluid or otherwise found in humans that serve as a recognition or binding site to cause specific physiologic, pathophysiologic or pharmacologic effects. The term "receptor" also means a cellular macromolecule, or an assembly of macromolecules, that is concerned directly and specifically in chemical signaling between and within cells. Combination of a hormone, neurotransmitter, drug, ligand, or intracellular messenger with its receptor(s) initiates a change in cell function (Neubig et al, IUPHAR Committee on Receptor Nomenclature and Classification, Pharmacol Rev, 2003).

The term "opioid agonist" also referred to as "opioid receptor agonist" means a molecule that causes a specific physiologic, pathophysiologic or pharmacologic effect after binding to an opioid receptor, such actions a consequence of their agonist or agonistic effects. Opioid agonists are known or can be readily determined by individuals who skilled in the art.

The term "opioid receptor" includes mu ($\mu$), delta ($\delta$), kappa ($\kappa$) and/or nociceptin/orphanin FQ (N/OFQ) peptide (NOP) receptors, their subtypes and splice variants such as $\mu_1$, $\mu_2$, $\delta_1$, $\delta_2$, $\kappa_1$, $\kappa_2$ and $\kappa_3$, etc, regardless of whether they also bind to or influence other receptor systems (e.g., norepinephrine reuptake inhibition, serotonin reuptake inhibition, NMDA receptor antagonism).

As used herein, the term "serotonin surge protector", "SSP" or "SSP's" means pharmaceutical compositions that resist, deter or prevent crushing, shearing, grinding, chewing, dissolving, melting, needle aspiration, inhalation, insufflation or solvent extraction of the proserotonergic agent contained therein which is responsible for causing the serotonin syndrome through serotonin excess, thereby preventing or reducing the incidence and intensity of the serotonin syndrome when the SSP is combined in the same formulation with one or more proserotonergic agents. Preferred SSP's are selected from a group consisting of polymeric and/or nonpolymeric gel forming agents, viscosity enhancing agents, high viscosity liquids and high melting point waxes, hydrogenated Type I or Type II vegetable oils, polyoxyethylene stearates and distearates, glycerol monostearate, and non-polymeric, non-water soluble liquids, carbohydrate-based substances or poorly water soluble, high melting point (mp=40 to 100° C.) waxes and mixtures thereof. In some embodiments, SSP's include polyethylene oxides, polyvinyl alcohol, hydroxypropyl methyl cellulose, carbomers, ethylcellulose, cellulose acetate, cellulose acetate propionate, cellulose acetate butyrate, cellulose acetate phthalate and cellulose triacetate, cellulose ether, cellulose ester, cellulose ester ether, and cellulose, acrylic resins comprising copolymers synthesized from acrylic and methacrylic acid esters, the acrylic polymer may be selected from the group consisting of acrylic acid and methacrylic acid copolymers, methyl methacrylate copolymers, ethoxyetlryl methacrylates, cyanoetlryl methacrylate, poly(acrylic acid), poly(methaerylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), glycidyl methacrylate copolymers, microcrystalline cellulose with carboxymethylcellulose sodium, carboxymethylcellulose sodium, polyacrylic acid, locust bean flour, pectins, waxy corn starch, sodium alginate, guar flour, iota-carrageenan, karaya gum, gellan gum, galactomannan, tara stone flour, propylene glycol alginate, sodium hyaluronate, tragacanth, tara gum, fermented polysaccharide welan gum, xanthans, silicon dioxide, fumed silicon dioxide, coconut oil, hydrogenated palm kernel oil, hydrogenated cottonseed oil, hydrogenated palm kernel oil, hydrogenated palm oil, hydrogenated soybean oil and beeswax, and mixtures thereof. In some embodiments, SSP's include hydrophobic polymers, hydrophilic polymers, gums, protein derived materials, waxes, shellac, oils and mixtures thereof.

In some embodiments, "SSP's" include glyceryl behenate (e.g., Comptirol™ 888 ATO), glyceryl palmitostearate (e.g., Precirol™ ATO 5), stearoyl macrogolglycerides (Gelucire™ 50/13), lauroyl macrogolglycerides (Labrafil™ M 2130 CS).

In some embodiments, the dosage form must include, in addition to at least one proserotonergic agent, at least two SSP's.

In some embodiments, the dosage form must include, in addition to at least one proserotonergic agent, at least two SSP's selected from the group comprising: (a) polymeric and/or nonpolymeric gel forming agents; (b) viscosity enhancing agents; (c) high viscosity liquids; and (d) high melting point waxes. In some preferred embodiments, to qualify as an "SSP" requires a mixture of two or more compounds, wherein the two or more compounds are selected from at least two of the foregoing groups [i.e., (a), (b), (c), and (d), for example one compound from (a) and one compound from (b) or one compound from (a) and two compounds from (b)]. In some preferred embodiments, to qualify as an "SSP" requires a mixture of three or more of the foregoing compounds. In some preferred embodiments, to qualify as an "SSP" requires a mixture of three or more of the foregoing compounds, wherein the three or more compounds are selected from at least two of the foregoing groups [i.e., (a), (b), (c), and (d), for example one compound from (a) and two compounds from (b)]. In some preferred embodiments, to qualify as an "SSP" requires a mixture of three or more of the foregoing compounds, wherein the three or more compounds are selected from at least three of the foregoing groups [i.e., (a), (b), (c), and (d), for example one compound from (a), one compounds from (b), and one compounds from (c)].

In some embodiments, the SSP refers to one or more compounds selected from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes, and mixtures thereof. In some preferred embodiments, the SSP is a mixture of two or more compounds from the forgoing group [i.e., (a) to (d)]. In some preferred embodiments, to qualify as an "SSP" requires a mixture of two or more compounds, wherein the two or more compounds are selected from at least two of the foregoing groups [i.e., (a), (b), (c), and (d), for example one compound from (a) and one compound from (b)].

In some preferred embodiments, to qualify as an "SSP" requires a mixture of three or more of the foregoing compounds. In some preferred embodiments, to qualify as an "SSP" requires a mixture of three or more of the foregoing compounds, wherein the three or more compounds are selected from at least two of the foregoing groups [i.e., (a), (b), (c), and (d), for example one compound from (a) and two compounds from (b)]. In some preferred embodiments, to qualify as an "SSP" requires a mixture of three or more of the foregoing compounds, wherein the three or more compounds are selected from at least three of the foregoing groups [i.e., (a), (b), (c), and (d), for example one compound from (a), one compounds from (b), and one compounds from (c)].

As used herein, the term "SSP" also includes glyceryl behenate (e.g., Comptirol™ 888 ATO), glyceryl palmitostearate (e.g., Precirol™ ATO 5), stearoyl macrogolglycerides (Gelucire™ 50/13), lauroyl macrogolglycerides (Labrafil™ M 2130 CS).

As used herein and without being bound by theory, the term "proserotonergic agent", "proserotonergic", "proserotonergic agents" or "proserotonergic drugs" means drugs that directly or indirectly enhance the effects of serotonin, usually through reuptake inhibition, direct or indirect agonism, enhancement of effects of serotonergic drugs or other known or unknown mechanism, or through effects at receptors or by mechanisms other than serotonin effect enhancement or in addition to serotonin effect enhancement, such that they have the potential to produce the serotonin syndrome, said serotonin syndrome characterized by one or more adverse signs and symptoms, including hyperthermia, tachycardia, shivering, diaphoresis, mydriasis, tremor, myoclonus, hyperreflexia, hypertension, hyperactive bowel sounds, agitation, hypervigilance, pressured speech, delirium, muscular rigidity, hypertonicity, metabolic acidosis, rhabdomyolysis, elevated levels of AST, ALT and creatinine, seizures, renal failure, and disseminated intravascular coagulopathy (DIC). For the purposes of the invention, proserotonergic drugs include drugs selected from a group consisting of selective serotonin-reuptake inhibitors (SSRIs), selective serotonin-norepinephrine reuptake inhibitors (SNRIs), serotonin reuptake inhibitors, norepinephrine reuptake inhibitors, tricyclic, tetarcyclic and non-tricyclic antidepressants, monoamine oxidase (MAO) inhibitors, antiepileptics, opioid analgesics, tramadol, antiemetics, bariatric medications, sibutramine, antibiotics, antimigraine drugs, antivirals, and cough suppressants, and mixtures thereof given in the form of an acid, base or, optionally, in the form of a pharmaceutically acceptable salt, prodrug, ester, analog, derivative, solvate, complex, polymorph, hydrate, racemate or an individual diastereoisomers or enantiomeric isomers thereof or mixture thereof. In some embodiments, the proserotonergic agent includes citalopram, fluoxetine, fluvoxamine, paroxetine, sertaline, venlafaxine, milnacipran, buspirone, clomipramine, nefazodone, trazadone, clorgiline, isocarboxazid, moclobemide, phenelzine, selegiline, valproate, fentanyl, levorphanol, meperidine, pentazocine, tramadol, granisetron, metoclopramide, ondansetron, sumatriptan, sibutramine, linezolide, ritonavir, dextromethorphan, dextrorphan, tryptophan, hypericum perforatum (St. John's wort), panax ginseng (ginseng) and lithium.

Without being bound by theory, proserotonergic agents include selective serotonin-reuptake inhibitors (SSRIs), e.g., citalopram, ecitalopram, fluoxetine, fluvoxamine, nefazodone, paroxetine, and sertaline; selective serotonin-norepinephrine reuptake inhibitors (SNRIs), e.g, bicifadine, venlafaxine, milnacipran, mirtazepine and nefazodone; tricyclic and non-tricyclic antidepressants, e.g., buspirone, clomipramine, trazadone; monoamine oxidase (MAO) inhibitors, e.g., clorgiline, isocarboxazid, moclobemide, phenelzine and selegiline; antiepileptics, e.g., valproate; analgesics, e.g., fentanyl, levorphanol, meperidine, pentazocine, tramadol, other opioid analgesics (see below); antiemetic agents, e.g., granisetron, metoclopramide and ondansetron; antimigraine drugs, e.g., sumatriptan; bariatric medications, e.g., sibutramine; antibiotics, e.g., linezolide (a MAOI) and ritonavir (via CYP-450 3A4 inhibition); antitussives, e.g. dextromethorphan; dietary supplements and herbal products, e.g., tryptophan, Hypericum perforatum (St. John's wort), Panax ginseng (ginseng); lithium; and drugs that are serotonin receptor agonists.

Opioid analgesics include alfentanil, allylprodine, alphaprodine, anileridine, apomorphine, apocodeine, benzylmorphine, bezitramide, buprenorphine, butorphanol, carfentanil, clonitazene, codeine, cyclazocine, cyclorphen, cyprenorphine, desmethyltramadol, desomorphine, dextromoramide, dezocine, diampromide, dihydrocodeine, dihydromorphine, dimenoxadol, dimepheptanol, dimethylthiambutene, dioxyaphetyl butyrate, dipipanone, eptazocine, ethoheptazine, ethylmethylthiambutene, ethylmorphine, etonitazene, fentanyl, heroin, hydrocodone, hydroxymethylmorphinan, hydromorphone, hydroxypethidine, isomethadone, ketobemidone, levallorphan, levorphanol, levomethadone, levophenacylmorphan, lofentanil, meperidine, meptazinol, metazocine, methadone, methylmorphine, metopon, morphine, myrophine, nalbuphine, narceine, nicomorphine, norlevorphanol, normethadone, nalorphine, normorphine, norpipanone, ohmefentanyl, opium, oxycodone, oxymorphone, papavereturn, pentazocine, phenadoxone, phenomorphan, phenazocine, phenoperidine, pholcodine, piminodine, piritramide, propheptazine, promedol, profadol, properidine, propiram, propoxyphene, remifentanil, sufentanil, tapentadol, tramadol, tramadol metabolites, tilidine, naltrexone, naloxone, nalmefene, methylnaltrexone, naloxone methiodide, nalorphine, naloxonazine, nalide, nalmexone, nalbuphine, nalorphine dinicotinate, naltrindole (NTI), naltrindole isothiocyanate, (NTII), naltriben (NTB), nor-binaltorphimine (nor-BNI), racemorphan, beta-funaltrexamine (b-FNA), BNTX, cyprodime, ICI-174,864, LY117413, MR2266, etorphine, DAMGO, CTOP, diprenorphine, naloxone benzoylhydrazone, bremazocine, ethylketocyclazocine, U50,488, U69, 593, spiradoline, DPDPE, [D-Ala2,Glu4] deltorphin, DSLET, Met-enkephalin, Leu-enkephalin, (3-endorphin, dynorphin A, dynorphin B, a-neoendorphin, or an opioid having the same pentacyclic nucleus as nalmefene, naltrexone, buprenorphine, levorphanol, meptazinol, pentazocine or dezocine. Opioids include the unsalified drug or the pharmaceutically acceptable salts, esters, analogs, derivatives, solvates, complexes, polymorphs, hydrates, as racemates or an individual diastereoisomers or enantiomeric isomers thereof or mixture thereof. Opioid agonists also include drugs that bind to opioid receptors to exert agonist activity. Opioid agonists also include drugs that are listed in the United States Controlled Substances Act of 1970, as amended, and regulations thereof, and drugs listed in the United States Psychotropic Substances Act of 1978, as amended, and regulations thereof.

In a preferred embodiment, the opioid of the invention is selected from a group consisting of alfentanil, anileridine, buprenorphine, brifentanil, butorphanol, carfentanil, codeine, dextromoramide, dezocine, dihydrocodeine, dihydromorphine, fentanyl, heroin, hydrocodone, hydromorphone, hydroxypethidine, isomethadone, ketobemidone, levorphanol, levomethadone, lofentanil, meperidine, meptazinol, metazocine, methadone, 4-methoxymethylfentanyl, 3-methylfentanyl, metopon, mirfentanil, morphine, morphine-6-glucuronide, nalbuphine, norlevorphanol, normethadone, ohmefentanyl, opium, oxycodone, oxymorphone, pentazocine, phenazocine, propiram, propoxyphene, remifentanil, sufentanil, tapentadol, trefentanil, tramadol, tilidine, any opioid having agonist activity at an opioid receptor belonging to the phenanthrene, morphinan, benzomorphan, methadone, phenylpiperidine, propionanilide 4-anilidopiperidine, 4-aryl piperidines, and 4-Heteroarylpiperidines class, any opioid having agonist activity at an opioid receptor having the same pentacyclic nucleus as nalmefene, naltrexone, buprenorphine, levorphanol, meptazinol, pentazocine and dezocine, any opioid having agonist activity at an opioid receptor which is a fentanyl analog, or their pharmaceutically acceptable salts, prodrugs, esters, analogs, derivatives, solvates, complexes, polymorphs, hydrates and metabolites, as racemates or an individual diastereoisomers or enantiomeric isomers thereof or mixtures thereof.

Notwithstanding anything to the contrary in this application and without being bound by theory, in some embodiments, the term "proserotonergic agent", "proserotonergic", "proserotonergic agents" or "proserotonergic drugs" means drugs that have the potential to produce the serotonin syndrome by mechanisms other than causing a serotonin surge, serotonin excess or serotonin effect. Proserotonergic agents have the potential to produce the serotonin syndrome through unknown mechanism, or through effects at receptors or by mechanisms other than serotonin effect enhancement or in addition to serotonin effect enhancement.

In some embodiments, the invention excludes milnacipran as the proserotonergic agent. In some embodiments, the invention excludes selective serotonin-reuptake inhibitors (SSRIs), selective serotonin-norepinephrine reuptake inhibitors (SNRIs), serotonin reuptake inhibitors, norepinephrine reuptake inhibitors, tricyclic, tetarcyclic and non-tricyclic antidepressants, monoamine oxidase (MAO) inhibitors, and mixtures thereof as proserotonergic agents.

In some embodiments, the invention excludes milnacipran. In some embodiments, the invention excludes antiepileptics and mixtures thereof as proserotonergic agents.

In some embodiments, the invention excludes milnacipran. In some embodiments, the invention excludes antiemetics, bariatric medications, sibutramine, antibiotics, antimigraine drugs, antivirals, and cough suppressants, and mixtures thereof as proserotonergic agents.

In some embodiments, the invention excludes milnacipran. In some embodiments, the invention excludes citalopram, fluoxetine, fluvoxamine, paroxetine, sertaline, venlafaxine, milnacipran, buspirone, clomipramine, nefazodone, trazadone, clorgiline, isocarboxazid, moclobemide, phenelzine, selegiline, valproate, fentanyl, levorphanol, meperidine, pentazocine, tramadol, granisetron, metoclopramide, ondansetron, sumatriptan, sibutramine, linezolide, ritonavir, dextromethorphan, dextrorphan, tryptophan, hypericum perforatum (St. John's wort), panax ginseng (ginseng) and lithium and mixtures thereof as proserotonergic agents.

In some embodiments, the invention excludes citalopram, ecitalopram, fluoxetine, fluvoxamine, nefazodone, paroxetine, sertaline, bicifadine, venlafaxine, milnacipran, mirtazepine, nefazodone, buspirone, clomipramine, trazadone, clorgiline, isocarboxazid, moclobemide, phenelzine and selegiline, and mixtures thereof as proserotonergic agents.

In some embodiments, the invention excludes extended and/or delayed release prosertonergic agents. In some embodiments, the invention excludes extended and/or delayed release prosertonergic agents intended to provide a therapeutic effect of approximately 24 hours.

In some embodiments, the invention includes as proserotonergic agents only opioid agonists, or opioid agonists in immediate release form or opioid analgesics in extended release form.

In some embodiments, the invention includes as proserotonergic agents only opioid agonists, said proserotonergic agents not known to provide clinically meaningful or significant serotonergic effects.

In some embodiments, the invention includes as proserotonergic agents only opioid agonists, said proserotonergic agents not known in the prior art to be therapeutically effective selective serotonin-reuptake inhibitors (SSRIs), selective serotonin-norepinephrine reuptake inhibitors (SNRIs), serotonin reuptake inhibitors, norepinephrine reuptake inhibitors, antidepressants, tricyclic, tetarcyclic and non-tricyclic antidepressants or monoamine oxidase (MAO) inhibitors.

In some embodiments, the invention includes as proserotonergic agents only opioid agonists, said proserotonergic agents not generally considered to produce common serotonergic side effects effects (for example, those seen with selective serotonin-reuptake inhibitors (SSRIs), selective serotonin-norepinephrine reuptake inhibitors (SNRIs), serotonin reuptake inhibitors, norepinephrine reuptake inhibitors, antidepressants, tricyclic, tetarcyclic and non-tricyclic antidepressants).

In some embodiments, the invention includes as proserotonergic agents opioid agonists, said proserotonergic agents not known to produce the serotonin syndrome.

In some embodiments, the invention excludes modified, extended and/or delayed release opioids as prosertonergic agents, said opioids intended to provide a therapeutic effect of approximately 24 hours.

In some embodiments, the invention excludes opioids in bead, spehroid or multiparticulate matrices as prosertonergic agents.

In some embodiments, the invention excludes modified, extended and/or delayed release opioids in bead, spehroid or multiparticulate matrices as prosertonergic agents.

In some embodiments, the invention excludes modified, extended and/or delayed release opioids in bead, spehroid or multiparticulate matrices as prosertonergic agents, said opioids intended to provide a therapeutic effect of approximately 24 hours.

In some embodiments, the invention includes prosertonergic agent dosage forms, said dosage form only in the form of liquid filled capsules which solidify at room temperature.

In some embodiments, the invention includes only opioid agonists as prosertonergic agent dosaage forms, said dosage form only in the form of liquid filled capsules which solidify at room temperature.

Prosertonergic agents include the drugs, their pharmaceutically acceptable salts, esters, analogs, derivatives, solvates, complexes, polymorphs, hydrates, as a racemates or an individual diastereoisomers or enantiomeric isomers thereof or mixture thereof.

All modes of administration and co-administration are contemplated in the present invention, including oral, subcutaneous, direct intravenous, slow intravenous infusion, continuous intravenous infusion, intravenous or epidural patient controlled analgesia (PCA and PCEA), intramuscular, intrathecal, epidural, intracistemal, intramuscular, intraperitoneal, transdermal, topical, transmucosal, buccal, sublingual, transmucosal, inhalation, intranasal, epidural, intraatricular, intranasal, rectal or ocular routes.

The term "pharmaceutically acceptable salt" as used herein refers to a salt which is toxicologically safe for human and animal administration. Nonlimiting examples of salts include hydrochlorides, hydrobromides, hydroiodides, sulfates, bisulfates, nitrates, citrates, tartrates, bitartrates, phosphates, malates, maleates, napsylates, fumarates, succinates, acetates, terephlhalates, pamoates and pectinates. Preferably, the pharmaceutically acceptable salt of levorphanol is a tartrate. Preferably, the pharmaceutically acceptable salt of morphine is a hydrochloride, a sulfate or a tartrate.

The present invention anticipates the use of more than one proserotonergic agent, given in the same formulation of in a different formulation, for use to treat, prevent or ameliorate the same disease or a different disease.

In one embodiment of the invention, the proserotonergic drug tramadol is given alone as an immediate release formulation. In another embodiment, tramadol is given as an extended release formulation. In another embodiment, extended release tramadol is administered with fluoxetine. In another embodiment, levorphanol is administered alone as an extended release formulation. In another embodiment, extended release levorphanol is administered with venlafaxine.

The term "controlled release" as used herein is intended to distinguish it from immediate release dosage forms. Controlled release means a formulation or composition intended for any route of administration, including oral, buccal, rectal, transdermal, epidural, intramuscular, subcutaneous, inhaled and the like, which is prepared in such a manner as to allow for delayed, gradual, modulated and/or prolonged release of the µ-opioid receptor agonist and/or levorphanol. As used herein, controlled release is interchangeable with "extended release", "sustained release", "pulsatile release", "modified release", "depot" and the like.

To further evaluate this invention, tramadol was selected as the initial a prototype drug. Tramadol serves as an excellent prototype drug as it: 1) has been implicated when used alone in the serotonin syndrome; 2) has been implicated in the serotonin syndrome when used in combination with other drugs; 3) has significant proserotonergic and opioid effects, both of which have been implicated in the serotonin syndrome; 4) is water soluble and therefore prone to easy extraction and gastrointestinal absorption; 4) is available in both immediate release and extended release formulations, which if tampered with may dump an entire days contents into the systemic circulation, thereby increasing the incidence and severity of the serotonin syndrome.

Tramadol is a synthetic, centrally acting analgesic which exerts its analgesic effects by inhibiting reuptake of norepinephrine and serotonin and by activation of µ-opioid receptors. Tramadol binds to the µ-opioid receptor, although its principal active (M1) metabolite, mono-O-demethyl-tramadol is up to 6 times more potent in producing analgesia and 200 times more potent in µ-opioid binding (Ultram Package Insert). During its intentional or inadvertent non-medical use, tramadol, especially the extended release tramadol is likely to be crushed. Since tramadol produces dose dependent seizures and dose dependent serotonin syndrome, there is the potential for a compounded risk.

The occurrence of serotonin syndrome has been well documented with tramadol given alone, with serious and potentially fatal consequences (Clarkson et al, 2004; Garrett, 2004; Kitson and Carr, 2005). The sudden exposure of patients to large concentrations of tramadol from crushed solid dosage forms of Tramadol ER, especially in the face of ubiquitous use of SSRI's and SNRI's in chronic pain may have important medical consequences. (Clarkson et al, 2004; Gonzalez-Pinto et al, 2001; Houlihan, 2004; Egberts et al, 1997; Kesavan and Sobala, 1999; Lange-Asschenfeldt, 2002; Mahlberg et al, 2004; Mittino et al, 2004).

EXAMPLES

Materials in the series of experiments below included the following: Aerosil 200, Lot 1412033, ex Degussa Huls, Aerosil COK84, Lot 2258, ex Degussa Huls, Beeswax, Lot A018035701, ex Acros Organics, Cetyl alcohol (1-hexadecanol), Lot A019258301, ex Acros Organics, Cithrol GMS 0400, Lot 6483-0103, ex Croda, Fractionated coconut oil, Lot 165544, ex A E Connock Gelucire 44/14, Lot 22009, ex Gattefosse, Gelucire 50/02, Lot 19255, ex Gattefosse, Gelucire 50/13, Lot 20529, ex Gattefosse, Hydrokote 112 Lot 048M3, ex Abitech Corp, Hydrokote AP5, Lot 340J1, ex Abitech Corp, Hydrokote M, Lot 126J2, ex Abitech Corp, Methocel AM4, Lot Q101012N01, ex Colorcon, Methocel K100M, Lot QA15012N01, ex Colorcon, Methocel K15M, Lot QK02012N11, ex Colorcon, Paraffin wax, Lot P/0680/90, ex Fisher Scientific, PEG 400, Lot 310354, ex NOF Corp, Pluriol E6005 (PEG 6000), Lot 97193, ex BASF, Pharmacoat 606 (hypromellose USP), Lot 308522, ex Shin-Etsu Chemical Co Ltd., Poloxamer 124 (Pluronic L44), Lot WPWV-645B, ex BASF., Poloxamer 188 (Lutrol F68), Lot 0306043523, ex BASF, Propoylene glycol, Lot 09521H0, ex Aldrich, Propranolol HCl, Lot 044K1219, ex Sigma, Shellac, Lot 4010 2465 2056, ex Syntapharm, Size 1 clear/clear gelatin capsules, Lot C14893, ex Capsugel, Starch 1500, Lot IN 500578, ex Colorcon, Sterotex N F, Lot 324M2, ex Abitech Corp., Tramadol HCl, Lot 3TRMDNOD105 & 3TRMD-NOE056, ex Chemagis Ltd, Zein (Paroxite), Lot 5041C, ex Variati & Co.

Equipment in the series of experiments below included the following: Caleva 9ST dissolution apparatus with ERWEKA P thermostatically controlled water heater, Copley ZT54 disintegration apparatus, Haake DC5 water bath, Heidolph bench mixer, HiBar bench filling machine, Qualiseal bench banding machine, Silverson SL2 bench high shear mixer, Thermo Electron Vision uv/visible spectrometry data acquisition program with Vision Security, Unicam UV2-400 spectrophotometer, Watson Marlow 205U peristaltic pump 650µ nominal s/s Laboratory test sieve, 600µ s/s certified Laboratory test sieve from Endecotts Ltd, London, Whatman 25 mm 45µ filters used in combination with a 5 ml Luer lock syringe.

Example 1

Binary Mix Compatibility Trials

Binary mixes were prepared of tramadol HCL in potential excipients (in some instances a third material, fractionated coconut oil was used to bring two non melting materials into intimate contact). The mixes were stored in sealed amber glass bottles under conditions of 40° C./75% RH for four weeks then examined by HPLC for signs of interaction or degradation. Excipients were chosen from materials considered to potentially cover the range of material properties that were likely to be required by this project. Materials were chosen for properties such as dissolution rate i.e. from materials that are relatively soluble in aqueous media to totally insoluble materials; their potential as viscosity/release rate modifiers, including such materials as different HPMC (viscosity) grades and Aerosils for contributing thixotropic properties. Mixes containing 25% w/w tramadol HCL were prepared for each excipient. Samples were prepared by mixing tramadol HCl with the melted excipient or for non melting excipients materials were placed in contact by blending with a 50/50 mix of excipient and fractionated coconut oil. Samples of each excipient were also stored in sealed amber glass bottles at 40° C./75% RH as control samples. The project objective describes a target of 15 binary mixes, however, 25 different mixes were made during this trial to maximize the range of excipients available for formulation.

Dissolution Testing

Initially two test formulations were prepared as noted below. The capsules for this and all other small scale capsule preparations were manufactured by the melting and mixing of the ingredients in a water bath or on a hot plate then hand filling capsules to the target weight. All capsules used were size 1 gelatin capsules.

| Material | % w/w | Quantity per cap mg |
|---|---|---|
| Formulation 052/014 | | |
| Poloxamer 188 | 62.8 | 282.7 |
| HPMC K100M | 17.9 | 80.3 |
| Aerosol COK 84 | 2.7 | 12.0 |
| Tramadol HCl | 16.6 | 74.9 |
| Capsule fill weight | | 450 |

-continued

| Material | % w/w | Quantity per cap mg |
|---|---|---|
| Formulation 052/015 | | |
| Gelucire 50/02 | 58.3 | 233.3 |
| HPMC Pharmacoat 606 | 19.9 | 79.8 |
| Aerosil COK 84 | 3.0 | 12.0 |
| Tramadol HCl | 18.7 | 74.9 |
| Capsule fill weight | | 400 |

The target fill weight was set as 400 mg for a size 1 capsule. Formulation 052/014 was initially targeted on a 400 mg fill, however, the mix proved too viscous to fill. Additional poloxamer 188 had to be added to reduce the mix viscosity to a level that could be encapsulated. The addition of extra poloxamer 188 required that the fill weight be increased to 450 mg. This quantity could be hand filled into a capsule and would meet the requirements of this preliminary trial, however, such a quantity would be excessive for machine filling into a size 1 capsule.

The tramadol HCl dissolution release profile was determined, for each formulation. Full dissolution testing is carried out using six individual capsule sets. Preliminary screening trials used between two and six capsules per test. This permitted several candidate formulations to be screened at once and clearly unsuitable formulations eliminated quickly. Potentially useful formulations could be modified further first before going on to six capsule sample dissolution testing.

Tramadol HCl in aqueous solution shows an absorbance maximum between 240 nm and 290 nm with the maximum at 271 nm. It starts to show increasingly strong absorbance below the minimum at 240 nm to 200 nm (the limit of the instrument) however absorbance in this area is shown by many compounds so observation in the more definitive region of 240 nm to 290 was selected with 270-272 nm chosen as the preferential wavelength of observation. A plot of the UV spectrum of tramadol HCl in water is shown in FIG. 1.

Dissolution testing was carried out using the USP paddle method on a Caleva 9ST dissolution apparatus with an ERWEKA P, thermostatically controlled, water heater. Each solution was continuously cycled through a Unicam UV2-400 spectrophotometer using a Watson Marlow 205U peristaltic pump and the solution absorbance in a 1 cm silica cell, at 271 nm, recorded against the absorbance of a placebo or SIF blank with the data captured by Thermo Electron Vision UV/visible spectrometry data acquisition software protected by Vision Security. The spectrophotometer was fitted with a six cell autochanger permitting continuous automatic recording of cell solution absorbances. The capsules were weighed down with 316 stainless steel sinking wire, wrapped round each capsule. Each solution passed through a filter as it was pumped from the dissolution bath. Except where otherwise specified, the dissolution medium was 600 ml of Simulated Intestinal Fluid (SIF) USP without the inclusion of enzyme. This dissolution set up was selected to give a final absorbance value, with full release of tramadol HCl, of not more than 1.5 absorbance units (au). Typically, the final absorbance of a test solution did not exceed 1.0 au. A placebo blank was used in the reference cell. This comprised of a capsule containing the same proportion and quantity of each material used in the active test capsules but without the tramadol HCl. This ensured that the reference solution contained the same quantity (and thus gave the same background absorbance) as the excipients in the active capsules.

Binary Mix Compatibility Study

Different materials were tested for compatibility with Tramadol HCl. The results of storage in sealed amber glass bottles under conditions of 40° C./75% RH for four weeks then subsequent analysis by HPLC for degradants or impurities are as below.

| | Material | Assay % | Peaks from stresses excipient | Impurities/Degradants % area normalized | Comments |
|---|---|---|---|---|---|
| 1 | Gelucire 44/14 | 127.9 | none | none | |
| 1 | Gelucire 44/14 REPEAT SAMPLE | 71.2 | none | none | Mean 2 samples 99.5% |
| 2 | Gelucire 50/13 | 106.3 | none | none | |
| 3 | Gelucire 43/01 | | | | Not available |
| 4 | Poloxamer 188 | 101.9 | none | none | |
| 5 | Poloxamer 124 (Pluronic L44) | 98.6 | none | none | Separated suspension re-mixed before sampling |
| 6 | PEG 6000 | 96.6 | none | none | |
| 7 | PEG 400 | 100.7 | none | none | |
| 8 | Propylene glycol | 96.5 | none | none | |
| 9 | Beeswax (refined yellow) | 2.1 | none | none | Material insoluble in sample diluent |
| 10 | Starch 1500 (+Miglyol) | 97.3 | none | none | Separated suspension re-mixed before sampling |
| 11 | Cetyl alcohol 1-hexadecanol | 4.5 | none | none | Solution produced was a thick slime Very hard to take HPLC sample |
| 12 | Paraffin wax | 15.0 | none | none | Material insoluble in sample diluent |
| 13 | Miglyol (fractionated coconut oil) | 102.3 | none | none | Separated suspension re-mixed before sampling |
| 14 | HPMC Methocel K15MP (+Miglyol) | 104.0 | none | none | |
| 15 | HPMC Methocel K100MP (+Miglyol) | 98.9 | none | none | Separated of components re-mixed before sampling |
| 16 | Methocel A (+Miglyol) | 101.1 | none | none | |
| 17 | Hydrokote 112 | 104.2 | None | None | |

-continued

| | Material | Assay % | Peaks from stresses excipient | Impurities/Degradants % area normalized | Comments |
|---|---|---|---|---|---|
| 18 | Hydrokote AP5 | 101.2 | None | None | |
| 19 | Hydrokote M | 102.8 | None | none | |
| 20 | Shellac (+Miglyol) | 99.8 | Peaks at 5.065, 10.702 and 12.491 minutes | RT 5.057 = 0.1% – excipient RT 10.436 = 0.1% RT 10.704 = 0.5% – excipient RT 12.488 = 0.3% – excipient RT 15.043 = 0.1% RT 15.402 = 0.1% | Yellow semisolid Excipient insoluble in diluent |
| 20 | Shellac UNSTRESSED | N/A | Main peaks: 5.035, 10.393, 10.656, 12.455 Several small peaks in time zone 14 to 18 minutes | N/A | Conclude: peaks present in stressed Shellac were present before stress test |
| 21 | Zein (+Miglyol) | 100.5 | Peak at 7.083 minutes | RT 7.080 = 0.1% – excipient | Yellow semisolid |
| 22 | Aerosil COK 84 (+Miglyol) | 100.2 | none | None | |
| 23 | Aerosil 200 (+Miglyol) | 101.9 | none | none | |
| 24 | Cithrol GMS | 99.3 | Not available Control sample 96.4% assay | none | Solution produced a viscous mix |
| 25 | Sterotex | 62.9 | none | none | Solution produced a viscous mix |
| 25 | Sterotex REPEAT SAMPLE | 32.7 | none | none | Mean 2 samples 47.8% |
| 26 | Gelucire 50/02 | 104.1 | none | none | Solution produced a viscous mix |

The results above show that none of the excipients tested show any detectable signs of degradation or interaction after one month storage under conditions of 40° C./75% RH. It was therefore possible to use any of these materials as formulation ingredients.

Initial Test Formulation Dissolution Testing

Preliminary test formulations were prepared based on poloxamer 188 and Gelucire 50/02. The formulation compositions are as below.

| Material | % w/w | Quantity per cap mg |
|---|---|---|
| Formulation 052/014 | | |
| Poloxamer 188 | 62.8 | 282.7 |
| HPMC K100M | 17.9 | 80.3 |
| Aerosol COK 84 | 2.7 | 12.0 |
| Tramadol HCl | 16.6 | 74.9 |
| Capsule fill weight | | 450 |
| Formulation 052/015 | | |
| Gelucire 50/02 | 58.3 | 233.3 |
| HPMC Pharmacoat 606 | 19.9 | 79.8 |
| Aerosol COK 84 | 3.0 | 12.0 |
| Tramadol HCl | 18.7 | 74.9 |
| Capsule fill weight | | 400 |
| Placebo for 052/014 | | |
| Poloxamer 188 | 75.4 | 282.4 |
| HPMC K100M | 21.4 | 80.0 |
| Aerosol COK 84 | 3.2 | 12.0 |
| Capsule fill weight | | 374.4 |
| Placebo for 052/015 | | |
| Gelucire 50/02 | 71.5 | 232.2 |
| HPMC Pharmacoat 606 | 24.8 | 80.6 |
| Aerosol COK 84 | 3.7 | 12.1 |
| Capsule fill weight | | 325 |

The release profiles, determined from dissolution testing in SIF are shown in FIGS. 2 and 3. Some HPMC gel remained at the end of the trial in sample 052/014 (poloxamer 188 based) but all poloxamer 188 and tramadol HCl had dissolved very quickly. Plot 2 shows that release took place over a 2-5 hr time span. This release rate is too fast to be useable in this project so the use of poloxamer 188 as a base excipient was discarded. The material of formulation 052/015 remained as a plug at the end of dissolution testing. It appears that the tramadol HCl and HPMC dissolved and migrates out through the Gelucire 50/02 over a period of 10-12 hr. This is shorter than the project targeted release time of 18-24 hr but Gelucire 50/02 was retained as a material worth testing further.

Example 2

Dissolution Testing of a Modified Gelucire 50/02 Formulation

Methocel K100M, a very high viscosity HPMC, was substituted for Pharmacoat 606, a very low viscosity HPMC, to investigate whether this substitution using a much higher viscosity HPMC would significantly slow the release rate of tramadol HCl from the formulation. The active and reference placebo capsules' formulations are shown in FIG. 4. It should be noted that the relative viscosity of HPMC is based on the viscosity of a 2% aqueous solution at 20° C. measured in mPas (millipascal Seconds). The numbers and letters in the HPMC's designation indicate (different manufacturers use slightly different conventions) the HPMC's 2% viscosity in mPas (1 mPas=1 centipoise (cps)), e.g. Pharmacoat 606 (Pharmacoat 6 is the HPMC type with the final 6 referring to the 2% viscosity) has a viscosity of 6 mPas (6 centipoise) as a 2% solution while Methocel K100M (Methocel K is the HPMC type and 100M is the 2% viscosity using the letter M as the convention for a multiplication factor of 1000) has a viscosity of 100,000 mPas (100 Pascal Seconds) as a 2% solution.

| Material | % w/w | Quantity per cap mg |
|---|---|---|
| Formulation 052/019 | | |
| Gelucire 50/02 | 58.2 | 232.9 |
| Methocel K 100M | 19.9 | 79.4 |
| Aerosil COK 84 | 3.0 | 12.0 |
| Tramadol HCl | 18.7 | 75.0 |
| Capsule fill weight | | 400 |
| Placebo for 052/019 | | |
| Gelucire 50/02 | 71.6 | 232.8 |
| HPMC Pharmacoat 606 | 24.6 | 79.8 |
| Aerosil COK 84 | 3.8 | 12.4 |
| Capsule fill weight | | 325 |

The dissolution rate had been slowed down slightly compared with 052/015 from 10-12 hr to approximately 15-18 hr, however, this mix was a thick cream and was probably too viscous to machine fill as this exact formulation.

Example 3

Dissolution Testing of Tramadol HCl in Gelucire 50/02 without Additional Excipients Initial dissolution trials on formulations were performed as 'sighting' trials to give some idea of the range of profiles possible for 75 mg of tramadol HCl in a matrix made up to 400 mg. The two major excipients used, poloxamer 188 and Gelucire 50/02 are at opposite ends of the water solubility/dispersibility scale so would give a good indication of the range of release rates potentially available. Poloxamer 188 is readily water soluble while Gelucire 50/02 is highly lipophilic and only very slowly dispersible in water. The Gelucire 50/02 formulation 052/019 dissolution release rate, shown in FIG. 5, is close to that desired for this project. This formulation does incorporate materials which would modify (increase) the release rate so samples were prepared containing only tramadol HCl and Gelucire 50/02 to determine the slowest release rate that could be achieved with Gelucire 50/02. Samples were prepared according to the formulation below and their release rate determined.

| Material | % w/w | Quantity per cap mg |
|---|---|---|
| Formulation 052/024 | | |
| Gelucire 50/02 | 81.2 | 325.0 |
| Tramadol HCl | 18.8 | 75.0 |
| Capsule fill weight | | 400 |
| Placebo for 052/024 | | |
| Gelucire 50/02 | 100 | 325 |

A single capsule was initially tested then a further five capsules were also tested. All the data has been incorporated into the single plot shown below. The profile with the extended time scale is that of the first capsule tested.

These experiments indicate that full release takes place in the order of 30 hr. The outlying profiles was considered to be potentially due to uneven distribution of tramadol HCl in these hand mixed preparations but it was not deemed worthwhile to investigate this further at this stage. Gelucire 50/02 melts over a range centered on 50° C. and is hard enough to be crumbled into a powder. This makes formulations susceptible to abuse (by powdering, extraction, dose dumping, snorting etc) and it would be essential to include abuse deterrent materials such as HPMC and Aerosils in the final formulation. The release rate indicated by these profiles fall within the acceptable range of release rates worthy of further consideration at this stage of the project, however, as only two materials had been examined (with one rejected) by this stage it was decided to investigate other materials before narrowing the selection of potential formulations.

Example 4

Dissolution Testing of Tramadol HCl in Gelucire 50/02 in SIF Containing Pancreatin The Gelucire range of materials is described as polyglycolized glycerides consisting of mono-, di- and triglycerides and of mono- and di-fatty acid esters of polyethylene glycol (PEG) with a range of HLB (hydrophilic lipophilic balance) values from 1 to 14. A material with a value of 14 is at the hydrophilic end of the scale where the material is easily water dispersible; 1 or 2 is at the other end of the scale and the material is extremely slowly water dispersible, at best.

Gelucire 50/02 (the $O_2$ suffix shows the HLB value to be 2) is highly lipophilic and only disperses very slowly in aqueous media. These materials are potentially digestible so it is possible that a formulation that shows very slow release in vitro, in purely aqueous media such as SIF, could show dramatically faster release due to digestion, as opposed to dispersion, in vivo in the presence of enzymes.

An experiment was performed to look for any indications that the presence of an enzyme, pancreatin, modified the release rate of tramadol HCl in Gelucire 50/02. This experiment encountered difficulties as pancreatin in solution absorbs strongly over a range exceeding that of tramadol HCl's 240 nm to 290 nm band and pancreatin in suspension tended to block the solution filters.

The dissolution profile of capsules containing formulation 052/024 was recorded using UV absorbance determination. The pancreatin level was reduced to one fifth of that specified in the USP method so that solution absorbance values did not significantly exceed 1 au. The results shown below were very erratic, however, as this was intended as no more than a check on whether this family of materials (atypical of future excipients) was susceptible to acceleration of release rate by digestion it was decided not to divert the project into the development of an HPLC assay for tramadol HCL in the presence of pancreatin at this stage.

The profile (FIG. 6) shows an initial dip due to suspended/dissolved pancreatin affecting the reference cell. The absorbance of the mix appears to stop increasing after approximately 30 hr which does indicate that the tramadol HCl is fully released after this time. This corresponds well with the release time of tramadol HCl in this excipient tested in SIF in the absence of pancreatin (FIG. 5). This suggests that, at the level of pancreatin used, no major variation in dissolution release rate is observed in the presence of pancreatin. The Gelucire 50/02 units were allowed to be stirred in this medium for a further two days. The units maintained their shape and size for the entire period adding some confirmatory evidence that the Gelucire 50/02 content remained substantially unchanged (undigested).

Example 5

Dissolution Testing of Propranolol HCl in Gelucire 50/02 in SIF Containing Pancreatin The above trial using Gelucire 50/02, as the base excipient, in SIF containing pancreatin suffered from the pancreatin UV absorbance overlapping and being of greater intensity than the tramadol HCl absorbance in the monitored 290 nm region. An alternative model compound was found in propranolol HCl, as a substitute for the tramadol HCl. Propranolol HCl has similar solubility and similar UV specific absorbance to tramadol HCl but has its UV absorbance maximum at 319 nm, just outside the absorbance window of tramadol. This allowed the testing of the propranolol HCl analogue of the above formulation, 052/024, to be tested in the presence of pancreatin with reduced interference.

The propranolol HCl analogue was subjected to dissolution testing in 600 ml of SIF, with and without (full strength) pancreatin. Six capsule samples were tested in each case. FIGS. 7 and 8 shows data for dissolution with and without pancreatin while FIG. 9 shows the combined averaged data of dissolution in the absence and presence of pancreatin.

The pancreatin in suspension caused difficulties with filter blockage in both test and reference vessels leading to irregularities appearing in the data for propranolol HCl in SIF in the presence of pancreatin. Overall, despite the irregularities in the data, it is concluded that there is no difference detected in the overall rate of release for Gelucire 50/02 between dissolution in SIF in the absence or presence of pancreatin. This supports the conclusion reached for the similar experiment carried out using tramadol HCl in Gelucire 50/02.

Example 6

Dissolution Testing of Current Tramadol HCl Sustained Release Products

Tramadol HCl is available in commercial sustained release products. (for this purpose extended release, controlled release, modified release and sustained release are considered as having the same meaning). These products contain different doses of tramadol HCl, typically 150 mg, from the dosage unit under development in this project but it was considered useful to broaden our knowledge of such products and to obtain a dissolution release profile using our current conditions. It was also intended that proprietary products such as these were used later in this project as comparators during product tampering and extraction tests.

Zydol XL 150 from Pfizer for once a day administration and Dromadol SR by IVAX for twice a day administration are two proprietary products which both contain 150 mg of tramadol HCl in a sustained release formulation. Two tablets of each product had their dissolution profile determined in 600 ml of SIF without added enzyme with UV monitoring at 271 nm according to the standard method used in this development project. The combined release profiles are shown in FIG. 10. All tablets were substantially whole at the end of the test period. The release profiles match so closely that it is not possible to distinguish visually one tablet type from the other. Under the above conditions full release takes of the order of 40 hr and, as the tablets contain double the dose of the experimental formulations, the final absorbance is approximately double that shown in earlier plots. The slight dip in the plot about 17 hr is considered to be an artifact of the method.

Example 7

Indicative Dissolution Testing of Potential Dosage Unit Base Excipients

Previous trials demonstrated that the hard fats and slowly dissolving materials were the best choice of base material (a base excipient is the predominant excipient in a dosage unit) for a 75 mg tramadol HCl sustained release dosage unit. This identified seven other materials, from those tested in the compatibility trial, as potential base excipients. Six of these were formulated as binary mixtures with tramadol HCl and filled into capsules to a fill weight of 400 mg containing 75 mg tramadol HCl as had been carried out previously. The final material, beeswax, was formulated with the additional presence of HPMC as an unmodified formulation was unlikely to show any significant release due to the known insolubility of beeswax in aqueous media. All formulations had their dissolution profiles determined using single capsule samples for initial screening. The materials and formulations used are as below. The reference cell contained 600 mL of SIF.

| Material | % w/w | Quantity per cap mg |
|---|---|---|
| Formulation 052/034-1 | | |
| Cetyl alcohol | 81.2 | 325.0 |
| Tramadol HCl | 18.8 | 75.0 |
| Capsule fill weight | | 400 |
| Formulation 052/035-2 | | |
| Hydrokote 112 | 81.2 | 324.8 |
| Tramadol HCl | 18.8 | 75.2 |
| Capsule fill weight | | 400 |
| Formulation 052/035-3 | | |
| Hydrokote AP5 | 81.3 | 325.2 |
| Tramadol HCl | 18.7 | 74.8 |
| Capsule fill weight | | 400 |
| Formulation 052/035-4 | | |
| Hydrokote M | 81.3 | 325.4 |
| Tramadol HCl | 18.7 | 74.6 |
| Capsule fill weight | | 400 |
| Formulation 052/035-5 | | |
| Cithrol GMS | 81.6 | 326.2 |
| Tramadol HCl | 18.4 | 73.8 |
| Capsule fill weight | | 400 |
| Formulation 052/035-6 | | |
| Sterotex NF | 81.2 | 324.9 |
| Tramadol HCl | 18.8 | 75.1 |
| Capsule fill weight | | 400 |
| Formulation 052/035-7 | | |
| Beeswax | 61.2 | 244.8 |
| Methocel K 100M | 20.1 | 80.5 |
| Tramadol HCl | 18.7 | 74.7 |
| Capsule fill weight | | 400 |

The above tests were carried out using only filtered SIF in the reference cell. Absorbance values obtained may be composed of two components, namely, absorbance due to tramadol HCl and absorbance due to dissolved excipient. 75 mg of Tramadol HCl in SIF gives an absorbance of 0.74 au therefore the absorbance must reach 0.7 au (allowing for inter capsule variation) before it is possible for all the tramadol HCl to have been dissolved. Absorbances significantly in excess of 0.7 au will have some contribution from excipient dissolution.

FIGS. 11 and 12 show that Hydrokote and Hydrokote AP5 dissolve rapidly and release their tramadol HCl in approximately 2 hours. This is too fast a release rate for the requirements of this project so these excipients were not able to be used as base excipients.

The other excipients were in two groups. Cithrol GMS, Cetyl alcohol and the beeswax/HPMC combination showed release rates that were slightly slower than the target of total release in 18-24 hr while the Hydrokote 112 and Sterotex NF were significantly slower. One of the requirements of this project is to develop dosage units with demonstrable deterrence to physical or solvent based tampering. Materials were to be incorporated into formulations to enhance resistance. As it was likely that these materials would accelerate release then all of the materials mentioned in this paragraph were suitable for further consideration.

Example 8

Dissolution Testing of Modified Tramadol HCl Formulations

The base excipients Cithrol GMS, Hydrokote 112, Cetyl alcohol, Sterotex NF and beeswax showed potential as formulation base excipients in the trial above. These materials, in binary combination (beeswax as a ternary combination), gave dissolution release rates slower than the 18-24 hr target.

In this trial HPMCs were incorporated into the formulations to accelerate release and provide a level of tamper deterrence. Up to this point formulations contained tramadol HCl, a water soluble material, with a water insoluble base excipient which could make separation by extraction relatively easy. HPMC has been chosen as a material which might enhance tamper resistance as it has the property of being water soluble and thus would 'follow' tramadol HCl during attempted aqueous extraction, making separation of the tramadol HCl more difficult. HPMC comes in high viscosity grades which can impart a viscous nature to aqueous extracts of dosage units i.e. if anyone tries to extract the tramadol HCl with a small amount of water in a small spoon then, at best, they will produce an unpleasant mixture with a 'gummy' appearance which will tend to block attempts at filtration. Additionally, HPMC behaves in an unusual manner in aqueous solution. Most water soluble materials increase in solubility as the water temperature rises. HPMC is most soluble in cold water, becoming less soluble with temperature increase until, at about 40° C., it becomes totally insoluble. Solutions of HPMC, that are heated to 40° C. or above, turn into solid gels. This means that although an HPMC may be added to increase release rates from a dosage unit, it can actively deter abuse by extraction. If an individual tries to extract tramadol HCl with warm or hot water then the HPMC will become completely insoluble and actively resist the diffusion of tramadol HCl through the relatively impermeable base excipient.

Several formulations were produced incorporating a high viscosity HPMC, Methocel K 100M, into the matrix. The formulations tested and the release profiles obtained are shown below.

| Material | % w/w | Quantity per cap mg |
|---|---|---|
| Formulation 052/039-1 | | |
| Cetyl alcohol | 71.2 | 284.9 |
| Methocel K 100M | 10.0 | 40.0 |
| Tramadol HCl | 18.8 | 75.1 |
| Capsule fill weight | | 400 |
| Formulation 052/039-2 | | |
| Hydrokote 112 | 57.0 | 227.9 |
| Methocel K 100M | 24.5 | 97.9 |
| Tramadol HCl | 18.6 | 74.2 |
| Capsule fill weight | | 400 |
| Formulation 052/040-5 | | |
| Hydrokote 112 | 66.1 | 264.4 |
| Methocel K 100M | 15.1 | 60.3 |
| Tramadol HCl | 18.8 | 75.3 |
| Capsule fill weight | | 400 |
| Formulation 052/039-3 | | |
| Cithrol GMS | 71.0 | 284.0 |
| Methocel K 100M | 10.2 | 40.8 |
| Tramadol HCl | 18.8 | 75.2 |
| Capsule fill weight | | 400 |
| Formulation 052/040-4 | | |
| Sterotex NF | 56.5 | 225.8 |
| Methocel K 100M | 25.1 | 100.4 |
| Tramadol HCl | 18.4 | 73.8 |
| Capsule fill weight | | 400 |

FIG. 13 is based on using only SIF in the reference cell. As described previously, the flattening of the curve, having reached an absorbance of at least 0.7 au, indicates full release of tramadol HCl from the dosage unit. Materials dissolving or suspending in the dissolution media may increase the recorded absorbance significantly above 0.7 as is clearly seen above for the Sterotex NF plot. FIG. 13 shows that all formulations release all/almost all tramadol HCl within approximately 17-27 hr. This is satisfactory at this stage in the project. An example of the data and scatter for a five capsule dissolution set of results produced using one of the formulations used in the combined plot above (cetyl alcohol 052/039-1) is shown in FIG. 14.

Example 9

Dissolution Testing of Modified Tramadol HCl in Sterotex NF Formulations

The future processing of formulations at manufacturing scale required to be considered at this stage. Some formulations had too low a viscosity, as a melt, to maintain insoluble excipients in suspension and others were so viscous that, although they could be hand filled for the purposes of these trials, they were so viscous that they would cause great difficulty during manufacture on full scale machinery. Formulations, unstable due to low viscosity, could have their viscosity increased using low levels of thixotrope but formulations of excessive viscosity required that excipients were reduced or substituted.

An Aerosil was chosen as both a thixotrope and contributor to abuse deterrence. Aerosil is the commercial name for fumed silicon dioxide manufactured by Degussa Hüls. They produce a range of Aerosils with differing properties. These include different particle size, hydrophobic or hydrophilic characteristics or blended with additional materials such as aluminum oxide for specific purposes. Aerosil COK84 was chosen as the Aerosil of choice for this project. Aerosil COK 84 is a mixture of fumed silicon dioxide and highly dispersed aluminum oxide in a 5:1 ratio. This material effectively thickens aqueous systems and other polar liquids. In this project Aerosil COK 84 will increase viscosity in a formulation, however, if attempts are made to add a small quantity of water to produce a solution (e.g. for injection) the Aerosil COK 84 will contribute to increase the viscosity of any solution produced as it is specifically designed to thicken aqueous systems. Silicon dioxide and aluminum oxide, additionally, do not melt below 100° C. (or even 1000° C.) and are insoluble. The thickening effect of this Aerosil is unaffected by heat thus an abuser attempting to melt a dosage unit will find that the structure and shape of the dosage unit tends to remain unchanged when sufficient Aerosil is incorporated even though the melting point of all other excipients has been exceeded.

Formulations were modified by having Aerosil COK 84 added in some instances to improve process characteristics and enhance abuse resistance while others had the HPMC grade substituted to bring the dissolution release rate towards the target range or to adjust the formulation properties to that required for commercial production.

The Sterotex NF formulation above, 052/040-4, contained 25% of a very high viscosity HPMC which produced a mix that could be hand filled but was excessively viscous for machine encapsulation. This formulation was modified with a lower quantity of a lower viscosity grade HPMC with the aim of producing a machine fillable formulation of similar release rate

| Material | % w/w | Quantity per cap mg |
|---|---|---|
| Formulation 052/058 | | |
| Sterotex NF | 66.2 | 264.9 |
| Methocel K 15M | 15.0 | 60.0 |
| Tramadol HCl | 18.8 | 75.0 |
| Capsule fill weight | | 400 |
| Placebo for 052/058 | | |
| Sterotex NF | 81.5 | 265 |
| Methocel K 15M | 18.5 | 60.0 |
| Capsule fill weight | | 325 |

The dissolution profile of a four capsule sample is shown in FIGS. 15 and 16. The above profiles indicate release in 25-30 hr. (Later data will demonstrate that full release of 75 mg tramadol HCl from Sterotex NF results in an absorbance of approximately 0.8 au under the above conditions). This formulation was quite thin with fast separation of the insoluble ingredients and required an increase in viscosity. This undoubtedly contributed to the variation between individual profiles. The dosage unit was swollen after dissolution testing but retained its original shape and was tough to break up. This demonstrated that the tramadol HCl has diffused out from the dosage unit rather than released after dosage unit dissolution or disintegration.

Example 10

Dissolution Testing of Further Modified Tramadol HCl in Sterotex NF Formulations Aerosil COK 84 was added to the tramadol HCl in Sterotex NF formulations. Formulations containing quantities of Aerosil COK 84 in excess of 2% w/w were too viscous for machine filling so formulation 052/058 was modified to contain 2% Aerosil COK 84 and subjected to dissolution testing against a placebo without tramadol HCl but which contained the same quantities of all other ingredients.

| Material | % w/w | Quantity per cap mg |
|---|---|---|
| Formulation 052/060 | | |
| Sterotex NF | 63.9 | 255.4 |
| Methocel K 15M | 15.2 | 61.0 |
| Aerosil COK 84 | 2.1 | 8.6 |
| Tramadol HCl | 18.9 | 75.5 |
| Capsule fill weight | | 400 |

The dosage units had expanded and were soft and easily broken up after dissolution testing. The average release profile was not significantly different from that of formulation 052/058, with release in approximately 25-30 hr, however, there was less variation between individual samples indicating that low viscosity of 052/058 was a major contributor to individual sample variation (FIGS. 17 and 18).

Example 11

Dissolution Testing of Tramadol HCl in Hydrokote 112 with HPMC and Aerosil COK 84

FIG. 13 shows the plot for a formulation based on Hydrokote 112 containing 15% Methocel K 100M, formulation 052/040-5. Trials indicated that Aerosil COK 84 could be incorporated at 1.5% w/w to produce a flowing light cream. The above formulation was modified to contain 1.5% Aerosil COK 84 and to compare release profiles for formulations containing equal quantities of Methocel K 15M or the much higher viscosity grade Methocel K 100M. Formulations were prepared as below.

| Material | % w/w | Quantity per cap mg |
|---|---|---|
| Formulation 052/062-1 | | |
| Hydrokote 112 | 64.7 | 258.7 |
| Methocel K 100M | 15.0 | 60.1 |
| Aerosil COK 84 | 2.1 | 8.6 |
| Tramadol HCl | 1.6 | 6.3 |
| Capsule fill weight | | 400 |
| Formulation 052/062-2 | | |
| Hydrokote 112 | 64.7 | 258.6 |
| Methocel K 15M | 15.0 | 60.2 |
| Aerosil COK 84 | 2.1 | 8.6 |
| Tramadol HCl | 1.5 | 6.2 |
| Capsule fill weight | | 400 |

Three capsule samples of each formulation had their dissolution absorbance profiles measured in 600 mL of SIF, without enzyme at 271 nm, using the USP paddle apparatus, at 75 rpm, as carried out previously. The combined individual and averaged profiles are shown in FIGS. 19 and 20. Both dosage units were soft and crumbling at the end of dissolution testing. Both gave acceptable release times for the tramadol HCl of 25-30 hr. As would be expected, the lower viscosity grade dissolution was slightly faster than that of the formulation containing the higher viscosity grade.

Example 12

Dissolution Testing of a Formulation Containing 250 mg Tramadol HCl in Sterotex NF A dosage unit containing 250 mg of tramadol HCl was considered as a future possibility for this type of slow release dosage form so a preliminary investigation was carried out to estimate the likelihood of this being achievable.

Tramadol HCl is highly water soluble. This can lead to difficulty in producing a slow release formulation as, with the preferred largest capsule size as a size 0, the largest quantity of formulated material that can be filled as a liquid fill is approximately 550 mg. This means that the formulation will contain approximately 45% as the very soluble tramadol HCl.

The objective of this exercise was to determine whether 250 mg tramadol HCl could be formulated to 500-550 mg in a mix, with the properties to enable machine filling, and having a release rate that delivered the tramadol HCl into solution over at least 18-24 hr. If the formulation released tramadol at a much slower rate then this was completely acceptable as the release rate could be accelerated by the incorporation of materials such as HPMC. Difficulties would arise if the release rate could not achieve 18-24 hr release with only the base excipient.

Sterotex NF was chosen as the base excipient for this trial as, at the 18.8% w/w tramadol HCl level (FIG. 12), it was the 'slowest' of the excipients under examination and able to deliver extremely slow release. A formulation targeted on 500 mg dosage was too viscous to be filled. Diluting to a total mass of 550 mg and the addition of a small quantity of Aerosil COK 84 gave a flowing cream that could be machine filled.

| Formulation 052/066 | | |
|---|---|---|
| Material | % w/w | Quantity per cap mg |
| Sterotex NF | 52.8 | 290.5 |
| Aerosil COK 84 | 1.8 | 10.0 |
| Tramadol HCl | 45.4 | 249.6 |
| Capsule fill weight | | 550 |

The dissolution profile of a six capsule set was obtained in the previous manner. The only difference from previous conditions was that the dissolution medium volume had been increased to 1 liter. At this level, total release of the 250 mg of tramadol HCl would give an absorbance of at least 1.5 au. A placebo containing all materials in identical quantities without tramadol HCl was used as the reference.

The individual plots (FIGS. 21 and 22) showed some atypical behaviour due to bubble generation in the flow through cells. Despite this, the clear observation is that this formulation released less than a quarter of its tramadol HCl content over the 38 hr period of the dissolution trial. This release time and the percentage released comfortably exceeds the minimum requirement of release of all tramadol HCl in not less than 18-24 hr. This trial demonstrates that it should be feasible to produce a similar slow release, liquid filled dosage unit to the objective of this project, containing up to 250 mg tramadol HCl in a total formulated mass of up to 550 mg.

Example 13

Dissolution Testing of Tramadol HCl in Beeswax Based Formulations

Previous beeswax based formulations (052/035-7), containing 20% Methocel K 100M released in a period of approximately 40 hr. This exceeded the 18-24 hr target range of the study, however, it was considered useful to include a slightly slower, in vitro, formulation to broaden the range of formulations that would eventually be subject to an in vivo trial.

Two other beeswax formulations were prepared to compare the quantity and type of HPMC that should be incorporated and the effect of Aerosil COK 84 inclusion. It was found that up to 2% Aerosil COK 84 could be included and the material remained as a potentially machine fillable mix. 25% HPMC was found to produce an excessively viscous mix. Two formulas were tested containing 20 and 23% w/w of the lower viscosity Methocel K 15M HPMC. The formulations subjected to dissolution testing were as below.

| Material | % w/w | Quantity per cap mg |
|---|---|---|
| Formulation 052/068 | | |
| Beeswax | 59.4 | 237.6 |
| Methocel K 15M | 19.9 | 79.5 |
| Aerosil COK 84 | 2.0 | 8.2 |
| Tramadol HCl | 18.7 | 74.7 |
| Capsule fill weight | | 400 |
| Formulation 052/070 | | |
| Beeswax | 56.3 | 225.0 |
| Methocel K 15M | 23.0 | 92.0 |
| Aerosil COK 84 | 2.0 | 8.0 |
| Tramadol HCl | 18.7 | 75.0 |
| Capsule fill weight | | 400 |

The dissolution profiles of both formulations were obtained using 600 mL of SIF and the USP paddle method with monitoring at 271 nm, unchanged from previous dissolution trials. Placebos containing all materials in identical quantities without tramadol HCl were used as the reference in each case. The dissolution profiles obtained shown in FIGS. 23, 24, 25, 26 and 27.

Tramadol HCl was released over approximately 40 hr in both cases. The dissolution of 052/070, containing 23% Methocel K 15M, was allowed to continue running for 95 hr to confirm the final absorbance achieved. It would have been expected that formulation 052/070, containing slightly more soluble matter, would have shown the faster release. It appears that there is little real difference in release rates at this level of HPMC content so the formulation containing 20% Methocel K 15M was selected for use.

Example 14

HPLC Analysis of Tramadol HCl During Dissolution Testing

Tramadol HCl release during dissolution testing had been monitored to this point using the absorbance of the dissolution media at 271 nm (absorbance maximum for tramadol HCl at longest wavelength) as a function of the quantity of tramadol HCl released into solution. This approach was reasonable as the excipients used in formulations were either almost insoluble or had negligible absorbance at this wavelength. It was considered that tramadol HCl was fully released when the absorbance of the solution became constant. For 75 mg tramadol formulations and the system used, this meant that the absorbance would be in excess of 0.7 au. The absorbance profile would be composed of absorbance from tramadol HCl plus a small contribution from absorbance/scattering from the other excipients.

This trial subjected all of the formulations under consideration, at this point, to dissolution testing of two capsule samples (or two×two) with concurrent sampling and HPLC analysis for tramadol HCL. Sufficient samples for HPLC analysis were taken over the course of a dissolution run to allow a plot of absorbance profile versus quantity of tramadol HCl released to be constructed. This permitted the assumptions on absorbance profile versus release profile to be tested. The formulations tested are detailed below. FIG. 28 shows the combined absorbance profiles for three formulation followed by individual plots combining the percentage (of 75 mg) released into solution as determined by HPLC with the initial absorbance plot overlaid and normalized on the first or nearest position to 100% tramadol HCl release by HPLC (FIGS. 29, 30, 31, 32, 33, 34, 35, 36, 37, 38, 39, 40 and 41). This allows comparison of the quantity of tramadol HCl released and the quantity that would have been estimated from the absorbance plot as having been released. Note: The formulation reference details the exact quantities used in a particular set of samples. The same basic formula e.g. 55% of X plus 20% of Y plus 18% of Z, may appear as different formulation references as the quantities in a particular set vary slightly due to weighing variations.

| Material | % w/w | Quantity per cap mg |
|---|---|---|
| Formulation 052/072-1 | | |
| Beeswax | 59.3 | 237.0 |
| HPMC Pharmacoat 606 | 20.0 | 79.8 |
| Aerosil COK 84 | 2.0 | 8.0 |
| Tramadol HCl | 18.8 | 75.1 |
| Capsule fill weight | | 400 |
| Formulation 052/072-2 (Same as 052/019) | | |
| Gelucire 50/02 | 68.2 | 272.6 |
| Methocel K 100M | 10.0 | 40.1 |
| Aerosil COK 84 | 3.0 | 12.1 |
| Tramadol HCl | 18.7 | 74.8 |
| Capsule fill weight | | 400 |
| Formulation 052/073-3 | | |
| Cetyl alcohol | 67.9 | 271.5 |
| Methocel K 100M | 9.8 | 39.2 |
| Aerosil COK 84 | 3.9 | 15.8 |
| Tramadol HCl | 18.4 | 73.6 |
| Capsule fill weight | | 400 |
| Formulation 052/073-4 (Similar to 052/060) | | |
| Sterotex NF | 64.2 | 256.8 |
| Methocel K 15M | 15.0 | 60.1 |
| Aerosil COK 84 | 2.0 | 7.9 |
| Tramadol HCl | 18.8 | 75.2 |
| Capsule fill weight | | 400 |
| Formulation 052/073-5 | | |
| Cithrol GMS | 68.3 | 273.0 |
| Methocel K 100M | 10.0 | 40.1 |
| Aerosil COK 84 | 3.0 | 12.0 |
| Tramadol HCl | 18.7 | 74.9 |
| Capsule fill weight | | 400 |

| Material | % w/w | Quantity per cap mg |
|---|---|---|
| Formulation 052/074-6 | | |
| Hydrokote 112 | 63.2 | 252.7 |
| Methocel K 15M | 15.1 | 60.2 |
| Aerosil COK 84 | 3.0 | 12.2 |
| Tramadol HCl | 18.7 | 74.9 |
| Capsule fill weight | | 400 |
| Formulation 052/074-7 | | |
| Beeswax | 59.2 | 236.9 |
| Methocel K 15M | 20.0 | 80.1 |
| Aerosil COK 84 | 2.0 | 8.1 |
| Tramadol HCl | 18.7 | 74.9 |
| Capsule fill weight | | 400 |

TABLE 2

Formulation Release Data Summary from HPLC

| Formula | Base excipient | HPMC and % w/w | 100% release after approx (ex HPLC data) |
|---|---|---|---|
| 052/072-1 | Beeswax | 20% Pharmacoat 606 | 70-75% in 45 hr |
| 052/072-2 | Gelucire 50/02 | 10% Methocel K 100M | 15 hr |
| 052/073-3 | Cetyl alcohol | 10% Methocel K 100M | 15 hr |
| 052/073-4 | Sterotex NF | 15% Methocel K 15M | 38 hr |
| 052/073-5 | Cithrol GMS | 10% Methocel K 100M | 20 hr |
| 052/074-6 | Hydrokote 112 | 15% Methocel K 15M | 40 hr |
| 052/074-7 | Beeswax | 20% Methocel K 15M | 25 hr |

Overall the HPLC data correlated well with absorbance data confirming that the modification of formulations based on their absorbance profiles, minimising delays that HPLC analysis would cause if applied to every sample, was a viable and acceptable approach. The above formulations cover a broad range of release profiles exceeding the 18-24 hr guide value for this project. At the present stage only the first beeswax formulation (52/072-1) is to be discontinued. Further modifications may arise during tamper resistance testing.

Example 15

Formulations 052/074-7, 052/093-3, 052/073-5 and 052/074-6 were remanufactured with Aerosil COK 84 replaced in each with Aerosil 200. The change in Aerosil did not modify the dissolution profile or the tamper deterrence of the drug.

Tamper Resistance Testing

The serotonin syndrome is a potentially life-threatening adverse drug experience that results from therapeutic drug use, intentional self-poisoning or inadvertent interactions between drugs. The syndrome is not an idiopathic iatrogenic reaction. Instead, it is a predictable consequence of serotonin excess in both the central and peripheral nervous systems. A wide variety of proserotonergic drugs, taken alone or in combination have been implicated in the causation of the serotonin syndrome.

Serotonin syndrome occurs with the initiation of therapy with a serotonergic agent., the addition of a second serotonergic agents and intentional or accidental overdose with one or several serotonergic agents. Serotonergic agents are frequently used in patients with primary psychopathology (major depression, schizophrenia) and in individuals with chronic pain who have comorbid depression. Such populations are particularly predisposed to concomitant therapy with multiple serotonergic drugs, other polypharmacy, drug and alcohol abuse and suicidal ideation. Consequently, patients receivining serotonergic agents are at particular risk for accidental or intentional overdose with one or several prescribed or street drugs implicated in the serotonin syndrome.

The common types of misuse of proserotonergic agents includes: 1) snorting, where the drug is inhaled as powdered dosage unit; 2) injection/ingestion (melting or extracting), where the drug is crushed and extracted or melted and the contents of a dosage unit then injects or swallows the liquid; 3) dose dumping by chewing, where the drug is chewed to increase the surface area and permit easy release of drug substance.

It is necessary to be able to measure resistance to the likely routes of abuse in a meaningful and relevant way. No standard set of tests exist with companies, interested in abuse resistance, generating their own particular set of tests. The series of tests chosen to evaluate abuse resistance and the source of the test were:

Extraction with Alcohol on Whole Dosage Unit

This method is based on US patent application 2004/0161382 A1 (P 11, [122]). Method: Place a whole dosage unit in 18 mL of 0.1N HCl in a 60 mL amber bottle and shake at 240 rpm on an orbital shaker for 30 min. After 30 min add 12 mL of ethanol (95-96%) to each bottle. Swirl by hand and remove a 1 mL sample from each bottle ($T_0$). Place the solutions back in the orbital shaker for further shaking at 240 rpm. Take 1 mL samples after 10, 20, 30, 40, 60 and 180 min of further shaking for each bottle. Analyze and graph the results on a linear scale of cumulative release (%) vs time (min).

Extraction with Alcohol on a Crushed or Cut Dosage Unit

Extension of test in above patent. Method: Place a tablet (after crushing with a single crush with a spatula) or a capsule (cut in half) in 18 mL of 0.1N HCl in a 60 mL amber bottle and shake at 240 rpm on an orbital shaker for 30 min. Continue the test as in 1) above.

Extraction into Water

This method is based on US patent application 2004/0161382 A1 (P12, [0130]). Method: Crush with a mortar and pestle and grind in 5 mL of water for 5 minutes. The resulting suspension is filtered through a 0.45 micron filter into a flask and diluted to 50 mL with water. Quantify Tramadol HCl concentration by HPLC.

Freeze and Crush

Method: Freeze the dosage unit in a domestic freezer for 24 hr, then grind with a mortar and pestle for five minutes. Sieve through a suitable sieve (ca 600 micron) and, by weighing, measure the percentage passing the sieve.

Taste of Base Excipient Mix (Organoleptic Test)

Method: Chew a placebo mix for five minutes and rate the taste on a 0-10 scale with 0 as bland to repulsive at 10. This method is relevant only to dosage units containing taste modifiers.

Extraction into Acid

Method: Crush with a mortar and pestle and heat to boiling in 5 mL of vinegar. The resulting suspension is filtered through a 0.45 micron filter into a flask and diluted to 50 mL with water. Quantify tramadol HCl concentration by HPLC.

Application Of Heat (melting temperature$\geq$50° C. or 55° C.)
Method: Heat the squashed contents of a dosage unit on a hot plate until melted. Determine the temperature of melting and test whether the mix becomes sufficiently fluid to be drawn up into a syringe via a 1.2 mm needle then expelled. The formulations tested were the last six of those listed in Table 2 (omits the first sample 052/072-1). Dromadol SR tablets were included into the testing for to allow comparison of the liquid filled dosage units with a commercial tramadol HCl prolonged release preparation. The results of testing are presented below.

Example 16

Extraction with Alcohol on Whole Dosage Unit

The results of this test are shown in FIG. 42.

Example 17

Extraction with Alcohol on Cut or Crushed Dosage Unit

The samples under test were reduced to four formulations plus the Dromadol SR comparator at this point. The Cetyl alcohol based formulation (052/073-3) and Gelucire 50/02 (052/072-2) were deselected due to their dissolution release time of approx 15 hr to 100% release and their high extractable fraction, as seen in FIG. 42. Formulations showing a slower than target in vitro release profile may possibly show more rapid release in vivo due to the presence of digestion materials but is seems unlikely that formulations showing a faster than desirable in vitro dissolution rate will show a retarded rate in vivo.

The above two tests demonstrate that whole dosage units release their contents into alcohol relatively slowly but once crushed or cut the waxy liquid fill dosage unit is much harder to extract than the tablet. One single crush turns the Dromadol tablet into an easily extractable powder. This feature would apply to any tablet. It should be noted that the apparent high quantity released at $T_0$ is due to the conditions specified in the method. The method requires an initial 30 min of shaking in 18 mL of 0.1N HCl before the addition of ethanol. The time is defined in the method as starting from the addition of ethanol. The tramadol HCl, shown as released at $T_0$, has dissolved during the 30 min pre ethanol addition sample preparation. This test demonstrates that the liquid fill formulations are clearly superior in abuse resistance by ethanol extraction to a sustained release tablet (FIG. 43).

Example 18

Extraction into Water Via Crushing and Grinding in Water

The four formulations continuing under test plus Dromadol SR tablets were crushed and ground for 5 minutes in 5 mL of water to simulate extraction in preparation for swallowing or injection. The material was then filtered (by pressurising a 45μ filter using an attached syringe) and diluted before quantifying by HPLC. The results are presented in Table 3 and 4 below with comments on the mix produced after grinding given below.

TABLE 3

| Product | Observations |
| --- | --- |
| Dromadol SR tablet | Ground easily and formed a mobile easily filtered solution. |
| Sterotex NF formulation 052/073-4 | Difficult to grind, forms a light paste that filtered slowly. |
| Cithrol GMS formulation 052/073-5 | Difficult to grind, forms a light paste that filtered very slowly. |
| Hydrokote 112 formulation 052/074-6 | Difficult to grind, forms a light paste that filtered very slowly. |
| Beeswax formulation 052/074-7 | Difficult to grind, forms a light paste that filtered relatively easily |

The Dromadol SR tablet crushed easily and produced a solution that filtered in a matter of seconds while the beeswax formed a light paste, with difficulty, which took approximately five minutes to filter. This difficulty of preparation was common to the other capsule samples with filtration time graduating from the five minutes of the beeswax sample to over 60 minutes for the Cithrol GMS sample. All liquid fill samples gave much greater difficulty in grinding and filtering than the tablet sample.

TABLE 4

Percentage release on extraction into water.

| Base excipient | Formulation | % released on extraction |
| --- | --- | --- |
| Dromadol SR tablets | n/a | 84.0 |
| Sterotex NF | 052/073-4 | 38.7 |
| Cithrol GMS | 052/073-5 | 17.1 |
| Hydrokote 112 | 052/074-6 | 24.5 |
| Beeswax | 052/074-7 | 30.1 |

The HPLC data shows that tramadol HCl was easily extracted from the tablet, as would be expected as a tablet crushes easily to give a large surface area from which extraction can take place. Extraction from the liquid fill formulation was reduced considerably due to the waxy nature of the base excipients and the inclusion of HPMC which caused the liquid extracts to turn into a filtration resistant light paste.

Example 19

Extraction into Acid Water Via Crushing and Grinding in Dilute Acetic Acid

Dilute acetic acid (6% w/w glacial acetic in water) was used to simulate the vinegar that drug abusers may use when extracting dosage units for injection. Dosage units were crushed forcibly 2-3 times in a mortar and pestle then transferred to a small beaker where 5 mL of the above dilute acetic acid was added. The mix was heated to boiling on a hotplate and held boiling for 5-10 s. The mix was allowed to cool to room temperature, the resulting solution filtered through a 45μ filter, as above, the solution diluted to volume and the content of tramadol HCl determined by HPLC. The assay results are shown below expressed as a percentage of the contents released into solution.

TABLE 5

Percentage release on extraction into dilute acid.

| Base excipient | Formulation | % released on extraction |
| --- | --- | --- |
| Dromadol SR tablets | n/a | 83.9 |
| Sterotex NF | 052/073-4 | 29.3 |
| Cithrol GMS | 052/073-5 | 41.7 |
| Hydrokote 112 | 052/074-6 | 30.2 |
| Beeswax | 052/074-7 | 17.6 |

Tramadol HCl was easily extracted from the tablet. All liquid fill formulations showed appreciably better resistance to extraction. The waxy mass of the four test formulations coalesced on melting and floated as a mass on the surface. The HPMC content of the mass is insoluble above 40° C. so, instead of its normal property of assisting release at room temperature, it actively prevents release at this temperature by helping to hold the molten mass together. The tramadol HCl migrates relatively slowly to the surface when boiling agitates the mass while the powdered tablet releases most of its content instantly. It is easily understood why the formulated capsule dosages give superior extraction resistance to that of tablets.

Example 20

Effect of Heat on Dosage Units

Tablets can be crushed and extracted easily while soft gel contents have been known to be liquefied by slight warming (to about 40° C.) and the contents injected directly. This test records the temperature at which the meltable excipients in a formulation have liquefied and tests whether this material can be sucked into a syringe and ejected as would take place during an injection. Formulated material was placed in a beaker then slowly warmed in a water bath. The mix temperature was recorded with a calibrated thermocouple. The results are listed in Table 5 below.

TABLE 6

Melting point range and potential for direct injection

| Base excipient | Excipient mp | Formulation | Formulation melted | Comment |
| --- | --- | --- | --- | --- |
| Sterotex NF | 61-66° C. | 052/073-4 | 65° C. | Light cream, can't suck into syringe, sets instantly in needle tip |

TABLE 6-continued

Melting point range and potential for direct injection

| Base excipient | Excipient mp | Formulation | Formulation melted | Comment |
|---|---|---|---|---|
| Cithrol GMS | 55-60° C. | 052/073-5 | 58° C. | Light cream, can't suck into syringe, sets instantly in needle tip |
| Hydrokote 112 | 43-46° C. | 052/074-6 | °45 C. | Viscous paste, can suck and eject about 5 mm of material from needle |
| Beeswax | 61-66° C. | 052/074-7 | 66° C. | Viscous paste, can't suck into syringe, sets instantly in needle tip |

All of the mixes melted around the melting points of the base excipients and, due to this elevated melting point, none could be effectively introduced into a syringe nor could be ejected (or injected).

Example 21

Modification to Increase Resistance to Powdering

It was observed during this trial that the Sterotex NF formulation can be powdered with careful crushing. This occurs to a lesser extent with the Cithrol GMS and Hydrokote 112 formulations. It was desirable to decrease the ease with which this formulation could be powdered. Both the Sterotex NF and Hydrokote 112 formulations gave full release of tramadol HCl in 38-40 hr during dissolution testing. It would therefore be acceptable to add modifiers that decrease the ease of crumbling formulated material into a powder even if these accelerated release. Several materials were tested including small levels of beeswax, adding hydrophilic liquids such as maltitol or glucose syrup or adding surfactants such as Crillet 4. The addition of hydrophilic liquids or surfactants immediately turned the mix into a lumpy unfillable mass by binding the powder content together. The use of these liquids was discontinued.

Formulations containing Sterotex NF with increased level of HPMC to accelerate dissolution plus 0, 5% and 10% beeswax were produced for examination of any change in resistance to powdering. The dissolution profiles of each formulation were recorded as the absorbance curve via UV monitoring at 271 nm as previously. The formulas used are show below. The dissolution results are show in FIG. 44.

| Material | % w/w | Quantity per cap mg |
|---|---|---|
| Formulation 052/087-1 | | |
| Sterotex NF | 60.3 | 241.0 |
| Methocel K 15M | 20.0 | 80.0 |
| Aerosil COK 84 | 1.0 | 4.0 |
| Beeswax | 0.0 | 0.0 |
| Tramadol HCl | 18.8 | 75.0 |
| Capsule fill weight | | 400 |
| Formulation 052/087-2 | | |
| Sterotex NF | 55.3 | 221.0 |
| Methocel K 15M | 20.0 | 80.0 |
| Aerosil COK 84 | 1.0 | 4.0 |
| Beeswax | 5.0 | 20.0 |
| Tramadol HCl | 18.8 | 75.0 |
| Capsule fill weight | | 400 |

| Material | % w/w | Quantity per cap mg |
|---|---|---|
| Formulation 052/087-3 | | |
| Sterotex NF | 50.3 | 201.2 |
| Methocel K 15M | 20.0 | 79.9 |
| Aerosil COK 84 | 1.0 | 4.0 |
| Beeswax | 10.0 | 40.0 |
| Tramadol HCl | 18.8 | 74.9 |
| Capsule fill weight | | 400 |

The Sterotex formulation without beeswax showed considerable variability. The addition of 5% or 10% beeswax significantly increased the rate of release to an approximate time for full release of 25 hr. There was no meaningful difference in release rate between either formulation containing added beeswax so the formulation containing 10% beeswax (052/087-3) was selected for inclusion in subsequent trials.

Example 22

Ease of Powdering and Percentage of Resultant Particles of 650 Micron or Less

Capsules were initially powdered at room temperature as an indicative guide and for comparison with subsequent frozen samples. The contents were removed from the capsules and ground until the finest powder achievable had been formed. The stated period of five minutes was not normally required and it was observed that excessive grinding could cause the particles to start to coalesce. The data obtained is shown in Table 7.

TABLE 7

Powder generation by grinding of formulated material at RT

| Base Excipient | Formulation | Comment | % as 650μ or less |
|---|---|---|---|
| Dromadol SR tablet | | | 64.2% |
| Dromadol SR tablet | | Repeat sample | 79.9% |
| Sterotex NF | 052/087-1 | 0% beeswax | 84.7% |
| Sterotex NF | 052/087-3 | Plus 10% beeswax | 84.8% |
| Cithrol GMS | 052/073-5 | | 86.9% |
| Hydrokote 112 | 052/074-6 | | 2.1% |
| Beeswax | 052/074-7 | | 1.9% |

The test was repeated using capsules that had been cooled in a domestic freezer. The results of this trial are shown in Table 8.

TABLE 8

Powder generation by grinding of formulated material cooled to domestic freezer temperatures

| Base Excipient | Formulation | Comment | % as 650µ or less |
|---|---|---|---|
| Dromadol SR tablet | | | 70.6% |
| Sterotex NF | 052/073-4 | | 78.8% |
| Sterotex NF | 052/087-3 | Plus 10% beeswax | 82.1% |
| Cithrol GMS | 052/073-5 | | 85.7% |
| Hydrokote 112 | 052/074-6 | | 5.5% |
| Beeswax | 052/074-7 | | 1.5% |

There was little significant difference, within experimental variation, between the results obtained at room temperature and that obtained from dosage units frozen to domestic freezer temperature (−20° C.). The Dromadol SR tablet ground to a fine powder relatively easily. The Sterotex NF and Cithrol GMS formulations also produced similar amounts of fine powder. The incorporation of 10% beeswax in one of the Sterotex NF formulations made to detectable difference. The beeswax and Hydrokote 112 formulations provided excellent resistance against powdering.

Example 23

Sterotex NF Formulation Modification to Enhance Resistance to Powdering

Further modifications were made to the Sterotex NF based formulation, using fractionated coconut oil, to improve resistance to powdering. Samples were prepared substituting 15, 20 and 25% of Sterotex NF for fractionated coconut oil. The formulations used were as listed below.

| Material | % w/w | Quantity per cap mg |
|---|---|---|
| Formulation 052/093-1 | | |
| Sterotex NF | 45.2 | 180.8 |
| Fractionated coconut oil | 15.0 | 59.9 |
| Methocel K 15M | 20.0 | 80.1 |
| Aerosil COK 84 | 1.0 | 4.1 |
| Tramadol HCl | 18.8 | 75.1 |
| Capsule fill weight | | 400 |
| Formulation 052/093-2 | | |
| Sterotex NF | 40.2 | 160.8 |
| Fractionated coconut oil | 20.0 | 79.9 |
| Methocel K 15M | 20.0 | 79.9 |
| Aerosil COK 84 | 1.0 | 4.2 |
| Tramadol HCl | 18.8 | 75.1 |
| Capsule fill weight | | 400 |
| Formulation 052/094-3 | | |
| Sterotex NF | 35.3 | 141.0 |
| Fractionated coconut oil | 25.0 | 100.0 |
| Methocel K 15M | 19.9 | 79.8 |
| Aerosil COK 84 | 1.0 | 4.1 |
| Tramadol HCl | 18.8 | 75.0 |
| Capsule fill weight | | 400 |

Example 24

The test to quantify the ease of powdering, Test 3, was repeated using capsules that had been cooled in a domestic freezer. The results of this trial are shown in table 8 below.

TABLE 9

Powder generation from Sterotex NF formulations containing fractionated coconut oil by grinding of formulated material cooled to domestic freezer temperatures

| Base Excipient | Formulation | Comment | % as 650µ or less |
|---|---|---|---|
| Sterotex NF | 052/073-4 | Data from Table 6 | 78.8% |
| Sterotex NF | 052/093-1 | Plus 15% fractionated coconut oil | 49.7% |
| Sterotex NF | 052/093-2 | Plus 20% fractionated coconut oil | 33.7% |
| Sterotex NF | 052/094-4 | Plus 25% fractionated coconut oil | 8.3% |

The addition of fractionated coconut oil produced the desired effect in decreasing the ability to grind cooled formulated mix into a powder. The hot mix remained a machine fillable light cream. The melting point of the 25% mix had decreased from the 65° C. melting point of a Sterotex NF mix with zero added fractionated coconut oil to an acceptable 62° C. for the mix containing 25%.

Example 25

Abuse Resistance Testing; Re-Evaluation of Modified Sterotex NF Combinations

Further testing was required, after revising the Sterotex NF formulation by substituting part of the Sterotex NF for fractionated coconut oil, to determine how this change had affected the other parameters.

Dissolution testing was carried out, in the same manner as previously, using the USP paddle method to obtain the dissolution profiles of the Sterotex NF formulations with and without additional fractionated coconut oil. This plot is shown below in FIG. 45

Example 26

Tests for ethanol extraction of whole and crushed or cut dosage units was also repeated. Sterotex NF with 25% fractionated coconut oil (052/094-3) was tested alongside the fractionated coconut oil free analogue (052/087-1). The opportunity was taken to test some additional relevant samples. The three previously tested formulations based on Cithrol GMS (052/073-5), Hydrokote 112 (052/074-6) and the beeswax formulation (052/074-7) were retested. Zydol XL 150 tablets were substituted for the previously used Dromadol SR tablets. Both of these are slow release formulations containing 150 mg of tramadol HCl. OxyContin extended release 80 mg tablets were included for comparison purposes as oxycodone extended release tablets are the subject of current concerns over tablet abuse and they provide another tablet comparator containing a similar quantity of water soluble active in a slow release formula. The results of ethanol extraction of whole dosage units and cut/crushed dosage units are shown below in FIGS. 46 and 47, respectively.

The Sterotex NF formulation containing 25% fractionated coconut oil did show increased susceptibility to ethanol extraction compared with the formulation without fractionated coconut oil however this was demonstrably much better than the tablets or the Cithrol GMS formulation so was considered as acceptable. The quantities extracted were broadly in line with that determined in the earlier ethanol extraction tests, shown in FIGS. 42 and 43. The Zydol XL 150 tablets showed comparable release to the Dromadol SR tablets in the earlier test. The OxyContin tablets showed much greater and faster release than any of the dosage units in either of these sets of tests.

Example 27

The abuse resistance test involving extraction into water by grinding a dosage unit in a mortar and pestle with subsequent filtration was repeated. All of the samples included in the above ethanol extraction tests were included. Table 10 shows the results of HPLC analysis of the filtrate expressed as the percentage of drug substance released. The results are also depicted in Left Panel of FIG. 58 (the bars from left to right are Formulation 052/094-3, Formulation 052/073-5, Formulation 052/074-7, Formulation 052/074-6, Zydol XL® 150 mg and OxyContin® 80 mg, respectively).

TABLE 10

Percentage release on extraction into water.

| Base excipient | Formulation | % released on extraction |
|---|---|---|
| Zydol XL 150 | n/a | 87.4 |
| Oxycontin 80 mg | n/a | 90.0 |
| Sterotex NF | 052/087-1 | 28.1 |
| Sterotex NF with 25% fr. coconut oil | 052/094-3 | 11.6 |
| Cithrol GMS | 052/073-5 | 15.3 |
| Hydrokote 112 | 052/074-6 | 23.1 |
| Beeswax | 052/074-7 | 18.6 |

Example 28

The abuse resistance test involving extraction into dilute acetic acid by heating to boiling was repeated. The same samples as immediately above were tested and the results of HPLC analysis of the resulting filtrates are shown in table 10.

TABLE 11

Percentage release on extraction into dilute acid.

| Base excipient | Formulation | % released on extraction |
|---|---|---|
| Zydol XL 150 | n/a | 87.4 |
| Oxycontin 80 mg | n/a | 82.2 |
| Sterotex NF | 052/087-1 | 10.8 |
| Sterotex NF with 25% fr. coconut oil | 052/094-3 | 7.0 |
| Cithrol GMS | 052/073-5 | 34.9 |
| Hydrokote 112 | 052/074-6 | 11.1 |
| Beeswax | 052/074-7 | 14.5 |

Both sets of results gave similar results for comparable formulations in this and the earlier set of tests. All liquid fill formulations were significantly superior to any of the three commercial tablets formulations.

Example 29

Ease of Powdering and Percentage of Resultant Particles of 600 Micron or Less

Initial powdering tests were carried out using a laboratory stainless steel sieve of nominal 650 micron size. The sieve size used had been qualitatively determined as a size that could differentiate between the powders generated. Initially much finer sieves had been tested but were found to be too fine e.g. a 45 micron sieve was tested but this was too fine resulting in almost zero powder passing through the sieve from any samples. As result of the initial tests, a certified sieve was obtained of 600 micron size for further trials. All of the above samples were subjected to the powdering test. The results are shown in Table 12.

TABLE 12

Powder generation of formulations and comparator tablets by grinding of dosage units cooled to domestic freezer temperatures

| Base Excipient | Formulation | Comment | % as 600µ or less. Sample 1 | % as 600µ or less. Sample 2 |
|---|---|---|---|---|
| Dromadol SR | n/a | | 48.1% | 51.9% |
| Zydol XL 150 | n/a | | 52.6% | 41.2% |
| Oxycontin 80 mg | n/a | | 66.6% | Not tested |
| Sterotex NF with 25% fr. coconut oil | 052/094-3 | With 25% fractionated coconut oil | 2.2% | 0.6% |
| Cithrol GMS | 052/073-5 | | 40.3% | 72.4% |
| Hydrokote 112 | 052/074-6 | | 7.3% | 2.6% |
| Beeswax | 052/074-7 | | 0.7% | 0.6% |

It should be noted that the lower results found in this trial than those reported previously are due to a slightly finer sieve size being used. The tablets all powdered relatively easily while the Sterotex NF, Hydrokote 112 and beeswax were very resistant to powdering. The Cithrol GMS gave a high quantity of powder. The same approach of adding a room temperature oil could be used on the Cithrol GMS as used on Sterotex NF however, with the Cithrol GMS formulation showing a release rate of approximately 20 hr, on the fast size of the target 24 hr, it was decided not to amend it at this stage.

Example 30

Dissolution Testing of Stored Samples

Samples of the above formulations were stored for a period of at least four weeks at room temperature (in some cases much longer) after which their dissolution release profile was re-determined. This was carried out to find out if there were any short term changes in the release rate. The tested formulations are shown in Table 13 and FIGS. 48 to 57.

TABLE 13

Formulations used for dissolution testing after a minimum of 4 weeks storage.

| Base Excipient | Formulation | Storage period days | Comment |
|---|---|---|---|
| Sterotex N | 052/087-1 | 75 | 20% HPMC |
| Sterotex NF with 25% fr. coconut oil | 052/094-3 | 71 | |
| Cithrol GMS | 052/073-5 | 95 | |
| Hydrokote 112 | 052/074-6 | 98 | |
| Beeswax | 052/074-7 | 83 | |

Example 31

The manufacturing methods described above was utilized to prepare a dosage form of the proserotonergic drug tramadol and filled in gelatin capsules (see FIG. 59).

| Excipients | Content |
| --- | --- |
| Sterotex NF | 141 mg |
| Methocel, K15M | 80 mg |
| Fractionated Coconut oil | 100 mg |
| Aerosil 200 | 4 mg |
| Tramadol HCl | 75 mg |
| Total Weight | 400 mg |

Example 33

The manufacturing methods described above was utilized to prepare a dosage form of the proserotonergic drug tramadol and filled in gelatin capsules (see FIG. 61).

| Excipients | Content |
| --- | --- |
| Hydrocote 112 | 253 mg |
| Methocel, K15M | 60 mg |
| Aerosil 200 | 12 mg |
| Tramadol HCl | 75 mg |
| Total Weight | 400 mg |

Example 34

The manufacturing methods described above was utilized to prepare a dosage form of the proserotonergic drug tramadol and filled in gelatin capsules (see FIG. 62).

| Excipients | Content |
| --- | --- |
| Cithrol GMS | 273 mg |
| Methocel, K100M | 40 mg |
| Aerosil 200 | 12 mg |
| Tramadol HCl | 75 mg |
| Total Weight | 400 mg |

Example 35

The manufacturing methods described above was utilized to prepare a dosage form of the proserotonergic drug levorphanol and filled in gelatin capsules (see FIG. 63).

| Excipients | Content |
| --- | --- |
| Beeswax | 237 mg |
| Methocel, K15M | 80 mg |
| Aerosil 200 | 8 mg |
| Tramadol HCl | 75 mg |
| Total Weight | 400 mg |

Example 36

The manufacturing methods described above was utilized to prepare a dosage form of the proserotonergic drug levorphanol and filled in gelatin capsules (see FIG. 64).

| Excipients | Content |
| --- | --- |
| Sterotex NF | 141 mg |
| Methocel, K15M | 80 mg |
| Fractionated Coconut oil | 100 mg |
| Aerosil 200 | 4 mg |
| Levorphanol Tartrate | 10 mg |
| Total Weight | 335 mg |

| Excipients | Content |
| --- | --- |
| Hydrocote 112 | 253 mg |
| Methocel, K15M | 60 mg |
| Aerosil 200 | 12 mg |
| Levorphanol Tartrate | 10 mg |
| Total Weight | 335 mg |

Example 37

The manufacturing methods described above was utilized to prepare a dosage form of the proserotonergic drug levorphanol and filled in gelatin capsules (see FIG. 65).

| Excipients | Content |
| --- | --- |
| Cithrol GMS | 273 mg |
| Methocel, K100M | 40 mg |
| Aerosil 200 | 12 mg |
| Levorphanol Tartrate | 10 mg |
| Total Weight | 335 mg |

Example 38

The manufacturing methods described above was utilized to prepare a dosage form of the proserotonergic drug levorphanol and filled in gelatin capsules (see FIG. 66).

| Excipients | Content |
| --- | --- |
| Beeswax | 237 mg |
| Methocel, K15M | 80 mg |
| Aerosil 200 | 8 mg |
| Levorphanol Tartrate | 10 mg |
| Total Weight | 335 mg |

The manufacturing methods described above and others are utilized for the preparation of other proserotonergic dosage form of the invention as shown in the prophetic examples below. Variations to the methods may be employed, in some embodiments, depending on the specific chemical, physicochemical, pharmaceutical and pharmacologic properties of the abusable drug, excipients and their interaction and other factors. Compositions and methods of the present invention in some embodiments provide protection against the serotonin syndrome; wherein the dosage form is prepared using serotonin surge protectors of the invention. Compositions and methods of the present invention in some embodiments provide simultaneous protection against the serotonin syndrome and against drug abuse; wherein the abusable proserotonergic dosage form is prepared using serotonin surge protectors of the invention. Compositions and methods of the present invention in some embodiments provide simultaneous protection against the serotonin syndrome and against drug abuse using substantially the same serotonin surge protectors; wherein the abusable proserotonergic dosage form is prepared using serotonin surge protectors of the invention. Compositions and methods of the present invention in some embodiments provide protection against the serotonin syndrome and also provide extended release of the proserotonergic agent; wherein the dosage form is prepared using serotonin surge protectors of the invention. Compositions and methods of the present invention in some embodiments provide protection against the serotonin syndrome and also provide extended release of the proserotonergic agent using substantially the same serotonin surge protectors; wherein the dosage form is prepared using serotonin surge protectors of the invention. Compositions and methods of the present invention in some embodiments provide protection against the serotonin syndrome and against drug abuse, and provide extended release of the proserotonergic agent; wherein the dosage form is prepared using serotonin surge protectors of the invention. Compositions and methods of the present invention in some embodiments provide protection against the serotonin syndrome and against drug abuse, and provide extended release of the proserotonergic agent; wherein the dosage form is prepared using substantially the same serotonin surge protectors of the invention.

Example 39

| Ingredients | Quantity (mg)/Dose |
|---|---|
| Beeswax | 200 |
| HPMC, Pharmacoat 606 | 62.5 |
| Aerosil COK 84 | 7.5 |
| Hydrocodone | 30 |
| Capsule fill weight | 300 |

Example 40

| Ingredients | Quantity (mg)/Dose |
|---|---|
| Gelucire 50/02 | 190 |
| Methocel K 100M | 35 |
| Aerosil COK 84 | 10 |
| Hydromorphone HCl | 15 |
| Capsule fill weight | 250 |

Example 41

| Ingredients | Quantity (mg)/Dose |
|---|---|
| Cetyl alcohol | 280 |
| Methocel K 100M | 50 |
| Aerosil COK 84 | 10 |
| Levorphanol | 10 |
| Capsule fill weight | 350 |

Example 42

| Ingredients | Quantity (mg)/Dose |
|---|---|
| Sterotex NF | 320 |
| Methocel K 15M | 60 |
| Aerosil COK 84 | 10 |
| Oxycodone | 10 |
| Capsule fill weight | 400 |

Example 43

| Ingredients | Quantity (mg)/Dose |
|---|---|
| Cithrol GMS | 320 |
| Methocel K 100M | 55 |
| Aerosil COK 84 | 15 |
| Oxymorphone | 10 |
| Capsule fill weight | 400 |

Example 44

| Ingredients | Quantity (mg)/Dose |
|---|---|
| Hydrokote 112 | 225 |
| Methocel K 15M | 50 |
| Aerosil COK 84 | 10 |
| Hydrocodone | 15 |
| Capsule fill weight | 300 |

Example 45

| Ingredients | Quantity (mg)/Dose |
|---|---|
| Beeswax | 225 |
| Methocel K 15M | 75 |
| Aerosil COK 84 | 10 |
| Dihydrocodeine | 15 |
| Capsule fill weight | 325 |

Example 46

| Ingredients | Quantity (mg)/Dose |
|---|---|
| Beeswax | 210 |
| HPMC, K 15M | 80 |
| Aerosil COK 84 | 8 |
| Hydromorphone | 2 |
| Capsule fill weight | 300 |

Example 47

| Ingredients | Quantity (mg)/Dose |
|---|---|
| Sterotex NF | 166 |
| HPMC, K 15M | 75 |
| Coconut oil | 75 |
| Aerosil COK 84 | 5 |
| Hydromorphone | 4 |
| Capsule fill weight | 325 |

Example 48

| Ingredients | Quantity (mg)/Dose |
|---|---|
| Cithrol GMS | 285 |
| HPMC, K 100M | 49 |
| Aerosil COK 84 | 10 |
| Hydromorphone | 6 |
| Capsule fill weight | 350 |

Example 49

| Ingredients | Quantity (mg)/Dose |
|---|---|
| Hydrokote 112 | 240 |
| HPMC, K 15M | 50 |
| Aerosil COK 84 | 10 |
| Oxycodone | 100 |
| Capsule fill weight | 400 |

Example 50

| Ingredients | Quantity (mg)/Dose |
|---|---|
| Beeswax | 195 |
| HPMC, Pharmacoat 606 | 45 |
| Aerosil COK 84 | 10 |
| Oxycodone | 150 |
| Capsule fill weight | 400 |

Example 51

| Ingredients | Quantity (mg)/Dose |
|---|---|
| Gelucire 50/02 | 190 |
| Methocel K 100M | 30 |
| Aerosil COK 84 | 10 |
| Hydromorphone HCl | 20 |
| Capsule fill weight | 250 |

Example 52

| Ingredients | Quantity (mg)/Dose |
|---|---|
| Cetyl alcohol | 290 |
| Methocel K 100M | 50 |
| Aerosil COK 84 | 10 |
| Hydrocodone | 50 |
| Capsule fill weight | 400 |

Example 53

| Ingredients | Quantity (mg)/Dose |
|---|---|
| Sterotex NF | 320 |
| Methocel K 15M | 60 |
| Aerosil COK 84 | 10 |
| Oxymorphone | 40 |
| Capsule fill weight | 430 |

Example 54

| Ingredients | Quantity (mg)/Dose |
|---|---|
| Cithrol GMS | 320 |
| Methocel K 100M | 68 |
| Aerosil COK 84 | 12 |
| Oxycodone | 60 |
| Capsule fill weight | 460 |

Example 55

| Ingredients | Quantity (mg)/Dose |
|---|---|
| Hydrokote 112 | 225 |
| Methocel K 15M | 50 |
| Aerosil COK 84 | 10 |
| Methadone | 40 |
| Capsule fill weight | 325 |

Example 56

| Ingredients | Quantity (mg)/Dose |
|---|---|
| Beeswax | 235 |
| Methocel K 15M | 75 |
| Aerosil COK 84 | 14 |
| Codeine S$O_4$ | 150 |
| Capsule fill weight | 474 |

Example 57

| Ingredients | Quantity (mg)/Dose |
|---|---|
| Beeswax | 200 |
| HPMC, K 15M | 90 |
| Aerosil COK 84 | 10 |
| Pentazocine | 100 |
| Capsule fill weight | 40 |

Example 58

| Ingredients | Quantity (mg)/Dose |
|---|---|
| Sterotex NF | 150 |
| HPMC, K15M | 75 |
| Coconut oil | 80 |
| Aerosil COK 84 | 10 |
| Anileridine | 100 |
| Capsule fill weight | 415 |

Example 59

| Ingredients | Quantity (mg)/Dose |
|---|---|
| Cithrol GMS | 290 |
| HPMC, K100M | 48 |
| Aerosil COK 84 | 12 |
| Oxycodone | 40 |
| Capsule fill weight | 390 |

Example 60

| Ingredients | Quantity (mg)/Dose |
|---|---|
| Hydrokote 112 | 270 |
| HPMC, K15M | 65 |
| Aerosil COK 84 | 15 |
| Oxycodone | 20 |
| Capsule fill weight | 370 |

Example 61

| Ingredients | Quantity (mg)/Dose |
|---|---|
| Beeswax | 177 |
| HPMC, Pharmacoat 606 | 60 |
| Aerosil COK 84 | 10 |
| Methadone | 23 |
| Capsule fill weight | 270 |

Example 62

| Ingredients | Quantity (mg)/Dose |
|---|---|
| Gelucire 50/02 | 190 |
| Methocel K 100M | 40 |
| Aerosil COK 84 | 10 |
| Methadone | 10 |
| Capsule fill weight | 250 |

Example 63

| Ingredients | Quantity (mg)/Dose |
|---|---|
| Cetyl alcohol | 270 |
| Methocel K 100M | 50 |
| Aerosil COK 84 | 10 |
| Meperidine | 20 |
| Capsule fill weight | 350 |

Example 64

| Ingredients | Quantity (mg)/Dose |
|---|---|
| Sterotex NF | 293 |
| Methocel K 15M | 45 |
| Aerosil COK 84 | 10 |
| Meperidine | 52 |
| Capsule fill weight | 400 |

Example 65

| Ingredients | Quantity (mg)/Dose |
|---|---|
| Cithrol GMS | 325 |
| Methocel K 100M | 55 |
| Aerosil COK 84 | 15 |
| hydromorphone | 5 |
| Capsule fill weight | 400 |

Example 66

| Ingredients | Quantity (mg)/Dose |
|---|---|
| Hydrokote 112 | 225 |
| Methocel K 15M | 50 |
| Aerosil COK 84 | 10 |
| Hydrocodone | 15 |
| Capsule fill weight | 300 |

Example 67

| Ingredients | Quantity (mg)/Dose |
|---|---|
| Beeswax | 225 |
| Methocel K 15M | 75 |
| Aerosil COK 84 | 10 |
| Hydrocodone | 20 |
| Capsule fill weight | 330 |

Example 68

| Ingredients | Quantity (mg)/Dose |
|---|---|
| Sterotex ® NF | 100 |
| Fractionated coconut oil | 70 |
| Beeswax | 100 |
| Methocel ® K 15M | 81 |
| Aerosil ® COK 84 | 4 |
| Hydromorphone HCl | 20 |
| Capsule fill weight | 375 |

Example 69

| Ingredients | Quantity (mg)/Dose |
|---|---|
| Sterotex ® NF | 135 |
| Fractionated coconut oil | 50 |
| Beeswax | 50 |
| Methocel ® K 15M | 60 |
| Aerosil ® COK 84 | 3 |
| Morphine HCl | 22 |
| Capsule fill weight | 320 |

Example 70

| Ingredients | Quantity (mg)/Dose |
|---|---|
| Sterotex ® NF | 130 |
| Fractionated coconut oil | 100 |
| Beeswax | 70 |
| HPMC, K15M | 20 |
| Methocel ® K 15M | 70 |
| Aerosil ® COK 84 | 4.5 |
| Levorphanol | 5.5 mg |
| Capsule fill weight | 400 |

Example 71

| Ingredients | Quantity (mg)/Dose |
|---|---|
| Sterotex ® NF | 150 |
| Fractionated coconut oil | 80 |
| Cithrol GMS | 120 |
| HPMC, K100M | 20 |
| Methocel ® K 15M | 80 |
| Aerosil ® COK 84 | 5 |
| Methadone | 60 |
| Capsule fill weight | 515 mg |

Example 72

| Ingredients | Quantity (mg)/Dose |
|---|---|
| Beeswax | 150 |
| HPMC, K15M | 80 |
| Aerosil COK 84 | 10 |
| Cithrol | 150 |
| Levorphanol Tartrate | 20 |
| Capsule fill weight | 410 |

Example 73

| Ingredients | Quantity (mg)/Dose |
|---|---|
| Beeswax | 150 |
| HPMC, K15M | 80 |
| Aerosil COK 84 | 15 |
| Hydrokote 112 | 75 |
| Morphine Sulfate | 60 |
| Capsule fill weight | 380 |

Example 74

| Ingredients | Quantity (mg)/Dose |
|---|---|
| Sterotex NF | 150 |
| HPMC, K15M | 75 |

-continued

| Ingredients | Quantity (mg)/Dose |
|---|---|
| Coconut oil | 75 |
| Aerosil COK 84 | 5 |
| Oxymorphone | 20 |
| Hydrokote 112 | 75 |
| Capsule fill weight | 400 |

Example 75

| Ingredients | Quantity (mg)/Dose |
|---|---|
| Cithrol GMS | 275 |
| HPMC, K100M | 50 |
| Aerosil COK 84 | 15 |
| Hydrokote 112 | 100 |
| Methadone | 60 |
| Capsule fill weight | 500 |

Example 76

| Ingredients | Quantity (mg)/Dose |
|---|---|
| Cithrol GMS | 275 |
| HPMC, K100M | 60 |
| Aerosil COK 84 | 15 |
| Gelucire 50/02 | 100 |
| Methadone | 25 |
| Capsule fill weight | 475 |

Example 77

| Ingredients | Quantity (mg)/Dose |
|---|---|
| Gelucire 50/02 | 140 |
| Methocel K 100M | 35 |
| Aerosil COK 84 | 15 |
| Sterotex ® NF | 75 |
| Fractionated coconut oil | 45 |
| Hydromorphone HCl | 15 |
| Capsule fill weight | 325 |

Example 78

| Ingredients | Quantity (mg)/Dose |
|---|---|
| Gelucire 50/02 | 100 |
| Methocel K 100M | 28 |

-continued

| Ingredients | Quantity (mg)/Dose |
|---|---|
| Aerosil COK 84 | 12 |
| Beeswax | 125 |
| HPMC, K15M | 65 |
| Levorphanol Tartrate | 30 |
| Capsule fill weight | 370 |

Example 79

| Ingredients | Quantity (mg)/Dose |
|---|---|
| Gelucire 50/02 | 200 |
| Methocel K 100M | 60 |
| Aerosil COK 84 | 20 |
| Cithrol GMS | 140 |
| Oxycodone HCl | 80 |
| Capsule fill weight | 500 |

Example 80

| Ingredients | Quantity (mg)/Dose |
|---|---|
| Sterotex ® NF | 200 |
| Fractionated coconut oil | 70 |
| Methocel ® K 15M | 81 |
| Aerosil ® COK 84 | 4 |
| Hydromorphone HCl | 20 |
| Capsule fill weight | 375 |

Example 81

| Ingredients | Quantity (mg)/Dose |
|---|---|
| Sterotex ® NF | 135 |
| Fractionated coconut oil | 50 |
| Methocel ® K 15M | 60 |
| Aerosil ® COK 84 | 3 |
| Hydromorphone HCl | 22 |
| Capsule fill weight | 270 |

Example 82

| Ingredients | Quantity (mg)/Dose |
|---|---|
| Sterotex ® NF | 170 |
| Fractionated coconut oil | 100 |
| Methocel ® K 15M | 70 |
| Aerosil ® COK 84 | 4.5 |
| Levorphanol | 5.5 mg |
| Capsule fill weight | 350 |

Example 83

| Ingredients | Quantity (mg)/Dose |
|---|---|
| Sterotex ® NF | 200 |
| Fractionated coconut oil | 90 |
| Methocel ® K 15M | 80 |
| Aerosil ® COK 84 | 5 |
| Hydrocodone | 25 |
| Capsule fill weight | 400 mg |

Example 84

| Ingredients | Quantity (mg)/Dose |
|---|---|
| Beeswax | 200 |
| HPMC, K15M | 80 |
| Aerosil COK 84 | 8 |
| Levorphanol Tartrate | 12 |
| Capsule fill weight | 300 |

Example 85

| Ingredients | Quantity (mg)/Dose |
|---|---|
| Sterotex NF | 150 |
| HPMC, K15M | 75 |
| Coconut oil | 75 |
| Aerosil COK 84 | 5 |
| Oxymorphone | 20 |
| Capsule fill weight | 325 |

Example 86

| Ingredients | Quantity (mg)/Dose |
|---|---|
| Cithrol GMS | 275 |
| HPMC, K100M | 40 |
| Aerosil COK 84 | 10 |
| Methadone | 25 |
| Capsule fill weight | 350 |

Example 87

| Ingredients | Quantity (mg)/Dose |
|---|---|
| Hydrokote 112 | 250 |
| HPMC, K15M | 60 |
| Aerosil COK 84 | 10 |
| Morphine | 30 |
| Capsule fill weight | 350 |

The manufacturing methods described above and others are utilized for the preparation of other dosage forms of the invention using the following proserotonergic drugs: (i) selective serotonin-reuptake inhibitors (SSRIs); (ii) selective serotonin-norepinephrine reuptake inhibitors (SNRIs); (iii) serotonin reuptake inhibitors; (iv) norepinephrine reuptake inhibitors; (v) tricyclic, tetarcyclic and non-tricyclic antidepressants; (vi) monoamine oxidase (MAO) inhibitors; (vii) antiepileptics; (viii) opioid analgesics; (ix) tramadol; (x) antiemetics; (xi) bariatric medications; (xii) sibutramine; (xiii) antibiotics; (xiv) antimigraine drugs; (xv) antivirals; (xvi) antitussives, and mixtures thereof given in the form of an acid, base or, optionally, in the form of a pharmaceutically acceptable salt, prodrug, ester, analog, derivative, solvate, complex, polymorph, hydrate, racemate or an individual diastereoisomers or enantiomeric isomers thereof or mixture thereof.

The manufacturing methods described above and others are utilized for the preparation of other dosage forms of the invention using the following proserotonergic drugs: citalopram, fluoxetine, fluvoxamine, paroxetine, sertaline, venlafaxine, milnacipran, buspirone, clomipramine, nefazodone, trazadone, clorgiline, isocarboxazid, moclobemide, phenelzine, selegiline, valproate, fentanyl, levorphanol, meperidine, pentazocine, tramadol, granisetron, metoclopramide, ondansetron, sumatriptan, sibutramine, linezolide, ritonavir, dextromethorphan, dextrorphan, tryptophan, hypericum perforatum (St. John's wort), panax ginseng (ginseng), lithium and mixtures thereof given in the form of an acid, base or, optionally, in the form of a pharmaceutically acceptable salt, prodrug, ester, analog, derivative, solvate, complex, polymorph, hydrate, racemate or an individual diastereoisomers or enantiomeric isomers thereof or mixture thereof.

The manufacturing methods described above and others are utilized for the preparation of other dosage forms of the invention using the following proserotonergic drugs: ecitalopram, bicifadine, milnacipran, mirtazepine, buspirone, clomipramine, trazadone, clorgiline, isocarboxazid, moclobemide, phenelzine, selegiline, valproate, granisetron, metoclopramide, ondansetron, sumatriptan, naratriptan, rizatriptan, frovatriptan, eletriptan, zolmitriptan, almotriptan, sibutramine, linezolide, ritonavir, dextromethorphan, dextrorphan, tryptophan, Hypericum perforatum (St. John's wort), Panax ginseng (ginseng), lithium, and mixtures thereof given in the form of an acid, base or, optionally, in the form of a pharmaceutically acceptable salt, prodrug, ester, analog, derivative, solvate, complex, polymorph, hydrate, racemate or an individual diastereoisomers or enantiomeric isomers thereof or mixture thereof.

The manufacturing methods described above and others are utilized for the preparation of other dosage forms of the invention using the following proserotonergic drugs: alfentanil, allylprodine, alphaprodine, anileridine, apomorphine, apocodeine, benzylmorphine, bezitramide, buprenorphine, butorphanol, carfentanil, clonitazene, codeine, cyclazocine, cyclorphen, cyprenorphine, desmethyltramadol, desomorphine, dextromoramide, dezocine, diampromide, dihydrocodeine, dihydromorphine, dimenoxadol, dimepheptanol, dimethylthiambutene, dioxyaphetyl butyrate, dipipanone, eptazocine, ethoheptazine, ethylmethylthiambutene, ethylmorphine, etonitazene, fentanyl, heroin, hydrocodone, hydroxymethylmorphinan, hydromorphone, hydroxypethidine, isomethadone, ketobemidone, levallorphan, levorphanol, levomethadone, levophenacylmorphan, lofentanil, meperidine, meptazinol, metazocine, methadone, methylmorphine, metopon, morphine, myrophine, nalbuphine, narceine, nicomorphine, norlevorphanol, normethadone, nalorphine, normorphine, norpipanone, ohmefentanyl, opium, oxycodone, oxymorphone, papavereturn, pentazocine, phenadoxone, phenomorphan, phenazocine, phenoperidine, pholcodine, piminodine, piritramide, propheptazine, promedol, profadol, properidine, propiram, propoxyphene, remifentanil, sufentanil, tapentadol, tramadol, tramadol metabolites, tilidine, naltrexone, naloxone, nalmefene, methylnaltrexone, naloxone methiodide, nalorphine, naloxonazine, nalide, nalmexone, nalbuphine, nalorphine dinicotinate, naltrindole (NTI), naltrindole isothiocyanate, (NTII), naltriben (NTB), nor-binaltorphimine (nor-BNI), racemorphan, beta-funaltrexamine (b-FNA), BNTX, cyprodime, ICI-174, 864, LY117413, MR2266, etorphine, DAMGO, CTOP, diprenorphine, naloxone benzoylhydrazone, bremazocine, ethylketocyclazocine, U50,488, U69, 593, spiradoline, DPDPE, [D-Ala2,Glu4] deltorphin, DSLET, Met-enkephalin, Leu-enkephalin, (3-endorphin, dynorphin A, dynorphin B, a-neoendorphin, or an opioid having the same pentacyclic nucleus as nalmefene, naltrexone, buprenorphine, levorphanol, meptazinol, pentazocine, dezocine and mixtures thereof given in the form of an acid, base or, optionally, in the form of a pharmaceutically acceptable salt, prodrug, ester, analog, derivative, solvate, complex, polymorph, hydrate, racemate or an individual diastereoisomers or enantiomeric isomers thereof or mixture thereof.

The manufacturing methods described above and others are utilized for the preparation of other dosage forms of the invention using the following proserotonergic drugs: alfentanil, anileridine, buprenorphine, brifentanil, butorphanol, carfentanil, codeine, dextromoramide, dezocine, dihydrocodeine, dihydromorphine, fentanyl, heroin, hydrocodone, hydromorphone, hydroxypethidine, isomethadone, ketobemidone, levorphanol, levomethadone, lofentanil, meperidine, meptazinol, metazocine, methadone, 4-methoxymethylfentanyl, 3-methylfentanil, metopon, mirfentanil, morphine, morphine-6-glucuronide, nalbuphine, norlevorphanol, normethadone, ohmefentanyl, opium, oxycodone, oxymorphone, pentazocine, phenazocine, propiram, propoxyphene, remifentanil, sufentanil, tapentadol, trefentanil, tramadol, tilidine, any opioid having agonist activity at an opioid receptor belonging to the phenanthrene, morphinan, benzomorphan, methadone, phenylpiperidine, propionanilide 4-anilidopiperidine, 4-aryl piperidines, and 4-Heteroarylpiperidines class, any opioid having agonist activity at an opioid receptor having the same pentacyclic nucleus as nalmefene, naltrexone, buprenorphine, levorphanol, meptazinol, pentazocine and dezocine, and mixtures thereof given in the form of an acid, base or, optionally, in the form of a pharmaceutically acceptable salt, prodrug, ester, analog, derivative, solvate, complex, polymorph, hydrate, racemate or an individual diastereoisomers or enantiomeric isomers thereof or mixture thereof.

These and other embodiments of the present invention will readily occur to those of ordinary skill in the art in view of the disclosure herein.

The included examples are illustrative but not limiting of the methods and composition of the present invention. Other suitable modifications and adaptations of the variety of conditions and parameters normally encountered and obvious to those skilled in the art are within the spirit and scope of the invention.

A wide variety of materials can be used for preparing the dosage form according to this invention. This invention therefore contemplates the use of materials other than those specifically disclosed herein, including those which may hereafter become known to the art to be capable of performing the necessary functions.

Having now fully described the invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A method of reducing the intensity of the serotonin syndrome in a human to whom levorphanol is being administered, the method comprising orally administering to the human a pharmaceutical composition comprising a blend of
    a) an effective amount of levorphanol and
    b) a serotonin surge protector (SSP) selected from the group consisting of:
        i) hydrogenated vegetable oils;
        ii) coconut oil products;
        iii) polyoxyethylene stearates;
        iv) polyoxyethylene distearates;
        v) glycerol monostearate; and
        vi) waxes that are poorly soluble in water and that have a melting point in the range from 40 to 100 degrees Celsius;
    the SSP being present in an amount sufficient to extend release of the levorphanol, relative to the same composition lacking the SSP,
wherein the blend has a melting point greater than 20 degrees Celsius.

2. The method of claim 1, wherein the blend comprises at least two of i)-vi).

3. The method of claim 1, wherein the blend comprises at least three of i)-vi).

4. The method of claim 1, wherein the blend further comprises
    c) a thixotrope in an amount sufficient to increase the viscosity of the blend when it is combined with a solvent.

5. The method of claim 4, wherein the thixotrope is selected from the group comprising silicon dioxide or a mixture of silicon dioxide and aluminum oxide.

6. The method of claim 4, wherein the blend further comprises
    d) a release rate modifier in an amount effective to modify the rate of release of levorphanol from the composition following administration of the composition to the human.

7. The method of claim 1, wherein the blend further comprises a release rate modifier in an amount effective to modify the rate of release of levorphanol from the composition following administration of the composition to the human.

8. The method of claim 7, wherein an aqueous solution of the release rate modifier exhibits a greater viscosity at 40 degrees Celsius than at approximately 20 degrees Celsius.

9. The method of claim 8, wherein the release rate modifier is soluble in water at approximately 20 degrees Celsius, but is substantially insoluble in water at 40 degrees Celsius.

10. The method of claim 7, wherein the release rate modifier is a hydroxypropyl methyl cellulose.

11. The method of claim 1, wherein the blend comprises a hydrogenated vegetable oil selected from the group consisting of hydrogenated cottonseed oil, hydrogenated palm oil, hydrogenated palm kernel oil, hydrogenated soybean oil, and combinations of these.

12. The method of claim 1, wherein the blend comprises a coconut oil product selected from the group consisting of coconut oil, fractionated coconut oil, cetyl alcohol, lauric acid and medium chain triglycerides, and combinations of these.

13. The method of claim 12, wherein the coconut oil product is fractionated coconut oil.

14. The method of claim 1, wherein the blend comprises at least one of
   i) a polyoxyethylene stearate selected from the group consisting of polyoxyl 2, 4, 6, 8, 12, 20, 30, 40, 50, 100 and 150 stearates and combinations of these and
   ii) a polyoxyethylene distearate selected from the group consisting of polyoxyl 4, 8, 12, 32 and 150 distearates and combinations of these.

15. The method of claim 1, wherein the blend comprises a wax selected from the group consisting of glyceryl behenate, glyceryl palmitostearate, glyceryl monostearate, stearoyl macrogolglycerides, lauroyl macrogolglycerides, carnauba waxes, petroleum waxes, cetyl ester waxes, hydrogenated castor oils, lanolin alcohols, cetostearyl alcohols, beeswaxes, and combinations of these.

16. A method of reducing the incidence of the serotonin syndrome in a human to whom levorphanol is being administered, the method comprising orally administering to the human a pharmaceutical composition comprising a blend of
   a) an effective amount of levorphanol and
   b) a serotonin surge protector (SSP) selected from the group consisting of:
      i) hydrogenated vegetable oils;
      ii) coconut oil products;
      iii) polyoxyethylene stearates;
      iv) polyoxyethylene distearates;
      v) glycerol monostearate; and
      vi) waxes that are poorly soluble in water and that have a melting point in the range from 40 to 100 degrees Celsius;
   the SSP being present in an amount sufficient to extend release of levorphanol, relative to the same composition lacking the SSP,
wherein the blend has a melting point greater than 20 degrees Ceisius,
whereby incidence of the serotonin syndrome in the human is decreased, relative to incidence of the serotonin syndrome in the same human being administered levorphanol alone.

17. The method of claim 16, wherein the blend comprises a pharmaceutically acceptable salt of levorphanol.

18. The method of claim 16, wherein the blend comprises levorphanol tartrate.

19. The method of claim 1, wherein the blend comprises a pharmaceutically acceptable salt of levorphanol.

20. The method of claim 1, wherein the blend comprises levorphanol tartrate.

* * * * *